US012583911B2

(12) United States Patent (10) Patent No.: US 12,583,911 B2
Arnoult et al. (45) Date of Patent: Mar. 24, 2026

(54) HUMAN IMMUNODEFICIENCY VIRUS GP120 BINDING PROTEINS

(71) Applicant: ViiV Healthcare UK (No.5) Limited, Stevenage (GB)

(72) Inventors: Eric Arnoult, Branford, CT (US); Tiancen Hu, Branford, CT (US); Mark R. Krystal, Branford, CT (US); James Schawalder, Durham, NC (US)

(73) Assignee: ViiV Healthcare UK (NO.5) Limited, Stevenage (GB)

( * ) Notice: Subject to any disclaimer, the term of this patent is extended or adjusted under 35 U.S.C. 154(b) by 51 days.

(21) Appl. No.: 18/498,114

(22) Filed: Oct. 31, 2023

(65) Prior Publication Data

US 2024/0166728 A1 May 23, 2024

Related U.S. Application Data

(60) Provisional application No. 63/421,737, filed on Nov. 2, 2022.

(51) Int. Cl.
| | |
|---|---|
| *C07K 16/10* | (2006.01) |
| *A61P 31/18* | (2006.01) |
| *C12N 15/63* | (2006.01) |
| *A61K 39/00* | (2006.01) |

(52) U.S. Cl.
CPC .......... *C07K 16/1063* (2013.01); *A61P 31/18* (2018.01); *C12N 15/63* (2013.01); *A61K 2039/505* (2013.01); *C07K 2317/14* (2013.01)

(58) Field of Classification Search
None
See application file for complete search history.

(56) References Cited

U.S. PATENT DOCUMENTS

2018/0237505 A1 8/2018 Ho et al.

FOREIGN PATENT DOCUMENTS

| WO | 9304693 A1 | 3/1993 |
|---|---|---|
| WO | 2015048770 A2 | 4/2015 |
| WO | 2016153572 A1 | 9/2016 |
| WO | 2018075564 A1 | 4/2018 |
| WO | 2020082045 A1 | 4/2020 |

OTHER PUBLICATIONS

Stryer, L., Biochemistry, 4th edition, W. H. Freeman and Company, 1995, pp. 18-23.*
Rudikoff et al., Proc Natl Acad Sci USA. Mar. 1982;79(6):1979-83.*
Winkler et al., J Immunol. Oct. 15, 2000;165(8):4505-14. doi: 10.4049/jimmunol.165.8.4505. PMID: 11035090.*
Janeway et al., Immunobiology, 3rd edition, Garland Publishing Inc, 1997, pp. 3:1-3:21.*
Edwards et al.,J Mol Biol. Nov. 14, 2003;334(1): 103-18.*
Llyod et al., Protein Eng Des Sel. Mar. 2009;22(3):159-68. doi: 10.1093/protein/gzn058. Epub Oct. 29, 2008.*
Goel et al., J Immunol. Dec. 15, 2004; 173(12):7358-67.*
Kanyavuz et al., Nat Rev Immunol. Jun. 2019;19(6):355-368. doi: 10.1038/S41577-019-0126-7.*
Chen et al., J Virol. Jan. 2014;88(2):1125-39. doi: 10.1128/JVI. 02566-13. Epub Nov. 6, 2013. PMID: 24198429 PMCID: PMC3911630.*
Chen et al., Antiviral Res. Oct. 2010;88(1):107-15. doi: 10.1016/j. antiviral.2010.08.004. Epub Aug. 13, 2010. PMID: 20709110 PMCID : PMC2954370.*
Falkenhagen A., and Joshi S., "HIV Entry and Its Inhibition by Bifunctional Antiviral Proteins," Molecular Therapy Nucleic Acids, Dec. 2018, vol. 13, pp. 347-364.
International Search Report and Written Opinion for International Application No. PCT/EP2023/080353, mailed Apr. 26, 2024, 20 Pages.
Lagenaur L.A., et al., "sCD4-17b Bifunctional Protein: Extremely Broad and Potent Neutralization of HIV-1 Env Pseudotyped Viruses from Genetically Diverse Primary Isolates," Retrovirology, 2010, vol. 7(11), pp. 1-13.
Magnus A.G.H., et al., "Nanoparticles Presenting Clusters of Cd4 Expose a Universal Vulnerability of Hiv-1 by Mimicking Target Cells," Proceedings of the National Academy of Sciences, Abstract, Jul. 20, 2020, vol. 117, No. 31, pp. 18719-18728, DOI: 10.1073/ pnas.2010320117, ISSN: 0027-8424, XP093132438.
Shigeyoshi H., et al., "Driving HIV-1 into a Vulnerable Corner by Taking Advantage of Viral Adaptation and Evolution," Frontiers in Microbiology, Mar. 16, 2017, vol. 8, Lausanne, Abstract, DOI: 10.3389/fmicb.2017.00390, ISSN: 1664-302X, XP093132471.
West A.P., et al., "Evaluation of CD4-CD4i Antibody Architectures Yields Potent, Broadly Cross-Reactive Anti-Human Immunodeficiency Virus Reagents," Journal of Virology, Jan. 2010, vol. 84(1), pp. 261-269.
Chen W., et al., "Engineered Single Human CD4 Domains as Potent HIV-1 Inhibitors and Components of Vaccine Immunogens," Journal of Virology, 2011, vol. 85(18), pp. 9395-9405.
Fisher R.A., et al., "HIV infection is blocked in vitro by recombinant soluble CD4," Nature, Jan. 7, 1988, vol. 331, pp. 76-78, Retrieved from [https://doi.org/10.1038/331076a0].
International Preliminary Report on Patentability for International Application No. PCT/EP2023/080353, mailed May 15, 2025, 14 Pages.

(Continued)

*Primary Examiner* — Michael Szperka

(74) *Attorney, Agent, or Firm* — Kelly A. Gauger

(57) ABSTRACT

Antigen binding proteins of the invention bind to Human Immunodeficiency Virus (HIV) envelope protein and are useful in treating and preventing HIV infection. In particular, the antigen binding proteins bind to two different epitopes on HIV envelope surface glycoprotein 120 (gp120): the V3 loop region and the CD4 binding site.

10 Claims, 8 Drawing Sheets

Specification includes a Sequence Listing.

(56)                    References Cited

OTHER PUBLICATIONS

Ivan B., et al., "CD4 Occupancy Triggers Sequential Pre-Fusion Conformational States of the HIV-1 Envelope Trimer with Relevance for Broadly Neutralizing Antibody Activity," PLOS Biology, 17(1), (2019), pp. 1-26.
Yoon H., et al., "CATNAP: A Tool to Compile, Analyze and Tally Neutralizing Antibody Panels," Nucleic Acids Research, vol. 43, (2015), pp. W213-W219.
McConnell A.D., et al., "A General Approach to Antibody Thermostabilization," mAbs, vol. 1274-1282.

* cited by examiner (A) Anti-V3 bNAb IgG (B) Anti-V3 bNAb IgG (C) Anti-V3 bNAb IgG (D)

HUMAN IMMUNODEFICIENCY VIRUS GP120 BINDING PROTEINS

CROSS-REFERENCE TO RELATED APPLICATIONS

This application claims the benefit under 35 U.S.C. § 119 (b) of U.S. Provisional Application No. 63/421,737, filed on Nov. 2, 2022, the contents of which is hereby incorporated by reference in its entirety.

FIELD OF THE INVENTION

The invention is directed to an antigen binding protein that binds to the Human

Immunodeficiency Virus (HIV) envelope and its use in treating or preventing HIV infection. The antigen binding protein of the invention binds to at least two different epitopes on the HIV envelope protein, in particular the V3 loop region (V3/glycan) and the CD4 binding site (CD4bs) of HIV envelope surface glycoprotein 120 (gp120).

BACKGROUND TO THE INVENTION

HIV, the virus that over time may result in Acquired Immunodeficiency Syndrome (AIDS), continues to be a serious public health challenge and has claimed 40.1 million lives so far. HIV attacks the body's immune system, targeting CD4-positive white blood cells, and leaves those infected vulnerable to opportunistic infections such as tuberculosis and fungal infections, severe bacterial infections and some cancers. Globally, 38.4 million people were living with HIV at the end of 2021, with 1.5 million people becoming newly infected (WHO, Key Facts HIV, July 2022).

Whilst there is currently no cure for HIV infection, it can be treated with antiretroviral therapy (ART), which includes a number of different types of drugs that prevent the virus from multiplying (nucleoside reverse transcriptase inhibitors (NRTIs), non-nucleoside reverse transcriptase inhibitors (NNRTIs), protease inhibitors, entry inhibitors and integrase inhibitors), allowing the body's immune system to recover sufficiently for the infected patient to be asymptomatic. 75% of people living with HIV in 2021 received some form of ART. However, ART often requires taking medication every day for life and has the risk of serious and debilitating side effects. Further, increased use of ART has also been accompanied by the emergence of drug resistance, the levels of which have steadily increased in recent years.

Broadly neutralizing antibodies (bNAbs) could potentially provide longer-term HIV suppression, but individual bNAbs have only had limited success in previous studies. This is in part because antibody-resistant virus either already existed in the patient or emerged soon after treatment began (NIH Research Matters, 14 Jun. 2022). Combinations of bNAbs are currently being investigated in the presence or absence of ART (Nature, 606, 368-374, 2022).

Further treatment options are needed for HIV infection, in particular drugs that are long-acting and effective against a wide spectrum of HIV strains so that patients taking them are less susceptible to drug resistance.

SEQUENCE LISTING

The instant application contains a Sequence Listing, which has been submitted electronically in computer readable form in an XML format and is hereby incorporated by reference in its entirety. Said XML file, created on Oct. 5, 2023, is named "70263WO01.xml" and is 398,770 bytes in size.

SUMMARY OF THE INVENTION

In a first aspect of the invention, an anti-HIV gp120-binding protein that binds to at least two different epitopes on human immunodeficiency virus (HIV) surface glycoprotein 120 (gp120) is provided.

In a second aspect of the invention, a bispecific anti-HIV gp120-binding protein comprising an anti-V3 bNAb and two copies of a CD4 domain is provided, wherein the C-terminus of one CD4 domain is attached directly or by a linker to the N-terminus of one of the anti-V3 bNAb heavy chains and the C-terminus of the other copy of the CD4 domain is attached directly or by a linker to the N-terminus of the other anti-V3 bNAb heavy chain.

In another aspect of the invention, a bispecific molecule that binds to human immunodeficiency virus (HIV) glycoprotein gp120 and human CD4 is provided, wherein the bispecific molecule comprises: (i) a first antigen-binding domain comprising an anti-V3 bNAb; (ii) a second antigen-binding domain comprising a CD4 domain, and (iii) a third antigen-binding domain comprising a CD4 domain.

In a third aspect of the invention, an anti-HIV gp120-binding protein having two identical heavy chains and two identical light chains is provided, comprising or consisting of: a heavy chain that is at least 95% identical to SEQ ID NO: 121 and a light chain that is at least 95% identical to SEQ ID NO:63.

In a fourth aspect of the invention, an anti-HIV gp120-binding protein consisting of two identical heavy chains of SEQ ID NO:121 and two identical light chains of SEQ ID NO:63 is provided.

In a fifth aspect of the invention, an anti-HIV gp120-binding protein comprising or consisting of a sequence that is at least 95% identical to any one of SEQ ID NOs: 152-157 is provided.

In a sixth aspect of the invention an anti-HIV gp120-binding protein consisting of SEQ ID NO: 155 is provided.

In further aspects of the invention, pharmaceutical compositions comprising anti-HIV gp120-binding proteins of the invention, methods of preventing HIV infection and methods of treating HIV infection with anti-HIV gp120-binding proteins of the invention, uses of anti-HIV gp120-binding proteins of the invention, methods of manufacturing anti-HIV gp120-binding proteins of the invention and kits comprising anti-HIV gp120-binding proteins of the invention are also provided.

DESCRIPTION OF DRAWINGS/FIGURES

FIG. 1 shows schematic designs of bispecific molecules of the invention. Human CD4 domains or variants thereof are fused, either directly or via linkers, to the N-termini of either the heavy chains (A), the light chains (B) or both chains (C) of anti-V3 bNAbs. Such designs facilitate concomitant binding of the human CD4 domain of the bispecific molecule and the V3 glycan binding domain of the bispecific molecule to HIV-1 gp120 and prevent HIV-1 virions from binding to and fusing with the cell membrane (D).

Figure 4A:
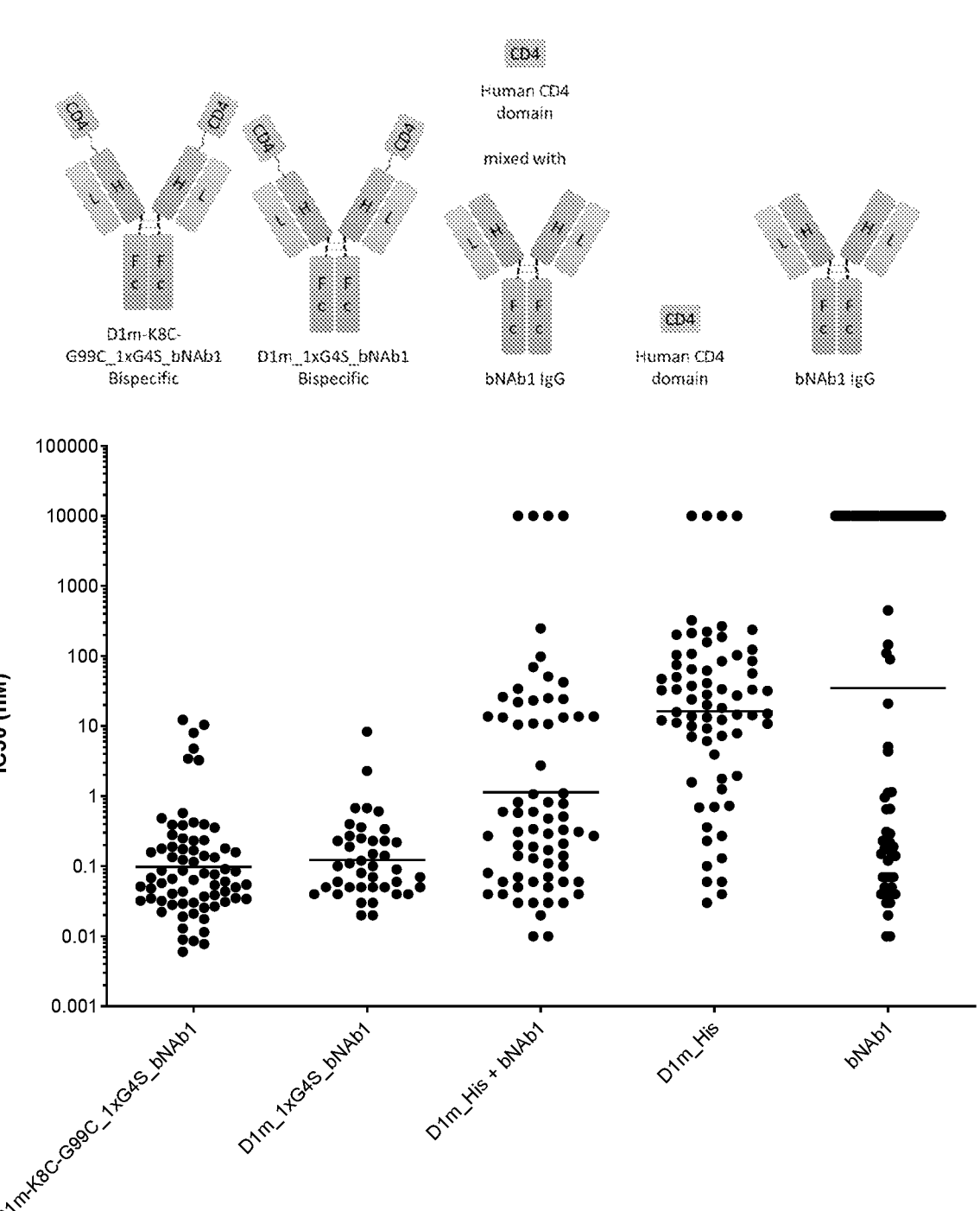
Figure 4B:
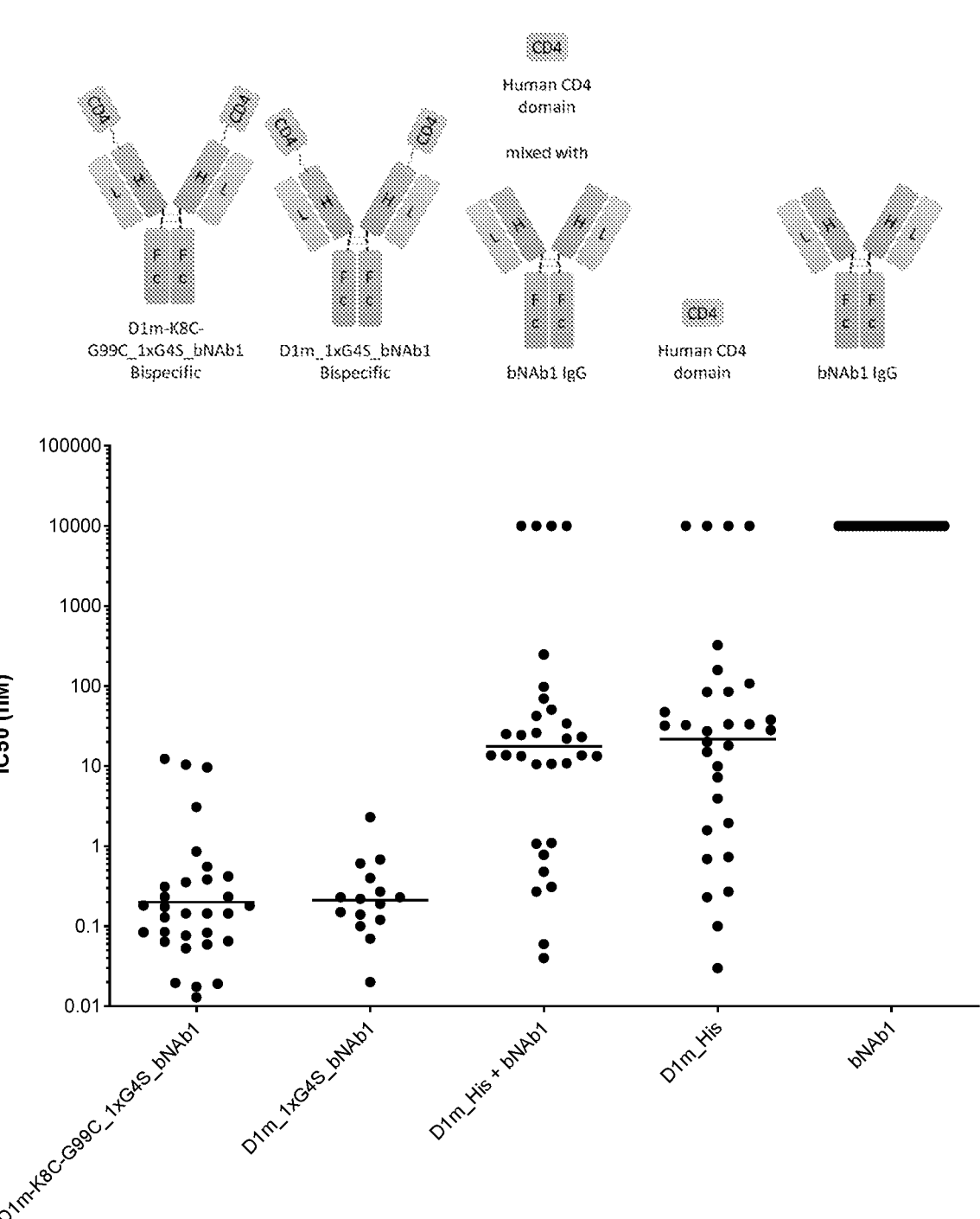

FIGS. 4A-4B show IC50 values (nM) of two bispecific molecules (SEQ ID NO: 121 and SEQ ID NO: 63; and SEQ ID NO: 102 and SEQ ID NO:63) of the invention having a variant human CD4 domain (D1m-K8C-G99C, SEQ ID NO:11; and D1m, SEQ ID NO:4 respectively) fused to each of the heavy chain N-termini of bNAb1 via a GGGGS (1xG4S) (SEQ ID NO:90) linker, and control molecules, against a panel of HIV-1 envelopes in a PSV assay (AC-TOne) (A) and a different panel of HIV-1 envelopes from bNAb1-resistant strains in a PSV assay (ACTOne) (B). Each dot represents one HIV envelope. The horizontal bars indicate geometric mean IC50.

Figure 5:
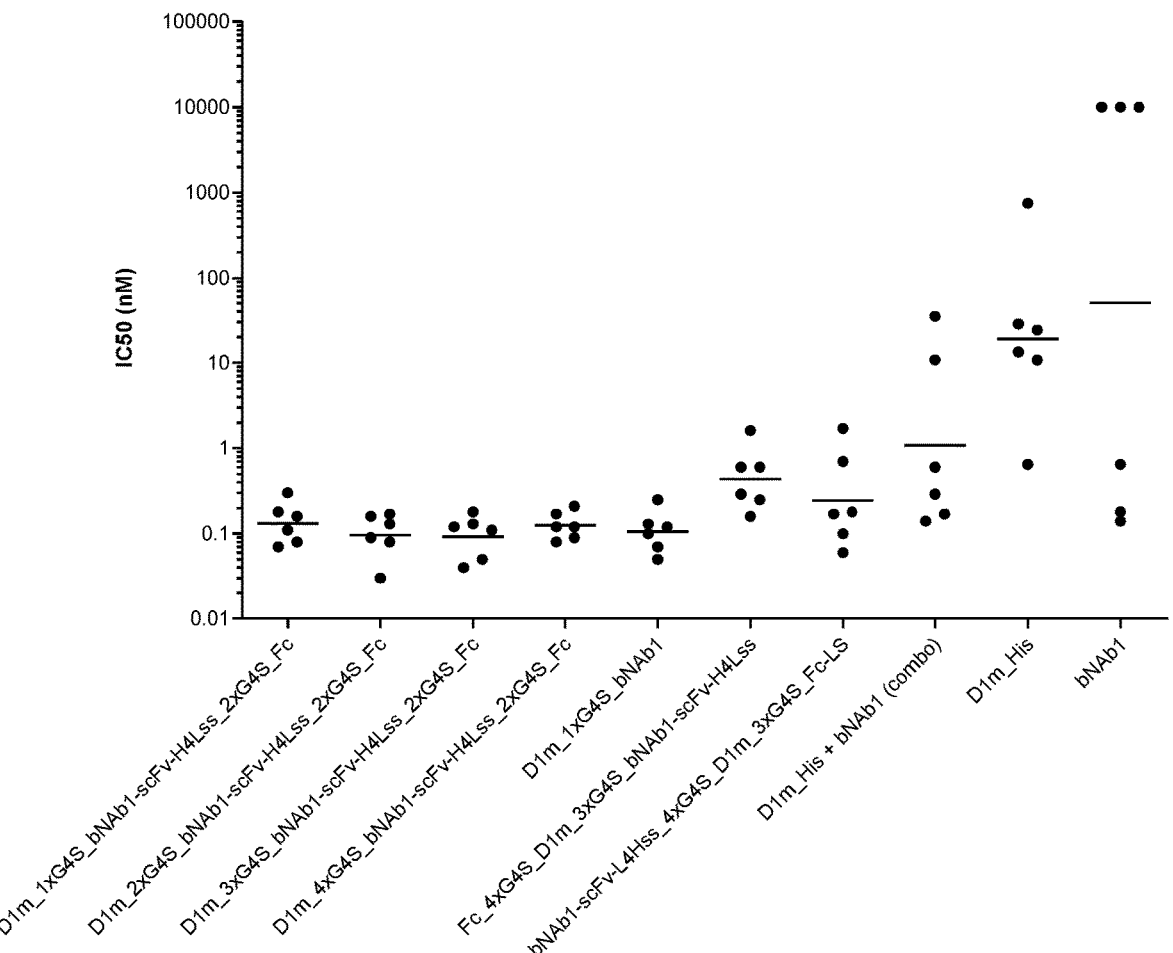

FIG. 5 shows IC50 values (nM) of single ORF versions of the most potent bispecific format (i.e. fusing CD4 D1 to the N-terminus of bNAb1 heavy chain), also referred to as scFv-Fc molecules (SEQ ID NOs: 152-157), in PSV assays (ACTOne cells). The horizontal bars indicate geometric mean IC50.

Figure 6:
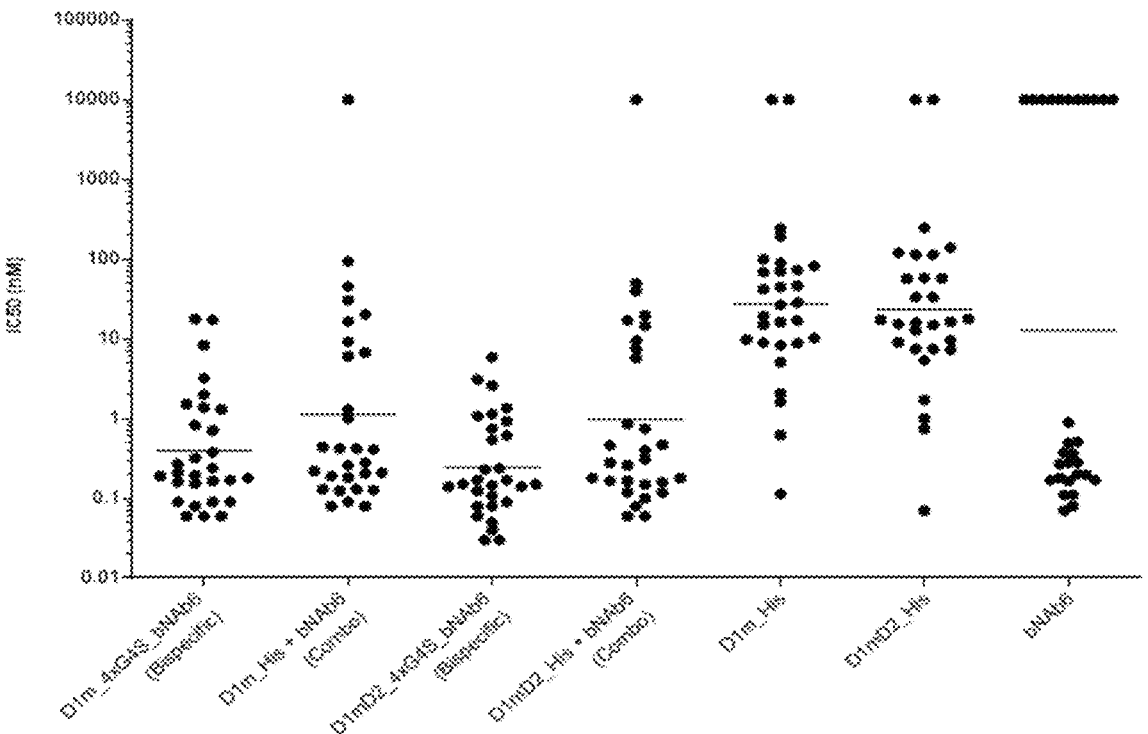

FIG. 6 shows IC50 values (nM) of two bispecific molecules (SEQ ID NO: 151 and SEQ ID NO: 89; and SEQ ID NO: 150 and SEQ ID NO: 89) of the invention having variant human CD4 domains (D1m, SEQ ID NO:4 and D1mD2, SEQ ID NO:2, respectively) fused to each of the heavy chain N-termini of bNAb6 (SEQ ID NO:88 and 89) via a 4xG4S linker (SEQ ID NO:93), and control molecules, against a panel of HIV-1 envelopes in a PSV assay (AC-TOne). Each dot represents one HIV envelope. The horizontal bars indicate geometric mean IC50.

Figure 7:
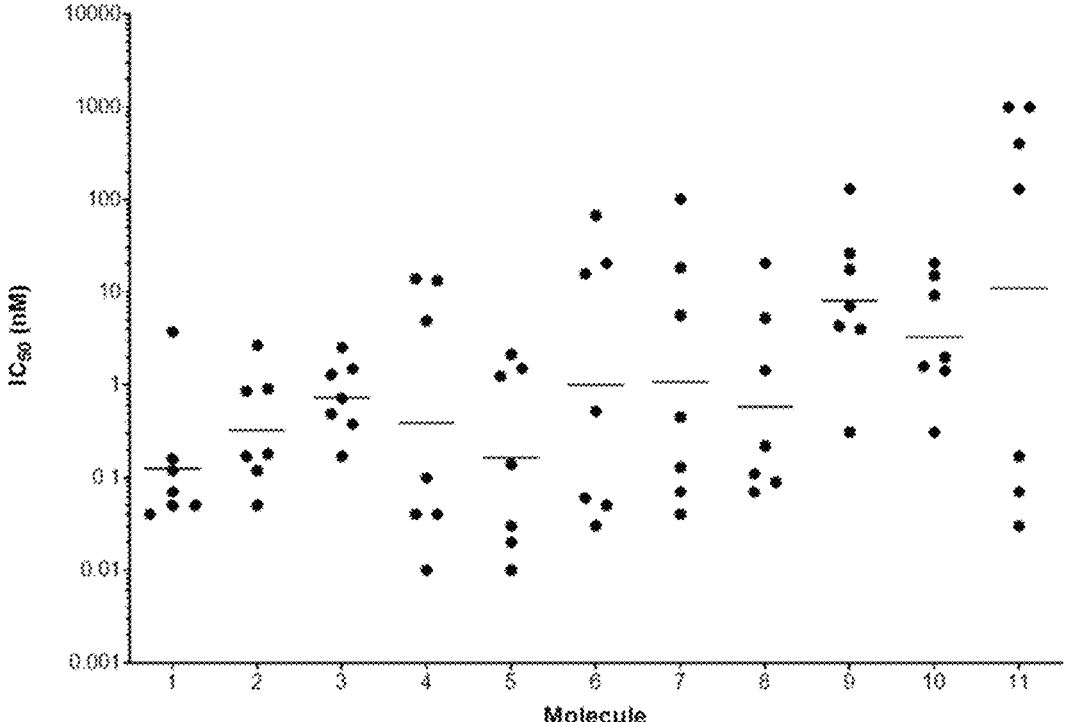

FIG. 7 shows IC50 values (nM) of different bNAb1-derived bispecific formats and control molecules against a panel of HIV-1 envelopes in a PSV assay (ACTone).

DETAILED DESCRIPTION OF THE INVENTION

Definitions

"Affinity", also referred to as "binding affinity", is the strength of binding at a single interaction site, i.e., of one molecule, e.g., an antigen binding protein, to another molecule, e.g., its target antigen, at a single binding site. The binding affinity of an antigen binding protein to its target may be determined by equilibrium methods (e.g., enzyme-linked immunoabsorbent assay (ELISA) or radioimmuno-assay (RIA)), or kinetics (e.g., BIACORE analysis).

"Alternative antibody formats" include alternative scaffolds in which one or more CDRs of the antigen binding protein can be arranged onto a suitable non-immunoglobulin protein scaffold or skeleton, such as an affibody, a SpA scaffold, an LDL receptor class A domain, an avimer (see, e.g., U.S. Patent Application Publication Nos. 2005/0053973, 2005/0089932, 2005/0164301) or an EGF domain.

"Antibody" is used herein to refer to a heterotetrameric glycoprotein with an approximate molecular weight of 150,000 daltons. An intact antibody is composed of two identical heavy chains (HCs) and two identical light chains (LCs) linked by covalent disulphide bonds. This H2L2 structure folds to form a 'Y' shape with three functional domains comprising two antigen-binding fragments, known as 'Fab' fragments (the 'top' of the 'Y'), and a fragment crystallisable 'Fc' (the 'bottom' of the 'Y'). The Fab fragment is composed of the variable domain at the amino-terminus, variable heavy (VH) or variable light (VL), and the constant domain at the carboxyl terminus, CH1 (heavy) and CL (light). The Fc fragment is composed of two domains formed by dimerization of paired CH2 and CH3 regions. The Fc may elicit effector functions by binding to receptors on immune cells or by binding C1q, the first component of the classical complement pathway. The five classes of antibodies IgM, IgA, IgG, IgE and IgD are defined by distinct heavy chain amino acid sequences, which are called $\mu$, $\alpha$, $\gamma$, $\in$ and $\delta$ respectively; each heavy chain can pair with either a K or A light chain. The majority of antibodies in the serum belong to the IgG class, there are four isotypes of human IgG (IgG1, IgG2, IgG3 and IgG4), the sequences of which differ mainly in their hinge region. In an embodiment, an anti-CD4bs antibody, as used herein, refers to an antibody that binds to a CD4 binding site "Antigen binding antibody fragments" or "antigen binding fragments" or "antibody fragments" as used herein include Fab, F(ab')$_2$, Fv, disulphide linked Fv, single chain Fv (scFv), disulphide-linked scFv, diabodies, TANDABS, etc. and modified versions of any of the foregoing (for a summary of alternative "antibody" formats see Holliger and Hudson, Nature Biotechnology, 23 (9), 1126-1136, 2005).

"Antigen binding protein" and "anti-gp120 binding protein" are used interchangeably herein and refer to antibodies and fragments thereof, alternative antibody formats, and other protein constructs, such as domains, that are capable of binding to HIV gp120. Envelope glycoprotein gp120 (or gp120) is a 120 kDa glycoprotein that is part of the outer layer of HIV. It presents itself as viral membrane spikes consisting of three molecules of gp120 linked together and anchored to the membrane by gp41 protein. Gp120 is essential for viral infection as it facilitates HIV entry into the host cell through its interaction with cell surface receptors. Gp120 is encoded by the HIV env gene. The env gene encodes a gene product of around 850 amino acids. The primary env product is the protein gp160, which gets cleaved into gp120 (about 480 amino acids) and gp41 (about 345 amino acids) in the endoplasmic reticulum by the cellular protease furin. The amino acid sequence of an exemplary gp160 from HIV clone WITO is provided below (SEQ ID NO: 363; the V3 loop is boldened and the potential N332 N-linked glycosylation site is boldened and underlined):

```
MKVMGTKKNYQHLWRWGIMLLGMLMMSSAAEQLWVTVYYGVPVWR

EANTTLFCASDAKAYDTEVHNVWATHACVPTDPNPQEVVMGNVTE

DFNMWKNNMVEQMHEDIISLWDQSLKPCVKLTPLCVTLHCTNVTI

SSTNGSTANVTMREEMKNCSFNTTTVIRDKIQKEYALFYKLDIVP

IEGKNTNTSYRLINCNTSVITQACPKVSFEPIPIHYCAPAGFAIL

KCNNKTFNGKGPCRNVSTVQCTHGIKPVVSTQLLLNGSLAEEDII

IRSENFTNNGKNIIVQLKEPVKINCTRPGNNTRRSINIGPGRAFY

ATGAIIGDIRKAHCNISTEQWNNTLTQIVDKLREQFGNKTIIFNQ

SSGGDPEVVMHTFNCGGEFFYCNSTQLFNSTWENNGTSTWNSTAD

NITLPCRIKQVINMWQEVGKAMYAPPIRGQIDCSSNITGLILTRD

GGSNSSQNETFRPGGGNMKDNWRSELYKYKVVKIEPLGIAPTRAK
```

```
-continued
RRVVQREKRAVTLGAVFLGFLGAAGSTMGAASLTLTVQARLLLSG

IVQQQSNLLRAIEAQQHMLQLTVWGIKQLQARVLAIERYLKDQQL

LGIWGCSGKLICTTTVPWNTSWSNKSYDYIWNNMTWMQWEREIDN

YTGFIYTLIEESQNQQEKNELELLELDKWASLWNWFNITNWLWYI

KLFIMIIGGLVGLRIVCAVLSIVNRVRQGYSPLSFQTRLPNPRGP

DRPEETEGEGGERDRDRSARLVNGFLAIIWDDLRSLCLFSYHRLR

DLLLIVARVVEILGRRGWEILKYWWNLLKYWSQELKNSAVSLLNV

TAIAVAEGTDRVIEIVQRAVRAILHIPTRIRQGFERALL
```

The amino acid of an exemplary gp120 is provided below (SEQ ID NO: 364; the V3 loop is boldened and the potential N332 N-linked glycosylation site is boldened and underlined):

```
AEQLWVIVYYGVPVWREANTTLFCASDAKAYDTEVHNVWATHACV

PTDPNPQEVVMGNVTEDFNMWKNNMVEQMHEDIISLWDQSLKPCV

KLTPLCVTLHCTNVTISSTNGSTANVTMREEMKNCSFNTTTVIRD

KIQKEYALFYKLDIVPIEGKNTNTSYRLINCNTSVITQACPKVSF

EPIPIHYCAPAGFAILKCNNKTFNGKGPCRNVSTVQCTHGIKPVV

STQLLLNGSLAEEDIIIRSENFTNNGKNIIVQLKEPVKINCTRPG

NNTRRSINIGPGRAFYATGAIIGDIRKAHCNISTEQWNNTLTQIV

DKLREQFGNKTIIFNQSSGGDPEVVMHTFNCGGEFFYCNSTQLFN

STWENNGTSTWNSTADNITLPCRIKQVINMWQEVGKAMYAPPIRG

QIDCSSNITGLILTRDGGSNSSQNETFRPGGGNMKDNWRSELYKY

KVVKIEPLGIAPTRAKRRVVQREKR
```

"Antigen binding site" and "paratope" are used interchangeably herein and refer to a particular site on an antigen binding protein that makes contact with and is capable of specifically binding to a site (i.e., epitope) on an antigen, e.g., HIV gp120. The antigen binding site may be formed by a single variable domain, or paired VH/VL domains as can be found on a standard antibody. Single-chain Fv (ScFv) domains can also provide antigen binding sites.

"Avidity" also referred to as functional affinity, is the cumulative strength of binding at multiple interaction sites, e.g., the sum total of the strength of binding of two molecules (or more) to one another at multiple sites, e.g., taking into account the valency of the interaction.

A "bispecific molecule" as used herein is an antigen binding protein that is capable of binding to two different epitopes on the same antigen, i.e., HIV gp120 protein. In particular, one epitope comprises part of or the whole of the V3 loop region of gp120 and the other epitope comprises part of or the whole of the CD4 binding site of gp120.

"Broadly neutralizing antibody" or "bNAb" as used herein, is meant an antibody that neutralizes more than one HIV-1 virus species (from diverse clades and different strains within a clade) in a neutralization assay. A broad neutralizing antibody may neutralize at least 2, 3, 4, 5, 6, 7, 8, 9 or more different strains of HIV-1, the strains belonging to the same or different clades.

"CD4 binding site" or "CD4-binding site" or "CD4bs" refers to a site on the HIV envelope protein gp120 that binds to CD4. (Cluster of differentiation factor 4). CD4 is a T-cell surface protein that serves as the primary receptor site for HIV during HIV infection. The CD4 binding site on gp120 is a highly conserved, discontinuous and conformational that comprises residues on either side of the HIV V4 loop (Curr HIV/AIDS Rep, 9 (1): 52-63, 2021) that binds to CD4.

A "CD4 domain" as used herein is a soluble recombinant form of human CD4 (Cluster of differentiation factor 4, a transmembrane glycoprotein found on T-cells), or a fragment thereof, that mimics the activity of native membrane-anchored human CD4 in its binding interactions with the HIV envelope protein. A CD4 domain of the present invention binds to the CD4-binding site of HIV gp120 and may block the ability of HIV gp120 to bind membrane-anchored CD4, e.g., on CD4+ T cells. A CD4 domain of the invention may induce a structural rearrangement in gp120 upon binding, including a structural rearrangement of part or all of the V3 region of gp120. This structural rearrangement in gp120 results in a high affinity binding site for a chemokine coreceptor (CXCR4 and/or CCR5) being exposed. Native CD4 comprises four domains that are exposed on the extracellular surface of the cell, D1, D2, D3 and D4; a transmembrane domain; and a cytoplasmic tail domain. D1 and D3 resemble Ig variable domains and D2 and D4 resemble Ig constant domains. CD4 domains of the invention include one or more of domains D1 to D4 of CD4, or variants thereof. Examples of CD4 domains of the invention include wild-type D1 (SEQ ID NO:3); "mD1.22" (SEQ ID NO:4), which is a variant of D1 of CD4 (Chen et al, JVI 88 (2): 1125-39, 2014); wild-type D1D2 (SEQ ID NO:1); "mD1.22-D2" (SEQ ID NO: 2), which is a variant of D1D2 (Fetzer et al., Journal of Virology, 92 (12), 2018); and further variants of mD1.22 (SEQ ID NOs: 5-21).

"CDRs" are defined as the complementarity determining region amino acid sequences of an antigen binding protein. These are the hypervariable regions of immunoglobulin heavy and light chains. There are three heavy chain and three light chain CDRs (or CDR regions) in the variable portion of an immunoglobulin. In one embodiment, the CDRs are defined based on the Kabat definition. In another embodiment, the CDRs are defined based on the Chothia definition. In a further embodiment, the Chothia definition is from Discovery Studio which uses the definitions from Chothia and Lesk, J Mol Biol. 196 (4): 901-17 (1987) and Morea et al, Methods, 20:267-279 (2000). In another embodiment, the Chothia definition is based on the Chothia from Abysis definition. In a further embodiment, the CDRs are defined based on the IMGT definition. In another embodiment, the CDRs are defined based on the Honegger definition. In another embodiment, the CDRs are defined based on the contact definition. Thus, "CDRs" as used herein refers to all three heavy chain CDRs, all three light chain CDRs, all heavy and light chain CDRs, or at least two CDRs.

"Domain" refers to a folded polypeptide structure that retains its tertiary structure independent of the rest of the polypeptide. Generally, domains are responsible for discrete functional properties of polypeptides and in many cases may be added, removed or transferred to other polypeptides without loss of function of the remainder of the protein and/or of the domain.

"Effector Function" as used herein refers to one or more of antibody-mediated effects including antibody-dependent cell-mediated cytotoxicity (ADCC), antibody-mediated complement activation including complement-dependent cytotoxicity (CDC), complement-dependent cell-mediated phagocytosis (CDCP), antibody dependent complement-mediated cell lysis (ADCML), and Fc-mediated phagocytosis or antibody-dependent cellular phagocytosis (ADCP).

"Epitope" as used herein refers to the portion of an antigen (e.g., gp120) that makes contact with and is capable of specifically binding to a particular site (paratope) on an antigen binding protein. An epitope may be linear or conformational/discontinuous. A conformational/discontinuous epitope comprises amino acid residues that are separated by other sequences, i.e., it does not comprise a continuous sequence in the antigen's primary amino acid sequence, but instead relies on the tertiary folding of the polypeptide. Although the residues within a confirmational/discontinuous epitope may be from different regions of the polypeptide chain, they are in close proximity in the three-dimensional structure of the antigen.

In the case of multimeric antigens, a conformational or discontinuous epitope may include residues from different polypeptide chains. Particular residues comprised within an epitope can be determined through computer modelling programs or via three-dimensional structures obtained through methods known in the art, such as X-ray crystallography.

Epitope mapping can be carried out using various techniques known to persons skilled in the art as described in publications such as Methods in Molecular Biology 'Epitope Mapping Protocols', by Mike Schutkowski and Ulrich Reineke (volume 524, 2009) and Johan Rockberg and Johan Nilvebrant (volume 1785, 2018). Exemplary methods include peptide-based approaches such as pepscan whereby a series of overlapping peptides are screened for binding using techniques such as ELISA or by in vitro display of large libraries of peptides or protein mutants, e.g., on phage. Detailed epitope information can be determined by structural techniques including X-ray crystallography, solution nuclear magnetic resonance (NMR) spectroscopy and cryogenic-electron microscopy (cryo-EM). Mutagenesis, such as alanine scanning, is an effective approach whereby loss of binding analysis is used for epitope mapping. Another method is hydrogen/deuterium exchange (HDX) combined with proteolysis and liquid-chromatography mass spectrometry (LC-MS) analysis to characterize discontinuous or conformational epitopes.

"Half-life" or "t1/2" refers to the time required for the serum concentration of an antigen binding protein to reach half of its original value. The serum half-life of proteins can be measured by pharmacokinetic studies according to the method described by Kim et al., 1994, Eur. J. of Immuno. 24:542-548. According to this method, radio-labelled protein is injected intravenously into mice and its plasma concentration is periodically measured as a function of time, for example, at about 3 minutes to about 72 hours after the injection. Other methods for pharmacokinetic analysis and determination of the half-life of a molecule will be familiar to those skilled in the art.

"HIV envelope protein" or "ENV" refers to a trimeric viral membrane-associated glycoprotein (gp) or 'spike'. It is found on both the viral membrane and the cell membrane of infected host cells. The env gene encodes the gp160 polypeptide which forms a homotrimer and is cleaved into gp120 and gp41 polypeptides. Gp120 is a surface (SU) glycoprotein responsible for binding to receptor molecules and the transmembrane (TM) glycoprotein, gp41, mediates fusion of the viral membrane with the plasma cell membrane. Over half of the mass of the trimeric envelope 'spike' is an N-linked glycan shield that hides most amino acid-based epitopes on gp120. Binding of the cell surface receptor CD4 to HIV gp120 induces a structural rearrangement creating a high affinity binding site for a chemokine coreceptor (CXCR4 and/or CCR5), on gp120. Following gp120 binding to CXCR4 or CCR5 further conformational changes are triggered which results in gp120 disengaging from gp41, allowing for the fusion peptide of gp41 to be inserted into the cell membrane, which in turn triggers a sequence of structural changes resulting in membrane fusion (Dimitrov et al., Biochemistry 44 (37): 12471-12479, 2005).

"Human immunodeficiency virus (HIV)" has been characterized into two types: HIV-1 and HIV-2. HIV-1 is more virulent and more infective than HIV-2 and is the cause of the majority of HIV infections globally, whereas HIV-2 is limited to a much smaller number of people, mostly in West Africa (Gilbert et al., Statistics in Medicine 22 (4): 573-593). Herein, when reference is made to "HIV" this is intended to mean "HIV-1". HIV virions are spherical with viral glycoprotein "spikes", the HIV envelope protein, protruding outwards. A conical capsid exists within the virion, enclosing a ribonucleoprotein complex comprising two copies of positive-sense single stranded RNA tightly bound to nucleocapsid proteins and enzymes needed for viral replication.

A "linker" is an amino acid sequence that links one domain in a polypeptide to another domain in a polypeptide. For example, a linker within the meaning of the invention includes an amino acid sequence that joins a CD4 domain to a bNAb heavy chain or a bNAb light chain. In an embodiment, the linker is not cleavable under intracellular conditions.

"Multi-specific antigen binding protein" or "MSABP" refers to an antigen binding protein that comprises at least two different antigen binding sites. Each of these antigen-binding sites is capable of binding to a different epitope, which may be present on the same antigen or different antigens. In an embodiment, the multi-specific antigen binding proteins of the invention are bispecific molecules capable of binding to two different epitopes on the HIV envelope protein. In particular, one epitope may comprise part of or the whole of the V3 loop region of gp120 and the other epitope may comprise part of or the whole of the CD4 binding site of gp120.

Symmetric formats of MSABPs combine multiple binding specificities in a single polypeptide chain or single HL pair including Fc-fusion proteins of fragment-based formats and formats whereby antibody fragments are fused to regular antibody molecules. Examples of symmetric formats may include DVD-Ig, TVD-Ig, CODV-Ig, (scFv)$_4$-Fc, IgG-(scFv)$_2$, Tetravalent DART-Fc, F(ab)$_4$CrossMab, IgG-HC-scFv, IgG-LC-scFv, mAb-dAb etc.

"Neutralizes" as used throughout the present specification means that the biological activity of HIV is reduced in the presence of an antigen binding protein as described herein in comparison to the biological activity of HIV in the absence of the antigen binding protein, in vitro or in vivo. For example, a neutralizing antigen binding protein of the invention may inhibit HIV entry into a target cell and reduce viral load in a patient infected with HIV.

"Percent identity" or "% identity" between a query amino acid sequence and a subject amino acid sequence is the "Identities" value, expressed as a percentage, that is calculated using a suitable algorithm (e.g., BLASTP, FASTA, Needleman-Wunsch, Smith-Waterman, LALIGN, or GenePAST/KERR) or software (e.g., DNASTAR Lasergene, GenomeQuest, EMBOSS needle or EMBOSS infoalign), over the entire length of the query sequence after a pair-wise global sequence alignment has been performed using a suitable algorithm (e.g., Needleman-Wunsch or GenePAST/KERR) or software (e.g. DNASTAR Lasergene or GenePAST/KERR). Importantly, a query amino acid sequence may be described by an amino acid sequence disclosed herein, in particular in one or more of the claims.

The query sequence may be 100% identical to the subject sequence, or it may include up to a certain integer number of amino acid alterations as compared to the subject sequence such that the % identity is less than 100%. For example, the query sequence is at least 50, 60, 70, 75, 80, 85, 90, 95, 96, 97, 98, or 99% identical to the subject sequence. In the case of amino acid sequences, such alterations include at least one amino acid residue deletion, substitution (including conservative and non-conservative substitutions), or insertion, wherein said alterations may occur at the amino- or carboxy-terminal positions of the query sequence or anywhere between those terminal positions, interspersed either individually among the amino acid residues in the query sequence or in one or more contiguous groups within the query sequence.

For antibody sequences, the % identity may be determined across the entire length of the query sequence, including the CDRs. Alternatively, the % identity may exclude one or more or all of the CDRs, for example all of the CDRs are 100% identical to the subject sequence and the % identity variation is in the remaining portion of the query sequence, e.g., the framework sequence, so that the CDR sequences are fixed and intact.

"Protein scaffold" as used herein includes, but is not limited to, an immunoglobulin (Ig) scaffold, for example an IgG scaffold, which may be a four chain or two chain antibody, or which may comprise only the Fc region of an antibody, or which may comprise one or more constant regions from an antibody, which constant regions may be of human origin.

The protein scaffold may be an Ig scaffold, for example an IgG, or IgA scaffold. The IgG scaffold may comprise some or all the domains of an intact antibody (i.e., CH1, CH2, CH3, VH, VL). The antigen binding protein may comprise an IgG scaffold selected from IgG1, IgG2, IgG3, IgG4 or IgG4PE. For example, the scaffold may be IgG1. The scaffold may consist of, or comprise, the Fc region of an antibody, or is a part thereof.

The protein scaffold may be a non-Ig scaffold. The protein scaffold may be a derivative of a scaffold selected from the group consisting of CTLA-4, lipocalin, Protein A derived molecules such as Z-domain of Protein A (Affibody, SpA), A-domain (Avimer/Maxibody); heat shock proteins such as GroEI and GroES; transferrin (trans-body); ankyrin repeat protein (DARPin); peptide aptamer; C-type lectin domain (Tetranectin); human γ-crystallin and human ubiquitin (affilins); PDZ domains; scorpion toxin kunitz type domains of human protease inhibitors; and fibronectin/adnectin; which has been subjected to protein engineering in order to obtain binding to an antigen, such as gp120.

"Single variable domain" refers to a folded polypeptide domain comprising sequences characteristic of antibody variable domains. It therefore includes complete antibody variable domains such as VH, VHH and VL and modified antibody variable domains, for example, in which one or more loops have been replaced by sequences that are not characteristic of antibody variable domains, or antibody variable domains that have been truncated or comprise N- or C-terminal extensions, as well as folded fragments of variable domains that retain at least the binding activity and specificity of the full-length domain. A single variable domain as defined herein is capable of binding an antigen or epitope independently of a different variable region or domain. A "domain antibody" or "DAB" may be considered the same as a human "single variable domain". A single variable domain may be a human single variable domain, but also includes single variable domains from other species such as rodent (for example, as disclosed in WO 00/29004), nurse shark and Camelid VHHs Camelid VHHs are immunoglobulin single variable domain polypeptides that are derived from species including camel, llama, alpaca, dromedary, and guanaco, which produce heavy chain only antibodies naturally devoid of light chains. Such VHH domains may be humanised according to standard techniques available in the art, and such domains are considered to be "single variable domains".

"Stabilizing mutation" refers to a change of an amino acid residue in a polypeptide sequence that increases the thermal thermostability of said polypeptide. Increased thermostability may be reflected in a melting temperature (Tm) increase of, for example, between 1 and 50° C. CD4 domains with stabilizing mutations include SEQ ID NOs: 5-21.

A "variant sequence" substantially retains the biological characteristics of the unmodified protein. In the case of an antibody sequence disclosed herein, the VH or VL (or HC or LC) sequence may be a variant sequence with up to 10 amino acid substitutions, additions or deletions. For example, the variant sequence may have up to 9, 8, 7, 6, 5, 4, 3, 2 or 1 amino acid substitution(s), addition(s) or deletion(s). The sequence variation may exclude one or more or all of the CDRs, for example the CDRs are the same as the VH or VL (or HC or LC) sequence and the variation is in the remaining portion of the VH or VL (or HC or LC) sequence, so that the CDR sequences are fixed and intact.

"V3 loop region", "V3/glycan" or "V3" as used herein refers to the third variable region (V3) of HIV gp120. Comparison of predicted amino acid sequences from several different isolates has shown that sequence heterogeneity of gp120 is clustered in five variable regions (designated V1, V2, V3, V4, and V5.) The V3 region contains post-translational modifications, such as glycosylation, and is essential for viral infectivity. The V3 region, although only 35 amino acids long, exhibits considerable sequence variability. Additionally, variability in potential N-linked glycosylation sites allow for further variability in the variable regions of gp120. Together, the V3 region and the N-linked glycosylation sites within and adjacent to the region are understood to comprise the "V3 loop region," "V3/glycan" or V3" as used herein. For example, one site of glycosylation (e.g., oligomannose such as Man-5 to Man-9) is centered on amino acid residue N332 of gp120. Other sites of potential N-linked glycosylation within and adjacent to the V3 loop region include K295, N301, N386, N392 of gp120. The V3 loop is generally considered to be in the region between cysteine residues C296 and C331 of gp120, while some N-linked glycosylation sites are located directly adjacent to the V3 loop. The V3 loop comprises a highly conserved tetrapeptide sequence, GPGR (residues 312 to 315) (Ivanhoff et al., Virology, 187 (2) 1992). HIV-1 cellular entry depends on the interaction of the V3 loop region with an HIV co-receptor, commonly CCR5 or CXCR4. The V3 loop comprises: (i) the base (residues 296-299), (ii) the stem (residues 300-303 and 321-326), and (iii) the crown (residues 304-320) (Friedrich et al., Nature Communications 12, 6705 (2021)). A consensus sequence of the V3 region of gp120 (Milich et al., *J Virol.*, 67 (9): 5623-5634 (1993)) is provided below:

```
                                      (SEQ ID NO: 361)
CTRPNNNTRKSIHIGPGRAFYTTGEIIGDIRQAHC
```

It is understood that the consensus sequence describes the highest frequency of residues emerging on each position of this region across multiple subtypes, but that the V3 loop region of a particular strain may exhibit sequence variability.

A "V3-bNAb" or "anti-V3 bNAb" is a bNAb that binds within the V3 loop region. A V3-bNAb may also be referred to herein as an anti-V3 antibody. A V3-bNAb may bind the N332 glycan in the V3 loop region and/or other N-linked glycosylation sites within and adjacent to the V3 loop region.

STATEMENT OF THE INVENTION

An antigen binding protein of the invention binds to the Human Immunodeficiency Virus (HIV) envelope protein. In particular, the antigen binding protein binds to HIV envelope surface glycoprotein 120 (gp120) and is, therefore, also referred to herein as an anti-gp120 binding protein. The anti-gp120 binding protein of the invention binds to at least two different epitopes on gp120, including the V3 loop region (V3) and the CD4 binding site (CD4bs) of gp120.

Bispecific molecules of the invention that bind to the V3 loop region and the CD4bs of gp120 have been shown to effectively neutralize HIV and exhibit significantly better anti-viral activity than monospecific molecules that only bind to the V3 loop region or the CD4bs of gp120, and mixtures of these monospecific molecules. Without being bound by any particular theory, we postulate that the bispecific molecules of the invention bind the two different epitopes in the same or neighboring HIV envelope protein trimers at the same time, such that the bispecific molecules achieve stronger binding (increased avidity) to the HIV envelope proteins. This may be as a result of the high local concentration of the bispecific molecules' binding sites (paratopes) being "pre-positioned" around their target binding sites (epitopes) on the HIV envelope compared to their monospecific counterparts, which in turn leads to stronger anti-viral activity.

Binding to the CD4 Binding Site (CD4bs) of HIV Gp120

The antigen binding protein of the invention comprises one or more paratopes that bind to the CD4bs of HIV gp120. Binding domains comprising such paratopes may be include by CD4 domains, as well as other anti-CD4bs domains, including those of anti-CD4bs antibodies and CD4bs-binding fragments thereof. Non-Ig constructs that bind to CD4bs are also part of the invention, such as single chain variable fragments (scFvs). In particular, non-Ig constructs such as scFv comprising one or more CDRs, preferably the three light chain CDRs or the three heavy chain CDRs, or a set of six CDRs of such anti-CD4bs antibodies are also part of the invention.

In an embodiment of the invention, the antigen binding protein of the invention comprises an anti-CD4bs antibody or CD4bs-binding fragment thereof, wherein such antibody or fragment thereof comprises a paratope that binds to the CD4bs of HIV gp120. In a further embodiment, the anti-CD4bs antibody is selected from the group consisting of: b12, HJ16, CH103-106, VRCO1-03, VRC-PG04, VRC-PG04b, VRC-CH30-34, 3BNC117, 3BNC60, NIH45-46, 12A12, 12A21, 8ANC131, 8ANC134, 1NC9, and 1B2530.

In an alternative or additional embodiment of the invention, a paratope that binds to the CD4bs of HIV gp120 is formed by a polypeptide domain that binds to the CD4bs of HIV gp120. In a more particular embodiment, the polypeptide domain is a CD4 domain.

CD4 Domains

CD4 domains of the invention include SEQ ID NOs: 1-21.

In an embodiment of the invention, the CD4 domain is a CD4 D1 domain. In an embodiment, the CD4 domain is a human CD4 domain. CD4 D1 domains include human wild-type D1 (SEQ ID NO:3), mD1.22 (SEQ ID NO:4) also known as D1m, and further variants of mD1.22 (SEQ ID NOs: 5-21).

In an embodiment of the invention, the CD4 domain is a CD4 D1D2 domain. In an embodiment, the CD4 domain is a human CD4 D1D2 domain. CD4 D1D2 domains include human wild-type D1D2 (SEQ ID NO:1) and mD1.22-D2 (SEQ ID NO:2).

In an aspect of the invention, a stabilized CD4 domain is provided. In an embodiment of the invention, a stabilized CD4 D1 domain is provided. In an embodiment, the CD4 domain is thermally stable, i.e., thermostable. In an embodiment, the CD4 domain is a thermostable CD4 D1 domain.

In an embodiment of the invention, the CD4 domain comprises one or more stabilizing mutations. In an embodiment, the stabilizing mutations are in the CD4 D1 domain. In an embodiment, the CD4 D1 domain comprises one or more mutations selected from the group consisting of: K8C, K8I, K8V, T11C, E13C, K21C, Q25E, H27C, H27D, G38C, N52W, R58N, R58T, R58V, L61M, G65C, 170C, K72C, E87G, E91H, E91Q, and G99C. In an embodiment, the CD4 D1 domain comprises K8I. In an embodiment, the CD4 D1 domain comprises K8V. In an embodiment, the CD4 D1 domain comprises T1C and K72C. In an embodiment, the CD4 D1 domain comprises K8C and G99C.

CD4 domains of the invention comprising novel and inventive stabilizing mutations include SEQ ID NOs: 5-21.

Increased thermostability may be reflected in a melting temperature (Tm) increase of, for example, between 1 and 50° C.; in particular between 1 and 30° C.; in particular between 1 and 25° C., in particular between 1 and 21° C., more particularly between 5 and 21° C. The Tm increase is determined by measuring the Tm of the CD4 domain(s) comprising one or more stabilizing mutations and subtracting the Tm of the corresponding CD4 domain(s) without said mutation(s). For example, measuring the Tm of a stabilized CD4 D1 domain and subtracting the Tm of the wild-type CD4 D1 domain. In an embodiment, the Tm increase is about 8° C. In an embodiment, the Tm increase is about 9° C. In an embodiment, the Tm increase is about 12° C. In an embodiment, the Tm increase is about 21° C.

In an embodiment, the Tm of the CD4 domain is above 70° C. In an embodiment, the Tm of the CD4 domain is between 70° C. and 95° C. In an embodiment, the Tm of the CD4 domain is between 75° C. and 95° C. In an embodiment, the Tm of the CD4 domain is between 75° C. and 91° C. In an embodiment, the Tm of the CD4 domain is about 76° C., about 77° C., about 78° C., about 79° C., about 80° C., about 81° C., about 82° C., about 83° C., about 84° C., about 85° C., about 86° C., about 87° C., about 88° C., about 89° C., or about 90° C. In an embodiment, the Tm of the CD4 domain is about 90° C. In an embodiment, the Tm of the CD4 domain is about 89° C.

Tm may be determined by routine methods known in the art or as set out in the Examples. In an embodiment, Tm is determined using the Prometheus System (NanoTemper, München Germany).

Binding to the V3 Loop Region of HIV Gp120

The antigen binding protein of the invention comprises one or more paratopes that bind to the V3 loop region of HIV gp120. Binding domains comprising such paratopes include an anti-V3 bNAb or a V3-binding fragment thereof, as well as a non-Ig construct that binds to V3.

An antigen binding protein of the invention may comprise heavy chain CDRs (CDRH1, CDRH2, and CDRH3) as set out in any row of Table 1. An antigen binding protein of the invention may comprise light chain CDRs (CDRL1, CDRL2, and CDRL3) as set out in any row of Table 1. An antigen binding protein of the invention may comprise a set of six CDRs (CDRH1, CDRH2, CDRH3, CDRL1, CDRL2 and CDRL3) as set out in any row of Table 1.

An antigen binding protein of the invention may comprise heavy chain CDRs (CDRH1, CDRH2, and CDRH3) of any one of PGT121-123, PGT125-131, PGT135-137, QA013.2, 10-1074, 10-1074LS, PGT121.414.LS and 2G12. An antigen binding protein of the invention may comprise light chain CDRs (CDRL1, CDRL2, and CDRL3) of any one of PGT121-123, PGT125-131, PGT135-137, QA013.2, 10-1074, 10-1074LS, PGT121.414.LS and 2G12. An antigen binding protein of the invention may comprise a set of six CDRs (CDRH1, CDRH2, CDRH3, CDRL1, CDRL2 and CDRL3) of any one of PGT121-123, PGT125-131, PGT135-137, QA013.2, 10-1074, 10-1074LS, PGT121.414.LS and 2G12.

An antigen binding protein of the invention may comprise a VH domain as set out in Table 2. An antigen binding protein of the invention may comprise a VL domain as set out in Table 2. An antigen binding protein of the invention may comprise a pair of variable domains (a VH and a VL) as set out in any row of Table 2.

Anti-V3 bNAbs

An antigen binding protein of the invention may comprise an anti-V3 bNAb or a V3-binding fragment thereof. An anti-V3 antibody includes an antibody comprising a set of CDRs (CDRH1, CDRH2, CDRH3, CDRL1, CDRL2 and CDRL3) as set out in any row of Table 1.

TABLE 1

SEQ ID NOs for the complementarity determining regions
(CDRs) of broadly neutralizing antibodies (bNAbs) 1-6

| | CDRH1 | CDRH2 | CDRH3 | CDRL1 | CDRL2 | CDRL3 |
|---|---|---|---|---|---|---|
| bNAb1 | 22 | 23 | 24 | 25 | 26 | 27 |
| bNAb2 | 28 | 29 | 30 | 31 | 32 | 33 |
| bNAb3 | 34 | 35 | 36 | 37 | 38 | 39 |
| bNAb4 | 40 | 41 | 42 | 43 | 44 | 45 |
| bNAb5 | 46 | 47 | 48 | 49 | 50 | 51 |
| bNAb6 | 52 | 53 | 54 | 55 | 56 | 57 |
| bNAb7 | 159 | 160 | 161 | 162 | 163 | 164 |
| bNAb8 | 165 | 166 | 167 | 168 | 169 | 170 |
| bNAb9 | 171 | 172 | 173 | 174 | 175 | 176 |
| bNAb10 | 177 | 178 | 179 | 180 | 181 | 182 |
| bNAb11 | 183 | 184 | 185 | 186 | 187 | 188 |
| bNAb12 | 189 | 190 | 191 | 192 | 193 | 194 |
| bNAb13 | 195 | 196 | 197 | 198 | 199 | 200 |
| bNAb14 | 201 | 202 | 203 | 204 | 205 | 206 |
| bNAb15 | 207 | 208 | 209 | 210 | 211 | 212 |
| bNAb16 | 213 | 214 | 215 | 216 | 217 | 218 |
| bNAb17 | 219 | 220 | 221 | 222 | 223 | 224 |
| bNAb18 | 225 | 226 | 227 | 228 | 229 | 230 |
| bNAb19 | 231 | 232 | 233 | 234 | 235 | 236 |
| bNAb20 | 237 | 238 | 239 | 240 | 241 | 242 |
| bNAb21 | 243 | 244 | 245 | 246 | 247 | 248 |
| bNAb23 | 249 | 250 | 251 | 252 | 253 | 254 |

In a particular embodiment, the anti-V3 antibody or V3-binding fragment thereof, comprises the CDRs of bNAb1. In an embodiment, the anti-V3 antibody or V3-binding fragment thereof, comprises a CDRH1 of SEQ ID NO:22, a CDRH2 of SEQ ID NO:23, a CDRH3 of SEQ ID NO: 24, a CDRL1 of SEQ ID NO: 25, a CDRL2 of SEQ ID NO:26 and a CDRL3 of SEQ ID NO:27.

An anti-V3 bNAb may be an antibody comprising a pair of variable domains (a VH and a VL) as set out in any row of Table 2.

An anti-V3 bNAb may be an antibody comprising a heavy chain (HC), with or without M428L/N434S (EU numbering) 'LS' mutations, and a light chain (LC) as set out in any row of Table 2. In an embodiment, the HC comprises LS.

TABLE 2

SEQ ID NOs for the variable regions (VH and VL)
and the heavy chains (HC) and light chains (LC)
of bNAbs 1-6. 'LS' refers to M428L/N434S
(EU numbering) mutations in the Fc portion of the bNAb.

| | VH | VL | HC without 'LS' | HC with 'LS' | LC |
|---|---|---|---|---|---|
| bNAb1 | 58 | 59 | 61 | 62 | 63 |
| bNAb1* | | 60* | | | 64* |
| bNAb2 | 65 | 66 | 67 | 68 | 69 |
| bNAb3 | 70 | 71 | 72 | 73 | 74 |
| bNAb4 | 75 | 76 | 77 | 78 | 79 |
| bNAb5 | 80 | 81 | 82 | 83 | 84 |
| bNAb6 | 85 | 86 | 87 | 88 | 89 |
| bNAb7 | 255 | 256 | 257 | 258 | 259 |
| bNAb8 | 260 | 261 | 262 | 263 | 264 |
| bNAb9 | 265 | 266 | 267 | 268 | 269 |
| bNAb10 | 270 | 271 | 272 | 273 | 274 |
| bNAb11 | 275 | 276 | 277 | 278 | 279 |
| bNAb12 | 280 | 281 | 282 | 283 | 284 |
| bNAb13 | 285 | 286 | 287 | 288 | 289 |
| bNAb14 | 290 | 291 | 292 | 293 | 294 |
| bNAb15 | 295 | 296 | 297 | 298 | 299 |
| bNAb16 | 300 | 301 | 302 | 303 | 304 |
| bNAb17 | 305 | 306 | 307 | 308 | 309 |
| bNAb18 | 310 | 311 | 312 | 313 | 314 |
| bNAb19 | 315 | 316 | 317 | 318 | 319 |
| bNAb20 | 320 | 321 | 322 | 323 | 324 |
| bNAb21 | 325 | 326 | 327 | 328 | 329 |
| bNAb22# | 330 | | 331 | 332 | |
| bNAb23 | 334 | 335 | 336 | 337 | 338 |

*a light chain variant with F32Y in the VL and LC #a heavy chain variant with {~TC to inserts definition}

In an embodiment, the anti-V3 antibody or V3-binding fragment thereof, comprises a VH domain of SEQ ID NO:58 and a VL domain of SEQ ID NO:59 or 60. In an embodiment, the anti-V3 antibody or V3-binding fragment thereof, comprises a VH domain of SEQ ID NO:58 and a VL domain of SEQ ID NO:59. In an embodiment, the anti-V3 antibody or V3-binding fragment thereof, comprises a VH domain of SEQ ID NO: 65 and a VL domain of SEQ ID NO:66. In an embodiment, the anti-V3 antibody or V3-binding fragment thereof, comprises a VH domain of SEQ ID NO: 70 and a VL domain of SEQ ID NO:71. In an embodiment, the anti-V3 antibody or V3-binding fragment thereof, comprises a VH domain of SEQ ID NO:75 and a VL domain of SEQ ID NO: 76. In an embodiment, the anti-V3 antibody or V3-binding fragment thereof, comprises a VH domain of SEQ ID NO:80 and a VL domain of SEQ ID NO:81. In an embodiment, the anti-V3 antibody or V3-binding fragment thereof, comprises a VH domain of SEQ ID NO:85 and a VL domain of SEQ ID NO:86. In an embodiment, the anti-V3 antibody or V3-binding fragment thereof, comprises a VH domain of SEQ ID NO:225 and a VL domain of SEQ ID NO:226. In an embodiment, the anti-V3 antibody or V3-binding fragment thereof, comprises a VH domain of SEQ ID NO:260 and a VL domain of SEQ ID NO:261. In an embodiment, the anti-V3 antibody or V3-binding fragment thereof, comprises a VH domain of SEQ ID NO:265 and a VL domain of SEQ ID NO: 266. In an embodiment, the anti-V3 antibody or V3-binding fragment thereof, comprises a VH domain of SEQ ID NO:270 and a VL domain of SEQ ID NO:271. In an embodiment, the anti-V3 antibody or V3-binding fragment thereof, comprises a VH domain of SEQ ID NO:275 and a VL domain of SEQ ID NO:276. In an embodiment, the anti-V3 antibody or V3-binding fragment thereof, comprises a VH domain of SEQ ID NO:280 and a VL domain of SEQ ID NO: 281. In an embodiment, the anti-V3 antibody or V3-binding fragment thereof, comprises a VH domain of SEQ ID NO:285 and a VL domain of SEQ ID NO:286. In an embodiment, the anti-V3 antibody or V3-binding fragment thereof, comprises a VH domain of SEQ ID NO: 290 and a VL domain of SEQ ID NO:291. In an embodiment, the anti-V3 antibody or V3-binding fragment thereof, comprises a VH domain of SEQ ID NO:295 and a VL domain of SEQ ID NO:296. In an embodiment, the anti-V3 antibody or V3-binding fragment thereof, comprises a VH domain of SEQ ID NO:300 and a VL domain of SEQ ID NO:301. In an embodiment, the anti-V3 antibody or V3-binding fragment thereof, comprises a VH domain of SEQ ID NO:305 and a VL domain of SEQ ID NO: 306. In an embodiment, the anti-V3 antibody or V3-binding fragment thereof, comprises a VH domain of SEQ ID NO:310 and a VL domain of SEQ ID NO:311. In an embodiment, the anti-V3 antibody or V3-binding fragment thereof, comprises a VH domain of SEQ ID NO:320 and a VL domain of SEQ ID NO:321. In an embodiment, the anti-V3 antibody or V3-binding fragment thereof, comprises a VH domain of SEQ ID NO:225 or SEQ ID NO:330 and a VL domain of SEQ ID NO:326. In an embodiment, the anti-V3 antibody or V3-binding fragment thereof, comprises a VH domain of SEQ ID NO:334 and a VL domain of SEQ ID NO:335.

In an embodiment, the anti-V3 antibody comprises a HC of SEQ ID NO:61 or 62 and a LC of SEQ ID NO:63 or 64. In an embodiment, the anti-V3 antibody comprises a HC of SEQ ID NO: 62 and a LC of SEQ ID NO:63. In an embodiment, the anti-V3 antibody comprises a HC of SEQ ID NO:67 or 68 and a LC of SEQ ID NO:69. In an embodiment, the anti-V3 antibody comprises a HC of SEQ ID NO:72 or 73 and a LC of SEQ ID NO:74. In an embodiment, the anti-V3 antibody comprises a HC of SEQ ID NO:77 or 78 and a LC of SEQ ID NO:79. In an embodiment, the anti-V3 antibody comprises a HC of SEQ ID NO:82 or 83 and a LC of SEQ ID NO: 84. In an embodiment, the anti-V3 antibody comprises a HC of SEQ ID NO:87 or 88 and a LC of SEQ ID NO:89 In an embodiment, the anti-V3 antibody comprises a HC of SEQ ID NO:257 or 258 and a LC of SEQ ID NO:259. In an embodiment, the anti-V3 antibody comprises a HC of SEQ ID NO:262 or 263 and a LC of SEQ ID NO:264. In an embodiment, the anti-V3 antibody comprises a HC of SEQ ID NO: 267 or 268 and a LC of SEQ ID NO:269. In an embodiment, the anti-V3 antibody comprises a HC of SEQ ID NO:272 or 273 and a LC of SEQ ID NO:274. In an embodiment, the anti-V3 antibody comprises a HC of SEQ ID NO:277 or 278 and a LC of SEQ ID NO: 279. In an embodiment, the anti-V3 antibody comprises a HC of SEQ ID NO:282 or 283 and a LC of SEQ ID NO: 284. In an embodiment, the anti-V3 antibody comprises a HC of SEQ ID NO: 292 or 293 and a LC of SEQ ID NO:294. In an embodiment, the anti-V3 antibody comprises a HC of SEQ ID NO: 297 or 298 and a LC of SEQ ID NO:299. In an embodiment, the anti-V3 antibody comprises a HC of SEQ ID NO:302 or 303 and a LC of SEQ ID NO:304. In an embodiment, the anti-V3 antibody comprises a HC of SEQ ID NO:307 or 308 and a LC of SEQ ID NO: 309. In an embodiment, the anti-V3 antibody comprises a HC of SEQ ID NO:312 or 313 and a LC of SEQ ID NO:314. In an embodiment, the anti-V3 antibody comprises a HC of SEQ ID NO: 317 or 318 and a LC of SEQ ID NO:319. In an embodiment, the anti-V3 antibody comprises a HC of SEQ ID NO:322 or 323 and a LC of SEQ ID NO:324. In an embodiment, the anti-V3 antibody comprises a HC of SEQ ID NO:327, 328, 331 or 332 and a LC of SEQ ID NO:329. In an embodiment, the anti-V3 antibody comprises a HC of SEQ ID NO:336 or 337 and a LC of SEQ ID NO: 329.

Anti-V3 bNAbs known in the art include PGT121-123, PGT125-131, PGT135-137, DH270.6, QA013.2, 10-1074, 10-1074LS, PGT121.414.LS and 2G12, 438-B11, 447-52D, BG18, DH270.6, ePGT121v1, ePGT121v2, ePGT121v3, EPTC112, and F425-B4e8. In an embodiment, the anti-V3 antibody or V3-binding fragment thereof, comprises the six CDRs of any one of PGT121-123, PGT125-131, PGT135-137, DH270.6, QA013.2, 10-1074, 2G12, 438-B11, 447-52D, BG18, DH270.6, ePGT121v1, ePGT121v2, ePGT121v3, EPTC112, and F425-B4e8. In an embodiment, the anti-V3 antibody or V3-binding fragment thereof, comprises the VH domain and the VL domain any one of PGT121-123, PGT125-131, PGT135-137, DH270.6, QA013.2, 10-1074, 2G12, 438-B11, 447-52D, BG18, DH270.6, ePGT121v1, ePGT121v2, ePGT121v3, EPTC112, and F425-B4e8.

An antigen binding protein of the invention may comprise an anti-V3 scFv of any one of the aforementioned anti-V3 bNAbs. In an embodiment, the scFv comprises a VH and VL pair as set out in Table 2. In an embodiment, the scFv comprises a VH and VL pair of any one of PGT121-123, PGT125-131, PGT135-137, QA013.2, 10-1074, 10-1074LS, PGT121.414.LS and 2G12. In an embodiment, the C-terminus of the VH domain is attached directly or via a linker to the N-terminus of the VL domain. In an embodiment, the C-terminus of the VL domain is attached directly or via a linker to the N-terminus of the VH domain. In an embodiment, the scFv comprises a VH domain of SEQ ID NO:58 and a VL domain of SEQ ID NO:59. In an embodiment, the scFv comprises a VH domain of SEQ ID NO:65 and a VL domain of SEQ ID NO:66. In an embodiment, the scFv comprises a VH domain of SEQ ID NO:70 and a VL domain of SEQ ID NO: 71. In an embodiment, the scFv comprises a VH domain of SEQ ID NO:75 and a VL domain of SEQ ID NO: 76. In an embodiment, the scFv comprises a VH domain of SEQ ID NO:80 and a VL domain of SEQ ID NO:81. In an embodiment, the scFv comprises a VH domain of SEQ ID NO: 85 and a VL domain of SEQ ID NO:86.

An anti-V3 scFv may be fused to an Fc domain. In an embodiment, the scFv is fused to a human Fc domain directly or via a linker (scFv-Fc).

Linkers

Examples of suitable linkers include amino acid sequences that are from 1 amino acid to 150 amino acids in length. In particular, from 1 to 140 amino acids, from 1 to 130 amino acids, from 1 to 120 amino acids, from 1 to 110 amino acids, from 1 to 100 amino acids, from 1 to 90 amino acids, from 1 to 80 amino acids, from 1 to 70 amino acids, from 1 to 60 amino acids, from 1 to 50 amino acids, from 1 to 40 amino acids, from 1 to 30 amino acids, from 1 to 20 amino acids, from 1 to 10 amino acids, from 5 to 30 amino acids.

In an embodiment, the linker is an amino acid sequence from 5 to 30 amino acids in length. In an embodiment, the linker is an amino acid sequence as set forth in any one of SEQ ID NOs: 90 to 95. In an embodiment, the linker is an amino acid sequence as set forth in SEQ ID NO: 90. In an embodiment, the linker is a multimer of the amino acid sequence as set forth in SEQ ID NO:90. In an embodiment, the linker is [SEQ ID NO:90]ⁿ", wherein n is an integer from 1 to 6. In an embodiment, the linker is an amino acid sequence as set forth in SEQ ID NO:91. In an embodiment, the linker is an amino acid sequence as set forth in SEQ ID NO:92. In an embodiment, the linker is an amino acid sequence as set forth in SEQ ID NO:93. In an embodiment, the linker is an amino acid sequence as set forth in SEQ ID NO:94. In an embodiment, the linker is an amino acid sequence as set forth in SEQ ID NO:95.

Any of the aforementioned linkers may be incorporated into an antigen binding protein of the invention. In particular, any of the aforementioned linkers may be used to join a domain within the antigen binding protein to another domain within the antigen binding protein. In particular, any of the aforementioned linkers may be used to join a domain within the antigen binding protein that binds to the CD4-binding site of HIV gp120 to another domain within the antigen binding protein that binds to the V3 loop region of HIV gp120. Further, any of the aforementioned linkers may be used to join a CD4 domain as disclosed herein to a bNAb as disclosed herein. In an embodiment, the linker is an amino acid sequence as set forth in any one of SEQ ID NOs: 90 to 95. In an embodiment, the linker is an amino acid sequence as set forth in SEQ ID NO:90.

In an embodiment, a linker is used to join the C-terminus of a CD4 domain to the N-terminus of a bNAb heavy chain variable domain. In an embodiment, a linker is used to join the C-terminus of a CD4 domain to the N-terminus of a bNAb light chain variable domain. In an embodiment, a linker is used to join the C-terminus of a CD4 domain to the N-terminus of a bNAb heavy chain variable domain and a linker is used to join the C-terminus of a CD4 domain to the N-terminus of a bNAb light chain variable domain. In an embodiment, a linker is used to join the C-terminus of a CD4 domain to the N-terminus of a bNAb heavy chain variable domain and an identical linker is used to join the C-terminus of a CD4 domain to the N-terminus of a bNAb light chain variable domain. In an embodiment, the linker is an amino acid sequence as set forth in any one of SEQ ID NOs: 90 to 95. In an embodiment, the linker is an amino acid sequence as set forth in SEQ ID NO:90.

In an embodiment, a linker is used to join the N-terminus of a CD4 domain to the C-terminus of a bNAb heavy chain. In an embodiment, a linker is used to join the N-terminus of a CD4 domain to the C-terminus of a bNAb heavy chain variable domain. In an embodiment, a linker is used to join the N-terminus of a CD4 domain to the C-terminus of a bNAb light chain. In an embodiment, a linker is used to join the N-terminus of a CD4 domain to the C-terminus of a bNAb light chain variable domain. In an embodiment, a linker is used to join the N-terminus of a CD4 domain to the C-terminus of an Fc domain. In an embodiment, the linker is an amino acid sequence as set forth in any one of SEQ ID NOs: 90 to 95. In an embodiment, the linker is an amino acid sequence as set forth in SEQ ID NO:90.

In an embodiment of the invention, the domain of the antigen binding protein that binds to the CD4-binding site of HIV gp120 is joined directly to another domain within the antigen binding protein that binds to the V3 loop region of HIV gp120, i.e., a linker is not used. In an embodiment, a CD4 domain as disclosed herein is joined directly to a bNAb as disclosed herein.

Any of the aforementioned linkers may be used to join a VH and VL pair as disclosed herein to form a scFv. In an embodiment, the linker between the VH domain and the VL domain of the scFv is selected from the group consisting of SEQ ID NOs: 90-95. In a particular embodiment, the linker between the VH domain and the VL domain of the scFv is SEQ ID NO:93.

Any of the aforementioned linkers may be used to join a scFv as disclosed herein to an Fc domain. In an embodiment, the scFv is fused to a human Fc via a linker selected from the group consisting of SEQ ID NO:90-95. In an embodiment, the scFv is fused to a human Fc via a linker of SEQ ID NO:91.

Bispecific Molecules

A bispecific molecule of the invention comprises one or more paratopes that bind to the CD4bs of HIV gp120 and one or more paratopes that bind to the V3 loop region of HIV gp120.

Paratopes that bind to the CD4bs of HIV gp120 may be formed by CD4 domains disclosed herein, as well as other CD4bs-binding domains disclosed herein, including those of anti-CD4bs antibodies and CD4bs-binding fragments thereof, and non-Ig constructs that bind to CD4bs.

Paratopes that bind to the V3 loop region of HIV gp120 may be formed by anti-V3 antibodies and V3-binding fragments thereof disclosed herein, as well as non-Ig constructs that bind to V3 disclosed herein.

In an embodiment, the bispecific molecule comprises a paratope that binds to the CD4bs of HIV gp120 that is formed by an anti-CD4bs antibody or CD4bs-binding fragment thereof and a paratope that binds to the V3 loop region of HIV gp120 that is formed by an anti-V3 antibody or a V3-binding fragment thereof.

In an embodiment, the bispecific molecule comprises an anti-CD4bs antibody or CD4bs-binding fragment thereof and an anti-V3 antibody or a V3-binding fragment thereof.

In an embodiment, the bispecific molecule comprises a CD4 domain and a paratope that binds to the V3 loop region of HIV gp120 that is formed by an anti-V3 antibody or a V3-binding fragment thereof.

In an embodiment, the bispecific molecule comprises a CD4 domain and an anti-V3 antibody or a V3-binding fragment thereof.

In an embodiment, the bispecific molecule comprises a CD4 domain of any one of SEQ ID NOs: 1-21 and an anti-V3 antibody or a V3-binding fragment thereof.

In an embodiment, the bispecific molecule comprises a CD4 domain of SEQ ID NO: 11 and an anti-V3 antibody or a V3-binding fragment thereof.

In an embodiment, the bispecific molecule comprises a CD4 domain and an anti-V3 antibody, selected from the group consisting of: PGT121-123, PGT125-131, PGT135-137, QA013.2, 10-1074, 10-1074LS, PGT121.414.LS and 2G12, or a V3-binding fragment thereof.

In an embodiment, the bispecific molecule comprises a CD4 domain of any one of SEQ ID NOs: 1-21 and an anti-V3 antibody selected from the group consisting of: PGT121-123, PGT125-131, PGT135-137, QA013.2, 10-1074, 10-1074LS, PGT121.414.LS and 2G12, or a V3-binding fragment thereof.

In an embodiment, the bispecific molecule comprises a CD4 domain of SEQ ID NO: 11 and an anti-V3 antibody selected from the group consisting of: PGT121-123, PGT125-131, PGT135-137, QA013.2, 10-1074, 10-1074LS, PGT121.414.LS and 2G12, or a V3-binding fragment thereof.

In an embodiment, the bispecific molecule comprises a CD4 domain and an anti-V3 antibody comprising a set of CDRs (CDRH1, CDRH2, CDRH3, CDRL1, CDRL2 and CDRL3) as set out in any row of Table 1, or a V3-binding fragment thereof.

In an embodiment, the bispecific molecule comprises a CD4 domain of any one of SEQ ID NOs: 1-21 and an anti-V3 antibody comprising a set of CDRs (CDRH1, CDRH2, CDRH3, CDRL1, CDRL2 and CDRL3) as set out in any row of Table 1, or a V3-binding fragment thereof.

In an embodiment, the bispecific molecule comprises a CD4 domain of SEQ ID NO:11 and an anti-V3 antibody comprising a set of CDRs (CDRH1, CDRH2, CDRH3, CDRL1, CDRL2 and CDRL3) as set out in any row of Table 1 or a V3-binding fragment thereof.

In an embodiment, the bispecific molecule comprises a CD4 domain of SEQ ID NO: 11 and an anti-V3 antibody comprising a CDRH1 of SEQ ID NO:22, a CDRH2 of SEQ ID NO:23, a CDRH3 of SEQ ID NO:24, a CDRL1 of SEQ ID NO: 25, a CDRL2 of SEQ ID NO:26 and a CDRL3 of SEQ ID NO:27, or a V3-binding fragment thereof.

In an embodiment, the bispecific molecule comprises a CD4 domain and an anti-V3 antibody comprising a pair of variable domains (a VH and a VL) as set out in any row of Table 2, or a V3-binding fragment thereof.

In an embodiment, the bispecific molecule comprises a CD4 domain of any one of SEQ ID NOs: 1-21 and an anti-V3 antibody comprising a pair of variable domains (a VH and a VL) as set out in any row of Table 2, or a V3-binding fragment thereof.

In an embodiment, the bispecific molecule comprises a CD4 domain of SEQ ID NO: 11 and an anti-V3 antibody comprising a pair of variable domains (a VH and a VL) as set out in any row of Table 2, or a V3-binding fragment thereof.

In an embodiment, the bispecific molecule comprises a CD4 domain and an anti-V3 antibody or a V3-binding fragment thereof comprising a VH domain of SEQ ID NO:58 and a VL domain of SEQ ID NO:59 or 60.

In an embodiment, the bispecific molecule comprises a CD4 domain of any one of SEQ ID NOs: 1-21 and an anti-V3 antibody comprising a VH domain of SEQ ID NO:58 and a VL domain of SEQ ID NO:59 or 60.

In an embodiment, the bispecific molecule comprises a CD4 domain of SEQ ID NO:11 and an anti-V3 antibody comprising a VH domain of SEQ ID NO:58 and a VL domain of SEQ ID NO: 59 or 60.

In an embodiment, the bispecific molecule comprises a CD4 domain of any one of SEQ ID NOs: 1-21 and an anti-V3 antibody comprising a VH domain of SEQ ID NO:65 and a VL domain of SEQ ID NO:66.

In an embodiment, the bispecific molecule comprises a CD4 domain of SEQ ID NO: 11 and an anti-V3 antibody comprising a VH domain of SEQ ID NO:65 and a VL domain of SEQ ID NO: 66.

In an embodiment, the bispecific molecule comprises a CD4 domain of any one of SEQ ID NOs: 1-21 and an anti-V3 antibody comprising a VH domain of SEQ ID NO: 70 and a VL domain of SEQ ID NO:71.

In an embodiment, the bispecific molecule comprises a CD4 domain of SEQ ID NO:11 and an anti-V3 antibody comprising a VH domain of SEQ ID NO:70 and a VL domain of SEQ ID NO: 71.

In an embodiment, the bispecific molecule comprises a CD4 domain of any one of SEQ ID NOs: 1-21 and an anti-V3 antibody comprising a VH domain of SEQ ID NO:75 and a VL domain of SEQ ID NO:76.

In an embodiment, the bispecific molecule comprises a CD4 domain of SEQ ID NO:11 and an anti-V3 antibody comprising a VH domain of SEQ ID NO:75 and a VL domain of SEQ ID NO: 76.

In an embodiment, the bispecific molecule comprises a CD4 domain of any one of SEQ ID NOs: 1-21 and an anti-V3 antibody comprising a VH domain of SEQ ID NO:80 and a VL domain of SEQ ID NO:81.

In an embodiment, the bispecific molecule comprises a CD4 domain of SEQ ID NO:11 and an anti-V3 antibody comprising a VH domain of SEQ ID NO:80 and a VL domain of SEQ ID NO: 81.

In an embodiment, the bispecific molecule comprises a CD4 domain of any one of SEQ ID NOs: 1-21 and an anti-V3 antibody comprising a VH domain of SEQ ID NO:85 and a VL domain of SEQ ID NO:86.

In an embodiment, the bispecific molecule comprises a CD4 domain of SEQ ID NO:11 and an anti-V3 antibody comprising a VH domain of SEQ ID NO:85 and a VL domain of SEQ ID NO: 86.

An anti-V3 antibody as described above may be an antibody comprising a heavy chain (HC), with or without M428L/N434S (EU numbering) 'LS' mutations. In an embodiment, the HC comprises LS.

In an embodiment, the bispecific molecule comprises a CD4 domain of any one of SEQ ID NOs: 1-21 and an anti-V3 antibody comprising a HC of SEQ ID NO:61 or 62 and a LC of SEQ ID NO: 63 or 64.

In an embodiment, the bispecific molecule comprises a CD4 domain of SEQ ID NO:11 and an anti-V3 antibody comprising a HC of SEQ ID NO:61 or 62 and a LC of SEQ ID NO:63 or 64.

In an embodiment, the bispecific molecule comprises a CD4 domain of any one of SEQ ID NOs: 1-21 and an anti-V3 antibody comprising a HC of SEQ ID NO:62 and a LC of SEQ ID NO: 63.

In an embodiment, the bispecific molecule comprises a CD4 domain of SEQ ID NO:11 and an anti-V3 antibody comprising a HC of SEQ ID NO:62 and a LC of SEQ ID NO:63.

In an embodiment, the bispecific molecule comprises a CD4 domain of any one of SEQ ID NOs: 1-21 and an anti-V3 antibody comprising a HC of SEQ ID NO:67 or 68 and a LC of SEQ ID NO: 69.

In an embodiment, the bispecific molecule comprises a CD4 domain of SEQ ID NO: 11 and an anti-V3 antibody comprising a HC of SEQ ID NO:67 or 68 and a LC of SEQ ID NO:69.

In an embodiment, the bispecific molecule comprises a CD4 domain of any one of SEQ ID NOs: 1-21 and an anti-V3 antibody comprising a HC of SEQ ID NO:72 or 73 and a LC of SEQ ID NO: 74.

In an embodiment, the bispecific molecule comprises a CD4 domain of SEQ ID NO:11 and an anti-V3 antibody comprising a HC of SEQ ID NO:72 or 73 and a LC of SEQ ID NO:74.

In an embodiment, the bispecific molecule comprises a CD4 domain of any one of SEQ ID NOs: 1-21 and an anti-V3 antibody comprising a HC of SEQ ID NO:77 or 78 and a LC of SEQ ID NO: 79.

In an embodiment, the bispecific molecule comprises a CD4 domain of SEQ ID NO:11 and an anti-V3 antibody comprising a HC of SEQ ID NO:77 or 78 and a LC of SEQ ID NO:79.

In an embodiment, the bispecific molecule comprises a CD4 domain of any one of SEQ ID NOs: 1-21 and an anti-V3 antibody comprising a HC of SEQ ID NO:82 or 83 and a LC of SEQ ID NO: 84.

In an embodiment, the bispecific molecule comprises a CD4 domain of SEQ ID NO:11 and an anti-V3 antibody comprising a HC of SEQ ID NO:82 or 83 and a LC of SEQ ID NO:84.

In an embodiment, the bispecific molecule comprises a CD4 domain of any one of SEQ ID NOs: 1-21 and an anti-V3 antibody comprising a HC of SEQ ID NO:87 or 88 and a LC of SEQ ID NO: 89

In an embodiment, the bispecific molecule comprises a CD4 domain of SEQ ID NO:11 and an anti-V3 antibody comprising a HC of SEQ ID NO:87 or 88 and a LC of SEQ ID NO:89.

In an embodiment, the bispecific molecule comprises an anti-V3 bNAb as disclosed herein and two copies of a CD4 domain as disclosed herein, wherein the C-terminus of one CD4 domain is attached directly or by a linker to the N-terminus of one of the anti-V3 bNAb heavy chains and the C-terminus of the other copy of the CD4 domain is attached directly or by a linker to the N-terminus of the other anti-V3 bNAb heavy chain.

In an embodiment, the bispecific molecule comprises an anti-V3 bNAb as disclosed herein and two copies of a CD4 domain as disclosed herein, wherein the C-terminus of one CD4 domain is attached directly or by a linker to the N-terminus of one of the anti-V3 bNAb light chains and the C-terminus of the other copy of the CD4 domain is attached directly or by a linker to the N-terminus of the other anti-V3 bNAb light chain.

In an embodiment, the bispecific molecule comprises an anti-V3 bNAb as disclosed herein and four copies of a CD4 domain as disclosed herein, wherein the C-terminus of the first CD4 domain is attached directly or by a linker to the N-terminus of one of the anti-V3 bNAb heavy chains, the C-terminus of the second CD4 domain is attached directly or by a linker to the N-terminus of the other anti-V3 bNAb heavy chains, the third CD4 domain is attached directly or by a linker to the N-terminus of one of the anti-V3 bNAb light chains, and the fourth CD4 domain is attached directly or by a linker to the N-terminus of the other anti-V3 bNAb light chains.

In an embodiment, the bispecific molecule comprises an anti-V3 bNAb as disclosed herein and two copies of a CD4 domain as disclosed herein, wherein the N-terminus of first CD4 domain is attached directly or by a linker to the C-terminus of one of the anti-V3 bNAb heavy chains and the N-terminus of the other copy of the CD4 domain is attached directly or by a linker to the C-terminus of the other anti-V3 bNAb heavy chain.

In an embodiment, the bispecific molecule comprises an anti-V3 bNAb as disclosed herein and two copies of a CD4 domain of SEQ ID NO: 11, wherein the C-terminus of one CD4 domain is attached by a linker of SEQ ID NO: 90 to the N-terminus of one of the anti-V3 bNAb heavy chains and the C-terminus of the other copy of the CD4 domain is attached by a linker of SEQ ID NO: 90 to the N-terminus of the other anti-V3 bNAb heavy chain.

In an embodiment, the bispecific molecule comprises an anti-V3 bNAb as disclosed herein and two copies of a CD4 domain of SEQ ID NO: 11, wherein the C-terminus of one CD4 domain is attached by a linker of SEQ ID NO: 90 to the N-terminus of one of the anti-V3 bNAb light chains and the C-terminus of the other copy of the CD4 domain is attached by a linker of SEQ ID NO: 90 to the N-terminus of the other anti-V3 bNAb light chain.

In an embodiment, the bispecific molecule comprises an anti-V3 bNAb as disclosed herein and four copies of a CD4 domain of SEQ ID NO:11, wherein the C-terminus of the first CD4 domain is attached by a linker of SEQ ID NO: 90 to the N-terminus of one of the anti-V3 bNAb heavy chains, the C-terminus of the second CD4 domain is attached by a linker of SEQ ID NO: 90 to the N-terminus of the other anti-V3 bNAb heavy chains, the third CD4 domain is by a linker of SEQ ID NO: 90 to the N-terminus of one of the anti-V3 bNAb light chains, and the fourth CD4 domain is attached by a linker of SEQ ID NO: 90 to the N-terminus of the other anti-V3 bNAb light chains.

In an embodiment, the bispecific molecule comprises an anti-V3 bNAb as disclosed herein and two copies of a CD4 domain of SEQ ID NO: 11, wherein the N-terminus of the first CD4 domain is attached by a linker of SEQ ID NO: 90 to the C-terminus of one of the anti-V3 bNAb heavy chains and the N-terminus of the other copy of the CD4 domain is attached by a linker of SEQ ID NO: 90 to the C-terminus of the other anti-V3 bNAb heavy chain.

In an embodiment, the bispecific molecule comprises an anti-V3 bNAb comprising a VH of SEQ ID NO:58 and a VL of SEQ ID NO:59, and two copies of a CD4 domain of SEQ ID NO: 11, wherein the C-terminus of one CD4 domain is attached by a linker of SEQ ID NO: 90 to the N-terminus of one of the anti-V3 bNAb heavy chains and the C-terminus of the other copy of the CD4 domain is attached by a linker of SEQ ID NO: 90 to the N-terminus of the other anti-V3 bNAb heavy chain.

In an embodiment, the bispecific molecule an anti-V3 bNAb comprising a VH of SEQ ID NO: 58 and a VL of SEQ ID NO:59, and two copies of a CD4 domain of SEQ ID NO: 11, wherein the C-terminus of one CD4 domain is attached by a linker of SEQ ID NO: 90 to the N-terminus of one of the anti-V3 bNAb light chains and the C-terminus of the other copy of the CD4 domain is attached by a linker of SEQ ID NO: 90 to the N-terminus of the other anti-V3 bNAb light chain.

In an embodiment, the bispecific molecule comprises an anti-V3 bNAb comprising a VH of SEQ ID NO:58 and a VL of SEQ ID NO:59, and four copies of a CD4 domain of SEQ ID NO: 11, wherein the C-terminus of the first CD4 domain is attached by a linker of SEQ ID NO: 90 to the N-terminus of one of the anti-V3 bNAb heavy chains, the C-terminus of the second CD4 domain is attached by a linker of SEQ ID NO: 90 to the N-terminus of the other anti-V3 bNAb heavy chains, the third CD4 domain is by a linker of SEQ ID NO: 90 to the N-terminus of one of the anti-V3 bNAb light chains, and the fourth CD4 domain is attached by a linker of SEQ ID NO: 90 to the N-terminus of the other anti-V3 bNAb light chains.

In an embodiment, the bispecific molecule comprises an anti-V3 bNAb comprising a VH of SEQ ID NO:58 and a VL of SEQ ID NO:59, and two copies of a CD4 domain of SEQ ID NO: 11, wherein the N-terminus of the first CD4 domain is attached by a linker of SEQ ID NO: 90 to the C-terminus of one of the anti-V3 bNAb heavy chains and the N-terminus of the other copy of the CD4 domain is attached by a linker of SEQ ID NO: 90 to the C-terminus of the other anti-V3 bNAb heavy chain.

In an embodiment, the bispecific molecule comprises a HC of any one of SEQ ID NOs: 96-107, 116, 117 or 119-135; and a LC of SEQ ID NO:63.

In an embodiment, the bispecific molecule comprises a HC of SEQ ID NO:62; and a LC of any one of SEQ ID NOs: 108-115 and 118.

In an embodiment, the bispecific molecule comprises a HC of SEQ ID NO:68; and a LC of SEQ ID NO: 142 or 143.

In an embodiment, the bispecific molecule comprises a HC of any one of SEQ ID NOs: 136-141; and a LC of SEQ ID NO:69.

In an embodiment, the bispecific molecule comprises a HC of SEQ ID NO: 144 or 145; and a LC of SEQ ID NO:74.

In an embodiment, the bispecific molecule comprises a HC of SEQ ID NO: 146 or 147; and a LC of SEQ ID NO:79.

In an embodiment, the bispecific molecule comprises a HC of SEQ ID NO: 148 or 149; and a LC of SEQ ID NO:84.

In an embodiment, the bispecific molecule comprises a HC of SEQ ID NO: 150 or 151; and a LC of SEQ ID NO:89.

In an embodiment, the bispecific molecule consists of two heavy chains and two light chains, wherein the heavy chain is at least 95% identical to SEQ ID NO: 121 and the light chain that is at least 95% identical to SEQ ID NO:63.

In an embodiment, the bispecific molecule consists of two heavy chains and two light chains, wherein the heavy chain is at least 96% identical to SEQ ID NO: 121 and the light chain that is at least 96% identical to SEQ ID NO:63.

In an embodiment, the bispecific molecule consists of two heavy chains and two light chains, wherein the heavy chain is at least 97% identical to SEQ ID NO: 121 and the light chain that is at least 97% identical to SEQ ID NO:63.

In an embodiment, the bispecific molecule consists of two heavy chains and two light chains, wherein the heavy chain is at least 98% identical to SEQ ID NO:121 and the light chain that is at least 98% identical to SEQ ID NO:63.

In an embodiment, the bispecific molecule consists of two heavy chains and two light chains, wherein the heavy chain is at least 99% identical to SEQ ID NO: 121 and the light chain that is at least 99% identical to SEQ ID NO:63.

In an embodiment, the bispecific molecule consists of two heavy chains of SEQ ID NO: 121 and two light chains of SEQ ID NO:63.

An antigen binding protein of the invention may comprise an anti-V3 scFv of any one of the aforementioned anti-V3 bNAbs. In an embodiment, the scFv comprises a VH and VL pair as set out in Table 2. In an embodiment, the scFv comprises a VH and VL pair of any one of PGT121-123, PGT125-131, PGT135-137, QA013.2, 10-1074, 10-1074LS, PGT121.414.LS and 2G12. In an embodiment, the C-terminus of the VH domain is attached directly or via a linker to the N-terminus of the VL domain. In an embodiment, the C-terminus of the VL domain is attached directly or via a linker to the N-terminus of the VH domain. In an embodiment, the linker between the VH domain and the VL domain of the scFv is selected from the group consisting of SEQ ID NOs: 90-95. In an embodiment, the linker between the VH domain and the VL domain of the scFv is SEQ ID NO:93.

In an embodiment, the scFv comprises a VH domain of SEQ ID NO:58 and a VL domain of SEQ ID NO:59. In an embodiment, the scFv comprises a VH domain of SEQ ID NO:65 and a VL domain of SEQ ID NO: 66. In an embodiment, the scFv comprises a VH domain of SEQ ID NO: 70 and a VL domain of SEQ ID NO:71. In an embodiment, the scFv comprises a VH domain of SEQ ID NO:75 and a VL domain of SEQ ID NO:76. In an embodiment, the scFv comprises a VH domain of SEQ ID NO:80 and a VL domain of SEQ ID NO:81. In an embodiment, the scFv comprises a VH domain of SEQ ID NO:85 and a VL domain of SEQ ID NO:86. In an embodiment, a linker of SEQ ID NO:93 joins the VH domain and the VL domain of the scFv. In an embodiment, a linker of SEQ ID NO:93 joins the C terminal of the VH domain to the N terminal of the VL domain to form the scFv. In an embodiment, a linker of SEQ ID NO:93 joins the C terminal of the VL domain to the N terminal of the VH domain to form the scFv.

An anti-V3 scFv may be fused to an Fc domain. In an embodiment, the scFv is fused to a human Fc domain directly or via a linker (scFv-Fc). In an embodiment, the C-terminus of the scFv is fused to the N-terminus of a human Fc domain via a linker selected from the group consisting of SEQ ID NOs: 90-95. In an embodiment, the N-terminus of the scFv is fused to the C-terminus of a human Fc domain via a linker selected from the group consisting of SEQ ID NOs: 90-95. In an embodiment, the scFv is fused to a human Fc domain via a linker of SEQ ID NO: 91. In an embodiment, the Fc domain comprises a half-life extending mutation. In an embodiment the half-life extending mutation is LS.

A scFv-Fc may be fused directly or via a linker to a CD4 domain. In an embodiment, the scFv-Fc is fused via a linker selected from the group consisting of SEQ ID NOs: 90-95 to a CD4 domain.

In an embodiment, the antigen binding protein comprises or consists of: (1) a scFv comprising a VH and VL pair as set out in any row of Table 2, wherein the VH and VL domain are joined to form a scFV via a linker selected from the group consisting of SEQ ID NOs: 90-95; (2) a CD4 domain selected from the group consisting of SEQ ID NOs: 1-21; and (3) and Fc domain comprising LS half-life extending mutations; wherein (1), (2) and (3) are joined together in any order directly or via a linker, and wherein each linker is selected from the group consisting of SEQ ID NOs: 90-95.

In an embodiment, the antigen binding protein comprises or consists of: (1) a scFv comprising a VH and VL pair as set out in any row of Table 2, wherein the VH and VL domain are joined to form a scFV via a linker of SEQ ID NO:93; (2) a CD4 domain selected from the group consisting of SEQ ID NOs: 1-21; and (3) and Fc domain comprising LS half-life extending mutations; wherein (1), (2) and (3) are joined together in any order via a linker between each domain, and wherein the linker is SEQ ID NOs: 90.

In an embodiment, the bispecific molecule of the invention comprises a sequence that is at least 95%, 96%, 97%, 98%, 99% or 100% identical to any one of SEQ ID NOs: 152-157. In an embodiment, an antigen binding protein of the invention consists of a sequence that is at least 95%, 96%, 97%, 98%, 99% or 100% identical to any one of SEQ ID NOs: 152-157. In an embodiment, an antigen binding protein of the invention comprises or consists of SEQ ID NO: 152. In an embodiment, an antigen binding protein of the invention comprises or consists of SEQ ID NO:153. In an embodiment, an antigen binding protein of the invention comprises or consists of SEQ ID NO: 154. In an embodiment, an antigen binding protein of the invention comprises or consists of SEQ ID NO: 155. In an embodiment, an antigen binding protein of the invention comprises or consists of SEQ ID NO: 156. In an embodiment, an antigen binding protein of the invention comprises or consists of SEQ ID NO: 157.

Production Methods

Antigen binding proteins may be prepared by any of a number of conventional techniques. For example, antigen binding proteins may be purified from cells that naturally express them (e.g., an antibody can be purified from a hybridoma that produces it), or produced in recombinant expression systems.

A number of different expression systems and purification regimes can be used to generate the antigen binding proteins of the invention. Generally, host cells are transformed with a recombinant expression vector encoding the desired antigen binding protein. The expression vector may be maintained by the host as a separate genetic element or integrated into the host chromosome depending on the expression system. A wide range of host cells can be employed, including Prokaryotes (including Gram-negative or Gram-positive bacteria, for example *Escherichia coli*, Bacilli sp., *Pseudomonas* sp., *Corynebacterium* sp.), Eukaryotes including yeast (for example *Saccharomyces cerevisiae, Pichia pastoris*), fungi (for example *Aspergillus* sp.), or higher Eukaryotes including insect cells and cell lines of mammalian origin (for example, CHO, NS0, PER.C6, HEK293, HeLa).

The host cell may be an isolated host cell. The host cell is usually not part of a multicellular organism (e.g., plant or animal). The host cell may be a non-human host cell.

Appropriate cloning and expression vectors for use with bacterial, fungal, yeast, and mammalian host cells are known in the art.

The cells can be cultured under conditions that promote expression of the antigen binding protein using a variety of equipment such as shake flasks, spinner flasks, and bioreactors. The polypeptide(s) is (are) recovered by conventional protein purification procedures. Protein purification procedures typically consist of a series of unit operations comprised of various filtration and chromatographic processes developed to selectively concentrate and isolate the antigen binding protein. The purified antigen binding protein may be formulated in a pharmaceutically acceptable composition.

Fc Modifications

Fc engineering methods can be applied to modify the functional or pharmacokinetics properties of an antigen binding protein, in particular an antibody. Effector function may be altered by making mutations in the Fc region that increase or decrease binding to C1q or Fcγ receptors and modify CDC or ADCC activity respectively. Modifications to the glycosylation pattern of an antibody can also be made to change the effector function.

The interaction between the Fc region of an antigen binding protein or antibody and various Fc receptors (FcR), including FcγRI (CD64), FcγRII (CD32), FcγRIII (CD16), FcRn, C1q, and type II Fc receptors is believed to mediate the effector functions of the antigen binding protein or antibody. Significant biological effects can be a consequence of effector functionality. Usually, the ability to mediate effector function requires binding of the antigen binding protein or antibody to an antigen and not all antigen binding proteins or antibodies will mediate every effector function.

Effector function can be assessed in a number of ways including, for example, evaluating ADCC effector function of antibody coated to target cells mediated by Natural Killer (NK) cells via FcγRIII, or monocytes/macrophages via FcγRI, or evaluating CDC effector function of antibody coated to target cells mediated by complement cascade via C1q. For example, an antigen binding protein of the present invention can be assessed for ADCC effector function in a Natural Killer cell assay. Examples of such assays can be found in Shields et al, 2001, The Journal of Biological Chemistry, Vol. 276, p. 6591-6604; Chappel et al, 1993, The Journal of Biological Chemistry, Vol 268, p. 25124-25131; Lazar et al, 2006, PNAS, 103; 4005-4010.

Examples of assays to determine CDC function include those described in J Imm Meth, 1995, 184:29-38.

The effects of mutations on effector functions (e.g., FcRn binding, FcγRs and C1q binding, CDC, ADCML, ADCC, ADCP) can be assessed, e.g., as described in Grevys et al., J Immunol. 2015 Jun. 1; 194 (11): 5497-5508, or Tam et al., Antibodies 2017, 6 (3); Monnet et al., 2014 mAbs, 6:2, 422-436.

Throughout this specification, amino acid residues in Fc regions, in antibody sequences or full-length antigen binding protein sequences, are numbered according to the EU index numbering convention.

The long half-life of IgG antibodies is reported to be dependent on their binding to FcRn. Therefore, substitutions that increase the binding affinity of IgG to FcRn at pH 6.0 while maintaining the pH dependence of the interaction with target, by engineering the constant region, have been extensively studied (Ghetie et al., Nature Biotech. 15:637-640, 1997; Hinton et al., JBC 279:6213-6216, 2004; Dall'Acqua et al., 10 J Immunol 117:1129-1138, 2006). The in-vivo half-life of antigen binding proteins of the present invention may be altered by modification of a heavy chain constant domain or an FcRn binding domain therein.

In adult mammals, FcRn, plays a key role in maintaining serum antibody levels by acting as a protective receptor that binds and salvages antibodies of the IgG isotype from degradation. IgG molecules are endocytosed by endothelial cells and, if they bind to FcRn, are recycled out of the cells back into circulation. In contrast, IgG molecules that enter the cells and do not bind to FcRn and are targeted to the lysosomal pathway where they are degraded.

FcRn is believed to be involved in both antibody clearance and the transcytosis across tissues (see Junghans R. P (1997) Immunol.Res 16. 29-57 and Ghetie et al (2000) Annu. Rev. Immunol. 18, 739-766). Human IgG1 residues determined to interact directly with human FcRn include Ile253, Ser254, Lys288, Thr307, Gln311, Asn434 and His435. Mutations at any of these positions may enable increased serum half-life and/or altered effector properties of antigen binding proteins of the invention.

Antigen binding proteins of the present invention may have amino acid modifications that increase the affinity of the constant domain or fragment thereof for FcRn. Increasing the half-life (i.e., serum half-life) of therapeutic and diagnostic IgG antibodies and other bioactive molecules has many benefits including reducing the amount and/or frequency of dosing of these molecules. In one embodiment, an antigen binding protein of the invention comprises all or a portion (an FcRn binding portion) of an IgG constant domain having one or more of the following amino acid modifications.

For example, with reference to IgG1, M252Y/S254T/T256E (commonly referred to as "YTE" mutations) and M428L/N434S (commonly referred to as "LS" mutations) increase FcRn binding at pH 6.0 (Wang et al. 2018). In an embodiment, an antigen binding protein of the invention comprises an Fc domain with the LS mutations. In an embodiment, an antigen binding protein of the invention comprises a bNAb in which the LS mutations are present in both of the heavy chain Fc domains.

Half-life and FcRn binding can also be extended by introducing H433K and N434F mutations (commonly referred to as "HN" or "NHance" mutations) (with reference to IgG1) (WO2006/130834).

Additionally, various publications describe methods for obtaining physiologically active molecules with modified half-lives, either by introducing an FcRn-binding polypeptide into the molecules (WO97/43316, U.S. Pat. Nos. 5,869, 046, 5,747,035, WO96/32478 and WO91/14438) or by fusing the molecules with antibodies whose FcRn-binding affinities are preserved, but affinities for other Fc receptors have been greatly reduced (WO99/43713), or fusing with FcRn binding domains of antibodies (WO00/09560, U.S. Pat. No. 4,703,039).

Post-Translational Modifications

The skilled person will appreciate that, upon production of an antigen binding protein, such as a bispecific molecule of the invention in a host cell, post-translational modifications may occur. For example, this may include the cleavage of certain leader sequences, the addition of various sugar moieties in various glycosylation patterns, non-enzymatic glycation, deamidation, oxidation, disulfide bond scrambling and other cysteine variants such as free sulfhydryls, racemized disulfides, thioethers and trisulfide bonds, isomerisation, C-terminal lysine clipping, and N-terminal glutamine cyclisation. The present invention encompasses the use of antigen binding proteins that have been subjected to, or have undergone, one or more post-translational modifications. Thus an antigen binding protein of the invention includes an "antigen binding protein" as defined earlier that has undergone a post-translational modification such as described herein.

Glycation is a post-translational non-enzymatic chemical reaction between a reducing sugar, such as glucose, and a free amine group in the protein, and is typically observed at the epsilon amine of lysine side chains or at the N-Terminus of the protein. Glycation can occur during production and storage only in the presence of reducing sugars.

Deamidation can occur during production and storage, is an enzymatic reaction primarily converting asparagine (N) to iso-aspartic acid (iso-aspartate) and aspartic acid (aspartate) (D) at approximately 3:1 ratio. This deamidation reaction is therefore related to isomerization of aspartate (D) to iso-aspartate. The deamidation of asparagine and the isomerisation of aspartate, both involve the intermediate succinimide. To a much lesser degree, deamidation can occur with glutamine residues in a similar manner. Deamidation can occur in a CDR, in a Fab (non-CDR region), or in the Fc region.

Oxidation can occur during production and storage (i.e., in the presence of oxidizing conditions) and results in a covalent modification of a protein, induced either directly by reactive oxygen species or indirectly by reaction with secondary by-products of oxidative stress. Oxidation happens primarily with methionine residues, but may occur at tryptophan and free cysteine residues. Oxidation can occur in a CDR, in a Fab (non-CDR) region, or in the Fc region.

Disulfide bond scrambling can occur during production and basic storage conditions. Under certain circumstances, disulfide bonds can break or form incorrectly, resulting in unpaired cysteine residues (—SH). These free (unpaired) sulfhydryls (—SH) can promote shuffling.

The formation of a thioether and racemization of a disulphide bond can occur under basic conditions, in production or storage, through a beta elimination of disulphide bridges back to cysteine residues via a dehydroalanine and persulfide intermediate. Subsequent crosslinking of dehydroalanine and cysteine results in the formation of a thioether bond or the free cysteine residues can reform a disulphide bond with a mixture of D- and L-cysteine.

Trisulfides result from insertion of a sulfur atom into a disulphide bond (Cys-S—S—S-Cys) and are formed due to the presence of hydrogen sulphide in production cell culture.

N-terminal glutamine (Q) and glutamate (glutamic acid) (E) in the heavy chain and/or light chain is likely to form pyroglutamate (pGlu) via cyclization. Most pGlu formation happens in the production bioreactor, but it can be formed non-enzymatically, depending on pH and temperature of processing and storage conditions. Cyclization of N-terminal Q or E is commonly observed in natural human antibodies.

C-terminal lysine clipping is an enzymatic reaction catalyzed by carboxypeptidases, and is commonly observed in recombinant and natural human antibodies. Variants of this process include removal of lysine from one or both heavy chains due to cellular enzymes from the recombinant host cell. Upon administration to the human subject/patient is likely to result in the removal of any remaining C-terminal lysines.

Pharmaceutical Compositions

Antigen binding proteins as described herein may be incorporated into pharmaceutical compositions for use in the treatment or prevention of HIV infection. In one embodiment, the pharmaceutical composition comprises an antigen binding protein in combination with one or more pharmaceutically acceptable carriers and/or excipients.

Such compositions comprise a pharmaceutically acceptable carrier as known and called for by acceptable pharmaceutical practice.

Pharmaceutical compositions may be administered by injection or continuous infusion (examples include, but are not limited to, intravenous, intraperitoneal, intradermal, subcutaneous, intramuscular, intraocular, and intraportal). In one embodiment, the composition is suitable for intravenous administration. In one embodiment, the composition is suitable for subcutaneous administration.

Pharmaceutical compositions may be suitable for topical administration (which includes, but is not limited to, epicutaneous, inhaled, intranasal or ocular administration) or enteral administration (which includes, but is not limited to, oral, vaginal, or rectal administration).

The pharmaceutical composition may be included in a kit containing the antigen binding protein together with other medicaments, for example dolutegravir or cabotegravir, and/or with instructions for use. For convenience, the kit may comprise the reagents in predetermined amounts with instructions for use. The kit may also include devices used for administration of the pharmaceutical composition.

The terms "individual", "subject" and "patient" are used herein interchangeably. In one embodiment the subject is a human.

The antigen binding proteins described herein may be used in methods of treatment or prevention of HIV infection and AIDs. The antigen binding proteins described herein may be used in the manufacture of medicaments for the treatment or prevention of HIV infection and AIDs. The antigen binding proteins described may be used in an effective amount for therapeutic, prophylactic or preventative treatment. A therapeutically effective amount of the antigen binding protein described herein is an amount effective to ameliorate or reduce one or more symptoms of HIV infection. A prophylactically effective amount of the antigen binding protein described herein is an amount effective to prevent one or more symptoms of HIV infection.

Combinations

Antigen binding proteins of the present invention may be employed alone or in combination with other therapeutic agents, or a prodrug thereof. Combination therapies according to the present invention thus comprise the administration of an antigen binding protein and the administration of at least one other agent which may be useful in the treatment or prevention of HIV infection and/or AIDS. An antigen binding protein of the present invention and the other therapeutic agent may be formulated and administered together in a single pharmaceutical composition or may be formulated and administered separately. When formulated and administered separately, administration may occur simultaneously or sequentially in any order.

Antigen binding proteins as described herein may be combined with, for example, one or more of an antiretroviral agent, an anti-infective agent, an immunomodulator, and other HIV entry inhibitors.

Antiretroviral agents include Nucleoside Reverse Transcriptase Inhibitors (NRTIs), Non-Nucleoside Reverse Transcriptase Inhibitors (NNRTIs), Nucleoside Reverse Transcriptase Translocation Inhibitors (NRTTIs), Protease Inhibitors (PIs), Entry Inhibitors (EI), Integrase Strand Transfer Inhibitors (INSTI), Maturation Inhibitors (MIS), and Capsid Inhibitors (CIs).

NRTIs may include, but are not limited to: abacavir, adefovir, adefovir dipivoxil, alovudine, amdoxovir, apricitabine, calanolide A, censavudine, didanosine, elvucitabine, emtricitabine, fozivudine, lamivudine, racivir, stampidine, stavudine, tenofovir disoproxil fumerate, tenofovir alafenamide, todoxil, zalcitabine, and zidovudine.

NNRTIs may include, but are not limited to, HBY 097 (Hoechst/Bayer), capravirine, delaviridine, doravirine, efavirenz, etravirine, immunocal, lersivirine, loviride, nevirapine, oltipraz, and rilpivirine.

NRTTIs include, but are not limited to, islatravir.

PIs may include, but are not limited to, amprenavir, atazanavir, brecanavir, cobicistat, darunavir, fosamprenavir, indinavir, lasinavir, lopinavir, palinavir, nelfinavir, ritonavir, saquinavir, and tipranavir.

EIs are discussed in DRUGS OF THE FUTURE 1999, 24 (12), 1355-1362; CELL, Vol. 9, 243-246, Oct. 29, 1999; and DRUG DISCOVERY TODAY, Vol. 5, No. 5, May 2000, pp. 183-194; and Meanwell et al., Current Opinion in Drug Discovery & Development (2003), 6 (4), 451-461. In particular, the antigen binding proteins of the invention can be utilized in combination with attachment inhibitors, fusion inhibitors, and chemokine receptor antagonists aimed at either the CCR5 or CXCR4 coreceptor. HIV attachment inhibitors are also set forth in U.S. Pat. Nos. 7,354,924 and 7,745,625. EIs may include, but are not limited to, cenicriviroc, enfuvirtide, fostemsavir, ibalizumab, leronlimab, maraviroc, vicriviroc and VIR-576.

INSTIs may include, but are not limited to, bictegravir, cabotegravir, dolutegravir, elvitegravir, and raltegravir. In an embodiment, the INSTI is dolutegravir or cabotegravir. In an embodiment, the INSTI is cabotegravir.

Maturation inhibitors may include, but are not limited to, bevirimat, BMS-955176, GSK3640254, GSK3739937, PA-344 and PA-457. It will be understood that GSK3640254 is a compound as described in Dicker I, Jeffrey J L, Protack T, et al., Antimicrob Agents Chemother. 2022; 66 (1). GSK3739937, also known as VH3739937, is the compound of clinical trial NCT04493684.

Capsid inhibitors may include, but are not limited to, GSK4004280, GSK4011499, and lencapavir.

Anti-infective agents include, but are not limited to, clindamycin with primaquine, daunorubicin, fluconazole, intraconazole, nystatin pastille, ornidyl eflornithine, megestrol acetate, pentamidine isethionate, piritrexim, trimethoprim, trimetrexate, recombinant human erythropoietin, recombinant human growth hormone, spiramycin, testosterone and total enteral nutrition, Immunomodulators include, but are not limited to, acemannan, alpha-2-interferon, AS-101, bropirimine, CL246, 738, FP-21399, gamma interferon, granulocyte macrophage colony stimulating factor, HIV core particle immunostimulant, interleukin-2, immune globulin, IMREG-1, IMREG-2, imuthiol diethyl dithio carbamate, methionine enkephalin, MTP-PE muramyl tripeptide, remune, recombinant soluble human CD4, rCD4-IgG hybrids, SK&F106528, thymopentin, and tumour necrosis factor (TNF).

The antigen binding proteins of the present invention may also be used in combination with agents that induce HIV expression, such as latency reversing agents. Several latency reversing agents include, but are not limited to, the following: histone deacetylase inhibitors (e.g., vorinostat, panobinostat, romidepin), histone crotonyl transferase inhibitors (sodium corotonate), protein kinase C agonists (e.g., bryostatin, ingenol B), disulfiram, TLR7 agonists (e.g., GS-9620), and bromodomain inhibitors (e.g., JQ1, iBET151).

The antigen binding proteins of the present invention may also be used in combination with other agents that induce HIV expression, such as agents for clearance therapy. Several examples of agents for clearance therapy, or of immunological combinations for clearance, include, but are not limited to, the following: bNAbs, CD4-Ig, eCD4-Ig, and dual-affinity re-targeting (DART) proteins.

Antigen binding proteins of the invention may be used in combination with broadly neutralizing HIV-1 antibodies, including 1NC9, 1B2530, 2F5, 2G12, 3NBC60, 3BNC117, 4E10, 8ANC131, 8ANC134, 10-1074, 10-1074LS, 10E8, 12A12, 12A21, b12, CAP206-CH12, CH01-04, CH103-106, elipovimab (formerly known as GS-9722), HJ16, M66.6, N6LS (also known as VRC-HIVMAB091-00-AB and the compound of clinical trial NCT03538626), NIH45-46, PG9, PG16, PGT121-123, PGT125-131, PGT135-137, PGT141-145, PGT121.414.LS, PGT151 2G12, QA013.2, VRC01-03, VRC-PG04, VRC-PG04b, VRC-CH30-34.

Other agents that may be combined with antigen binding proteins of the invention include BIT225, GSK4000422/VH4000422, and S-648414 (the compound of clinical trial NCT04147715).

The scope of combinations of compounds of this invention with HIV agents is not limited to those mentioned above but includes in principle any combination with any pharmaceutical composition useful for the treatment and/or prevention of HIV infection and/or AIDS.

The invention is illustrated by the following clauses:

1. An anti-HIV gp120-binding protein that binds to at least two different epitopes on human immunodeficiency virus (HIV) surface glycoprotein 120 (gp120).

2. The anti-HIV gp120-binding protein of clause 1, wherein one of the at least two epitopes comprises one or more amino acid residues of the CD4-binding site of HIV gp120.

3. The anti-HIV gp120-binding protein of clause 1 or clause 2, wherein one of the at least two epitopes comprises one or more amino acid residues of the V3 loop region (V3) of HIV gp120.

4. The anti-HIV gp120-binding protein of clause 3, wherein one of the at least two epitopes comprises a cluster of mannose glycans centered on N332 of HIV gp120.

5. The anti-HIV gp120-binding protein of any one of the preceding clauses that binds to the CD4-binding site of HIV gp120 and the V3 loop region of HIV gp120.

6. The anti-HIV gp120-binding protein of any one of the preceding clauses, comprising a CD4-domain.

7. The anti-HIV gp120-binding protein of clause 6, wherein the CD4 domain is a CD4 D1 domain or CD4 D1D2 domain.

8. The anti-HIV gp120-binding protein of clause 6 or clause 7, wherein the CD4 domain comprises one or more stabilizing mutations.

9. The anti-HIV gp120-binding protein of clause 8, wherein the CD4 domain has a Tm of between 70° C. and 95° C.

10. The anti-HIV gp120-binding protein of any one of clauses 6 to 9, wherein the CD4 D1 domain comprises one or more mutations selected from the group consisting of: K8C, K8I, K8V, T11C, E13C, K21C, Q25E, H27C, H27D, G38C, N52W, R58N, R58T, R58V, L61M, G65C, 170C, K72C, E87G, E91H, E91Q, and G99C.

11. The anti-HIV gp120-binding protein of clause 9, wherein the CD4 domain has a Tm of about 90° C.

12. The anti-HIV gp120-binding protein of clause 10 or clause 11, wherein the CD4 domain comprises K8C and G99C.

13. The anti-HIV gp120-binding protein of clause 6, comprising any one of SEQ ID NOs: 1-21.

14. The anti-HIV gp120-binding protein of any one of clauses 6 to 13, comprising SEQ ID NO: 11.

15. The anti-HIV gp120-binding protein of any one of clauses 3 to 14, comprising a set of 6 CDRs (CDRH1, CDRH2, CDRH3, CDRL1, CDRL2 and CDRL3) as set forth in any row of Table 1.

16. The anti-HIV gp120-binding protein of clause 15, comprising a CDRH1 of SEQ ID NO: 22, a CDRH2 of SEQ ID NO:23, a CDRH3 of SEQ ID NO:24, a CDRL1 of SEQ ID NO: 25, a CDRL2 of SEQ ID NO:26 and a CDRL3 of SEQ ID NO:27.

17. The anti-HIV gp120-binding protein of any one of the preceding clauses, comprising an immunoglobulin (Ig) scaffold.

18. The anti-HIV gp120-binding protein of clause 15, clause 16 or clause 17, comprising a heavy chain variable (VH) domain and a light chain variable (VL) domain pair as set forth in any row of Table 2.

19. The anti-HIV gp120-binding protein of clause 18, comprising a VH domain of SEQ ID NO: 58 and a VL domain of SEQ ID NO:59 or SEQ ID NO:60.

20. The anti-HIV gp120-binding protein of any one of clauses 17 to 19, comprising an Fc domain.

21. The anti-HIV gp120-binding protein of clause 20, wherein the Fc domain comprises a mutation that increases the half-life of the anti-HIV gp120-binding protein compared to the same anti-HIV gp120-binding protein without said mutation.

22. The anti-HIV gp120-binding protein of clause 21, wherein the Fc domain comprises any one of the following sets of mutations (EU numbering):
M428L and N434S (LS);
L309D, Q311H and N434S (DHS);
M252Y, S254T and T256E (YTE); and
H433K and N434F (HN).

23. The anti-HIV gp120-binding protein of clause 22, wherein the Fc domain comprises LS.

24. The anti-HIV gp120-binding protein of any one of the preceding clauses comprising a broadly neutralizing antibody (bNAb).

25. The anti-HIV gp120-binding protein of clause 24, wherein the bNAb is an anti-V3 bNAb.

26. The anti-HIV gp120-binding protein of clause 25, wherein the anti-V3 bNAb comprises a heavy chain (HC) and a light chain (LC) pair as set forth in any row of Table 2.

27. The anti-HIV gp120-binding protein of clause 26, wherein the HC comprises SEQ ID NO: 61 or SEQ ID NO: 62 and the LC comprises SEQ ID NO: 63 or SEQ ID NO:64.

28. The anti-HIV gp120-binding protein of clause 27, wherein the HC comprises SEQ ID NO: 62 and the LC comprises SEQ ID NO:63.

29. The anti-HIV gp120-binding protein of any one of clauses 17 to 19, comprising an anti-V3 bNAb scFv.

30. The anti-HIV gp120-binding protein of clause 29, wherein the scFv comprises a VH domain of SEQ ID NO:58 and a VL domain of SEQ ID NO:59.

31. The anti-HIV gp120-binding protein of clause 29 or clause 30, wherein the C-terminus of the VH domain is fused directly or via a linker to the N-terminus of the VL domain.

32. The anti-HIV gp120-binding protein of clause 29 or clause 30, wherein the C-terminus of the VL domain is fused directly or via a linker to the N-terminus of the VH domain.

33. The anti-HIV gp120-binding protein of clause 31 or clause 32, wherein the linker between the VH domain and the VL domain of the scFv is selected from the group consisting of SEQ ID NOs: 90-95.

34. The anti-HIV gp120-binding protein of clause 33, wherein the linker between the VH domain and the VL domain of the scFv is SEQ ID NO:93.

35. The anti-HIV gp120-binding protein of any one of clauses 29 to 34, wherein the scFv is fused to a human Fc domain directly or via a linker (scFv-Fc).

36. The anti-HIV gp120-binding protein of clause 35, wherein the scFv is fused to a human Fc via a linker selected from the group consisting of SEQ ID NO:90-95.

37. The anti-HIV gp120-binding protein of clause 35, wherein the scFv is fused to a human Fc via a linker of SEQ ID NO:91.

38. The anti-HIV gp120-binding protein of any one of clauses 35 to 37, wherein the Fc domain is as defined in any one of clauses 21 to 23.

39. The anti-HIV gp120-binding protein of any one of clauses 35 to 38, comprising any one of SEQ ID NOs: 152-157.

40. A bispecific anti-HIV gp120-binding protein comprising an anti-V3 bNAb and two copies of a CD4 domain, wherein the C-terminus of one CD4 domain is attached directly or by a linker to the N-terminus of one of the anti-V3 bNAb heavy chains and the C-terminus of the other copy of the CD4 domain is attached directly or by a linker to the N-terminus of the other anti-V3 bNAb heavy chain.

41. The bispecific protein according to clause 40, wherein each CD4 domain is attached via a linker to each of the heavy chains.

42. The bispecific protein according to clause 41, wherein the linker is selected from the group consisting of SEQ ID NOs: 90 to 95.

43. The bispecific protein according to clause 42, wherein the linker is SEQ ID NO:90.

44. The bispecific protein according to any one of clauses 40 to 43, wherein the CD4 domain is selected from the group consisting of SEQ ID NO:1-21.

45. The bispecific protein according to clause 44, wherein the CD4 domain is SEQ ID NO: 11.

46. The bispecific protein according to any one of clauses 40 to 45, wherein the anti-V3 bNAb is selected from the group consisting of bNAb1, bNAb1*, bNAb2, bNAb3, bNAb4, bNAb5 and bNAb6 as set forth in Table 2.

47. The bispecific protein according to clause 46, wherein the anti-V3 bNAb is bNAb1.

48. The bispecific protein according to any one of clauses 40 to 47, wherein the anti-V3 bNAb Fc comprises LS.

49. An anti-HIV gp120-binding protein having two identical heavy chains and two identical light chains, comprising or consisting of:
    a heavy chain that is at least 95% identical to SEQ ID NO:121 and
    a light chain that is at least 95% identical to SEQ ID NO:63.

50. An anti-HIV gp120-binding protein consisting of two heavy chains of SEQ ID NO: 121 and two light chains of SEQ ID NO:63.

51. An anti-HIV gp120-binding protein comprising or consisting of a sequence that is at least 95% identical to any one of SEQ ID NOs: 152-157.

52. An anti-HIV gp120-binding protein consisting of SEQ ID NO:155.

53. A pharmaceutical composition comprising the anti-HIV gp120-binding protein as defined in any one of the preceding clauses and a pharmaceutically acceptable excipient.

54. A method of treating or preventing an HIV infection in a human comprising administering to the human an anti-HIV gp120-binding protein according to any one of clauses 1 to 52, or a pharmaceutical composition according to clause 53, whereby viral load in the human is decreased.

55. An anti-HIV gp120-binding protein according to any one of clauses 1 to 52, or a pharmaceutical composition according to clause 53, for use in treating or preventing an HIV infection in a human.

56. Use of an anti-HIV gp120-binding protein according to any one of clauses 1 to 52, or a pharmaceutical composition according to clause 53, in the manufacture of a medicament for treating or preventing an HIV infection in a human.

57. A kit comprising in separate containers: an anti-HIV gp120-binding protein according to any one of clauses 1 to 52 and an anti-viral drug that inhibits cellular entry, replication, or transcription of HIV in a human.

58. The kit according to clause 57, wherein the antiviral drug is selected from the group consisting of: Nucleoside Reverse Transcriptase Inhibitors (NRTIs), Non-Nucleoside Reverse Transcriptase Inhibitors (NNRTIs), Protease Inhibitors (PIs), Entry Inhibitors, Integrase Strand Transfer Inhibitors (INSTI), Maturation Inhibitors (MIs), Capsid Inhibitors (CIs) and Nucleoside Reverse Transcriptase Translocation Inhibitors (NRTTIs)

59. The kit according to clause 58, wherein the antiviral drug is an INSTI.

60. The kit according to clause 59, wherein the INSTI is dolutegravir or cabotegravir.

61. A nucleic acid sequence that encodes an anti-HIV gp120-binding protein according to any one of clauses 1 to 52.

62. An expression vector that comprises the nucleic acid sequence of clause 61.

63. A host cell that comprises the nucleic acid sequence of clause 61 or the expression vector of clause 62.

64. A host cell that comprises two expression vectors:
    a first expression vector comprising a nucleic acid sequence encoding a heavy chain of SEQ ID NO:121; and
    a second expression vector comprising a nucleic acid sequence encoding a light chain of SEQ ID NO:63.

65. A method of producing an anti-HIV gp120-binding protein, comprising culturing the host cell as defined in clauses 63 or 64 under conditions suitable for expression of said nucleic acid sequence or vector, whereby an anti-HIV gp120-binding protein is produced.

66. A soluble CD4 domain having a Tm above 70° C.

67. A soluble CD4 domain comprising one or more stabilizing mutations selected from the group consisting of K8C, K8I, K8V, T11C, E13C, K21C, Q25E, H27C, H27D, G38C, N52W, R58N, R58T, R58V, L61M, G65C, I70C, K72C, E87G, E91H, E91Q, and G99C.

68. The soluble CD4 domain of clause 66 or clause 67 having a Tm of between 70° C. and 95° C.

69. The soluble CD4 domain of clause 68 having a Tm of about 90° C.

70. The soluble CD4 domain of any one of clauses 66 to 69, comprising K8C and G99C.

71. The soluble CD4 domain of any one of clauses 66 to 68, comprising K8I.

72. The soluble CD4 domain of any one of clauses 66 to 68, comprising K8V.

73. The soluble CD4 domain of any one of clauses 66 to 68, comprising T11C and K72C 74. The soluble CD4 domain of any one of clauses 66 to 68, comprising any one of SEQ ID NOs: 5-21.

75. The soluble CD4 domain of clause 74, comprising SEQ ID NO:11.

76. The soluble CD4 domain of any one of clauses 66 to 75, wherein the CD4 domain is fused directly or via a linker to a human Fc domain.

77. The soluble CD4 domain of clause 76, wherein the Fc domain comprises LS.

78. The soluble CD4 domain of clause 76 or clause 77, wherein the linker is selected from the group consisting of SEQ ID NOs: 90-95.

EXAMPLES

Example 1—Antigen Binding Protein Production

Plasmids encoding the antigen binding proteins of the invention were expressed in EXPI293 or FREESTYLE 293-F cells using the manufacturer's standard protocol (ThermoFisher Scientific, Waltham, MA). The expressed medium was harvested by centrifugation (4000 rpm for 10 min) and the antigen binding proteins were purified by filtration through a 0.22 μm filter (Millipore Sigma, Burlington, MA) and fast protein liquid chromatography (FPLC) (ÄKTA™ Pure, Cytiva, Marlborough MA). The medium was then passed through a Mabselect SuRe column (Cytiva, Marlborough MA) to capture the antigen binding proteins and the column was washed sequentially with phosphate-buffered saline (PBS) before elution.

The antigen binding proteins were then exchanged into a final buffer by using dialysis, a desalting column and preparative size exclusion column (SEC). The purity of the antigen binding proteins was evaluated by using sodium dodecyl sulphate-polyacrylamide gel electrophoresis (SDS-PAGE) and on a size exclusion column on a high-performance liquid chromatography system (SEC-HPLC).

Antigen binding protein concentrations were determined by measuring absorbance at 280 nm wavelength (A280) on a NanoDrop machine (ThermoFisher Scientific, Waltham, MA), and their molecular mass was measured by using liquid chromatography-mass spectrometry (LC-MS) to confirm their identity.

The endotoxin level in the final purified products was measured on an ENDOSAFE system (Charles River Labs, Wilmington MA) to make sure it was sufficiently low (usually <1 EU (Endotoxin Unit)/mg of protein) for downstream anti-viral studies.

Example 2—Anti-Viral Activity

The anti-viral activity of the antigen binding proteins was measured in a pseudotyped virus (PSV) assay. Pseudotyped HIV-1 virus (PSV) contains deletions in the genome that make it unable to produce infectious virions, but it can be used to measure the activity of cell entry inhibitors (i.e., molecules that prevent the binding of HIV-1 virions to the target cell membrane and/or prevent entry of HIV-1 into target cells), which include the antigen binding proteins of the invention.

PSV was produced in HEK-293T cells (ATCC, Manassas VA) by co-transfecting expression plasmids encoding the HIV-1 gp160 envelope gene and an HIV-1 backbone plasmid using TRANSIT-2020 transfection reagent (Mirus Bio, Madison WI). A panel of HIV-1 PSVs expressing different gp160 envelope trimers was generated to evaluate the effectiveness of the antigen binding proteins of the invention against a wide spectrum of HIV-1 strains.

i. ACTOne Cells

The genome of PSV used in this assay contains a luciferase gene that is expressed once the virus enters cells. Accordingly, the luminescence signal (after adding a substrate of luciferase) can be used to determine the level of viral infection.

The 50% tissue culture infectious dose (TCID) of a single thawed aliquot of each batch of PSV was determined in ACTOne cells. The ACTOne cell-line used in this assay was derived in-house from a genetically engineered 293T cell clone that expresses CD4, CXCR4, and CCR5. Cells were maintained in growth medium composed of Dulbecco's modified Eagle's medium (DMEM, Life Technologies) at 37° C. in a humidified 5% $CO_{2-95}$% air environment. Cell monolayers were split by treatment with Trypsin-EDTA (0.05%).

To run the anti-viral assay, ACTOne cells were detached by treating the cell culture flask with trypsin (trypsinization) and resuspended in growth medium containing 2% of DMSO to a density of $2.5 \times 10^5$ cells/ml. One hundred μl of such cells was added to 10 μl of antigen binding protein pre-loaded in a 96-well plate. Ninety μl of PSV was then added to each well. The assay plates were incubated at 37° C. in a humidified incubator at 5% $CO_2$ level. Plates were developed after 72 hours of incubation by adding 50 μl of BRIGHTGLO luciferase reagent (Promega, Madison WI) to each well, and transferring the plates to an ENVISION multilabel plate reader (PerkinElmer, Waltham MA) to measure the luminescence and determine the level of virus that had infected the cells. The higher the luminescence signal, the higher the level of infection.

Raw data were analyzed using an in-house template in an IDBS system to calculate half-maximal inhibitory concentration (IC50) values which reflects the activity of the antigen binding proteins of the invention at inhibiting viral entry (the smaller the number is, the more active the molecule is).

ii. TZM.bl Cells

Alternatively, the PSV assay was carried out using a luciferase-based assay in a TZM.bl cell line. The TZM-bl cell line is derived from a Hela cell clone that was engineered to express CD4, CCR5 and CXCR4 and to contain integrated reporter genes for firefly luciferase and *E. coli* β-galactosidase under the control of an HIV-1 long terminal repeat (Wei et al., Antimicrobial agents and chemotherapy 46:1896-905 (2002)) permitting sensitive and accurate measurements of infection.

The detailed materials and methodology have been described elsewhere (Mentefiori, Curr. Protoc. Immunol., 2005, Chapter 12; Seaman et al., Journal of Virology, February 2010, 84 (3), p. 1439-1452). In brief, the assay measures the reduction in luciferase reporter gene expression in TZM.bl cells following a single round of virus infection.

Five-fold serial dilutions of the antigen binding proteins of the invention, from 50 μg/ml to 3.2 ng/ml, were performed in duplicate in 10% DMEM growth medium (100 u/well). An amount of 200 TCID50 (50% tissue culture infectious dose) of virus was added to each well in a volume of 50 μl, and the plates were incubated for 1 h at 37° C.

TZM.bl cells were then added ($1 \times 10^4$/well in a 100-μl volume) in 10% D-MEM growth medium containing DEAE-dextran (Sigma, St. Louis, MO) at a final concentration of 11 μg/ml. Assay controls included TZM.bl cells alone (cell control) and TZM.bl cells with virus (virus control).

Following a 48-hour incubation at 37° C., 150 μl of assay medium was removed from each well and 100 μl of BRIGHTGLO luciferase reagent (Promega, Madison, WI) was added. The cells were allowed to lyse for 2 min, and then 150 μl of the cell lysate was transferred to a 96-well black solid plate, and luminescence was measured using a Victor 3 luminometer (Perkin Elmer).

The 50% and 80% inhibitory concentration (IC50 and IC80) values were calculated as the serum dilution that caused a 50% and 80% reduction respectively, in relative luminescence units (RLU) compared to the level in the virus control wells after subtraction of cell control RLU. All data were analyzed with 5-parameter curve fitting using neutralizing antibody analysis software provided by the CAVD Vaccine Immunology Statistical Center.

Example 3—Stability of Soluble CD4 Domains

All soluble human CD4 domains tested contain a set of "base" mutations in human CD4 domain 1 (D1) over the wild-type sequence (SEQ ID NO:3) that enable the folding of human CD4 D1 on its own. Soluble CD4 D1 with this set of mutations is known as mD1.22 (Chen et al., J Virol. 2014 January; 88 (2): 1125-39) and the mutations therein consist of: L5Y, S23N, A55V, I76P, L96V, and F98V (SEQ ID NO:4, also referred to as D1m herein).

To achieve better developability and pharmacokinetics, further mutations were introduced into mD1.22 (SEQ ID NO:4) to enhance its thermal stability. The additional stabilizing mutations were designed based on several methodologies: 1) computational simulation by using Free Energy Perturbation (FEP+, Schrodinger, New York, NY USA); 2) computational simulation by using disulfide-bond scan in Molecular Operating Environment program (MOE, Chemical Computing Group, Montreal Canada); and 3) panning a library of human CD4 D1 with each residue mutated, one by one, to the other 19 types of amino acids (site saturation mutagenesis, TWIST BioScience, San Francisco, CA USA) using phage display under thermally challenging conditions (i.e., incubating the phage at room temperature, 70° C., and 80° C., then selecting the CD4 domain variants that can still bind to recombinant HIV-1 gp120 (CN54 strain, Acro Biosystems, Beijing China)).

The best performing variants (SEQ ID NOs: 5-21) were fused with 6×His tag at their C-termini, expressed and purified from mammalian cells using methods as described in Example 1, except that purification was via a Ni-NTA resin (Cytiva, Marlborough MA) instead of Mabselect SuRe column, with standard protocol from the vendor.

These purified CD4 D1 variants (with C-terminal 6xHis tag) were then evaluated to determine their melting temperature (Tm, using Prometheus System, NanoTemper, München Germany), which indicates thermal stability, as well as their anti-viral activity against HIV-1 pseudotyped virus (see Example 2 above for methods using ACTOne cells).

Figure 2:
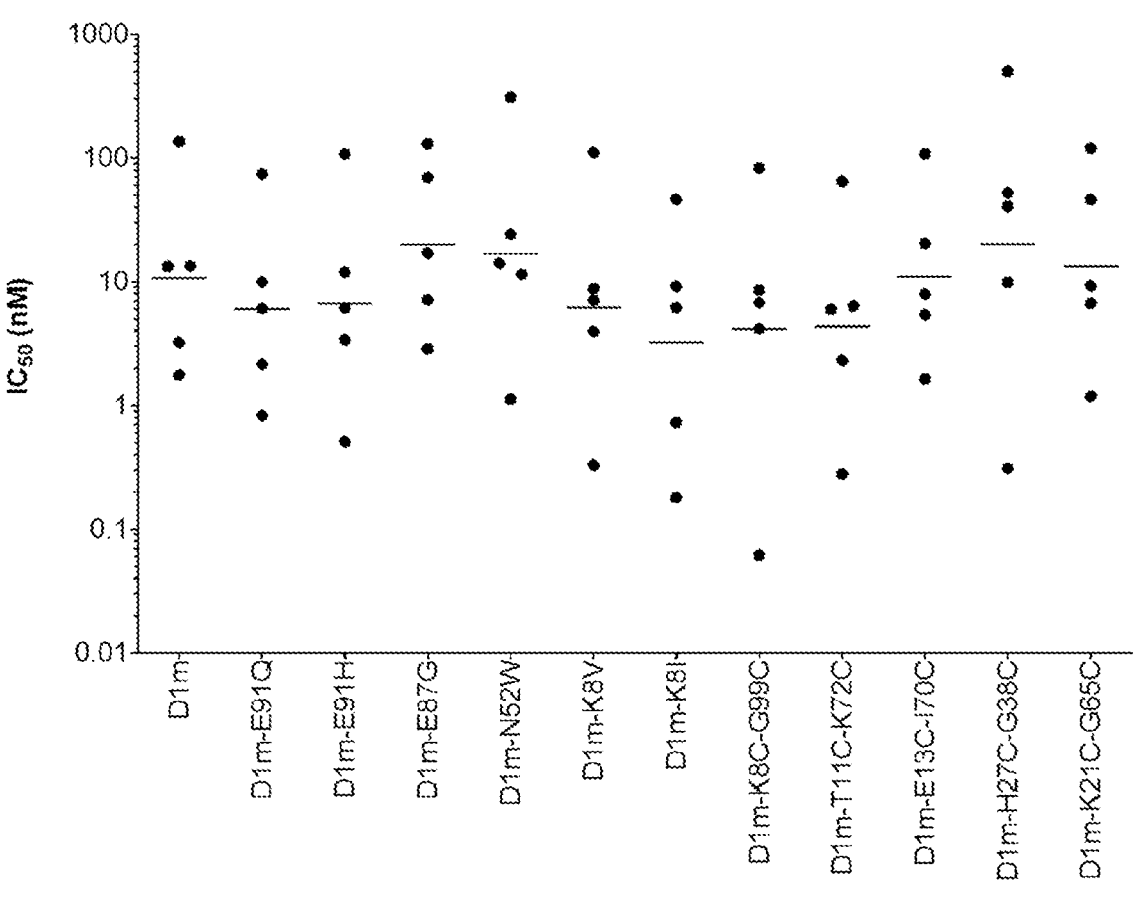
FIG. 2 shows IC50 values (nM) of soluble CD4 domains (SEQ ID NOs: 4-15) against a panel of HIV-1 envelopes in a PSV assay (ACTOne), together with the Tm for each soluble CD4 domain. The horizontal bars indicate geometric mean IC50.

As shown in Table 3 below and in FIG. 2, several CD4 D1 variants (SEQ ID NO:5-15) showed dramatically improved thermal stability over the "baseline" or "control" CD4 D1 (D1m, SEQ ID NO:4), while maintaining similar anti-viral activity.

TABLE 3

Melting temperature of soluble CD4 domains

| CD4 Domain | SEQ ID NO | Tm (° C.) |
|---|---|---|
| D1m | 4 | 68.2 |
| D1m-E91Q | 6 | 72.4 |
| D1m-E91H | 7 | 72.6 |
| D1m-E87G | 8 | 71.9 |
| D1m-N52W | 9 | 72 |
| D1m-K8V | 5 | 77.1 |
| D1m-K8I | 10 | 75.9 |

TABLE 3-continued

Melting temperature of soluble CD4 domains

| CD4 Domain | SEQ ID NO | Tm (° C.) |
|---|---|---|
| D1m-K8C-G99C | 11 | 88.8 |
| D1m-T11C-K72C | 12 | 79.9 |
| D1m-E13C-I70C | 13 | 78.8 |
| D1m-H27C-G38C | 14 | 90.1 |
| D1m-K21C-G65C | 15 | 80.1 |

Example 4—Antigen Binding Protein Format and Linker Length

The fusion position of the CD4 domain in the anti-V3 bNAbs (e.g., whether to fuse the CD4 domain to the light chain or heavy chain or both, whether to fuse the CD4 domain to the N-terminus or C-terminus of these chains, or whether to fuse the CD4 domain in the middle of the heavy chain (in between CH1 and CH2 domains)) has an effect on the anti-viral potency of the resulting bispecific as shown in Table 4.1 and Table 5 below.

Figure 3A:
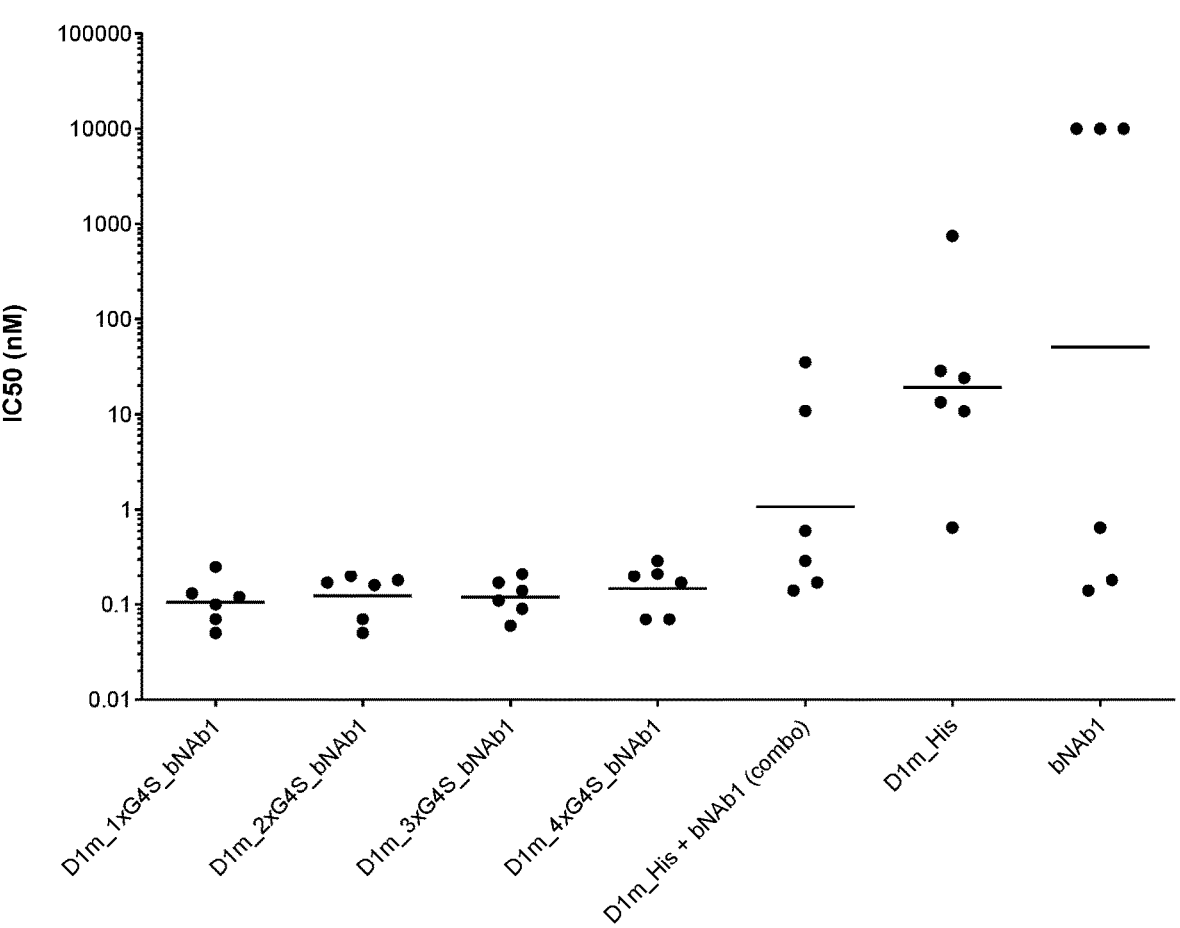
FIGS. 3A-3B show that linker length between the CD4 domain and bNAb1 heavy chain N-terminus does not particularly affect anti-viral activity in a PSV assay (ACTOne) (A) but does change the PK of the resultant bispecific molecules in a humanized mouse model (Tg32-hFcRn strain) (B). Thermal stability of the CD4 domain also affects the PK of the bispecific molecules (B).

We observed that the most potent bispecific molecule resulted from fusing CD4 D1 to the N-terminus of the heavy chain of bNAb1 (molecule 1 in Table 4.1, which neutralized 6 envelopes with IC50<160 pM and 1 envelope with IC50 about 3 nM in PSV assay). In this bispecific format, the linker length between the CD4 domain and bNAb1 heavy chain N-terminus does not particularly affect anti-viral activity (FIG. 3A), but changes the pharmacokinetics (PK) of the resultant bispecific molecules dramatically (FIG. 3B).

Figure 3B:
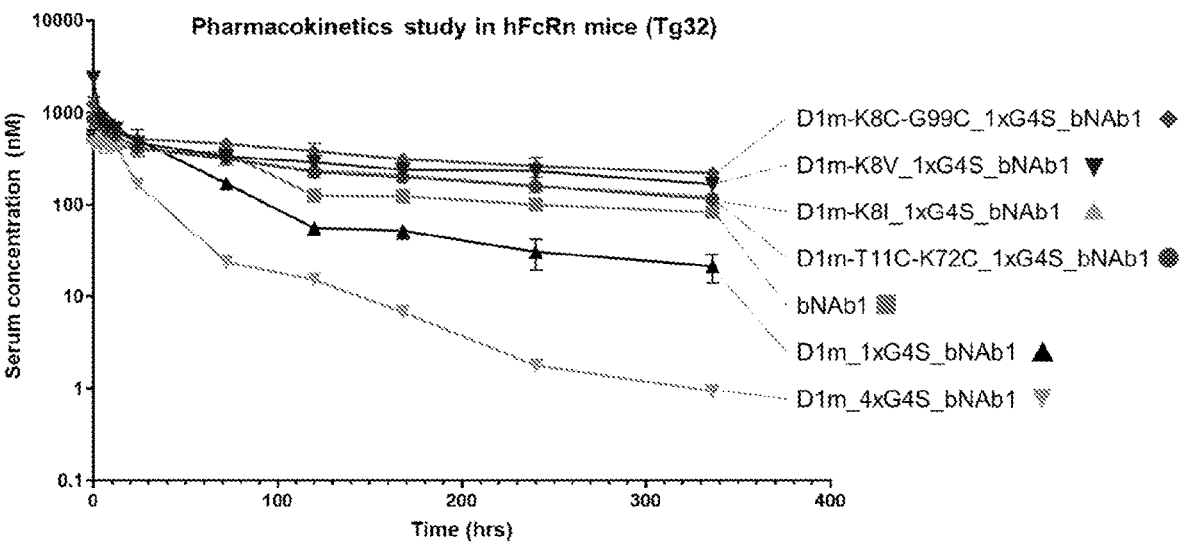

As shown in FIG. 3B, the shorter-linker bispecific (D1m_1xG4S_bNAb1, SEQ ID NOs: 102 and 63) showed much better PK (longer half-life and lower clearance rate) than the longer-linker bispecific (D1m_4xG4S_bNAb1, SEQ ID NOs: 105 and 63)) in a humanized mouse model (Tg32 strain where human neonatal Fc receptor (hFcRn) replaced the corresponding mouse gene (mFcRn), The Jackson Laboratory, Bar Harbor, Maine USA).

TABLE 4.1

(see also FIG. 7) IC50 (nM) of different bNAb1-derived bispecific formats and control molecules against a panel of HIV-1 envelopes in a PSV assay (ACTOne cells)

| Envelope | bNAb1-Derived Molecules | | | | | | | | | | |
|---|---|---|---|---|---|---|---|---|---|---|---|
| | 1 | 2 | 3 | 4 | 5 | 6 | 7 | 8 | 9 | 10 | 11 |
| 42368 | 0.16 | 0.91 | 1.49 | 4.90 | 1.24 | 15.73 | 5.60 | 1.44 | 4.32 | 1.58 | >500 |
| CC1/85 | 0.04 | 0.05 | 0.49 | 0.01 | 0.01 | 0.03 | 0.04 | 0.07 | 7.02 | 1.98 | 0.03 |
| NL4-3 | 0.05 | 0.17 | 0.17 | 0.10 | 0.14 | 0.52 | 0.45 | 0.22 | 0.31 | 0.31 | 131.20 |
| T278.50 | 0.12 | 0.12 | 1.29 | 0.04 | 0.02 | 0.06 | 0.13 | 0.11 | 3.99 | 1.43 | 0.17 |
| X2088.C9 | 0.07 | 0.86 | 0.72 | 13.28 | 1.50 | 67.68 | 18.25 | 5.25 | 17.49 | 9.20 | 402.35 |
| ZM106.9 | 0.05 | 0.18 | 0.38 | 0.04 | 0.03 | 0.05 | 0.07 | 0.09 | 26.02 | 15.14 | 0.07 |
| CAP45.2.00.G3 | 3.73 | 2.68 | 2.53 | 13.89 | 2.13 | 20.44 | 102.16 | 20.41 | 131.43 | 20.48 | >500 |

Table 4.1 Molecule Key:

1 = D1m-K8C-G99C_1xG4S_bNAb1 (SEQ ID NOs: 121 + 63)

2 = D1m-K8C-G99C_1xG4S_bNAb1-LC (SEQ ID NOs: 62 + 115)

3 = D1m-1xG4S_bNAb1-BothChains (SEQ ID NOs: 102 + 109)

4 = bNAb1-mid_1xG4S_D1m-K8C-G99C (SEQ ID NOs: 116 + 63)

5 = bNAb1-HC_1xG4S_D1m-K8C-G99C (SEQ ID NOs: 117 + 63)

6 = bNAb1-LC_1xG4S_D1m-K8C-G99C (SEQ ID NOs: 62 + 118)

7 = D1m_His (SEQ ID NO: 4*) + bNAb1 (SEQ ID NOS: 62 + 63) (combo)

8 = D1m-K8C-G99C_Fc (SEQ ID NO: 158) + bNAb1 (SEQ ID NOs: 62 + 63) (combo)

9 = D1m_His (SEQ ID NO: 4*)

10 = D1m-K8C-G99C_Fc (SEQ ID NO: 158)

11 = bNAb1 (SEQ ID NOS: 62 + 63)

*plus a 6xHis tag (six C-terminal histidine residues)

TABLE 4.2

IC50 (nM) of a bNAb1-derived bispecific against entry inhibitor resistant envelopes in a PSV assay (ACTOne cells)

| Type | Envelope | bNAb1-derived bispecific |
|---|---|---|
| 10E8-insensitive | KER2008.12 | 0.05 |
| | T266-60 | 0.06 |
| | ZM106.9 | 0.05 |
| | X2088.c9 | 0.07 |
| | MB539.2B7 | 0.04 |
| | JR2 with W680R and K683Q | 0.03 |
| N6-insensitive | BL01 | 0.07 |
| | T278-50 | 0.12 |
| | 6471_V1_C16 | 0.06 |
| | CH0219_E4 | 0.08 |

TABLE 4.2-continued

IC50 (nM) of a bNAb1-derived bispecific against entry inhibitor resistant envelopes in a PSV assay (ACTOne cells)

| Type | Envelope | bNAb1-derived bispecific |
|---|---|---|
| Temsavir- and Ibalizumab-insensitive | 21-116102 | 0.36 |
| | 21-116108 | 0.01 |
| Maraviroc-insensitive | MP5.7 | 0.13 |
| | MP11.38 | 0.05 |
| | MP35.2 | 0.13 |
| | MP49.20 | 0.02 |
| | MP53.36 | 0.04 |

Table 4.2 Molecule Key:
1 = D1m-K8C-G99C_1xG4S_bNAb1 (SEQ ID NOs: 121 + 63)

TABLE 5

IC50 (nM) of different bNAb2-, bNAb3- and bNAb4-derived bispecific formats and control molecules against a panel of HIV-1 envelopes in PSV assay (ACTOne cells)

| Envelope | bNAb2-Derived Molecules | | | | | | | bNAb3-Derived Molecules | | |
|---|---|---|---|---|---|---|---|---|---|---|
| | 1 | 2 | 3 | 4 | 5 | 6 | 7 | 8 | 9 | 10 |
| 42368 | 1.79 | 0.75 | 1.24 | 269.20 | 4.59 | 2.03 | >500 | 0.37 | 0.17 | 5.01 |
| CC1/85 | 0.64 | 0.46 | 0.33 | 107.46 | 9.44 | 1.98 | >500 | 0.29 | 0.07 | 4.07 |
| NL4-3 | 0.44 | 0.26 | 0.42 | 8.44 | 0.80 | 0.22 | 150.32 | 0.08 | 0.07 | 0.11 |
| T278.50 | 0.16 | 0.10 | 0.09 | 0.48 | 0.30 | 0.14 | 0.43 | 0.02 | 0.03 | 0.02 |
| X2088.C9 | 0.06 | 0.05 | 0.05 | 0.07 | 0.02 | 0.09 | 0.09 | 0.06 | 0.03 | 0.05 |
| ZM106.9 | 0.05 | 0.02 | 0.02 | 0.04 | 0.01 | 0.02 | 0.03 | 0.03 | 0.03 | 0.01 |
| CAP45.2.00.G3 | 0.10 | 0.10 | 0.11 | 2.49 | 12.51 | 3.63 | 36.53 | 1.69 | 0.25 | 96.75 |
| HIV-2-AID | 14.16 | 19.13 | 20.28 | 136.88 | >500 | * | >500 | * | * | * |
| HIV-2-ATM88 | 1.34 | 1.22 | 2.28 | 2.06 | 70.58 | * | >500 | * | * | * |
| HIV-2-HCC-01 | 35.94 | 17.47 | 24.36 | >500 | >500 | * | >500 | * | * | * |

| Envelope | bNAb3-Derived Molecules | | bNAb4-Derived Molecules | | | | CD4 Controls | |
|---|---|---|---|---|---|---|---|---|
| | 11 | 12 | 13 | 14 | 15 | 16 | 17 | 18 |
| 42368 | 2.12 | >500 | 0.50 | 8.78 | 3.42 | >500 | 4.32 | 1.58 |
| CC1/85 | 1.15 | 38.33 | 0.10 | 1.39 | 0.77 | 2.36 | 7.02 | 1.98 |
| NL4-3 | 0.06 | 0.15 | 0.19 | 0.86 | 0.48 | 327.61 | 0.31 | 0.31 |
| T278.50 | 0.02 | 0.01 | 0.13 | 0.23 | 0.41 | 0.47 | 3.99 | 1.43 |
| X2088.C9 | 0.03 | 0.03 | 0.03 | 0.01 | 0.04 | 0.02 | 17.49 | 9.20 |
| ZM106.9 | 0.03 | 0.03 | 0.03 | 0.02 | 0.03 | 0.03 | 26.02 | 15.14 |
| CAP45.2.00.G3 | 61.81 | >500 | 13.18 | 469.16 | 42.98 | >500 | 131.43 | 20.48 |
| HIV-2-AID | * | * | * | * | * | * | 103.54 | 24.35 |
| HIV-2-ATM88 | * | * | * | * | * | * | 3.93 | 2.72 |
| HIV-2-HCC-01 | * | * | * | * | * | * | >500 | >300 |

* not tested

Table 5 Molecule Key:
1 = D1m-K8C-G99C_2xG4S_bNAb2 (SEQ ID NOs: 137 + 69)
2 = D1m-K8C-G99C_3xG4S_bNAb2 (SEQ ID NOs: 138 + 69)
3 = D1m-K8C-G99C_4xG4S_bNAb2 (SEQ ID NOs: 139 + 69)
4 = bNAb2-LC_1xG4S_D1m-K8C-G99C (SEQ ID NOs: 68 + 143)
5 = bNAb2 (SEQ ID NOs: 68 + 69) + D1m_His (SEQ ID NO: 4*) (combo)
6 = bNAb2 (SEQ ID NOs: 68 + 69) + D1m-K8C-G99C_Fc (SEQ ID NO: 158) (combo)
7 = bNAb2 (SEQ ID NOs: 68 + 69)
8 = D1m-K8C-G99C_1xG4S_bNAb3 (SEQ ID NOs: 144 + 74)
9 = D1m-K8C-G99C_4xG4S_bNAb3 (SEQ ID NOs: 145 + 74)
10 = bNAb3 (SEQ ID NOs: 73 + 74) + D1m_His (SEQ ID NO: 4*) (combo)
11 = bNAb3 (SEQ ID NOs: 73 + 74) + D1m-K8C-G99C_Fc (SEQ ID NO: 158) (combo)
12 = bNAb3 (SEQ ID NOs: 73 + 74)
13 = D1m-K8C-G99C_4xG4S_bNAb4 (SEQ ID NOs: 147 + 79)
14 = bNAb4 (SEQ ID NOs: 78 + 79) + D1m_His (SEQ ID NO: 4*) (combo)
15 = bNAb4 (SEQ ID NOs: 78 + 79) + D1m-K8C-G99C_Fc (SEQ ID NO: 158) (combo)
16 = bNAb4 (SEQ ID NOs: 78 + 79)
17 = D1m_His (SEQ ID NO: 4*)
18 = D1m-K8C-G99C_Fc (SEQ ID NO: 158)
*plus a 6xHis tag (six C-terminal histidine residues)

Thermal stabilization of CD4 D1 (see Example 3 above) further enhanced the PK of the bispecific molecules (D1m-KBC-G99C_1xG4S_bNAb1, SEQ ID NOs: 121 and 63; D1m-T11C-K72C_1xG4S_bNAb1, SEQ ID NOs: 122 and 63; D1m-K8I_1xGAS_bNAb1, SEQ ID NOs: 119 and 63; and D1m-KBV_1xGAS_bNAb1, SEQ ID NOs: 120 and 63) as shown in Table 6 below.

TABLE 6

The effect of (1) linker length between the CD4 domain and bNAb1 heavy chain, and (2) thermal stability of CD4 D1, on the PK of bispecific molecules in hFcRn mice (Tg32)

| Molecule (SEQ ID NOs) | Tm of CD4 D1 (° C.) | Half-life (days) | Clearance (ml/day/kg) |
|---|---|---|---|
| bNAb1 (62 + 63) | — | 5.8 | 21.6 |
| D1m_4xG4S_bNAb1 (105 + 63) | 68.2 | 2.2 | 144 |
| D1m_1xG4S_bNAb1 (102 + 63) | 68.2 | 4.1 | 31.7 |
| D1m-K8C-G99C_1xG4S_bNAb1 (121 + 63) | 88.8 | 10.2 | 7.4 |
| D1m-T11C-K72C_1xG4S_bNAb1 (122 + 63) | 79.9 | 8.9 | 12.9 |
| D1m-K8I_1xG4S_bNAb1 (119 + 63) | 75.9 | 9.3 | 12 |
| D1m-K8V_1xG4S_bNAb1 (120 + 63) | 77.1 | 7.3 | 12.8 |

Accordingly, the best molecules for further development contain shorter linker lengths between the CD4 domain and bNAb (1xG4S) and contain a thermally stable CD4 domain(s).

Example 5—Anti-Viral Activity of bNAb1-derived Bispecific Molecules

As shown in FIG. 4A, bispecific molecules (D1m_1xG4S_bNAb1 bispecific having SEQ ID NOs: 102 and 63; and D1m-K8C-G99C_1xG4S_bNAb1 bispecific having SEQ ID NOs: 121 and 63) with human CD4 domains (CD4 D1m, SEQ ID NO:4, and a K8C and G99C variant thereof, SEQ ID NO: 11, respectively) fused to the N-termini of each of the heavy chains of bNAb1 (SEQ ID NOs: 62 and 63) via a GGGGS linker (SEQ ID NOs: 90) showed dramatically and consistently higher activity (fully neutralized all envelopes tested with geometric mean IC50~ 0.1 nM) than the two individual components (human CD4 domain and bNAb1) alone and their mixture (did not neutralize all envelopes tested, geometric mean IC50 much higher than the bispecific molecules). This clearly shows that the fusion strategy provides strong anti-viral synergy.

Interestingly, soluble CD4 has been considered to have negative synergy with bNAb1 (Ivan et al., Plos Biol. 17 (1), January 2019), based on the result that mixing soluble CD4 with bNAb1 can weaken its anti-viral activity. We found that when soluble CD4 is fused with bNAb1 instead of being mixed, the anti-viral activity is enhanced dramatically.

FIG. 4B shows the anti-viral activity of the bispecific molecules (SEQ ID NOs: 102 and 63; and SEQ ID NOs: 121 and 63) and control molecules against a panel of PSV strains insensitive to bNAb1. It can be seen that that the bispecific molecules (fully neutralized all envelopes tested with geometric IC50~0.2 nM) are much more potent than the individual components alone and their mixture (did not neutralize all envelopes tested, geometric mean IC50>10 nM), indicating strong anti-viral synergy. Such synergy is most obvious against the strains that are insensitive to both CD4 and bNAb1, where only the bispecific molecules showed complete inhibition of viral entry with good activity, while neither soluble CD4 domain nor bNAb1 nor their mixture exhibited significant activity.

Figure 1:
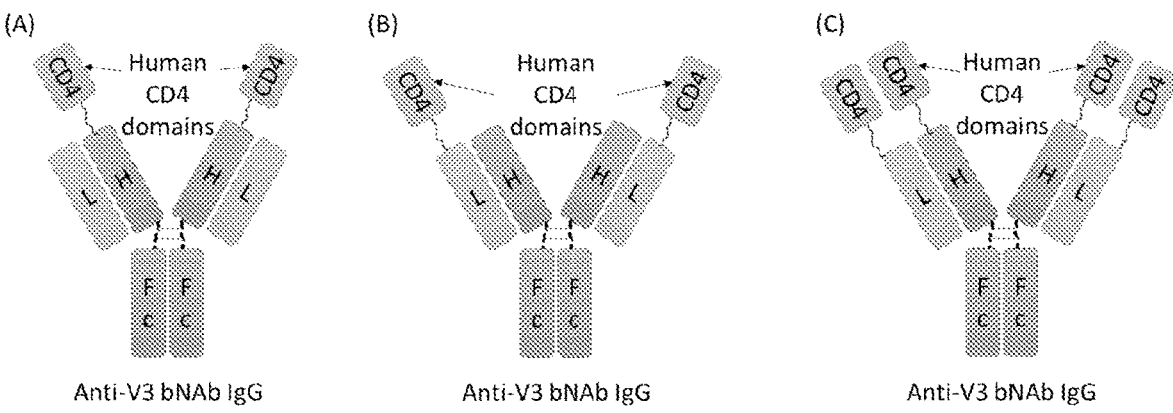
Figure 1:
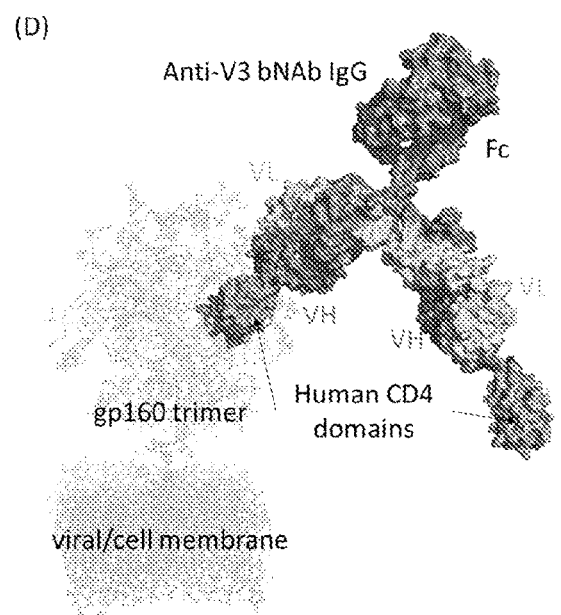

As shown in Table 4.1 above, although all of the bispecific molecules tested are able to inhibit viral entry, the most consistent and potent bispecific molecule is when the CD4 domain is fused to the N-termini of each of the heavy chains of bNAb1, which correlates well with the structure-based design (FIG. 1D).

Furthermore, as shown in Table 4.2 above, when tested in PSV assay against the HIV-1 envelopes insensitive to several entry inhibitors (10E8, N6, Temsavir, Ibalizumab, and Maraviroc), the bispecific molecule (SEQ ID NOs: 121 and 63) fully neutralized all these envelopes with IC50s <400 pM.

In addition, the most potent bispecific format (i.e. fusing CD4 D1 to the N-terminus of bNAb1 heavy chain) was converted to a single open-reading-frame (ORF) version, by replacing the Fab arm with a scFv fragment of bNAb1. As shown in FIG. 5, several such single-ORF molecules, also referred to as scFv-Fc molecules (SEQ ID NOs: 152-157), showed equivalent potency as the leading bispecific format in PSV assays (ACTOne cells).

Given that these single-ORF molecules are each encoded by a single <2 kb gene and contain an Fc domain for an increased half-life, they can be readily delivered by gene therapy vehicles, such as adeno-associated virus (AAV), enabling them to be constantly secreted into circulation at a therapeutic concentration. Such a strategy would result in an 'ultra-long' acting therapy against HIV-1.

Example 6—Anti-Viral Activity of bNAb6-Derived Bispecific Molecules

FIG. 6 and Table 7 below show the anti-viral activity of bNAb6-derived bispecific molecules and control molecules.

The plot of IC50 values (FIG. 6) from PSV assays (ACTOne) clearly shows that when CD4 domain 1 (D1m, SEQ ID NO:4) or domains 1 and 2 (D1mD2, SEQ ID NO:2) is fused to the N-termini of the bNAb6 (SEQ ID NOs: 88 and 89) heavy chain, the resultant molecule is much more active than a simple mixture of soluble CD4 domain and bNAb6 antibody, indicating strong synergy.

Table 7 shows the anti-viral activity of the bispecific molecules (D1m_4xG4S_bNAb6, SEQ ID NOs: 151 and SEQ ID NOs: 89; D1mD2_4xG4S_bNAb6, SEQ ID NO:150 and SEQ ID NO:89; and D1m-K8C-G99C_1xG4S_bNAb6 (SEQ ID NOs: 362+89)) and control molecules against HIV-1 strains resistant to bNAb6 antibody. As can be seen, the bNAb6-derived bispecific molecules are much more potent than the mixtures against double-resistant or insensitive strains.

TABLE 7

IC50 (nM) of bNAb6-derived bispecific formats and control molecules
against a panel of HIV-1 envelopes in PSV assay (ACTOne cells)

| | bNAb6-Derived Molecules | | | | | | |
|---|---|---|---|---|---|---|---|
| Envelope | 1 | 2 | 3 | 4 | 5 | 6 | 7 |
| CAP45.2.00.G3 | 17.79 | >500 | 5.90 | >500 | 131.43 | >500 | >500 |
| CH119 | 8.30 | 93.62 | 2.60 | 49.76 | 90.66 | 119.94 | >500 |
| BJOX2000 | 17.27 | 45.23 | 3.10 | 16.96 | 70.87 | 33.40 | >500 |
| X1632_S2_B10 | 1.38 | 20.26 | 0.75 | 19.70 | 16.25 | 14.94 | >500 |
| TRO11 | 1.99 | 16.55 | 1.14 | 14.64 | 68.43 | 17.27 | >500 |
| T278.50 | 0.71 | 9.26 | 1.08 | 9.51 | 3.99 | 16.02 | >500 |
| LAI | 1.52 | 6.76 | 0.93 | 7.46 | 8.79 | 5.41 | >500 |
| 42368 | 1.30 | 6.05 | 0.54 | 5.75 | 4.32 | 7.29 | >500 |
| NL4-3 | 0.17 | 1.31 | 0.11 | 0.75 | 0.31 | 0.74 | >500 |
| HXB2 | 0.06 | 0.08 | 0.03 | 0.06 | 0.11 | 0.07 | >500 |

| | bNAb6-Derived Molecules | | | |
|---|---|---|---|---|
| Envelope | 8 | 9 | 7 | 10 |
| X2088.C9 | 0.17 | 0.15 | 0.15 | 9.20 |
| ZM106.9 | 0.10 | 0.10 | 0.08 | 15.14 |
| 3637_V5_C3 | 103.00 | 328.50 | >500 | >500 |
| 3468_V1_C12 | 20.85 | 47.70 | >500 | 64.15 |
| Q461_E2 | 4.00 | 12.70 | >500 | 11.76 |
| 3326_V4_C3 | 72.10 | 483.00 | >500 | >500 |
| 42368 | 0.92 | 2.13 | >500 | 1.58 |
| NL4-3 | 0.27 | * | >500 | 0.31 |
| T278.50 | 1.33 | * | >500 | 1.43 |
| CAP45.2.00.G3 | 9.64 | * | >500 | 20.48 |
| CC1/85 | 0.42 | * | * | 1.98 |
| HIV-2-HCC-01 | 175.65 | * | * | >300 |

* not tested

Table 7 Molecule Key:

1 = D1m_4xG4S_bNAb6 (SEQ ID NOs: 151 + 89)

2 = D1m_His (SEQ ID NO: 4*) + bNAb6 (SEQ ID NOs: 88 + 89)

3 = D1mD2_4xG4S_bNAb6 (SEQ ID NOs: 150 + 89)

4 = D1mD2_His (SEQ ID NO: 2*) + bNAb6 (SEQ ID NOs: 88 + 89)

5 = D1m_His (SEQ ID NO: 4*)

6 = D1mD2_His (SEQ ID NO: 2*)

7 = bNAb6 (SEQ ID NOs: 88 + 89)

8 = D1m-K8C-G99C_1xG4S_bNAb6 (SEQ ID NOs: 362 + 89)

9 = bNAb6 (SEQ ID NOs: 88 + 89) + D1m-K8C-G99C_Fc (SEQ ID NO: 158) (combo)

10 = D1m-K8C-G99C_Fc (SEQ ID NO: 158)

*plus a 6xHis tag (six C-terminal histidine residues)

Example 7—Anti-Viral Activity of Further Anti-V3 bNAb-Derived Bispecific Molecules Additional bispecific molecules comprising CD4 domains fused to other anti-V3 bNAbs (bNAb2, bNAb3, bNAb4,) were tested, with the results shown in Table 5 above and Tables 8-23 below, a similar synergistic anti-viral activity was observed against one or more envelopes.

Accordingly, the strategy of fusing a soluble CD4 domain to anti-V3 loop bNAb can be generally applied to enhance the potency and spectrum of these bNAbs.

Conclusions

On the free HIV-1 virus, the V3 loop of gp120 is in its native "closed" state. The V3 loop is known to adopt various conformations (from different structures in Protein Data-bank), indicating its flexibility. During HIV-1 infection, the binding of gp120 to cell surface CD4 triggers conforma-tional changes of the V3 loop to "open" itself to bind co-receptors such as CXCR4 or CCR5.

Anti-V3 bNAbs mainly recognizes a pattern of glycans on the V3 loop of gp120, along with the backbone atoms of a few amino acid residues in the V3 loop (Krumm et al., Retrovirology 13 (8), 2016). Such "plasticity" of the V3 loop may facilitate the binding of anti-V3 loop bNAbs to this loop when it is "opened" by CD4 binding.

We hypothesize that when soluble CD4 and anti-V3 bNAbs are simply mixed together, the conformational change of the V3 loop triggered by soluble CD4 may be too transient for the anti-V3 bNAb to capture, therefore no synergistic activity is observed. But, in the context of bispecific molecules, when CD4 binds to the CD4 binding site (CD4bs) on gp120, the anti-V3 bNAb is at such high local concentration that it can immediately capture the exposed V3 loop glycans; this in turn could stabilize the binding of soluble CD4 to gp120 and form a positive feedback loop.

TABLE 8

IC50 (nM) of different bNAb5-derived bispecific
formats and control molecules against a panel
of HIV-1 envelopes in PSV assay (ACTOne cells)

| | bNAb5-Derived Molecules | | | CD4 Controls |
| Envelope | Bispecific | Combo | mAb | CD4 |
| --- | --- | --- | --- | --- |
| 42368 | 1.11 | 2.35 | >500 | 1.58 |
| CC1/85 | 0.67 | 2.53 | >500 | 1.98 |
| NL4-3 | 0.26 | 0.26 | 2.62 | 0.31 |
| T278.50 | 3.21 | 1.59 | 96.06 | 1.43 |
| X2088.C9 | 0.54 | 0.14 | 0.17 | 9.20 |
| ZM106.9 | 0.94 | 1.09 | 2.04 | 15.14 |
| CAP45.2.00.G3 | 44.41 | 63.82 | >500 | 20.48 |
| 25710 | 0.51 | 0.49 | 8.10 | 1.32 |
| TRO11 | 0.91 | 0.58 | 0.39 | 146.64 |
| 398F1 | 4.85 | 1.35 | 1.83 | 90.47 |
| CNE8 | 134.25 | 240.63 | 51.37 | 346.64 |
| X2278 | 0.60 | 5.46 | 9.53 | 44.56 |
| BJOX2000 | 1.11 | 1.86 | 126.82 | 2.34 |
| X1632 | 2.32 | 2.38 | >500 | 1.82 |
| CE1176 | 1.04 | 2.59 | 57.07 | 4.22 |
| 246F3 | 7.18 | 5.27 | 40.90 | 4.28 |
| CH119 | 2.63 | 3.22 | 63.54 | 3.25 |
| CE0217 | 2.42 | 2.19 | 409.83 | 2.53 |
| CNE55 | 20.92 | 36.59 | 3300.62 | 41.82 |
| JR-CSF | 0.31 | 0.45 | 0.64 | 5.47 |
| JRFL | 0.42 | 1.16 | 58.23 | 1.12 |

Table 8 Molecule Key:

Bispecific = D1m-K8C-G99C_1xG4S_bNAb5 (SEQ ID NOs: 148 + 84)

Combo = bNAb5 (SEQ ID NOs: 83 + 84) + D1m-K8C-G99C_Fc (SEQ ID NO: 158) (combo)

mAb = bNAb5 (SEQ ID NOs: 83 + 84)

CD4 = D1m-K8C-G99C_Fc (SEQ ID NO: 158)

TABLE 9

IC50 (nM) of different bNAb7-derived bispecific
formats and control molecules against a panel
of HIV-1 envelopes in PSV assay (ACTOne cells)

| | bNAb7-Derived Molecules | | | CD4 Controls |
| Envelope | Bispecific | Combo | mAb | CD4 |
| --- | --- | --- | --- | --- |
| 42368 | 1.38 | 2.40 | >500 | 1.58 |
| X2088.C9 | 0.09 | 0.19 | 0.22 | 9.20 |
| ZM106.9 | 0.03 | 0.03 | 0.04 | 15.14 |
| 3326_V4_C3 | 17.63 | >500 | >500 | >500 |
| 3637_V5_C3 | 260.71 | 388.10 | >500 | >500 |
| 3468_V1_C12 | 2.50 | 32.37 | >500 | 64.15 |
| 620345_C1 | 4.03 | 5.83 | >500 | 99.28 |
| 0260.v5.c36 | 0.16 | 0.22 | 0.75 | 119.29 |
| TH976_17 | 70.02 | 35.04 | >500 | 39.05 |
| Q461_E2 | 14.61 | 20.92 | >500 | 11.76 |
| 928_28 | 0.43 | 0.57 | 32.73 | 0.77 |
| YU-2 | 0.07 | 0.16 | 0.58 | 0.20 |
| 6471_V1_C16 | 0.59 | 0.50 | >500 | 5.07 |
| 93UG065 | 50.99 | 40.15 | >500 | 142.61 |
| CC1/85 | 0.21 | * | * | 1.98 |
| NL4-3 | 0.33 | * | * | 0.31 |
| T278.50 | 1.79 | * | * | 1.43 |
| CAP45.2.00.G3 | 0.22 | * | * | 20.48 |
| HIV-2-HCC-01 | 183.57 | * | * | >300 |

* not tested

Table 9 Molecule Key:

Bispecific = D1m-K8C-G99C_1xG4S_bNAb7 (SEQ ID NO: 338 + 259)

Combo = bNAb7 (SEQ ID NOs: 258 + 259) + D1m-K8C-G99C_Fc (SEQ ID NO: 158) (combo)

mAb = bNAb7 (SEQ ID NOs: 258 + 259)

CD4 = D1m-K8C-G99C_Fc (SEQ ID NO: 158)

TABLE 10

IC50 (nM) of different bNAb8-derived bispecific
formats and control molecules against a panel
of HIV-1 envelopes in PSV assay (ACTOne cells)

| | bNAb8-Derived Molecules | | | CD4 Controls |
| Envelope | Bispecific | Combo | mAb | CD4 |
| --- | --- | --- | --- | --- |
| X2088.C9 | 0.11 | 0.22 | 0.23 | 9.20 |
| ZM106.9 | 0.02 | 0.03 | 0.03 | 15.14 |
| 3637_V5_C3 | 104.00 | 305.50 | >500 | >500 |
| 3468_V1_C12 | 0.06 | 0.81 | 1.70 | 64.15 |
| Q461_E2 | 7.06 | 6.59 | >500 | 11.76 |
| 3326_V4_C3 | 75.70 | 367.00 | >500 | >500 |
| 42368 | 0.97 | 1.35 | >500 | 1.58 |
| CC1/85 | 0.14 | * | * | 1.98 |
| NL4-3 | 0.14 | * | * | 0.31 |
| T278.50 | 1.20 | * | * | 1.43 |
| CAP45.2.00.G3 | 2.72 | * | * | 20.48 |
| HIV-2-HCC-01 | 33.29 | * | * | >300 |

* not tested

Table 10 Molecule Key:

Bispecific = D1m-K8C-G99C_1xG4S_bNAb8 (SEQ ID NOs: 339 + 264)

Combo = bNAb8 (SEQ ID Nos: 263 + 264) + D1m-K8C-G99C_Fc (SEQ ID NO: 158) (combo)

mAb = bNAb8 (SEQ ID Nos: 263 + 264)

CD4 = D1m-K8C-G99C_Fc (SEQ ID NO: 158)

TABLE 11

IC50 (nM) of different bNAb9-derived bispecific
formats and control molecules against a panel
of HIV-1 envelopes in PSV assay (ACTOne cells)

| | bNAb9-Derived Molecules | | | CD4 Controls |
| Envelope | Bispecific | Combo | mAb | CD4 |
| --- | --- | --- | --- | --- |
| 42368 | 0.15 | 1.35 | >500 | 1.58 |
| X2088.C9 | 0.18 | 9.50 | >500 | 9.20 |
| ZM106.9 | 0.08 | 16.28 | >500 | 15.14 |
| 3326_V4_C3 | 3.87 | >500 | >500 | >500 |
| 3637_V5_C3 | 6.74 | >500 | >500 | >500 |
| 3468_V1_C12 | 1.51 | 23.22 | >500 | 64.15 |
| 620345_C1 | 1.02 | 3.25 | >500 | 99.28 |
| 0260.v5.c36 | 0.19 | 0.14 | 0.26 | 119.29 |
| TH976_17 | 20.42 | 27.24 | >500 | 39.05 |
| Q461_E2 | 0.55 | 18.54 | >500 | 11.76 |
| 928_28 | 0.20 | 0.42 | >500 | 0.77 |
| YU-2 | 0.12 | 0.09 | 0.36 | 0.20 |
| 6471_V1_C16 | 0.11 | 1.17 | >500 | 5.07 |
| 93UG065 | 0.18 | 31.44 | >500 | 142.61 |
| CC1/85 | 0.03 | * | * | 1.98 |
| NL4-3 | 0.07 | * | * | 0.31 |
| T278.50 | 0.14 | * | * | 1.43 |
| CAP45.2.00.G3 | 1.03 | * | * | 20.48 |
| HIV-2-HCC-01 | 1.68 | * | * | >300 |

* not tested

Table 11 Molecule Key:

Bispecific = D1m-K8C-G99C_1xG4S_bNAb9 (SEQ ID NOs: 340 + 269)

Combo = bNAb9 (SEQ ID NOs: 268 + 269) + D1m-K8C-G99C_Fc (SEQ ID NO: 158) (combo)

mAb = bNAb9 (SEQ ID NOs: 268 + 269)

CD4 = D1m-K8C-G99C_Fc (SEQ ID NO: 158)

TABLE 12

IC50 (nM) of different bNAb10-derived bispecific
formats and control molecules against a panel
of HIV-1 envelopes in PSV assay (ACTOne cells)

| | bNAb10-Derived Molecules | | | CD4 Controls |
| Envelope | Bispecific | Combo | mAb | CD4 |
| --- | --- | --- | --- | --- |
| 42368 | 0.17 | 2.29 | 189.62 | 1.58 |
| X2088.C9 | 0.17 | 9.94 | 233.05 | 9.20 |
| ZM106.9 | 0.09 | 24.96 | 71.31 | 15.14 |
| 3326_V4_C3 | 14.28 | >500 | >500 | >500 |
| 3637_V5_C3 | 0.36 | 439.54 | >500 | >500 |
| 3468_V1_C12 | 0.21 | 38.64 | 258.28 | 64.15 |
| 620345_C1 | 0.33 | 0.85 | >500 | 99.28 |
| 0260.v5.c36 | 0.17 | 0.29 | 0.48 | 119.29 |
| TH976_17 | 18.49 | 31.63 | >500 | 39.05 |
| Q461_E2 | 0.41 | 15.03 | >500 | 11.76 |
| 928_28 | 0.17 | 0.42 | 320.41 | 0.77 |
| YU-2 | 0.12 | 0.23 | 0.81 | 0.20 |
| 6471_V1_C16 | 0.12 | 1.23 | 91.84 | 5.07 |
| 93UG065 | 0.13 | 0.12 | 0.21 | 142.61 |
| CC1/85 | 0.04 | * | * | 1.98 |
| NL4-3 | 0.08 | * | * | 0.31 |
| T278.50 | 0.16 | * | * | 1.43 |
| CAP45.2.00.G3 | 4.55 | * | * | 20.48 |
| HIV-2-HCC-01 | 0.95 | * | * | >300 |

* not tested

Table 12 Molecule Key:
Bispecific = D1m-K8C-G99C_1xG4S_bNAb10 (SEQ ID Nos: 341 + 274)
Combo = bNAb10 (SEQ ID Nos: 273 + 274) + D1m-K8C-G99C_Fc (SEQ ID NO: 158)
(combo)
mAb = bNAb10 (SEQ ID Nos: 273 + 274)
CD4 = D1m-K8C-G99C_Fc (SEQ ID NO: 158)

TABLE 13

IC50 (nM) of different bNAb11-derived bispecific
formats and control molecules against a panel
of HIV-1 envelopes in PSV assay (ACTOne cells)

| | bNAb11-Derived Molecules | | | CD4 Controls |
| Envelope | Bispecific | Combo | mAb | CD4 |
| --- | --- | --- | --- | --- |
| 42368 | 0.48 | 2.65 | >500 | 1.58 |
| X2088.C9 | 0.15 | 7.06 | 95.12 | 9.20 |
| ZM106.9 | 0.07 | 14.74 | 73.68 | 15.14 |
| 3326_V4_C3 | 51.71 | 146.99 | >500 | >500 |
| 3637_V5_C3 | 6.73 | 410.00 | >500 | >500 |
| 3468_V1_C12 | 1.80 | 25.99 | >500 | 64.15 |
| 620345_C1 | 1.27 | 10.97 | 438.41 | 99.28 |
| 0260.v5.c36 | 0.20 | 0.42 | 0.57 | 119.29 |
| TH976_17 | 17.37 | 55.43 | >500 | 39.05 |
| Q461_E2 | 0.51 | 12.32 | >500 | 11.76 |
| 928_28 | 0.27 | 0.46 | >500 | 0.77 |
| YU-2 | 0.10 | 0.26 | 0.76 | 0.20 |
| 6471_V1_C16 | 0.25 | 0.71 | 253.40 | 5.07 |
| 93UG065 | 0.22 | 24.72 | 89.50 | 142.61 |
| CC1/85 | 0.09 | * | * | 1.98 |
| NL4-3 | 0.16 | * | * | 0.31 |
| T278.50 | 0.26 | * | * | 1.43 |
| CAP45.2.00.G3 | 5.82 | * | * | 20.48 |
| HIV-2-HCC-01 | 8.69 | * | * | >300 |

* not tested

Table 13 Molecule Key:
Bispecific = D1m-K8C-G99C_1xG4S_bNAb11 (SEQ ID NOs: 342 + 279)
Combo = bNAb11 (SEQ ID NOs: 278 + 279) + D1m-K8C-G99C_Fc (SEQ ID NO: 158)
(combo)
mAb = bNAb11 (SEQ ID NOs: 278 + 279)
CD4 = D1m-K8C-G99C_Fc (SEQ ID NO: 158)

TABLE 14

IC50 (nM) of different bNAb12-derived bispecific formats and control molecules
against a panel of HIV-1 envelopes in PSV assay (ACTOne cells)

| | bNAb12-Derived Molecules | | | | | | CD4 Controls |
| Envelope | Bispecific1 | Bispecific2 | Bispecific3 | Bispecific4 | Combo | mAb | CD4 |
| --- | --- | --- | --- | --- | --- | --- | --- |
| X2088.C9 | 0.59 | 13.09 | 4.43 | >500 | 7.37 | >500 | 9.20 |
| ZM106.9 | 0.13 | 0.13 | 0.27 | 3.37 | 1.55 | 1.85 | 15.14 |
| 3637_V5_C3 | 9.45 | 130.00 | 62.45 | >500 | 474.07 | >500 | >500 |
| 3468_V1_C12 | 0.82 | 2.94 | 4.41 | 103.85 | 16.30 | 343.72 | 64.15 |
| Q461_E2 | 0.26 | 0.3 | 0.5 | 4.5 | 5.16 | 41.90 | 11.76 |
| 3326_V4_C3 | 9.63 | 63.69 | 81.80 | >500 | 266.93 | >500 | >500 |
| 42368 | 0.15 | 6.2 | 1.3 | 167.0 | 1.84 | 344.45 | 1.58 |
| 620345_C1 | 0.33 | * | * | * | 2.13 | 179.12 | 99.28 |
| 0260.v5.c36 | 0.44 | * | * | * | 0.50 | 5.19 | 119.29 |
| TH976_17 | 29.83 | * | * | * | 36.40 | >500 | 39.05 |
| 928_28 | 0.46 | * | * | * | 0.48 | 482.30 | 0.77 |
| YU-2 | 0.21 | * | * | * | 0.29 | 77.41 | 0.20 |
| 6471_V1_C16 | 0.26 | * | * | * | 0.59 | >500 | 5.07 |
| 93UG065 | 0.42 | * | * | * | 0.86 | 3.17 | 142.61 |
| CC1/85 | 0.12 | * | * | * | * | * | 1.98 |
| NL4-3 | 0.14 | * | * | * | * | * | 0.31 |
| T278.50 | 0.19 | * | * | * | * | * | 1.43 |
| CAP45.2.00.G3 | 1.29 | * | * | * | * | * | 20.48 |
| HIV-2-HCC-01 | 4.04 | * | * | * | * | * | >300 |

* not tested

Table 14 Molecule Key:
Bispecific1 = D1m-K8C-G99C_1xG4S_bNAb12 (SEQ ID NOs: 343 + 284)
Bispecific2 = bNAb12_HC_1xG4S_D1m-K8C-G99C (SEQ ID NOs: 344 + 284)
Bispecific3 = D1m-K8C-G99C_1xG4S_LC-bNAb12 (SEQ ID NOs: 283 + 345)
Bispecific4 = bNAb12_LC_1xG4S_D1m-K8C-G99C (SEQ ID NOs: 283 + 346)
Combo = bNAb12 (SEQ ID NOs: 283 + 284) + D1m-K8C-G99C_Fc (SEQ ID NO: 158) (combo)
mAb = bNAb12 (SEQ ID NOs: 283 + 284)
CD4 = D1m-K8C-G99C_Fc (SEQ ID NO: 158)

TABLE 15

IC50 (nM) of different bNAb13-derived bispecific
formats and control molecules against a panel
of HIV-1 envelopes in PSV assay (ACTOne cells)

| Envelope | bNAb13-Derived Molecules | | | CD4 Controls |
|---|---|---|---|---|
| | Bispecific | Combo | mAb | CD4 |
| 42368 | 0.24 | 1.52 | >500 | 1.58 |
| X2088.C9 | 2.05 | 5.18 | >500 | 9.20 |
| ZM106.9 | 0.28 | 3.04 | 22.43 | 15.14 |
| 3326_V4_C3 | 52.07 | 191.00 | >500 | >500 |
| 3637_V5_C3 | 37.30 | 266.00 | >500 | >500 |
| 3468_V1_C12 | 4.25 | 25.00 | >500 | 64.15 |
| Q461_E2 | 0.50 | 4.14 | >500 | 11.76 |
| CC1/85 | 0.19 | * | * | 1.98 |
| 620345_C1 | 3.58 | * | >500 | 99.28 |
| 0260.v5.c36 | 0.36 | * | 18.10 | 119.29 |
| TH976_17 | 37.26 | * | >500 | 39.05 |
| 928_28 | 0.79 | * | 201.39 | 0.77 |
| YU-2 | 0.17 | * | 48.30 | 0.20 |
| 6471_V1_C16 | 0.16 | * | 133.35 | 5.07 |
| 93UG065 | 0.58 | * | 46.41 | 142.61 |
| NL4-3 | 0.21 | * | * | 0.31 |
| T278.50 | 0.34 | * | * | 1.43 |
| CAP45.2.00.G3 | 2.26 | * | * | 20.48 |
| HIV-2-HCC-01 | 11.13 | * | * | >300 |

* not tested

Table 15 Molecule Key:

Bispecific = D1m-K8C-G99C_1xG4S_bNAb13 (SEQ ID NOs: 347 + 289)

Combo = bNAb13 (SEQ ID NOs: 288 + 289) + D1m-K8C-G99C_Fc (SEQ ID NO: 158) (combo)

mAb = bNAb13 (SEQ ID NOs: 288 + 289)

CD4 = D1m-K8C-G99C_Fc (SEQ ID NO: 158)

TABLE 16

IC50 (nM) of different bNAb14-derived bispecific
formats and control molecules against a panel
of HIV-1 envelopes in PSV assay (ACTOne cells)

| Envelope | bNAb14-Derived Molecules | | | CD4 Controls |
|---|---|---|---|---|
| | Bispecific | Combo | mAb | CD4 |
| X2088.C9 | 1.26 | 1.73 | 2.79 | 9.20 |
| ZM106.9 | 0.62 | 1.08 | 1.26 | 15.14 |
| 3637_V5_C3 | 22.85 | 84.20 | >500 | >500 |
| 3468_V1_C12 | 17.35 | 35.05 | >500 | 64.15 |
| Q461_E2 | 2.77 | 11.40 | >500 | 11.76 |
| 3326_V4_C3 | 196.50 | >500 | >500 | >500 |
| 42368 | 1.15 | 1.84 | >500 | 1.58 |
| CC1/85 | 1.74 | * | * | 1.98 |
| NL4-3 | 0.29 | * | * | 0.31 |
| T278.50 | 6.81 | * | * | 1.43 |
| CAP45.2.00.G3 | 2.85 | * | * | 20.48 |
| HIV-2-HCC-01 | 98.75 | * | * | >300 |

* not tested

Table 16 Molecule Key:
Bispecific = D1m-K8C-G99C_1xG4S_bNAb14 (SEQ ID NOs: 348 + 294)
Combo = bNAb14 (SEQ ID NOs: 293 + 294) + D1m-K8C-G99C_Fc (SEQ ID NO: 158) (combo)
mAb = bNAb14 (SEQ ID NOs: 293 + 294)
CD4 = D1m-K8C-G99C_Fc (SEQ ID NO: 158)

TABLE 17

IC50 (nM) of different bNAb15-derived bispecific
formats and control molecules against a panel
of HIV-1 envelopes in PSV assay (ACTOne cells)

| Envelope | bNAb15-Derived Molecules | | | CD4 Controls |
|---|---|---|---|---|
| | Bispecific | Combo | mAb | CD4 |
| X2088.C9 | 1.19 | 0.95 | 2.58 | 9.20 |
| ZM106.9 | 0.68 | 0.40 | 1.34 | 15.14 |
| 3637_V5_C3 | 25.45 | 5.33 | 5.00 | >500 |
| 3468_V1_C12 | 22.00 | 35.80 | >500 | 64.15 |
| Q461_E2 | 2.81 | 5.98 | >500 | 11.76 |
| 3326_V4_C3 | 142.00 | >500 | >500 | >500 |
| 42368 | 1.11 | 1.55 | >500 | 1.58 |
| CC1/85 | 1.65 | * | * | 1.98 |
| NL4-3 | 0.36 | * | * | 0.31 |
| T278.50 | 7.66 | * | * | 1.43 |
| CAP45.2.00.G3 | 4.48 | * | * | 20.48 |
| HIV-2-HCC-01 | 142.16 | * | * | >300 |

* not tested

Table 17 Molecule Key:

Bispecific = D1m-K8C-G99C_1xG4S_bNAb15 (SEQ ID NOs: 349 + 299)

Combo = bNAb15 (SEQ ID NOs: 298 + 299) + D1m-K8C-G99C_Fc (SEQ ID NO: 158) (combo)

mAb = bNAb15 (SEQ ID NOs: 298 + 299)

CD4 = D1m-K8C-G99C_Fc (SEQ ID NO: 158)

TABLE 18

IC50 (nM) of different bNAb16-derived bispecific
formats and control molecules against a panel
of HIV-1 envelopes in PSV assay (ACTOne cells)

| Envelope | bNAb16-Derived Molecules | | | CD4 Controls |
|---|---|---|---|---|
| | Bispecific | Combo | mAb | CD4 |
| X2088.C9 | 0.25 | 2.02 | 289.00 | 9.20 |
| ZM106.9 | 2.42 | 11.63 | >500 | 15.14 |
| 3637_V5_C3 | 19.15 | 129.50 | >500 | >500 |
| 3468_V1_C12 | 11.21 | 26.75 | >500 | 64.15 |
| Q461_E2 | 2.03 | 6.06 | >500 | 11.76 |
| 3326_V4_C3 | 31.75 | 148.50 | >500 | >500 |
| 42368 | 0.69 | 1.92 | >500 | 1.58 |
| CC1/85 | 0.56 | * | * | 1.98 |
| NL4-3 | 0.14 | * | * | 0.31 |
| T278.50 | 2.29 | * | * | 1.43 |
| CAP45.2.00.G3 | 2.08 | * | * | 20.48 |
| HIV-2-HCC-01 | 237.46 | * | * | >300 |

* not tested

Table 18 Molecule Key:
Bispecific = D1m-K8C-G99C_1xG4S_bNAb16 (SEQ ID NOs: 350 +304)
Combo = bNAb16 (SEQ ID NOs: 303 + 304) + D1m-K8C-G99C_Fc (SEQ ID NO: 158) (combo)
mAb = bNAb16 (SEQ ID NOs: 303 + 304)
CD4 = D1m-K8C-G99C_Fc (SEQ ID NO: 158)

TABLE 19

IC50 (nM) of different bNAb17-derived bispecific
formats and control molecules against a panel
of HIV-1 envelopes in PSV assay (ACTOne cells)

| Envelope | bNAb17-Derived Molecules | | | CD4 Controls |
|---|---|---|---|---|
| | Bispecific | Combo | mAb | CD4 |
| X2088.C9 | 0.84 | 2.44 | >500 | 9.20 |
| ZM106.9 | 8.48 | 9.13 | >500 | 15.14 |
| 3637_V5_C3 | 45.75 | 97.90 | >500 | >500 |
| 3468_V1_C12 | 39.60 | 27.85 | >500 | 64.15 |
| Q461_E2 | 6.70 | 6.03 | >500 | 11.76 |
| 3326_V4_C3 | 287.50 | 171.50 | >500 | >500 |
| 42368 | 2.14 | 1.50 | >500 | 1.58 |
| CC1/85 | 0.91 | * | * | 1.98 |

TABLE 19-continued

IC50 (nM) of different bNAb17-derived bispecific
formats and control molecules against a panel
of HIV-1 envelopes in PSV assay (ACTOne cells)

| Envelope | bNAb17-Derived Molecules | | | CD4 Controls |
| | Bispecific | Combo | mAb | CD4 |
| --- | --- | --- | --- | --- |
| NL4-3 | 0.43 | * | * | 0.31 |
| T278.50 | 4.25 | * | * | 1.43 |
| CAP45.2.00.G3 | 1.39 | * | * | 20.48 |
| HIV-2-HCC-01 | 300.00 | * | * | >300 |

* not tested

Table 19 Molecule Key:

Bispecific = D1m-K8C-G99C_1xG4S_bNAb17 (SEQ ID NOs: 351 + 309)

Combo = bNAb17 (SEQ ID NOs: 308 + 309) + D1m-K8C-G99C_Fc (SEQ ID NO: 158) (combo)

mAb = bNAb17 (SEQ ID NOs: 308 + 309)

CD4 = D1m-K8C-G99C_Fc (SEQ ID NO: 158)

TABLE 20

IC50 (nM) of different bNAb18-derived bispecific
formats and control molecules against a panel
of HIV-1 envelopes in PSV assay (ACTOne cells)

| Envelope | bNAb18-Derived Molecules | | | CD4 Controls |
| | Bispecific | Combo | mAb | CD4 |
| --- | --- | --- | --- | --- |
| X2088.C9 | 0.63 | 0.26 | 0.20 | 9.20 |
| ZM106.9 | 0.25 | 0.08 | 0.11 | 15.14 |
| 3637_V5_C3 | 102.85 | 377.00 | >500 | >500 |
| 3468_V1_C12 | 26.60 | 38.60 | >500 | 64.15 |
| Q461_E2 | 3.16 | 9.98 | >500 | 11.76 |
| 3326_V4_C3 | 157.00 | 369.50 | >500 | >500 |
| 42368 | 0.94 | 2.18 | >500 | 1.58 |
| CC1/85 | 2.06 | * | * | 1.98 |
| NL4-3 | 0.33 | * | * | 0.31 |
| T278.50 | 5.83 | * | * | 1.43 |

TABLE 20-continued

IC50 (nM) of different bNAb18-derived bispecific
formats and control molecules against a panel
of HIV-1 envelopes in PSV assay (ACTOne cells)

| Envelope | bNAb18-Derived Molecules | | | CD4 Controls |
| | Bispecific | Combo | mAb | CD4 |
| --- | --- | --- | --- | --- |
| CAP45.2.00.G3 | 20.89 | * | * | 20.48 |
| HIV-2-HCC-01 | 93.74 | * | * | >300 |

* not tested

Table 20 Molecule Key:

Bispecific = D1m-K8C-G99C_1xG4S_bNAb18 (SEQ ID NOs: 352 + 314)

Combo = bNAb18 (SEQ ID NOs: 313 + 314) + D1m-K8C-G99C_Fc (SEQ ID NO: 158) (combo)

mAb = bNAb18 (SEQ ID NOs: 313 + 314)

CD4 = D1m-K8C-G99C_Fc (SEQ ID NO: 158)

TABLE 21

IC50 (nM) of different bNAb19-derived bispecific
formats and control molecules against a panel
of HIV-1 envelopes in PSV assay (ACTOne cells)

| Envelope | bNAb19-Derived Molecules | | | CD4 Controls |
| | Bispecific | Combo | mAb | CD4 |
| --- | --- | --- | --- | --- |
| X2088.C9 | 1.63 | 4.40 | >300 | 9.20 |
| ZM106.9 | 3.91 | 8.27 | >300 | 15.14 |
| 3637_V5_C3 | 16.50 | 168.00 | >300 | >500 |
| 3468_V1_C12 | 4.56 | 24.54 | >300 | 64.15 |
| Q461_E2 | 3.18 | 4.49 | >300 | 11.76 |
| 3326_V4_C3 | 130.00 | 241.67 | >300 | >500 |
| 42368 | 1.16 | 1.10 | >300 | 1.58 |
| CC1/85 | 0.52 | * | * | 1.98 |
| NL4-3 | 0.23 | * | * | 0.31 |
| T278.50 | 0.79 | * | * | 1.43 |
| CAP45.2.00.G3 | 5.54 | * | * | 20.48 |
| HIV-2-HCC-01 | 6.54 | * | * | >300 |

* not tested

Table 21 Molecule Key:

Bispecific = D1m-K8C-G99C_1xG4S_bNAb19 (SEQ ID NOs: 353 + 319)

Combo = bNAb19 (SEQ ID NOs: 318 + 319) + D1m-K8C-G99C_Fc (SEQ ID NO: 158) (combo)

mAb = bNAb19 (SEQ ID NOs: 318 + 319)

CD4 = D1m-K8C-G99C_Fc (SEQ ID NO: 158)

TABLE 22

IC50 (nM) of different bNAb20/21/22-derived bispecific formats and control
molecules against a panel of HIV-1 envelopes in PSV assay (ACTOne cells)

| Envelope | bNAb20-Derived Molecules | | | bNAb21-Derived Molecules | | | bNAb22-Derived Molecules | | | CD4 Controls |
| | 1 | 2 | 3 | 4 | 5 | 6 | 7 | 8 | 9 | 10 |
| --- | --- | --- | --- | --- | --- | --- | --- | --- | --- | --- |
| X2088.C9 | 0.03 | 0.04 | 0.04 | 0.02 | 0.02 | 0.02 | 0.04 | 0.03 | 0.04 | 9.20 |
| ZM106.9 | 0.01 | 0.02 | 0.02 | 0.01 | 0.01 | 0.01 | 0.01 | 0.01 | 0.01 | 15.14 |
| 3637_V5_C3 | 6.2 | 21.9 | 61.6 | 4.7 | 117.0 | 326.0 | 6.8 | 115.0 | 484.0 | >500 |
| 3468_V1_C12 | 0.01 | 0.02 | 0.02 | 0.01 | 0.01 | 0.01 | 0.01 | 0.02 | 0.01 | 64.15 |
| Q461_E2 | 0.9 | 5.9 | 72.1 | 0.4 | 10.0 | 186.0 | 2.0 | 7.1 | >500 | 11.76 |
| 3326_V4_C3 | 1.3 | 24.1 | 24.0 | 0.3 | 14.5 | 12.5 | 0.6 | 6.1 | 16.0 | >500 |
| 42368 | 0.5 | 3.7 | 59.4 | 0.2 | 1.9 | 128.0 | 0.7 | 1.2 | 391.0 | 1.58 |

Table 22 Molecule Key:

1 = D1m-K8C-G99C_1xG4S_bNAb20 (SEQ ID NOs: 354 + 324)

2 = bNAb20 (SEQ ID NOs: 323 + 324) + D1m-K8C-G99C_Fc (SEQ ID NO: 158) (combo)

3 = bNAb20 (SEQ ID NOs: 323 + 324)

4 = D1m-K8C-G99C_1xG4S_bNAb21 (SEQ ID NOs: 355 + 329)

5 = bNAb21 (SEQ ID NOs: 328 + 329) + D1m-K8C-G99C_Fc (SEQ ID NO: 158) (combo)

6 = bNAb21 (SEQ ID NOs: 328 + 329)

7 = D1m-K8C-G99C_1xG4S_bNAb22 (SEQ ID NOs: 356 + 366)

8 = bNAb22 (SEQ ID NOs: 332 + 366) + D1m-K8C-G99C_Fc (SEQ ID NO: 158) (combo)

9 = bNAb22 (SEQ ID NOs: 332 + 366)

10 = D1m-K8C-G99C_Fc (SEQ ID NO: 158)

TABLE 23

IC50 (nM) of different bNAb23-derived bispecific formats and control molecules against a panel of HIV-1 envelopes in PSV assay (ACTOne cells)

| Envelope | bNAb23-Derived Molecules | | | | | CD4 Controls |
|---|---|---|---|---|---|---|
| | 1 | 2 | 3 | 4 | 5 | 6 |
| X2088.C9 | 6.05 | 0.09 | 12.05 | 5.89 | >500 | 9.20 |
| ZM106.9 | 3.96 | 0.12 | 6.06 | 15.06 | 17.4 | 15.14 |
| 3637_V5_C3 | 129.50 | 2.26 | >500 | 294.00 | >500 | >500 |
| 3468_V1_C12 | 62.10 | 6.17 | 384.00 | 53.05 | >500 | 64.15 |
| Q461_E2 | 4.29 | 0.80 | 116.00 | 7.11 | >500 | 11.76 |
| 3326_V4_C3 | 44.90 | 3.94 | 108.00 | 173.00 | 15.3 | >500 |
| 42368 | 0.62 | 0.30 | 10.70 | 1.57 | >500 | 1.58 |

Table 23 Molecule Key:
1 = D1m-K8C-G99C_1xG4S_bNAb23 (SEQ ID NOs: 357 + 337)
2 = D1m-K8C-G99C_1xG4S_bNAb23-LC (SEQ ID NOs: 336 + 358)
3 = bNAb23-HC_1xG4S_D1m-K8C-G99C (SEQ ID NOs: 359 + 337)
4 = bNAb23 (SEQ ID NOs: 336 + 337) + D1m-K8C-G99C_Fc (SEQ ID NO: 158) (combo)
5 = bNAb23 (SEQ ID NOs: 336 + 337)
6 = D1m-K8C-G99C_Fc (SEQ ID NO: 158)

Example 8—Broad Spectrum Anti-Viral Activity of a bNAb1-derived Bispecific Molecule (SEQ ID NO:121 and SEO ID NO: 63)

A selected bispecific molecule derived from bNAb1 having two heavy chains (SEQ ID NO:121) and two light chains (SEQ ID NO:63) was independently tested against an external panel of pseudo-typed HIV-1 virus containing 119 HIV-1 envelopes and 1 control envelope in a PSV assay 15 (TMZ.bl—see Example 3 above), to further evaluate its breadth and potency. As shown in Table 24, the bispecific molecule completely and potently inhibited all of the 119 HIV-1 envelopes in this assay.

TABLE 24

IC50 and IC80 values (µg/ml) of bNAb1-derived bispecific molecule (SEQ ID NO: 121 and SEQ ID NO: 63) against 119 HIV-1 envelopes in PSV assay

| Virus ID | Clade* | IC50 | IC80 | MPI |
|---|---|---|---|---|
| 6535.3 | B | 0.007 | 0.021 | 100 |
| QH0692.42 | B | 0.020 | 0.066 | 100 |
| SC422661.8 | B | 0.013 | 0.032 | 100 |
| PVO.4 | B | 0.010 | 0.037 | 100 |
| TRO.11 | B | 0.011 | 0.026 | 100 |
| AC10.0.29 | B | 0.006 | 0.022 | 100 |
| RHPA4259.7 | B | 0.007 | 0.021 | 100 |
| THRO4156.18 | B | 0.027 | 0.095 | 100 |
| REJO4541.67 | B | 0.022 | 0.054 | 100 |
| TRJO4551.58 | B | 0.006 | 0.022 | 100 |
| WITO4160.33 | B | 0.024 | 0.099 | 100 |
| CAAN5342.A2 | B | 0.023 | 0.085 | 100 |
| WEAU_d15_410_787 | B (T/F) | 0.009 | 0.033 | 100 |
| 1006_11_C3_1601 | B (T/F) | 0.005 | 0.014 | 100 |
| 1054_07_TC4_1499 | B (T/F) | 0.014 | 0.041 | 100 |
| 1056_10_TA11_1826 | B (T/F) | 0.009 | 0.026 | 100 |
| 1012_11_TC21_3257 | B (T/F) | 0.004 | 0.015 | 100 |
| 6240_08_TA5_4622 | B (T/F) | 0.019 | 0.054 | 100 |
| 6244_13_B5_4576 | B (T/F) | 0.011 | 0.039 | 100 |
| 62357_14_D3_4589 | B (T/F) | 0.021 | 0.060 | 100 |
| SC05_8C11_2344 | B (T/F) | 0.016 | 0.045 | 100 |
| Du156.12 | C | 0.005 | 0.018 | 100 |
| Du172.17 | C | 0.010 | 0.029 | 100 |
| Du422.1 | C | 0.011 | 0.044 | 100 |
| ZM197M.PB7 | C | 1.148 | 5.807 | 100 |
| ZM214M.PL15 | C | 0.020 | 0.069 | 100 |
| ZM233M.PB6 | C | 0.046 | 0.171 | 100 |
| ZM249M.PL1 | C | 0.006 | 0.021 | 100 |

TABLE 24-continued

IC50 and IC80 values (µg/ml) of bNAb1-derived bispecific molecule (SEQ ID NO: 121 and SEQ ID NO: 63) against 119 HIV-1 envelopes in PSV assay

| Virus ID | Clade* | IC50 | IC80 | MPI |
|---|---|---|---|---|
| ZM53M.PB12 | C | 0.275 | 0.908 | 100 |
| ZM109F.PB4 | C | 0.036 | 0.132 | 100 |
| ZM135M.PL10a | C | 0.030 | 0.119 | 100 |
| CAP45.2.00.G3 | C | 0.260 | 2.976 | 100 |
| CAP210.2.00.E8 | C | 0.023 | 0.102 | 100 |
| HIV-001428-2.42 | C | 0.002 | 0.004 | 100 |
| HIV-0013095-2.11 | C | 0.016 | 0.042 | 100 |
| HIV-16055-2.3 | C | 0.044 | 0.159 | 100 |
| HIV-16845-2.22 | C | 0.042 | 0.147 | 100 |
| Ce1086_B2 | C (T/F) | 0.085 | 0.297 | 100 |
| Ce0393_C3 | C (T/F) | 0.008 | 0.022 | 100 |
| Ce1176_A3 | C (T/F) | 0.010 | 0.028 | 100 |
| Ce2010_F5 | C (T/F) | 0.206 | 0.693 | 100 |
| Ce0682_E4 | C (T/F) | 0.080 | 1.232 | 100 |
| Ce1172_H1 | C (T/F) | 0.005 | 0.015 | 100 |
| Ce2060_G9 | C (T/F) | 0.016 | 0.059 | 100 |
| Ce703010054_2A2 | C (T/F) | 0.342 | 1.030 | 100 |
| BF1266.431a | C (T/F) | 0.106 | 1.283 | 100 |
| 246F C1G | C (T/F) | 0.009 | 0.031 | 100 |
| 249M B10 | C (T/F) | 0.627 | 5.222 | 99 |
| ZM247v1(Rev-) | C (T/F) | 0.004 | 0.014 | 100 |
| 7030102001E5(Rev-) | C (T/F) | 0.010 | 0.025 | 100 |
| 1394C9G1(Rev-) | C (T/F) | 0.008 | 0.028 | 100 |
| Ce704809221_1B3 | C (T/F) | 0.014 | 0.060 | 100 |
| CNE19 | BC | 0.054 | 0.270 | 100 |
| CNE20 | BC | 0.001 | 0.004 | 100 |
| CNE21 | BC | 0.004 | 0.013 | 100 |
| CNE17 | BC | 0.023 | 0.073 | 100 |
| CNE30 | BC | 0.026 | 0.074 | 100 |
| CNE52 | BC | 0.018 | 0.043 | 100 |
| CNE53 | BC | 0.005 | 0.013 | 100 |
| CNE58 | BC | 0.008 | 0.022 | 100 |
| MS208.A1 | A | 1.457 | 6.230 | 100 |
| Q23.17 | A | 0.010 | 0.025 | 100 |
| Q461.e2 | A | 0.025 | 0.086 | 100 |
| Q769.d22 | A | 0.046 | 0.122 | 100 |
| Q259.d2.17 | A | 0.167 | 0.459 | 100 |
| Q842.d12 | A | 0.006 | 0.015 | 100 |
| 0260.v5.c36 | A | 0.031 | 0.111 | 100 |
| 3415.v1.c1 | A | 0.010 | 0.028 | 100 |
| 3365.v2.c20 | A | 0.011 | 0.036 | 100 |
| 191955_A11 | A (T/F) | 0.032 | 0.115 | 100 |
| 191084 B7-19 | A (T/F) | 0.009 | 0.027 | 100 |
| 9004SS_A3_4 | A (T/F) | 0.008 | 0.023 | 100 |
| T257-31 | CRF02_AG | 0.022 | 0.064 | 100 |
| 928-28 | CRF02_AG | 0.029 | 0.086 | 100 |
| 263-8 | CRF02_AG | 0.011 | 0.043 | 100 |
| T250-4 | CRF02_AG | 0.005 | 0.012 | 100 |
| T251-18 | CRF02_AG | 0.023 | 0.064 | 100 |
| T278-50 | CRF02_AG | 0.010 | 0.027 | 100 |
| T255-34 | CRF02_AG | 0.025 | 0.091 | 100 |
| 211-9 | CRF02_AG | 0.025 | 0.085 | 100 |
| 235-47 | CRF02_AG | 0.170 | 0.800 | 100 |
| 620345.c01 | CRF01_AE | 0.247 | 2.737 | 100 |
| CNE8 | CRF01_AE | 0.007 | 0.021 | 100 |
| C1080.c03 | CRF01_AE | 0.014 | 0.027 | 100 |
| R2184.c04 | CRF01_AE | 0.006 | 0.022 | 100 |
| R1166.c01 | CRF01_AE | 0.252 | 1.001 | 100 |
| R3265.c06 | CRF01_AE | 0.065 | 0.254 | 100 |
| C2101.c01 | CRF01_AE | 0.005 | 0.016 | 100 |
| C3347.c11 | CRF01_AE | 0.006 | 0.015 | 100 |
| C4118.c09 | CRF01_AE | 0.512 | 4.356 | 100 |
| CNE5 | CRF01_AE | 0.014 | 0.038 | 100 |
| BJOX009000.02.4 | CRF01_AE | 0.006 | 0.020 | 100 |
| BJOX015000.11.5 | CRF01_AE (T/F) | 0.013 | 0.035 | 100 |
| BJOX010000.06.2 | CRF01_AE (T/F) | 0.035 | 0.114 | 100 |
| BJOX025000.01.1 | CRF01_AE (T/F) | 0.035 | 0.140 | 100 |
| BJOX028000.10.3 | CRF01_AE (T/F) | 0.004 | 0.010 | 100 |
| X1193_c1 | G | 0.015 | 0.034 | 100 |
| P0402_c2_11 | G | 0.005 | 0.019 | 100 |
| X1254_c3 | G | 0.014 | 0.040 | 100 |
| X2088_c9 | G | 0.017 | 0.048 | 100 |
| X2131_C1_B5 | G | 0.014 | 0.039 | 100 |
| P1981_C5_3 | G | 0.014 | 0.038 | 100 |

55

TABLE 24-continued

IC50 and IC80 values (µg/ml) of bNAb1-derived
bispecific molecule (SEQ ID NO: 121 and SEQ ID
NO: 63) against 119 HIV-1 envelopes in PSV assay

| Virus ID | Clade* | IC50 | IC80 | MPI |
|---|---|---|---|---|
| X1632_S2_B10 | G | 0.027 | 0.097 | 100 |
| 3016.v5.c45 | D | 0.041 | 0.117 | 100 |
| A07412M1.vrc12 | D | 0.009 | 0.034 | 100 |
| 231965.c01 | D | 0.023 | 0.068 | 100 |
| 231966.c02 | D | 0.006 | 0.018 | 100 |
| 6405.v4.c34 | D | 0.029 | 0.082 | 100 |
| 3817.v2.c59 | CD | 0.025 | 0.063 | 100 |
| 6480.v4.c25 | CD | 0.008 | 0.024 | 100 |
| 6952.v1.c20 | CD | 0.037 | 0.109 | 100 |
| 6811.v7.c18 | CD | 0.004 | 0.014 | 100 |
| 89-F1_2_25 | CD | 0.035 | 0.110 | 100 |
| 3301.v1.c24 | AC | 0.005 | 0.018 | 100 |
| 6041.v3.c23 | AC | 0.109 | 0.553 | 100 |
| 6540.v4.c1 | AC | 0.002 | 0.012 | 100 |
| 6545.v4.c1 | AC | 0.011 | 0.031 | 100 |
| 0815.v3.c3 | ACD | 0.003 | 0.008 | 100 |
| 3103.v3.c10 | ACD | 0.012 | 0.027 | 100 |
| MuLV | Negative Control | >50 | >50 | 0 |

Example 9—Activity of bNAb1-Derived Bispecific
Molecules Against Laboratory and Clinical Isolates
of HIV-1 in Replicating Virus Assays Method Clinical and Laboratory Isolates All clinical and laboratory isolates were originally obtained from the NIH AIDS Reagent Program (currently NIH HIV Reagent Program, https:hivreagentprogram.org/). The proviral clone of $NL_{4-3}$ (obtained from NIH) was used to make the replicating reporter virus NLRepRluc, in which a section of the nef gene from the proviral clone of $NL_{4-3}$ was replaced with the *Renilla* luciferase gene. Virus was produced through transfection of HEK293T cells using Lipofectamine Plus (Invitrogen, Carlsbad, CA), according to the manufacturer's instructions. The replication-competent virus was harvested 3 days after transfection of HEK 293T cells with the modified pNLRepRluc proviral clone and titrated in MT-2 cells using luciferase activity as a biomarker.

Clinical isolates were initially propagated in human PBMC cells. T-tropic laboratory virus strains IIIB, $NL_{4-3}$, HXB2, LAI, MN and RF viruses were propagated in MT-2 cells, while M-tropic laboratory strains Bal and JR-FL were propagated in PM1 cells. Titers of virus stocks were determined in PBMC using a virus infectivity assay with a p24 antigen endpoint (p24 ELISA kit; PerkinElmer Life Sciences). All those viruses were further titered in MT2 or CCR5-B6 cells before experiments by using luciferase enzyme activity as an endpoint for 50% tissue culture infectious dose (TCID50) determination.

Cells

MT-2 cells were obtained from the American Type Culture Collection (ATCC) and were propagated in RPMI 1640 medium supplemented with 10% heat-inactivated fetal bovine serum (FBS), 100 units/ml of penicillin G, 100 µg/ml of streptomycin, 10 mM HEPES buffer pH 7.55 and 2-mM L-glutamine. HEK293T cells were ere obtained from the ATCC and propagated in DMEM media supplemented with 10% heat-inactivated FBS. The ACTOne cells were originally derived from HEK293T cells and express CD4, CCR5 and CXCR4. They are grown in DMEM media supplemented with 10% heat-inactivated FBS, 100 U/ml of penicillin G, 100 µg/ml of streptomycin, 5 g/ml blasticidin, 200 µg/ml G418 and 1.5 µg/ml puromycin. CCR5-B6 cells were generated in-house at ViiV Branford CT USA. To generate CCR5-B6 cells, human CCR5 lentiviral particles were used to infect the MT4-B6 cells (obtained from Bristol-Myers Squibb) that has an integrated copy of the LTR-fire-fly luciferase reporter (backbone: plenti-P2A-Puro, RC223291L3V, Origene) and stable cells were selected by using G418 (0.6 mg/ml) and puromycin (2 µg/ml). The CCR5-B6 cells express firefly luciferase from an HIV-1 LTR promoter after infection with HIV. They are grown in RPMI 1640 supplemented with 10% heat inactivated fetal bovine serum (FBS), 10 mM HEPES buffer pH 7.55, 2 mM L-glutamine, 100 units/ml penicillin G, and 100 µg/ml streptomycin, 2 µg/ml puromycin, 0.6 mg/ml G418.

Replicating Virus Assay

Assay Using NLRepRluc Virus

The NLRepRluc was used to infect MT-2 cells at a multiplicity of 0.01 for 1 hour before adding the proteins to the 96-well plates. Antibodies were serially diluted four-fold and 11 concentrations were plated in triplicate. After 4 days of incubation, cells were processed and quantitated for virus growth by the amount of expressed luciferase. Luciferase was quantitated using the ENDUREN substrate from Promega (Madison, WI) according to the manufacturer's instructions. Luciferase activity was measured immediately on an ENVISION multilabel plate reader (PerkinElmer, Waltham MA). $EC_{50}$ values were calculated by comparing the amount of luciferase produced in the presence of antigen binding protein compared to wells where no antigen binding protein (DMSO control) was added. A 5-parameter sigmoidal equation was used to fit the resulting signal vs. concentration curves, and the concentration of each antigen binding protein that produced 50% maximal inhibition ($EC_{50}$) was determined. The results of three independent experiments were averaged and plotted, with error bars corresponding to 1 standard deviation.

Replicating Virus Assay Using Laboratory Strains and Clinical Isolates

Replicating laboratory strains and clinical isolates were prepared as described above. MT2 cells or CCR5-B6 cells were resuspended in corresponding media and distributed to 96-well assay plates (26,000 cells/well in 100 uL; Corning, Tewksbury, MA) containing serial dilutions of inhibitors in DMSO (5 or 3-fold dilutions, columns 1-10). The blank controls were wells containing DMSO (column 11, 12). Replicating whole viruses of laboratory strains or clinic isolates were diluted in RPMI-1640 culture medium based on 50% tissue culture infectious dose (TCID50) determination such that undiluted stock virus was added to the first well, and 100 µl of viral culture medium were loaded to the wells already containing compounds and cells (total 200 µl/well), resulting in a final concentration of DMSO of 1%. Plates were incubated at 37° C. and 5% $CO_2$ for approximately 4 days. After that, *Renilla* luciferase activity was measured (Enduren reagent, Promega Corp., Madison, WI) on an EnVision Multilabel pate reader (Perkin Elmer, Inc., Waltham MA). The 50% effective concentration ($EC_{50}$) was calculated by using the exponential form of the median effect equation where $(Fa)=1/[1+ (ED_{50}/drug conc.)]$.

Results

Table 25.1 shows that the bNAb1-derived bispecific molecules are consistently about 10-fold more active than the mixture of the component parts (bNAb1 and CD4 domain), again indicating a clear anti-viral synergy result from fusing these component binding domains.

TABLE 25.1

| EC50 (nM) values of bNAb1-derived bispecific and control molecules against NL4-3 in a replicating virus assay | |
| --- | --- |
| Molecules (SEQ ID NO) | EC50 (nM) |
| D1m_1xG4S_bNAb1 (102 + 63) | 0.03 |
| D1m_2xG4S_bNAb1 (103 + 63) | 0.03 |
| D1m_3xG4S_bNAb1 (104 + 63) | 0.02 |
| D1m_4xG4S_bNAb1 (105 + 63) | 0.03 |
| D1m_His (4*) + bNAb1 (62 + 63) | 0.22 |
| D1m_His (4*) | 0.23 |
| bNAb1 (62 + 63) | >500 |

*plus a 6xHis tag (six C-terminal histidine residues)

A bNAb1-derived bispecific molecule (D1m-K8C-G99C_1xG4S_bNAb1, SEQ ID NOS: 121+63) was tested against a panel of 13 clinical and 8 laboratory HIV-1 isolates in a replicating virus assay using MT-2 and CCR5-B6 cells. As shown in Table 25.2, this molecule neutralized all strains, with EC50s less than 1 nM (geometric mean EC50 being 0.11 nM against clinical isolates and 0.26 nM against lab strains), demonstrating again its strong potency and breadth of activity.

TABLE 25.2

| EC50 (nM) of a bNAb1-derived bispecific against a panel of HIV-1 clinical isolates and laboratory strains in a replicating virus assay | | |
| --- | --- | --- |
| Isolates | Clade | bNAb1-Derived Bispecific |
| Clinical isolates | | |
| 93US141 | B | 0.04 |
| 93US144 | B | 0.07 |
| ASM34 | B | 0.15 |
| BK132 | B | 0.19 |
| BZ167 | B | 0.05 |
| CC1/85 | B | 0.2 |
| CM237 | B | 0.03 |
| ETH2220 | C | 0.08 |
| I-2496 | A | 0.15 |
| SE364 | C | 0.2 |
| UG268 | C | 0.06 |
| UG270 | D | 0.42 |
| US4 | B | 0.39 |
| Laboratory strains | | |
| HXB2 | | 0.04 |
| BaL | | 0.83 |
| IIIB/H9 | | 0.56 |
| IIIB/HOS | | 0.56 |
| JR-FL | | 0.04 |
| LAI | | 0.39 |
| MIN | | 0.15 |
| NL4-3 | | 0.39 |
| RF | | 0.56 |

Table 25.2 Molecule Key:
1 = D1m-K8C-G99C_1xG4S_bNAb1 (SEQ ID NOs: 121 + 63)

Example 10—In Vitro Resistance Barrier

To assess the resistance barrier of the bispecific molecules, we examined the relative rates at which HIV NL4-3 virus can escape inhibition by a panel of antibodies versus a DMSO control.

MT2 cells ($2.0 \times 10^5$/well in RPMI 1640+50 mg/ml penicillin and streptomycin+10 mM HEPES buffer pH 7.55+2 mM L-glutamine. +0.2% DMSO) were pre-infected at an MOI (multiplicity of infection) of 0.005 for 2.5 hours and then pelleted to remove unbound virus particles. One mL of infected cells was added to each well of a 24 well plate. Replicates of antibody dilutions at the concentrations of 20-, 30-, or 40-fold of IC50 values were then added (1 mL of a 2× stock) to achieve 2 mL assay volume.

Every 3-4 days images of the wells were captured and 1 ml of each well is removed and replaced by fresh preparations of each condition. This process was continued until there was viral breakthrough (observed cytopathic effect (CPE)>80%) or until there was a confirmed elimination of infected cells (via challenged elimination). When either condition was achieved, the sample was collected as pellet and supernatant (via centrifugation) and stored at −80° C. until genotypic analysis was performed to confirm the presence of resistance mutations. The days from infection to breakthrough were used to estimate the resistance barrier of a certain molecule. The longer it takes the virus to develop CPE, which indicates resistance, the higher the resistance barrier is.

Table 26 shows that, in this experimental setting, the bNAb1-derived bispecific molecule (SEQ ID NO: 105 and SEQ ID NO:63) exhibited a much higher resistance barrier than the soluble CD4 domain or bNAb1 alone at all concentrations. This again indicates synergy between soluble CD4 domains and bNAb1 when fused together.

TABLE 26

| Group | Molecule | Conc. (nM) | Average days before CPE |
| --- | --- | --- | --- |
| 20x EC50 | D1m_4xG4S_bNAb1 | 4.2 | 16 |
| | D1m_His | 8.4 | 4 |
| | bNAb1 | 18 | 4 |
| 30x EC50 | D1m_4xG4S_bNAb1 | 6.3 | 54 |
| | D1m_His | 12.5 | 5 |
| | bNAb1 | 27 | 4 |
| 40x EC50 | D1m_4xG4S_bNAb1 | 8.4 | 62 |
| | D1m_His | 16.7 | 7 |
| | bNAb1 | 36 | 4 |

Table 26 Molecule Key:

D1m_4xG4S_bNAb1 = SEQ ID NO: 105 and 63

D1m_His = SEQ ID NO: 4 plus a 6xHis tag (six C-terminal histidine residues)

bNAb1 = SEQ ID NOs: 62 and 63

Example 11—Anti-HIV-2 Activity of a bNAb1-Derived Bispecific Molecule (SEQ ID NO: 121 and SEQ ID NO:63) in Pseudotyped and Replicating Virus Assays HIV-2 differs from HIV-1 in that it originates from the transmission of simian immunodeficiency virus (SIV) from sooty mangabeys (SIVsmm) to human (Gao et al, J Virol. 1994; 68 (11): 7433-7447) whilst HIV-1 stems from the transmission from chimpanzees and western gorillas (HIV-1 group M and O, respectively). HIV-2 can also cause AIDS but is far less pathogenic and wide-spread than HIV-1 (de Silva et al, Trends Microbiol. 2008; 16 (12): 588-595; Da Silva et al, AIDS. 2008; 22 (10): 1195-1202). Though also using CD4 for infection (Sattentau et al, AIDS. 1988; 2 (2): 101-105), HIV-2 shares only 40% identity in the gp160 amino acid sequence with HIV-1, and is therefore less sensitive or insensitive to HIV-1 envelope-directed bnAbs (Kong et al, JVI 2012; 86 (2): 947-960). The bNAb1-derived bispecific molecule (SEQ ID NO:121 and SEQ ID NO: 63) showed strong potency and anti-viral synergy against the 2 HIV-2 Env-pseudotypes tested in PSV assays and the laboratory NIHZ strain examined in a replicating virus assay (Table 27), illustrating its exceptional breadth of anti-HIV activity and excellent synergy.

TABLE 27

IC50 (nM) of a bNAb1-derived bispecific and control molecules against HIV-2 strains

| Strain | Assay | bNAb1-derived molecules | | | |
|--------|-------|------|------|------|------|
| | | 1 | 2 | 3 | 4 |
| HIV-2-ATM88 | PSV | 0.07 | 3.93 | >500 | 10.53 |
| HIV-2-HCC-01 | PSV | 0.78 | >500 | >500 | >500 |
| HIV-2 NIHZ | Replicating virus | 2.68 | * | * | * |

* not tested

Table 27 Molecule Key:

1 = D1m-K8C-G99C_1xG4S_bNAb1 (SEQ ID NOs: 121 + 63)

2 = D1m_His (SEQ ID NO: 4*)

3 = bNAb1 (SEQ ID NOs: 62 + 63)

4 = D1m_His (SEQ ID NO: 4*) + bNAb1(SEQ ID NOs: 62 + 63) (combo)

*plus a 6xHis tag (six C-terminal histidine residues)

SEQUENCE LISTING

| SEQ ID NO | Name/Identifier | Description |
|-----------|-----------------|-------------|
| 1 | D1D2 | Human CD4 D1D2 (wild type) |
| 2 | D1mD2 | Human CD4 mD1.22-D2 (D1 mutations S23N, A55V, and L96V) |
| 3 | D1 | Human CD4 D1 (wild type) |
| 4 | D1m | Human CD4 mD1.22 (NCBI accession code: QHY83614.1; D1 mutations L5Y, S23N, A55V, I76P, L96V and F98V) |
| 5 | D1m-K8V | Human CD4 mD1.22 + K8V |
| 6 | D1m-E91Q | Human CD4 mD1.22 + E91Q |
| 7 | D1m-E91H | Human CD4 mD1.22 + E91H |
| 8 | D1m-E87G | Human CD4 mD1.22 + E87G |
| 9 | D1m-N52W | Human CD4 mD1.22 + N52W |
| 10 | D1m-K8I | Human CD4 mD1.22 + K8I |
| 11 | D1m-K8C-G99C | Human CD4 mD1.22 + K8C, G99C |
| 12 | D1m-T11C-K72C | Human CD4 mD1.22 + T11C, K72C |
| 13 | D1m-E13C-I70C | Human CD4 mD1.22 + E13C, I70C |
| 14 | D1m-H27C-G38C | Human CD4 mD1.22 + H27C, G38C |
| 15 | D1m-K21C-G65C | Human CD4 mD1.22 + K21C, G65C |
| 16 | D1m-Q25E | Human CD4 mD1.22 + Q25E |
| 17 | D1m-H27D | Human CD4 mD1.22 + H27D |
| 18 | D1m-R58V | Human CD4 mD1.22 + R58V |
| 19 | D1m-R58N | Human CD4 mD1.22 + R58N |
| 20 | D1m-R58T | Human CD4 mD1.22 + R58T |
| 21 | D1m-L61M | Human CD4 mD1.22 + L61M |
| 22 | bNAb1 CDRH1 | CDRH1 of bNAb1 |
| 23 | bNAb1 CDRH2 | CDRH2 of bNAb1 |
| 24 | bNAb1 CDRH3 | CDRH3 of bNAb1 |
| 25 | bNAb1 CDRL1 | CDRL1 of bNAb1 |
| 26 | bNAb1 CDRL2 | CDRL2 of bNAb1 |
| 27 | bNAb1 CDRL3 | CDRL3 of bNAb1 |
| 28 | bNAb2 CDRH1 | CDRH1 of bNAb2 |
| 29 | bNAb2 CDRH2 | CDRH2 of bNAb2 |
| 30 | bNAb2 CDRH3 | CDRH3 of bNAb2 |
| 31 | bNAb2 CDRL1 | CDRL1 of bNAb2 |
| 32 | bNAb2 CDRL2 | CDRL2 of bNAb2 |
| 33 | bNAb2 CDRL3 | CDRL3 of bNAb2 |
| 34 | bNAb3 CDRH1 | CDRH1 of bNAb3 |
| 35 | bNAb3 CDRH2 | CDRH2 of bNAb3 |
| 36 | bNAb3 CDRH3 | CDRH3 of bNAb3 |
| 37 | bNAb3 CDRL1 | CDRL1 of bNAb3 |
| 38 | bNAb3 CDRL2 | CDRL2 of bNAb3 |
| 39 | bNAb3 CDRL3 | CDRL3 of bNAb3 |
| 40 | bNAb4 CDRH1 | CDRH1 of bNAb4 |
| 41 | bNAb4 CDRH2 | CDRH2 of bNAb4 |

-continued

| SEQUENCE LISTING | | |
|---|---|---|
| SEQ ID NO | Name/Identifier | Description |
| 42 | bNAb4 CDRH3 | CDRH3 of bNAb4 |
| 43 | bNAb4 CDRL1 | CDRL1 of bNAb4 |
| 44 | bNAb4 CDRL2 | CDRL2 of bNAb4 |
| 45 | bNAb4 CDRL3 | CDRL3 of bNAb4 |
| 46 | bNAb5 CDRH1 | CDRH1 of bNAb5 |
| 47 | bNAb5 CDRH2 | CDRH2 of bNAb5 |
| 48 | bNAb5 CDRH3 | CDRH3 of bNAb5 |
| 49 | bNAb5 CDRL1 | CDRL1 of bNAb5 |
| 50 | bNAb5 CDRL2 | CDRL2 of bNAb5 |
| 51 | bNAb5 CDRL3 | CDRL3 of bNAb5 |
| 52 | bNAb6 CDRH1 | CDRH1 of bNAb6 |
| 53 | bNAb6 CDRH2 | CDRH2 of bNAb6 |
| 54 | bNAb6 CDRH3 | CDRH3 of bNAb6 |
| 55 | bNAb6 CDRL1 | CDRL1 of bNAb6 |
| 56 | bNAb6 CDRL2 | CDRL2 of bNAb6 |
| 57 | bNAb6 CDRL3 | CDRL3 of bNAb6 |
| 58 | bNAb1 VH | Heavy chain variable region of bNAb1 |
| 59 | bNAb1 VL | Light chain variable region of bNAb1 |
| 60 | bNAb1* VL | Light chain variable region of bNAb1 with F32Y mutation |
| 61 | bnAb1 HC | Full heavy chain of bNAb1 |
| 62 | bNAb1 HC + LS | Full heavy chain of bNAb1 with M428L/N434S mutations |
| 63 | bNAb1 LC | Full light chain of bNAb1 |
| 64 | bNAb1* LC | Full light chain of bNAb1 with F32Y mutation |
| 65 | bNAb2 VH | Heavy chain variable region of bNAb2 |
| 66 | bNAb2 VL | Light chain variable region of bNAb2 |
| 67 | bNAb2 HC | Full heavy chain of bNAb2 |
| 68 | bNAb2 HC + LS | Full heavy chain of bNAb2 with M428L/N434S mutations |
| 69 | bNAb2 LC | Full light chain of bNAb2 |
| 70 | bNAb3 VH | Heavy chain variable region of bNAb3 |
| 71 | bNAb3 VL | Light chain variable region of bNAb3 |
| 72 | bNAb3 HC | Full heavy chain of bNAb3 |
| 73 | bNAb3 HC + LS | Full heavy chain of bNAb3 with M428L/N434S mutations |
| 74 | bNAb3 LC | Full light chain of bNAb3 |
| 75 | bNAb4 VH | Heavy chain variable region of bNAb4 |
| 76 | bNAb4 VL | Light chain variable region of bNAb4 |
| 77 | bNAb4 HC | Full heavy chain of bNAb4 |
| 78 | bNAb4 HC + LS | Full heavy chain of bNAb4 with M428L/N434S mutations |
| 79 | bNAb4 LC | Full light chain of bNAb4 |
| 80 | bNAb5 VH | Heavy chain variable region of bNAb5 |
| 81 | bNAb5 VL | Light chain variable region of bNAb5 |
| 82 | bNAb5 HC | Full heavy chain of bNAb5 |
| 83 | bNAb5 HC + LS | Full heavy chain of bNAb5 with M428L/N434S mutations |
| 84 | bNAb5 LC | Full light chain of bNAb5 |
| 85 | bNAb6 VH | Heavy chain variable region of bNAb6 |
| 86 | bNAb6 VL | Light chain variable region of bNAb6 |
| 87 | bNAb6 HC | Full heavy chain of bNAb6 |
| 88 | bNAb6 HC + LS | Full heavy chain of bNAb6 with M428L/N434S mutations |
| 89 | bNAb6 LC | Full light chain of bNAb6 |
| 90 | 1xG4S | Linker |
| 91 | 2xG4S | Linker |
| 92 | 3xG4S | Linker |
| 93 | 4xG4S | Linker |
| 94 | 5xG4S | Linker |
| 95 | 6xG4S | Linker |
| 96 | D1mD2_0xG4S_bNAb1-HC | Human CD4 mD1.22-D2 fused to the N-terminus of bNAb1 heavy chain with no linker, Fc includes M428L/N434S |
| 97 | D1mD2_1xG4S_bNAb1-HC | Human CD4 mD1.22-D2 fused to the N-terminus of bNAb1 heavy chain with 1xG4S linker, Fc includes M428L/N434S |
| 98 | D1mD2_2xG4S_bNAb1-HC | Human CD4 mD1.22-D2 fused to the N-terminus of bNAb1 heavy chain with 2xG4S linker, Fc includes M428L/N434S |
| 99 | D1mD2_3xG4S_bNAb1-HC | Human CD4 mD1.22-D2 fused to the N-terminus of bNAb1 heavy chain with 3xG4S linker, Fc includes M428L/N434S |

-continued

| SEQ ID NO | Name/Identifier | Description |
|---|---|---|
| 100 | D1mD2_4xG4S_bNAb1-HC | Human CD4 mD1.22-D2 fused to the N-terminus of bNAb1 heavy chain with 4xG4S linker, Fc includes M428L/N434S |
| 101 | D1m_0xG4S_bNAb1-HC | Human CD4 mD1.22 fused to the N-terminus of bNAb1 heavy chain with no linker, Fc includes M428L/N434S |
| 102 | D1m_1xG4S_bNAb1-HC | Human CD4 mD1.22 fused to the N-terminus of bNAb1 heavy chain with 1xG4S linker, Fc includes M428L/N434S |
| 103 | D1m_2xG4S_bNAb1-HC | Human CD4 mD1.22 fused to the N-terminus of bNAb1 heavy chain with 2xG4S linker, Fc includes M428L/N434S |
| 104 | D1m_3xG4S_bNAb1-HC | Human CD4 mD1.22 fused to the N-terminus of bNAb1 heavy chain with 3xG4S linker, Fc includes M428L/N434S |
| 105 | D1m_4xG4S_bNAb1-HC | Human CD4 mD1.22 fused to the N-terminus of bNAb1 heavy chain with 4xG4S linker, Fc includes M428L/N434S |
| 106 | D1m_5xG4S_bNAb1-HC | Human CD4 mD1.22 fused to the N-terminus of bNAb1 heavy chain with 5xG4S linker, Fc includes M428L/N434S |
| 107 | D1m_6xG4S_bNAb1-HC | Human CD4 mD1.22 fused to the N-terminus of bNAb1 heavy chain with 6xG4S linker, Fc includes M428L/N434S |
| 108 | D1m_0xG4S_bNAb1-LC | Human CD4 mD1.22 fused to the N-terminus of bNAb1 light chain with no linker |
| 109 | D1m_1xG4S_bNAb1-LC | Human CD4 mD1.22 fused to the N-terminus of bNAb1 light chain with 1xG4S linker |
| 110 | D1m_2xG4S_bNAb1-LC | Human CD4 mD1.22 fused to the N-terminus of bNAb1 light chain with 2xG4S linker |
| 111 | D1m_3xG4S_bNAb1-LC | Human CD4 mD1.22 fused to the N-terminus of bNAb1 light chain with 3xG4S linker |
| 112 | D1m_4xG4S_bNAb1-LC | Human CD4 mD1.22 fused to the N-terminus of bNAb1 light chain with 4xG4S linker |
| 113 | D1m_5xG4S_bNAb1-LC | Human CD4 mD1.22 fused to the N-terminus of bNAb1 light chain with 5xG4S linker |
| 114 | D1m_6xG4S_bNAb1-LC | Human CD4 mD1.22 fused to the N-terminus of bNAb1 light chain with 6xG4S linker |
| 115 | D1m-K8C-G99C_1xG4S_bNAb1-LC | Human CD4 mD1.22 + K8C + G99C fused to the N-terminus of bNAb1 light chain with 1xG4S linker |
| 116 | bNAb1-HC-mid_1xG4S_D1m-K8C-G99C | Human CD4 mD1.22 + K8C + G99C fused in between the CH1 domain and hinge of bNAb1 heavy chain with 1xG4S linker, Fc includes M428L/N434S |
| 117 | bNAb1-HC_1xG4S_D1m-K8C-G99C | Human CD4 mD1.22 + K8C + G99C fused to the C-terminus of bNAb1 heavy chain with 1xG4S linker, Fc includes M428L/N434S |
| 118 | bNAb1-LC_1xG4S_D1m-K8C-G99C | Human CD4 mD1.22 + K8C + G99C fused to the C-terminus of bNAb1 light chain with 1xG4S linker |
| 119 | D1m-K8I_1xG4S_bNAb1-HC | Human CD4 mD1.22 + K8I fused to the N-terminus of bNAb1 heavy chain with 1xG4S linker, Fc includes M428L/N434S |
| 120 | D1m-K8V_1xG4S_bNAb1-HC | Human CD4 mD1.22 + K8V fused to the N-terminus of bNAb1 heavy chain with 1xG4S linker, Fc includes M428L/N434S |
| 121 | D1m-K8C-G99C_1xG4S_bNAb1-HC | Human CD4 mD1.22 + K8C + G99C fused to the N-terminus of bNAb1 heavy chain with 1xG4S linker, Fc includes M428L/N434S |
| 122 | D1m-T11C-K72C_1xG4S_bNAb1-HC | Human CD4 mD1.22 + T11C + K72C fused to the N-terminus of bNAb1 heavy chain with 1xG4S linker, Fc includes M428L/N434S |
| 123 | D1m-E91Q_1xG4S_bNAb1-HC | Human CD4 mD1.22 + E91Q fused to the N-terminus of bNAb1 heavy chain with 1xG4S linker, Fc includes M428L/N434S |

-continued

| SEQ ID NO | Name/Identifier | Description |
|---|---|---|
| 124 | D1m-E91H_1xG4S_bNAb1-HC | Human CD4 mD1.22 + E91H fused to the N-terminus of bNAb1 heavy chain with 1xG4S linker, Fc includes M428L/N434S |
| 125 | D1m-Q25E_1xG4S_bNAb1-HC | Human CD4 mD1.22 + Q25E fused to the N-terminus of bNAb1 heavy chain with 1xG4S linker, Fc includes M428L/N434S |
| 126 | D1m-H27D_1xG4S_bNAb1-HC | Human CD4 mD1.22 + H27D fused to the N-terminus of bNAb1 heavy chain with 1xG4S linker, Fc includes M428L/N434S |
| 127 | D1m-R58V_1xG4S_bNAb1-HC | Human CD4 mD1.22 + R58V fused to the N-terminus of bNAb1 heavy chain with 1xG4S linker, Fc includes M428L/N434S |
| 128 | D1m-R58N_1xG4S_bNAb1-HC | Human CD4 mD1.22 + R58N fused to the N-terminus of bNAb1 heavy chain with 1xG4S linker, Fc includes M428L/N434S |
| 129 | D1m-R58T_1xG4S_bNAb1-HC | Human CD4 mD1.22 + R58T fused to the N-terminus of bNAb1 heavy chain with 1xG4S linker, Fc includes M428L/N434S |
| 130 | D1m-L61M_1xG4S_bNAb1-HC | Human CD4 mD1.22 + L61M fused to the N-terminus of bNAb1 heavy chain with 1xG4S linker, Fc includes M428L/N434S |
| 131 | D1m-E13C-I70C_1xG4S_bNAb1-HC | Human CD4 mD1.22 + E13C + I70C fused to the N-terminus of bNAb1 heavy chain with 1xG4S linker, Fc includes M428L/N434S |
| 132 | D1m-H27C-G38C_1xG4S_bNAb1-HC | Human CD4 mD1.22 + H27C + G38C fused to the N-terminus of bNAb1 heavy chain with 1xG4S linker, Fc includes M428L/N434S |
| 133 | D1m-K21C-G65C_1xG4S_bNAb1-HC | Human CD4 mD1.22 + K21C + G65C fused to the N-terminus of bNAb1 heavy chain with 1xG4S linker, Fc includes M428L/N434S |
| 134 | D1m-E87G_1xG4S_bNAb1-HC | Human CD4 mD1.22 + E87G fused to the N-terminus of bNAb1 heavy chain with 1xG4S linker, Fc includes M428L/N434S |
| 135 | D1m-N52W_1xG4S_bNAb1-HC | Human CD4 mD1.22 + N52W fused to the N-terminus of bNAb1 heavy chain with 1xG4S linker, Fc includes M428L/N434S |
| 136 | D1m-K8C-G99C_1xG4S_bNAb2-HC | Human CD4 mD1.22 + K8C + G99C fused to the N-terminus of bNAb2 heavy chain with 1xG4S linker, Fc includes M428L/N434S |
| 137 | D1m-K8C-G99C_2xG4S_bNAb2-HC | Human CD4 mD1.22 + K8C + G99C fused to the N-terminus of bNAb2 heavy chain with 2xG4S linker, Fc includes M428L/N434S |
| 138 | D1m-K8C-G99C_3xG4S_bNAb2-HC | Human CD4 mD1.22 + K8C + G99C fused to the N-terminus of bNAb2 heavy chain with 3xG4S linker, Fc includes M428L/N434S |
| 139 | D1m-K8C-G99C_4xG4S_bNAb2-HC | Human CD4 mD1.22 + K8C + G99C fused to the N-terminus of bNAb2 heavy chain with 4xG4S linker, Fc includes M428L/N434S |
| 140 | bNAb2-HC-mid_1xG4S_D1m-K8C-G99C | Human CD4 mD1.22 + K8C + G99C fused in between the CH1 domain and hinge of bNAb2 heavy chain with 1xG4S linkers, Fc includes M428L/N434S |
| 141 | bNAb2-HC_1xG4S_D1m-K8C-G99C | Human CD4 mD1.22 + K8C + G99C fused to the C-terminus of bNAb2 heavy chain with 1xG4S linker, Fc includes M428L/N434S |
| 142 | D1m-K8C-G99C_1xG4S_bNAb2-LC | Human CD4 mD1.22 + K8C + G99C fused to the N-terminus of bNAb2 light chain with 1xG4S linker |
| 143 | bNAb2-LC_1xG4S_D1m-K8C-G99C | Human CD4 mD1.22 + K8C + G99C fused to the C-terminus of bNAb2 light chain with 1xG4S linker |
| 144 | D1m-K8C-G99C_1xG4S_bNAb3-HC | Human CD4 mD1.22 + K8C + G99C fused to the N-terminus of bNAb3 heavy chain with 1xG4S linker, Fc includes M428L/N434S |
| 145 | D1m-K8C-G99C_4xG4S_bNAb3-HC | Human CD4 mD1.22 + K8C + G99C fused to the N-terminus of bNAb3 heavy chain with 4xG4S linker, Fc includes M428L/N434S |
| 146 | D1m-K8C-G99C_1xG4S_bNAb4-HC | Human CD4 mD1.22 + K8C + G99C fused to the N-terminus of bNAb4 heavy chain with 1xG4S linker, Fc includes M428L/N434S |
| 147 | D1m-K8C-G99C_4xG4S_bNAb4-HC | Human CD4 mD1.22 + K8C + G99C fused to the N-terminus of bNAb4 heavy chain with 4xG4S linker, Fc includes M428L/N434S |

| SEQUENCE LISTING | | |
|---|---|---|
| SEQ ID NO | Name/Identifier | Description |
| 148 | D1m-K8C-G99C_1xG4S_bNAb5-HC | Human CD4 mD1.22 + K8C + G99C fused to the N-terminus of bNAb5 heavy chain with 1xG4S linker, Fc includes M428L/N434S |
| 149 | D1m-K8C-G99C_4xG4S_bNAb5-HC | Human CD4 mD1.22 + K8C + G99C fused to the N-terminus of bNAb5 heavy chain with 4xG4S linker, Fc includes M428L/N434S |
| 150 | D1mD2_4xG4S_bNAb6-HC | Human CD4 mD1.22-D2 fused to the N-terminus of bNAb6 heavy chain with 4xG4S linker, Fc includes M428L/N434S |
| 151 | D1m_4xG4S_bNAb6-HC | Human CD4 mD1.22 fused to the N-terminus of bNAb6 heavy chain with 4xG4S linker, Fc includes M428L/N434S |
| 152 | D1m_4xG4S_bNAb1-scFv-H4Lss_2xG4S_Fc | Human CD4 mD1.22 fused, via 4xG4S linker, to the N-terminus of bNAb1 scFv (VH-4xG4S-VL, with stabilizing disulfide bond G44C/HC-G100C/LC), which is fused, via 2xG4S linker, to the N-terminus of human Fc fragment including M428L/N434S |
| 153 | D1m_3xG4S_bNAb1-scFv-H4Lss_2xG4S_Fc | Human CD4 mD1.22 fused, via 3xG4S linker, to the N-terminus of bNAb1 scFv (VH-4xG4S-VL, with stabilizing disulfide bond G44C/HC-G100C/LC), which is fused, via 2xG4S linker, to the N-terminus of human Fc fragment including M428L/N434S |
| 154 | D1m_2xG4S_bNAb1-scFv-H4Lss_2xG4S_Fc | Human CD4 mD1.22 fused, via 2xG4S linker, to the N-terminus of bNAb1 scFv (VH-4xG4S-VL, with stabilizing disulfide bond G44C/HC-G100C/LC), which is fused, via 2xG4S linker, to the N-terminus of human Fc fragment including M428L/N434S |
| 155 | D1m_1xG4S_bNAb1-scFv-H4Lss_2xG4S_Fc | Human CD4 mD1.22 fused, via 1xG4S linker, to the N-terminus of bNAb1 scFv (VH-4xG4S-VL, with stabilizing disulfide bond G44C/HC-G100C/LC), which is fused, via 2xG4S linker, to the N-terminus of human Fc fragment including M428L/N434S |
| 156 | Fc_4xG4S_D1m_3xG4S_bNAb1-scFv-H4Lss | Human CD4 mD1.22 fused, via 3xG4S linker, to the N-terminus of bNAb1 scFv (VH-4xG4S-VL, with stabilizing disulfide bond G44C/HC-G100C/LC), which is fused, via 3xG4S linker, to the C-terminus of human Fc fragment including M428L/N434S |
| 157 | bNAb1-scFv-L4Hss_4xG4S_D1m_3xG4S_Fc | bNAb1 scFv (VL-4xG4S-VH, with stabilizing disulfide bond G44C/HC-G100C/LC) fused, via 4xG4S linker, to the N-terminus of human CD4 mD1.22, which is fused, via 3xG4S linker, to the N-terminus of human Fc fragment including M428L/N434S |
| 158 | D1m-K8C-G99C_Fc | Human CD4 mD1.22 + K8C, G99C with C-terminal Fc tag including M428L/N434S |
| 159 | bNAb7 CDRH1 | CDRH1 of bNAb7 |
| 160 | bNAb7 CDRH2 | CDRH2 of bNAb7 |
| 161 | bNAb7 CDRH3 | CDRH3 of bNAb7 |
| 162 | bNAb7 CDRL1 | CDRL1 of bNAb7 |
| 163 | bNAb7 CDRL2 | CDRL2 of bNAb7 |
| 164 | bNAb7 CDRL3 | CDRL3 of bNAb7 |
| 165 | bNAb8 CDRH1 | CDRH1 of bNAb8 |
| 166 | bNAb8 CDRH2 | CDRH2 of bNAb8 |
| 167 | bNAb8 CDRH3 | CDRH3 of bNAb8 |
| 168 | bNAb8 CDRL1 | CDRL1 of bNAb8 |
| 169 | bNAb8 CDRL2 | CDRL2 of bNAb8 |
| 170 | bNAb8 CDRL3 | CDRL3 of bNAb8 |
| 171 | bNAb9 CDRH1 | CDRH1 of bNAb9 |
| 172 | bNAb9 CDRH2 | CDRH2 of bNAb9 |
| 173 | bNAb9 CDRH3 | CDRH3 of bNAb9 |
| 174 | bNAb9 CDRL1 | CDRL1 of bNAb9 |
| 175 | bNAb9 CDRL2 | CDRL2 of bNAb9 |
| 176 | bNAb9 CDRL3 | CDRL3 of bNAb9 |
| 177 | bNAb10 CDRH1 | CDRH1 of bNAb10 |
| 178 | bNAb10 CDRH2 | CDRH2 of bNAb10 |
| 179 | bNAb10 CDRH3 | CDRH3 of bNAb10 |
| 180 | bNAb10 CDRL1 | CDRL1 of bNAb10 |
| 181 | bNAb10 CDRL2 | CDRL2 of bNAb10 |
| 182 | bNAb10 CDRL3 | CDRL3 of bNAb10 |

-continued

| SEQUENCE LISTING | | |
|---|---|---|
| SEQ ID NO | Name/Identifier | Description |
| 183 | bNAb11 CDRH1 | CDRH1 of bNAb11 |
| 184 | bNAb11 CDRH2 | CDRH2 of bNAb11 |
| 185 | bNAb11 CDRH3 | CDRH3 of bNAb11 |
| 186 | bNAb11 CDRL1 | CDRL1 of bNAb11 |
| 187 | bNAb11 CDRL2 | CDRL2 of bNAb11 |
| 188 | bNAb11 CDRL3 | CDRL3 of bNAb11 |
| 189 | bNAb12 CDRH1 | CDRH1 of bNAb12 |
| 190 | bNAb12 CDRH2 | CDRH2 of bNAb12 |
| 191 | bNAb12 CDRH3 | CDRH3 of bNAb12 |
| 192 | bNAb12 CDRL1 | CDRL1 of bNAb12 |
| 193 | bNAb12 CDRL2 | CDRL2 of bNAb12 |
| 194 | bNAb12 CDRL3 | CDRL3 of bNAb12 |
| 195 | bNAb13 CDRH1 | CDRH1 of bNAb13 |
| 196 | bNAb13 CDRH2 | CDRH2 of bNAb13 |
| 197 | bNAb13 CDRH3 | CDRH3 of bNAb13 |
| 198 | bNAb13 CDRL1 | CDRL1 of bNAb13 |
| 199 | bNAb13 CDRL2 | CDRL2 of bNAb13 |
| 200 | bNAb13 CDRL3 | CDRL3 of bNAb13 |
| 201 | bNAb14 CDRH1 | CDRH1 of bNAb14 |
| 202 | bNAb14 CDRH2 | CDRH2 of bNAb14 |
| 203 | bNAb14 CDRH3 | CDRH3 of bNAb14 |
| 204 | bNAb14 CDRL1 | CDRL1 of bNAb14 |
| 205 | bNAb14 CDRL2 | CDRL2 of bNAb14 |
| 206 | bNAb14 CDRL3 | CDRL3 of bNAb14 |
| 207 | bNAb15 CDRH1 | CDRH1 of bNAb15 |
| 208 | bNAb15 CDRH2 | CDRH2 of bNAb15 |
| 209 | bNAb15 CDRH3 | CDRH3 of bNAb15 |
| 210 | bNAb15 CDRL1 | CDRL1 of bNAb15 |
| 211 | bNAb15 CDRL2 | CDRL2 of bNAb15 |
| 212 | bNAb15 CDRL3 | CDRL3 of bNAb15 |
| 213 | bNAb16 CDRH1 | CDRH1 of bNAb16 |
| 214 | bNAb16 CDRH2 | CDRH2 of bNAb16 |
| 215 | bNAb16 CDRH3 | CDRH3 of bNAb16 |
| 216 | bNAb16 CDRL1 | CDRL1 of bNAb16 |
| 217 | bNAb16 CDRL2 | CDRL2 of bNAb16 |
| 218 | bNAb16 CDRL3 | CDRL3 of bNAb16 |
| 219 | bNAb17 CDRH1 | CDRH1 of bNAb17 |
| 220 | bNAb17 CDRH2 | CDRH2 of bNAb17 |
| 212 | bNAb17 CDRH3 | CDRH3 of bNAb17 |
| 222 | bNAb17 CDRL1 | CDRL1 of bNAb17 |
| 223 | bNAb17 CDRL2 | CDRL2 of bNAb17 |
| 224 | bNAb17 CDRL3 | CDRL3 of bNAb17 |
| 225 | bNAb18 CDRH1 | CDRH1 of bNAb18 |
| 226 | bNAb18 CDRH2 | CDRH2 of bNAb18 |
| 227 | bNAb18 CDRH3 | CDRH3 of bNAb18 |
| 228 | bNAb18 CDRL1 | CDRL1 of bNAb18 |
| 229 | bNAb18 CDRL2 | CDRL2 of bNAb18 |
| 230 | bNAb18 CDRL3 | CDRL3 of bNAb18 |
| 231 | bNAb19 CDRH1 | CDRH1 of bNAb19 |
| 232 | bNAb19 CDRH2 | CDRH2 of bNAb19 |
| 233 | bNAb19 CDRH3 | CDRH3 of bNAb19 |
| 234 | bNAb19 CDRL1 | CDRL1 of bNAb19 |
| 235 | bNAb19 CDRL2 | CDRL2 of bNAb19 |
| 236 | bNAb19 CDRL3 | CDRL3 of bNAb19 |
| 237 | bNAb20 CDRH1 | CDRH1 of bNAb20 |
| 238 | bNAb20 CDRH2 | CDRH2 of bNAb20 |
| 239 | bNAb20 CDRH3 | CDRH3 of bNAb20 |
| 240 | bNAb20 CDRL1 | CDRL1 of bNAb20 |
| 241 | bNAb20 CDRL2 | CDRL2 of bNAb20 |
| 242 | bNAb20 CDRL3 | CDRL3 of bNAb20 |
| 243 | bNAb21 and bNAb22 CDRH1 | CDRH1 of bNAb21 and bNAb22 |
| 244 | bNAb21 and bNAb22 CDRH2 | CDRH2 of bNAb21 and bNAb22 |
| 245 | bNAb21 and bNAb22 CDRH3 | CDRH3 of bNAb21 and bNAb22 |
| 246 | bNAb21 and bNAb22 CDRL1 | CDRL1 of bNAb21 and bNAb22 |
| 247 | bNAb21 and bNAb22 CDRL2 | CDRL2 of bNAb21 and bNAb22 |
| 248 | bNAb21 and bNAb22 CDRL3 | CDRL3 of bNAb21 and bNAb22 |
| 249 | bNAb23 CDRH1 | CDRH1 of bNAb23 |
| 250 | bNAb23 CDRH2 | CDRH2 of bNAb23 |
| 251 | bNAb23 CDRH3 | CDRH3 of bNAb23 |
| 252 | bNAb23 CDRL1 | CDRL1 of bNAb23 |
| 253 | bNAb23 CDRL2 | CDRL2 of bNAb23 |
| 254 | bNAb23 CDRL3 | CDRL3 of bNAb23 |
| 255 | bNAb7 VH | Heavy chain variable region of bNAb7 |
| 256 | bNAb7 VL | Light chain variable region of bNAb7 |

SEQUENCE LISTING

| SEQ ID NO | Name/Identifier | Description |
|---|---|---|
| 257 | bNAb7 HC | Full heavy chain of bNAb7 |
| 258 | bNAb7 HC + LS | Full heavy chain of bNAb7 with M428L/N434S mutations |
| 259 | bNAb7 LC | Full light chain of bNAb7 |
| 260 | bNAb8 VH | Heavy chain variable region of bNAb8 |
| 261 | bNAb8 VL | Light chain variable region of bNAb8 |
| 262 | bNAb8 HC | Full heavy chain of bNAb8 |
| 263 | bNAb8 HC + LS | Full heavy chain of bNAb8 with M428L/N434S mutations |
| 264 | bNAb8 LC | Full light chain of bNAb8 |
| 265 | bNAb9 VH | Heavy chain variable region of bNAb9 |
| 266 | bNAb9 VL | Light chain variable region of bNAb9 |
| 267 | bNAb9 HC | Full heavy chain of bNAb9 |
| 268 | bNAb9 HC + LS | Full heavy chain of bNAb9 with M428L/N434S mutations |
| 269 | bNAb9 LC | Full light chain of bNAb9 |
| 270 | bNAb10 VH | Heavy chain variable region of bNAb10 |
| 271 | bNAb10 VL | Light chain variable region of bNAb10 |
| 272 | bNAb10 HC | Full heavy chain of bNAb10 |
| 273 | bNAb10 HC + LS | Full heavy chain of bNAb10 with M428L/N434S mutations |
| 274 | bNAb10 LC | Full light chain of bNAb10 |
| 275 | bNAb11 VH | Heavy chain variable region of bNAb11 |
| 276 | bNAb11 VL | Light chain variable region of bNAb11 |
| 277 | bNAb11 HC | Full heavy chain of bNAb11 |
| 278 | bNAb11 HC + LS | Full heavy chain of bNAb11 with M428L/N434S mutations |
| 279 | bNAb11 LC | Full light chain of bNAb11 |
| 280 | bNAb12 VH | Heavy chain variable region of bNAb12 |
| 281 | bNAb12 VL | Light chain variable region of bNAb12 |
| 282 | bNAb12 HC | Full heavy chain of bNAb12 |
| 283 | bNAb12 HC + LS | Full heavy chain of bNAb12 with M428L/N434S mutations |
| 284 | bNAb12 LC | Full light chain of bNAb12 |
| 285 | bNAb13 VH | Heavy chain variable region of bNAb13 |
| 286 | bNAb13 VL | Light chain variable region of bNAb13 |
| 287 | bNAb13 HC | Full heavy chain of bNAb13 |
| 288 | bNAb13 HC + LS | Full heavy chain of bNAb13 with M428L/N434S mutations |
| 289 | bNAb13 LC | Full light chain of bNAb13 |
| 290 | bNAb14 VH | Heavy chain variable region of bNAb13 |
| 291 | bNAb14 VL | Light chain variable region of bNAb14 |
| 292 | bNAb14 HC | Full heavy chain of bNAb14 |
| 293 | bNAb14 HC + LS | Full heavy chain of bNAb14 with M428L/N434S mutations |
| 294 | bNAb14 LC | Full light chain of bNAb14 |
| 295 | bNAb15 VH | Heavy chain variable region of bNAb15 |
| 296 | bNAb15 VL | Light chain variable region of bNAb15 |
| 297 | bNAb15 HC | Full heavy chain of bNAb15 |
| 298 | bNAb15 HC + LS | Full heavy chain of bNAb15 with M428L/N434S mutations |
| 299 | bNAb15 LC | Full light chain of bNAb15 |
| 300 | bNAb16 VH | Heavy chain variable region of bNAb16 |
| 301 | bNAb16 VL | Light chain variable region of bNAb16 |
| 302 | bNAb16 HC | Full heavy chain of bNAb16 |
| 303 | bNAb16 HC + LS | Full heavy chain of bNAb16 with M428L/N434S mutations |
| 304 | bNAb16 LC | Full light chain of bNAb16 |
| 305 | bNAb17 VH | Heavy chain variable region of bNAb17 |
| 306 | bNAb17 VL | Light chain variable region of bNAb17 |
| 307 | bNAb17 HC | Full heavy chain of bNAb17 |
| 308 | bNAb17 HC + LS | Full heavy chain of bNAb17 with M428L/N434S mutations |
| 309 | bNAb17 LC | Full light chain of bNAb17 |
| 310 | bNAb18 VH | Heavy chain variable region of bNAb17 |
| 311 | bNAb18 VL | Light chain variable region of bNAb17 |
| 312 | bNAb18 HC | Full heavy chain of bNAb17 |
| 313 | bNAb18 HC + LS | Full heavy chain of bNAb17 with M428L/N434S mutations |
| 314 | bNAb18 LC | Full light chain of bNAb18 |
| 315 | bNAb19 VH | Heavy chain variable region of bNAb19 |
| 316 | bNAb19 VL | Light chain variable region of bNAb19 |

| SEQUENCE LISTING | | |
|---|---|---|
| SEQ ID NO | Name/Identifier | Description |
| 317 | bNAb19 HC | Full heavy chain of bNAb19 |
| 318 | bNAb19 HC + LS | Full heavy chain of bNAb19 with M428L/N434S mutations |
| 319 | bNAb19 LC | Full light chain of bNAb19 |
| 320 | bNAb20 VH | Heavy chain variable region of bNAb20 |
| 321 | bNAb20 VL | Light chain variable region of bNAb20 |
| 322 | bNAb20 HC | Full heavy chain of bNAb20 |
| 323 | bNAb20 HC + LS | Full heavy chain of bNAb20 with M428L/N434S mutations |
| 324 | bNAb20 LC | Full light chain of bNAb20 |
| 325 | bNAb21 VH | Heavy chain variable region of bNAb21 |
| 326 | bNAb21 VL | Light chain variable region of bNAb21 |
| 327 | bNAb21 HC | Full heavy chain of bNAb21 |
| 328 | bNAb21 HC + LS | Full heavy chain of bNAb21 with M428L/N434S mutations |
| 329 | bNAb21 LC | Full light chain of bNAb21 |
| 330 | bNAb22 VH | Full heavy chain of bNAb22 |
| 331 | bNAb22 HC | Full heavy chain of bNAb22 with M428L/N434S mutations |
| 332 | bNAb22 HV + LS | Full light chain of bNAb22 |
| 333 | bNAb23 VH | Heavy chain variable region of bNAb23 |
| 334 | bNAb23 VL | Light chain variable region of bNAb23 |
| 335 | bNAb23 HC | Full heavy chain of bNAb23 |
| 336 | bNAb23 HC + LS | Full heavy chain of bNAb23 with M428L/N434S mutations |
| 337 | bNAb23 LC | Full light chain of bNAb23 |
| 338 | D1m-K8C-G99C_1xG4S_bNAb7-HC | Human CD4 mD1.22 + K8C + G99C fused to the N-terminus of bNAb7 heavy chain with 1xG4S linker, Fc includes M428L/N434S |
| 339 | D1m-K8C-G99C_1xG4S_bNAb8-HC | Human CD4 mD1.22 + K8C + G99C fused to the N-terminus of bNAb8 heavy chain with 1xG4S linker, Fc includes M428L/N434S |
| 340 | D1m-K8C-G99C_1xG4S_bNAb9-HC | Human CD4 mD1.22 + K8C + G99C fused to the N-terminus of bNAb9 heavy chain with 1xG4S linker, Fc includes M428L/N434S |
| 341 | D1m-K8C-G99C_1xG4S_bNAb10-HC | Human CD4 mD1.22 + K8C + G99C fused to the N-terminus of bNAb10 heavy chain with 1xG4S linker, Fc includes M428L/N434S |
| 342 | D1m-K8C-G99C_1xG4S_bNAb11-HC | Human CD4 mD1.22 + K8C + G99C fused to the N-terminus of bNAb11 heavy chain with 1xG4S linker, Fc includes M428L/N434S |
| 343 | D1m-K8C-G99C_1xG4S_bNAb12-HC | Human CD4 mD1.22 + K8C + G99C fused to the N-terminus of bNAb12 heavy chain with 1xG4S linker, Fc includes M428L/N434S |
| 344 | bNAb12_HC_1xG4S_D1m-K8C-G99C | Human CD4 mD1.22 + K8C + G99C fused to the C-terminus of bNAb12 heavy chain with 1xG4S linker, Fc includes M428L/N434S |
| 345 | D1m-K8C-G99C_1xG4S_LC-bNAb12 | Human CD4 mD1.22 + K8C + G99C fused to the N-terminus of bNAb12 light chain with 1xG4S linker |
| 346 | bNAb12_LC_1xG4S_D1m-K8C-G99C-HC | Human CD4 mD1.22 + K8C + G99C fused to the C-terminus of bNAb12 light chain with 1xG4S linker |
| 347 | D1m-K8C-G99C_1xG4S_bNAb13-HC | Human CD4 mD1.22 + K8C + G99C fused to the N-terminus of bNAb13 heavy chain with 1xG4S linker, Fc includes M428L/N434S |
| 348 | D1m-K8C-G99C_1xG4S_bNAb14-HC | Human CD4 mD1.22 + K8C + G99C fused to the N-terminus of bNAb14 heavy chain with 1xG4S linker, Fc includes M428L/N434S |
| 349 | D1m-K8C-G99C_1xG4S_bNAb15-HC | Human CD4 mD1.22 + K8C + G99C fused to the N-terminus of bNAb15 heavy chain with 1xG4S linker, Fc includes M428L/N434S |
| 350 | D1m-K8C-G99C_1xG4S_bNAb16-HC | Human CD4 mD1.22 + K8C + G99C fused to the N-terminus of bNAb16 heavy chain with 1xG4S linker, Fc includes M428L/N434S |
| 351 | D1m-K8C-G99C_1xG4S_bNAb17-HC | Human CD4 mD1.22 + K8C + G99C fused to the N-terminus of bNAb17 heavy chain with 1xG4S linker, Fc includes M428L/N434S |
| 352 | D1m-K8C-G99C_1xG4S_bNAb18-HC | Human CD4 mD1.22 + K8C + G99C fused to the N-terminus of bNAb18 heavy chain with 1xG4S linker, Fc includes M428L/N434S |
| 353 | D1m-K8C-G99C_1xG4S_bNAb19-HC | Human CD4 mD1.22 + K8C + G99C fused to the N-terminus of bNAb19 heavy chain with 1xG4S linker, Fc includes M428L/N434S |

-continued

| | SEQUENCE LISTING | |
|---|---|---|
| SEQ ID NO | Name/Identifier | Description |
| 354 | D1m-K8C-G99C_1xG4S_bNAb20-HC | Human CD4 mD1.22 + K8C + G99C fused to the N-terminus of bNAb20 heavy chain with 1xG4S linker, Fc includes M428L/N434S |
| 355 | D1m-K8C-G99C_1xG4S_bNAb21-HC | Human CD4 mD1.22 + K8C + G99C fused to the N-terminus of bNAb21 heavy chain with 1xG4S linker, Fc includes M428L/N434S |
| 356 | D1m-K8C-G99C_1xG4S_bNAb22-HC | Human CD4 mD1.22 + K8C + G99C fused to the N-terminus of bNAb22 heavy chain with 1xG4S linker, Fc includes M428L/N434S |
| 357 | D1m-K8C-G99C_1xG4S_bNAb23-HC | Human CD4 mD1.22 + K8C + G99C fused to the N-terminus of bNAb23 heavy chain with 1xG4S linker, Fc includes M428L/N434S |
| 358 | D1m-K8C-G99C_1xG4S_bNAb23-LC | Human CD4 mD1.22 + K8C + G99C fused to the N-terminus of bNAb23 light chain with 1xG4S linker |
| 359 | bNAb23-HC_1xG4S_D1m-K8C-G99C | Human CD4 mD1.22 + K8C + G99C fused to the C-terminus of bNAb23 heavy chain with 1xG4S linker, Fc includes M428L/N434S |
| 360 | bNAb23_LC_1xG4S_D1m-K8C-G99C | Human CD4 mD1.22 + K8C + G99C fused to the C-terminus of bNAb23 light chain with 1xG4S linker |
| 361 | V3 loop | V3 loop consensus sequence |
| 362 | D1m-K8C-G99C_1xG4S_bNAb6-HC | Human CD4 mD1.22 + K8C + G99C fused to the N-terminus of bNAb6 heavy chain with 1xG4S linker, Fc includes M428L/N434S |
| 363 | Exemplary gp160 | Exemplary gp160 sequence |
| 364 | Exemplary gp120 | Exemplary gp120 sequence |
| 365 | bNAb22 VL | Light chain variable region of bNAb22 |
| 366 | bNAb22 LC | Full light chain of bNAb22 |

-continued

```
                                    SEQ ID NO: 1
KKVVLGKKGDTVELTCTASQKKSIQFHWKNSNQIKILGNQGSFLT

KGPSKLNDRADSRRSLWDQGNFPLIIKNLKIEDSDTYICEVEDQK

EEVQLLVFGLTANSDTHLLQGQSLTLTLESPPGSSPSVQCRSPRG

KNIQGGKTLSVSQLELQDSGTWTCTVLQNQKKVEFKIDIVVLA

SEQ ID NO: 2
KKVVLGKKGDTVELTCTASQKKNIQFHWKNSNQIKILGNQGSFLT

KGPSKLNDRVDSRRSLWDQGNFPLIIKNLKIEDSDTYICEVEDQK

EEVQLVVFGLTANSDTHLLQGQSLTLTLESPPGSSPSVQCRSPRG

KNIQGGKTLSVSQLELQDSGTWTCTVLQNQKKVEFKIDIVVLAF

SEQ ID NO: 3
KKVVLGKKGDTVELTCTASQKKSIQFHWKNSNQIKILGNQGSFLT

KGPSKLNDRADSRRSLWDQGNFPLIIKNLKIEDSDTYICEVEDQK

EEVQLLVFG

SEQ ID NO: 4
KKVVYGKKGDTVELTCTASQKKNIQFHWKNSNQIKILGNQGSFLT

KGPSKLNDRVDSRRSLWDQGNFPLIIKNLKPEDSDTYICEVEDQK

EEVQLVVVG

SEQ ID NO: 5
KKVVYGKVGDTVELTCTASQKKNIQFHWKNSNQIKILGNQGSFLT

KGPSKLNDRVDSRRSLWDQGNFPLIIKNLKPEDSDTYICEVEDQK

EEVQLVVVG
```

```
                                    SEQ ID NO: 6
KKVVYGKKGDTVELTCTASQKKNIQFHWKNSNQIKILGNQGSFLT

KGPSKLNDRVDSRRSLWDQGNFPLIIKNLKPEDSDTYICEVEDQK

QEVQLVVVG

SEQ ID NO: 7
KKVVYGKKGDTVELTCTASQKKNIQFHWKNSNQIKILGNQGSFLT

KGPSKLNDRVDSRRSLWDQGNFPLIIKNLKPEDSDTYICEVEDQK

HEVQLVVVG

SEQ ID NO: 8
KKVVYGKKGDTVELTCTASQKKNIQFHWKNSNQIKILGNQGSFLT

KGPSKLNDRVDSRRSLWDQGNFPLIIKNLKPEDSDTYICEVGDQK

EEVQLVVVG

SEQ ID NO: 9
KKVVYGKKGDTVELTCTASQKKNIQFHWKNSNQIKILGNQGSFLT

KGPSKLWDRVDSRRSLWDQGNFPLIIKNLKPEDSDTYICEVEDQK

EEVQLVVVG

SEQ ID NO: 10
KKVVYGKIGDTVELTCTASQKKNIQFHWKNSNQIKILGNQGSFLT

KGPSKLNDRVDSRRSLWDQGNFPLIIKNLKPEDSDTYICEVEDQK

EEVQLVVVG
```

```
                                    SEQ ID NO: 11
KKVVYGKCGDTVELTCTASQKKNIQFHWKNSNQIKILGNQGSFLT

KGPSKLNDRVDSRRSLWDQGNFPLIIKNLKPEDSDTYICEVEDQK

EEVQLVVVC
```

```
                                    SEQ ID NO: 12
KKVVYGKKGDCVELTCTASQKKNIQFHWKNSNQIKILGNQGSFLT

KGPSKLNDRVDSRRSLWDQGNFPLIICNLKPEDSDTYICEVEDQK

EEVQLVVVG
```

```
                                    SEQ ID NO: 13
KKVVYGKKGDTVCLTCTASQKKNIQFHWKNSNQIKILGNQGSFLT

KGPSKLNDRVDSRRSLWDQGNFPLCIKNLKPEDSDTYICEVEDQK

EEVQLVVVG
```

```
                                    SEQ ID NO: 14
KKVVYGKKGDTVELTCTASQKKNIQFCWKNSNQIKILCNQGSFLT

KGPSKLNDRVDSRRSLWDQGNFPLIIKNLKPEDSDTYICEVEDQK

EEVQLVVVG
```

```
                                    SEQ ID NO: 15
KKVVYGKKGDTVELTCTASQCKNIQFHWKNSNQIKILGNQGSFLT

KGPSKLNDRVDSRRSLWDQCNFPLIIKNLKPEDSDTYICEVEDQK

EEVQLVVVG
```

```
                                    SEQ ID NO: 16
KKVVYGKKGDTVELTCTASQKKNIEFHWKNSNQIKILGNQGSFLT

KGPSKLNDRVDSRRSLWDQGNFPLIIKNLKPEDSDTYICEVEDQK

EEVQLVVVG
```

```
                                    SEQ ID NO: 17
KKVVYGKKGDTVELTCTASQKKNIQFDWKNSNQIKILGNQGSFLT

KGPSKLNDRVDSRRSLWDQGNFPLIIKNLKPEDSDTYICEVEDQK

EEVQLVVVG
```

```
                                    SEQ ID NO: 18
KKVVYGKKGDTVELTCTASQKKNIQFHWKNSNQIKILGNQGSFLT

KGPSKLNDRVDSVRSLWDQGNFPLIIKNLKPEDSDTYICEVEDQK

EEVQLVVVG
```

```
                                    SEQ ID NO: 19
KKVVYGKKGDTVELTCTASQKKNIQFHWKNSNQIKILGNQGSFLT

KGPSKLNDRVDSNRSLWDQGNFPLIIKNLKPEDSDTYICEVEDQK

EEVQLVVVG
```

```
                                    SEQ ID NO: 20
KKVVYGKKGDTVELTCTASQKKNIQFHWKNSNQIKILGNQGSFLT

KGPSKLNDRVDSTRSLWDQGNFPLIIKNLKPEDSDTYICEVEDQK

EEVQLVVVG
```

```
                                    SEQ ID NO: 21
KKVVYGKKGDTVELTCTASQKKNIQFHWKNSNQIKILGNQGSFLT

KGPSKLNDRVDSRRSMWDQGNFPLIIKNLKPEDSDTYICEVEDQK

EEVQLVVVG
```

```
ACNSFWG                             SEQ ID NO: 22
```

```
SLSHCASYWNRGWTYHNPSLKS              SEQ ID NO: 23
```

```
FGGEVLRYTDWPKPAWVDL                 SEQ ID NO: 24
```

```
TGTSNNFVS                           SEQ ID NO: 25
```

```
DVNKRPS                             SEQ ID NO: 26
```

```
GSLVGNWDVI                          SEQ ID NO: 27
```

```
DSYWS                               SEQ ID NO: 28
```

```
YVHKSGDTNYSPSLKS                    SEQ ID NO: 29
```

```
TLHGRRIYGIVAFNEWFTYFYMDV            SEQ ID NO: 30
```

```
GEKSLGSRAVQ                         SEQ ID NO: 31
```

```
NNQDRPS                             SEQ ID NO: 32
```

```
HIWDSRVPTKWV                        SEQ ID NO: 33
```

```
SDHSWT                              SEQ ID NO: 34
```

```
DIHYNGATTYNPSLRS                    SEQ ID NO: 35
```

```
NAIRIYGVVALGEWFHYGMDV               SEQ ID NO: 36
```

```
SGAPLTSRFTY                         SEQ ID NO: 37
```

```
RSSQRSS                             SEQ ID NO: 38
```

```
QSSDTSDSYKM                         SEQ ID NO: 39
```

```
NYYWT                               SEQ ID NO: 40
```

```
YISDRESATYNPSLNS                    SEQ ID NO: 41
```

```
ARRGQRIYGVVSFGEFFYYYSMDV            SEQ ID NO: 42
```

```
GRQALGSRAVQ                         SEQ ID NO: 43
```

```
NNQDRPS                             SEQ ID NO: 44
```

```
HMWDSRSGFSWS                        SEQ ID NO: 45
```

```
GGEWGDKDYHWG                        SEQ ID NO: 46
```

```
SIHWRGTTHYKESLRR                    SEQ ID NO: 47
```

```
HRHHDVFMLVPIAGWFDV                  SEQ ID NO: 48
```

-continued

```
                                    SEQ ID NO: 49
RASQNINKNLA

SEQ ID NO: 50
ETYSKIA

SEQ ID NO: 51
QQYEEWPRT

SEQ ID NO: 52
DFYIH

SEQ ID NO: 53
WMNPQTGRTNTARNFQG

SEQ ID NO: 54
GGWISLYYDSSYYPNFDH

SEQ ID NO: 55
TGTKYDVGSHDLVS

SEQ ID NO: 56
EVNKRPS

SEQ ID NO: 57
CSFGGSATVV

SEQ ID NO: 58
QPQLQESGPTLVEASETLSLTCAVSGDSTAACNSFWGWVRQPPGK
GLEWVGSLSHCASYWNRGWTYHNPSLKSRLTLALDTPKNLVFLKL
NSVTAADTATYYCARFGGEVLRYTDWPKPAWVDLWGRGTLVTVSS

SEQ ID NO: 59
QSALTQPPSASGSPGQSITISCTGTSNNFVSWYQQHAGKAPKLVI
YDVNKRPSGVPDRFSGSKSGNTASLTVSGLQTDDEAVYYCGSLVG
NWDVIFGGGTKLTVL

SEQ ID NO: 60
QSALTQPPSASGSPGQSITISCTGTSNNYVSWYQQHAGKAPKLVI
YDVNKRPSGVPDRFSGSKSGNTASLTVSGLQTDDEAVYYCGSLVG
NWDVIFGGGTKLTVL

SEQ ID NO: 61
QPQLQESGPTLVEASETLSLTCAVSGDSTAACNSFWGWVRQPPGK
GLEWVGSLSHCASYWNRGWTYHNPSLKSRLTLALDTPKNLVFLKL
NSVTAADTATYYCARFGGEVLRYTDWPKPAWVDLWGRGTLVTVSS
ASTKGPSVFPLAPSSKSTSGGTAALGCLVKDYFPEPVTVSWNSGA
LTSGVHTFPAVLQSSGLYSLSSVVTVPSSSLGTQTYICNVNHKPS
NTKVDKKVEPKSCDKTHTCPPCPAPELLGGPSVFLFPPKPKDTLM
ISRTPEVTCVVVDVSHEDPEVKFNWYVDGVEVHNAKTKPREEQYN
STYRVVSVLTVLHQDWLNGKEYKCKVSNKALPAPIEKTISKAKGQ
PREPQVYTLPPSRDELTKNQVSLTCLVKGFYPSDIAVEWESNGQP
ENNYKTTPPVLDSDGSFFLYSKLTVDKSRWQQGNVFSCSVMHEAL
HNHYTQKSLSLSPGK

SEQ ID NO: 62
QPQLQESGPTLVEASETLSLTCAVSGDSTAACNSFWGWVRQPPGK
GLEWVGSLSHCASYWNRGWTYHNPSLKSRLTLALDTPKNLVFLKL
NSVTAADTATYYCARFGGEVLRYTDWPKPAWVDLWGRGTLVTVSS
ASTKGPSVFPLAPSSKSTSGGTAALGCLVKDYFPEPVTVSWNSGA
```

-continued

```
LTSGVHTFPAVLQSSGLYSLSSWVTVPSSSLGTQTYICNVNHKPS
NTKVDKKVEPKSCDKTHTCPPCPAPELLGGPSVFLFPPKPKDTLM
ISRTPEVTCVVVDVSHEDPEVKFNWYVDGVEVHNAKTKPREEQYN
STYRVVSVLTVLHQDWLNGKEYKCKVSNKALPAPIEKTISKAKGQ
PREPQVYTLPPSRDELTKNQVSLTCLVKGFYPSDIAVEWESNGQP
ENNYKTTPPVLDSDGSFFLYSKLTVDKSRWQQGNVFSCSVLHEAL
HSHYTQKSLSLSPGK

SEQ ID NO: 63
QSALTQPPSASGSPGQSITISCTGTSNNFVSWYQQHAGKAPKLVI
YDVNKRPSGVPDRFSGSKSGNTASLTVSGLQTDDEAVYYCGSLVG
NWDVIFGGGTKLTVLGQPKAAPSVTLFPPSSEELQANKATLVCLI
SDFYPGAVTVAWKADSSPVKAGVETTTPSKQSNNKYAASSYLSLT
PEQWKSHRSYSCQVTHEGSTVEKTVAPTECS

SEQ ID NO: 64
QSALTQPPSASGSPGQSITISCTGTSNNYVSWYQQHAGKAPKLVI
YDVNKRPSGVPDRFSGSKSGNTASLTVSGLQTDDEAVYYCGSLVG
NWDVIFGGGTKLTVLGQPKAAPSVTLFPPSSEELQANKATLVCLI
SDFYPGAVTVAWKADSSPVKAGVETTTPSKQSNNKYAASSYLSLT
PEQWKSHRSYSCQVTHEGSTVEKTVAPTECS

SEQ ID NO: 65
QMQLQESGPGLVKPSETLSLTCSVSGASISDSYWSWIRRSPGKGL
EWIGYVHKSGDTNYSPSLKSRVNLSLDTSKNQVSLSLVAATAADS
GKYYCARTLHGRRIYGIVAFNEWFTYFYMDVWGNGTQVTVSS

SEQ ID NO: 66
SDISVAPGETARISCGEKSLGSRAVQWYQHRAGQAPSLIIYNNQD
RPSGIPERFSGSPDSPFGTTATLTITSVEAGDEADYYCHIWDSRV
PTKWVFGGGTTLTVL

SEQ ID NO: 67
QMQLQESGPGLVKPSETLSLTCSVSGASISDSYWSWIRRSPGKGL
EWIGYVHKSGDTNYSPSLKSRVNLSLDTSKNQVSLSLVAATAADS
GKYYCARTLHGRRIYGIVAFNEWFTYFYMDVWGNGTQVTVSSAST
KGPSVFPLAPSSKSTSGGTAALGCLVKDYFPEPVTVSWNSGALTS
GVHTFPAVLQSSGLYSLSSVVTVPSSSLGTQTYICNVNHKPSNTK
VDKRVEPKSCDKTHTCPPCPAPELLGGPSVFLFPPKPKDTLMISR
TPEVTCVVVDVSHEDPEVKFNWYVDGVEVHNAKTKPREEQYNSTY
RVVSVLTVLHQDWLNGKEYKCKVSNKALPAPIEKTISKAKGQPRE
PQVYTLPPSRDELTKNQVSLTCLVKGFYPSDIAVEWESNGQPENN
YKTTPPVLDSDGSFFLYSKLTVDKSRWQQGNVFSCSVMHEALHNH
YTQKSLSLSPGK

SEQ ID NO: 68
QMQLQESGPGLVKPSETLSLTCSVSGASISDSYWSWIRRSPGKGL
EWIGYVHKSGDTNYSPSLKSRVNLSLDTSKNQVSLSLVAATAADS
GKYYCARTLHGRRIYGIVAFNEWFTYFYMDVWGNGTQVTVSSAST
```

-continued

KGPSVFPLAPSSKSTSGGTAALGCLVKDYFPEPVTVSWNSGALTS

GVHTFPAVLQSSGLYSLSSVVTVPSSSLGTQTYICNVNHKPSNTK

VDKRVEPKSCDKTHTCPPCPAPELLGGPSVFLFPPKPKDTLMISR

TPEVTCVVVDVSHEDPEVKFNWYVDGVEVHNAKTKPREEQYNSTY

RVVSVLTVLHQDWLNGKEYKCKVSNKALPAPIEKTISKAKGQPRE

PQVYTLPPSRDELTKNQVSLTCLVKGFYPSDIAVEWESNGQPENN

YKTTPPVLDSDGSFFLYSKLTVDKSRWQQGNVFSCSVLHEALHSH

YTQKSLSLSPGK

SEQ ID NO: 69

SDISVAPGETARISCGEKSLGSRAVQWYQHRAGQAPSLIIYNNQD

RPSGIPERFSGSPDSPFGTTATLTITSVEAGDEADYYCHIWDSRV

PTKWVFGGGTTLTVLGQPKAAPSVTLFPPSSEELQANKATLVCLI

SDFYPGAVTVAWKADSSPVKAGVETTTPSKQSNNKYAASSYLSLT

PEQWKSHKSYSCQVTHEGSTVEKTVAPTECS

SEQ ID NO: 70

QVQLRESGPGLVKPSETLSLSCTVSNDSRPSDHSWTWVRQSPGKA

LEWIGDIHYNGATTYNPSLRSRVRIELDQSIPRFSLKMTSMTAAD

TGMYYCARNAIRIYGVVALGEWFHYGMDVWGQGTAVTVSS

SEQ ID NO: 71

SSELTQPPSVSVSPGQTARITCSGAPLTSRFTYWYRQKPGQAPVL

IISRSSQRSSGWSGRFSASWSGTTVTLTIRGVQADDEADYYCQSS

DTSDSYKMFGGGTKLTVL

SEQ ID NO: 72

QVQLRESGPGLVKPSETLSLSCTVSNDSRPSDHSWTWVRQSPGKA

LEWIGDIHYNGATTYNPSLRSRVRIELDQSIPRFSLKMTSMTAAD

TGMYYCARNAIRIYGVVALGEWFHYGMDVWGQGTAVTVSSASTKG

PSVFPLAPSSKSTSGGTAALGCLVKDYFPEPVTVSWNSGALTSGV

HTFPAVLQSSGLYSLSSVVTVPSSSLGTQTYICNVNHKPSNTKVD

KRVEPKSCDKTHTCPPCPAPELLGGPSVFLFPPKPKDTLMISRTP

EVTCVVVDVSHEDPEVKFNWYVDGVEVHNAKTKPREEQYNSTYRV

VSVLTVLHQDWLNGKEYKCKVSNKALPAPIEKTISKAKGQPREPQ

VYTLPPSRDELTKNQVSLTCLVKGFYPSDIAVEWESNGQPENNYK

TTPPVLDSDGSFFLYSKLTVDKSRWQQGNVFSCSVMHEALHNHYT

QKSLSLSPGK

SEQ ID NO: 73

QVQLRESGPGLVKPSETLSLSCTVSNDSRPSDHSWTWVRQSPGKA

LEWIGDIHYNGATTYNPSLRSRVRIELDQSIPRFSLKMTSMTAAD

TGMYYCARNAIRIYGVVALGEWFHYGMDVWGQGTAVTVSSASTKG

PSVFPLAPSSKSTSGGTAALGCLVKDYFPEPVTVSWNSGALTSGV

HTFPAVLQSSGLYSLSSVVTVPSSSLGTQTYICNVNHKPSNTKVD

KRVEPKSCDKTHTCPPCPAPELLGGPSVFLFPPKPKDTLMISRTP

EVTCVVVDVSHEDPEVKFNWYVDGVEVHNAKTKPREEQYNSTYRV

VSVLTVLHQDWLNGKEYKCKVSNKALPAPIEKTISKAKGQPREPQ

-continued

VYTLPPSRDELTKNQVSLTCLVKGFYPSDIAVEWESNGQPENNYK

TTPPVLDSDGSFFLYSKLTVDKSRWQQGNVFSCSVLHEALHSHYT

QKSLSLSPGK

SEQ ID NO: 74

SSELTQPPSVSVSPGQTARITCSGAPLTSRFTYWYRQKPGQAPVL

IISRSSQRSSGWSGRFSASWSGTTVTLTIRGVQADDEADYYCQSS

DTSDSYKMFGGGTKLTVLGQPAAAPSVTLFPPSSEELQANKATLV

CLISDFYPGAVTVAWKADSSPVKAGVETTTPSKQSNNKYAASSYL

SLTPEQWKSHKSYSCQVTHEGSTVEKTVAPTEC

SEQ ID NO: 75

QVQLQESGPGLVKPSETLSVTCSVSGDSMNNYYWTWIRQSPGKGL

EWIGYISDRESATYNPSLNSRVVISRDTSKNQLSLKLNSVTPADT

AVYYCATARRGQRIYGVVSFGEFFYYYSMDVWGKGTTVTVSS

SEQ ID NO: 76

SYVRPLSVALGETARISCGRQALGSRAVQWYQHRPGQAPILLIYN

NQDRPSGIPERFSGTPDINFGTRATLTISGVEAGDEADYYCHMWD

SRSGFSWSFGGATRLTVL

SEQ ID NO: 77

QVQLQESGPGLVKPSETLSVTCSVSGDSMNNYYWTWIRQSPGKGL

EWIGYISDRESATYNPSLNSRVVISRDTSKNQLSLKLNSVTPADT

AVYYCATARRGQRIYGVVSFGEFFYYYSMDVWGKGTTVTVSSAST

KGPSVFPLAPSSKSTSGGTAALGCLVKDYFPEPVTVSWNSGALTS

GVHTFPAVLQSSGLYSLSSVVTVPSSSLGTQTYICNVNHKPSNTK

VDKRVEPKSCDKTHTCPPCPAPELLGGPSVFLFPPKPKDTLMISR

TPEVTCVVVDVSHEDPEVKFNWYVDGVEVHNAKTKPREEQYNSTY

RVVSVLTVLHQDWLNGKEYKCKVSNKALPAPIEKTISKAKGQPRE

PQVYTLPPSRDELTKNQVSLTCLVKGFYPSDIAVEWESNGQPENN

YKTTPPVLDSDGSFFLYSKLTVDKSRWQQGNVFSCSVMHEALHNH

YTQKSLSLSPGK

SEQ ID NO: 78

QVQLQESGPGLVKPSETLSVTCSVSGDSMNNYYWTWIRQSPGKGL

EWIGYISDRESATYNPSLNSRVVISRDTSKNQLSLKLNSVTPADT

AVYYCATARRGQRIYGVVSFGEFFYYYSMDVWGKGTTVTVSSAST

KGPSVFPLAPSSKSTSGGTAALGCLVKDYFPEPVTVSWNSGALTS

GVHTFPAVLQSSGLYSLSSVVTVPSSSLGTQTYICNVNHKPSNTK

VDKRVEPKSCDKTHTCPPCPAPELLGGPSVFLFPPKPKDTLMISR

TPEVTCVVVDVSHEDPEVKFNWYVDGVEVHNAKTKPREEQYNSTY

RVVSVLTVLHQDWLNGKEYKCKVSNKALPAPIEKTISKAKGQPRE

PQVYTLPPSRDELTKNQVSLTCLVKGFYPSDIAVEWESNGQPENN

YKTTPPVLDSDGSFFLYSKLTVDKSRWQQGNVFSCSVLHEALHSH

YTQKSLSLSPGK

SEQ ID NO: 79

SYVRPLSVALGETARISCGRQALGSRAVQWYQHRPGQAPILLIYN

NQDRPSGIPERFSGTPDINFGTRATLTISGVEAGDEADYYCHMWD

SRSGFSWSFGGATRLTVLGQPKAAPSVTLFPPSSEELQANKATLV

CLISDFYPGAVTVAWKADSSPVKAGVETTTPSKQSNNKYAASSYL

SLTPEQWKSHRSYSCQVTHEGSTVEKTVAPTECS

SEQ ID NO: 80

QLQMQESGPGLVKPSETLSLSCTVSGDSIRGGEWGDKDYHWGWVR

HSAGKGLEWIGSIHWRGTTHYKESLRRRVSMSIDTSRNWFSLRLA

SVTAADTAVYFCARHRHHDVFMLVPIAGWFDVWGPGVQVTVSS

SEQ ID NO: 81

EIVMTQSPDTLSVSPGETVTLSCRASQNINKNLAWYQYKPGQSPR

LVIFETYSKIAAFPARFVASGSGTEFTLTINNMQSEDVAVYYCQQ

YEEWPRTFGQGTKVDIK

SEQ ID NO: 82

QLQMQESGPGLVKPSETLSLSCTVSGDSIRGGEWGDKDYHWGWVR

HSAGKGLEWIGSIHWRGTTHYKESLRRRVSMSIDTSRNWFSLRLA

SVTAADTAVYFCARHRHHDVFMLVPIAGWFDVWGPGVQVTVSSAS

TKGPSVFPLAPSSKSTSGGTAALGCLVKDYFPEPVTVSWNSGALT

SGVHTFPAVLQSSGLYSLSSVVTVPSSSLGTQTYICNVNHKPSNT

KVDKRVEPKSCDKTHTCPPCPAPELLGGPSVFLFPPKPKDTLMIS

RTPEVTCVVVDVSHEDPEVKFNWYVDGVEVHNAKTKPREEQYNST

YRVVSVLTVLHQDWLNGKEYKCKVSNKALPAPIEKTISKAKGQPR

EPQVYTLPPSRDELTKNQVSLTCLVKGFYPSDIAVEWESNGQPEN

NYKTTPPVLDSDGSFFLYSKLTVDKSRWQQGNVFSCSVMHEALHN

HYTQKSLSLSPGK

SEQ ID NO: 83

QLQMQESGPGLVKPSETLSLSCTVSGDSIRGGEWGDKDYHWGWVR

HSAGKGLEWIGSIHWRGTTHYKESLRRRVSMSIDTSRNWFSLRLA

SVTAADTAVYFCARHRHHDVFMLVPIAGWFDVWGPGVQVTVSSAS

TKGPSVFPLAPSSKSTSGGTAALGCLVKDYFPEPVTVSWNSGALT

SGVHTFPAVLQSSGLYSLSSVVTVPSSSLGTQTYICNVNHKPSNT

KVDKRVEPKSCDKTHTCPPCPAPELLGGPSVFLFPPKPKDTLMIS

RTPEVTCVVVDVSHEDPEVKFNWYVDGVEVHNAKTKPREEQYNST

YRVVSVLTVLHQDWLNGKEYKCKVSNKALPAPIEKTISKAKGQPR

EPQVYTLPPSRDELTKNQVSLTCLVKGFYPSDIAVEWESNGQPEN

NYKTTPPVLDSDGSFFLYSKLTVDKSRWQQGNVFSCSVLHEALHS

HYTQKSLSLSPGK

SEQ ID NO: 84

EIVMTQSPDTLSVSPGETVTLSCRASQNINKNLAWYQYKPGQSPR

LVIFETYSKIAAFPARFVASGSGTEFTLTINNMQSEDVAVYYCQQ

YEEWPRTFGQGTKVDIKRTVAAPSVFIFPPSDEQLKSGTASVVCL

LNNFYPREAKVQWKVDNALQSGNSQESVTEQDSKDSTYSLSSTLT

LSKADYEKHKVYACEVTHQGLSSPVTKSFNRGEC

SEQ ID NO: 85

QVQLVQSGAQMKNPGASVKVSCAPSGYTFTDFYIHWLRQAPGQGL

QWMGWMNPQTGRTNTARNFQGRVTMTRDTSIGTAYMELRSLTSDD

TAIYYCTTGGWISLYYDSSYYPNFDHWGQGTLLLTVSS

SEQ ID NO: 86

QSALTQPASVSGSPGQSITISCTGTKYDVGSHDLVSWYQQYPGKV

PKYMIYEVNKRPSGVSNRFSGSKSGNTASLTISGLRAEDEADYYC

CSFGGSATVVCGGGTKVTVL

SEQ ID NO: 87

QVQLVQSGAQMKNPGASVKVSCAPSGYTFTDFYIHWLRQAPGQGL

QWMGWMNPQTGRTNTARNFQGRVTMTRDTSIGTAYMELRSLTSDD

TAIYYCTTGGWISLYYDSSYYPNFDHWGQGTLLLTVSSASTKGPSV

FPLAPSSKSTSGGTAALGCLVKDYFPEPVTVSWNSGALTSGVHTF

PAVLQSSGLYSLSSVVTVPSSSLGTQTYICNVNHKPSNTKVDKKV

EPKSCDKTHTCPPCPAPELLGGPSVFLFPPKPKDTLMISRTPEVT

CVVVDVSHEDPEVKFNWYVDGVEVHNAKTKPREEQYNSTYRVVSVL

TVLHQDWLNGKEYKCKVSNKALPAPIEKTISKAKGQPREPQVYTL

PPSRDELTKNQVSLTCLVKGFYPSDIAVEWESNGQPENNYKTTPP

VLDSDGSFFLYSKLTVDKSRWQQGNVFSCSVMHEALHNHYTQKSL

SLSPGK

SEQ ID NO: 88

QVQLVQSGAQMKNPGASVKVSCAPSGYTFTDFYIHWLRQAPGQGL

QWMGWMNPQTGRTNTARNFQGRVTMTRDTSIGTAYMELRSLTSDD

TAIYYCTTGGWISLYYDSSYYPNFDHWGQGTLLLTVSSASTKGPSV

FPLAPSSKSTSGGTAALGCLVKDYFPEPVTVSWNSGALTSGVHTF

PAVLQSSGLYSLSSVVTVPSSSLGTQTYICNVNHKPSNTKVDKKV

EPKSCDKTHTCPPCPAPELLGGPSVFLFPPKPKDTLMISRTPEVT

CVVVDVSHEDPEVKFNWYVDGVEVHNAKTKPREEQYNSTYRVVSV

LTVLHQDWLNGKEYKCKVSNKALPAPIEKTISKAKGQPREPQVYT

LPPSRDELTKNQVSLTCLVKGFYPSDIAVEWESNGQPENNYKTTP

PVLDSDGSFFLYSKLTVDKSRWQQGNVFSCSVLHEALHSHYTQKS

LSLSPGK

SEQ ID NO: 89

QSALTQPASVSGSPGQSITISCTGTKYDVGSHDLVSWYQQYPGKV

PKYMIYEVNKRPSGVSNRFSGSKSGNTASLTISGLRAEDEADYYC

CSFGGSATVVCGGGTKVTVLGQPKAAPSVTLFPPSSEELQANKAT

LVCLISDFYPGAVTVAWKADSSPVKAGVETTTPSKQSNNKYAASS

YLSLTPEQWKSHRSYSCQVTHEGSTVEKTVAPTECS

SEQ ID NO: 90

GGGGS

SEQ ID NO: 91

GGGGSGGGGS

SEQ ID NO: 92

GGGGSGGGGSGGGGS

-continued

SEQ ID NO: 93
GGGGSGGGGSGGGGSGGGGS

SEQ ID NO: 94
GGGGSGGGGSGGGGSGGGGSGGGGS

SEQ ID NO: 95
GGGGSGGGGSGGGGSGGGGSGGGGSGGGGS

SEQ ID NO: 96
KKVVLGKKGDTVELTCTASQKKNIQFHWKNSNQIKILGNQGSFLT

KGPSKLNDRVDSRRSLWDQGNFPLIIKNLKIEDSDTYICEVEDQK

EEVQLVVFGLTANSDTHLLQGQSLTLTLESPPGSSPSVQCRSPRG

KNIQGGKTLSVSQLELQDSGTWTCTVLQNQKKVEFKIDIVVLAFQ

PQLQESGPTLVEASETLSLTCAVSGDSTAACNSFWGWVRQPPGKG

LEWVGSLSHCASYWNRGWTYHNPSLKSRLTLALDTPKNLVFLKLN

SVTAADTATYYCARFGGEVLRYTDWPKPAWVDLWGRGTLVTVSSA

STKGPSVFPLAPSSKSTSGGTAALGCLVKDYFPEPVTVSWNSGAL

TSGVHTFPAVLQSSGLYSLSSVVTVPSSSLGTQTYICNVNHKPSN

TKVDKKVEPKSCDKTHTCPPCPAPELLGGPSVFLFPPKPKDTLMI

SRTPEVTCVVVDVSHEDPEVKFNWYVDGVEVHNAKTKPREEQYNS

TYRVVSVLTVLHQDWLNGKEYKCKVSNKALPAPIEKTISKAKGQP

REPQVYTLPPSRDELTKNQVSLTCLVKGFYPSDIAVEWESNGQPE

NNYKTTPPVLDSDGSFFLYSKLTVDKSRWQQGNVFSCSVLHEALH

SHYTQKSLSLSPGK

SEQ ID NO: 97
KKVVLGKKGDTVELTCTASQKKNIQFHWKNSNQIKILGNQGSFLT

KGPSKLNDRVDSRRSLWDQGNFPLIIKNLKIEDSDTYICEVEDQK

EEVQLVVFGLTANSDTHLLQGQSLTLTLESPPGSSPSVQCRSPRG

KNIQGGKTLSVSQLELQDSGTWTCTVLQNQKKVEFKIDIVVLAFG

GGGSQPQLQESGPTLVEASETLSLTCAVSGDSTAACNSFWGWVRQ

PPGKGLEWVGSLSHCASYWNRGWTYHNPSLKSRLTLALDTPKNLV

FLKLNSVTAADTATYYCARFGGEVLRYTDWPKPAWVDLWGRGTLV

TVSSASTKGPSVFPLAPSSKSTSGGTAALGCLVKDYFPEPVTVSW

NSGALTSGVHTFPAVLQSSGLYSLSSVVTVPSSSLGTQTYICNVN

HKPSNTKVDKKVEPKSCDKTHTCPPCPAPELLGGPSVFLFPPKPK

DTLMISRTPEVTCVVVDVSHEDPEVKFNWYVDGVEVHNAKTKPRE

EQYNSTYRVVSVLTVLHQDWLNGKEYKCKVSNKALPAPIEKTISK

AKGQPREPQVYTLPPSRDELTKNQVSLTCLVKGFYPSDIAVEWES

NGQPENNYKTTPPVLDSDGSFFLYSKLTVDKSRWQQGNVFSCSVL

HEALHSHYTQKSLSLSPGK

SEQ ID NO: 98
KKVVLGKKGDTVELTCTASQKKNIQFHWKNSNQIKILGNQGSFLT

KGPSKLNDRVDSRRSLWDQGNFPLIIKNLKIEDSDTYICEVEDQK

EEVQLVVFGLTANSDTHLLQGQSLTLTLESPPGSSPSVQCRSPRG

KNIQGGKTLSVSQLELQDSGTWTCTVLQNQKKVEFKIDIVVLAFG

GGGSGGGGSQPQLQESGPTLVEASETLSLTCAVSGDSTAACNSFW

-continued

GWVRQPPGKGLEWVGSLSHCASYWNRGWTYHNPSLKSRLTLALDT

PKNLVFLKLNSVTAADTATYYCARFGGEVLRYTDWPKPAWVDLWG

RGTLVTVSSASTKGPSVFPLAPSSKSTSGGTAALGCLVKDYFPEP

VTVSWNSGALTSGVHTFPAVLQSSGLYSLSSVVTVPSSSLGTQTY

ICNVNHKPSNTKVDKKVEPKSCDKTHTCPPCPAPELLGGPSVFLF

PPKPKDTLMISRTPEVTCVVVDVSHEDPEVKFNWYVDGVEVHNAK

TKPREEQYNSTYRVVSVLTVLHQDWLNGKEYKCKVSNKALPAPIE

KTISKAKGQPREPQVYTLPPSRDELTKNQVSLTCLVKGFYPSDIA

VEWESNGQPENNYKTTPPVLDSDGSFFLYSKLTVDKSRWQQGNVF

SCSVLHEALHSHYTQKSLSLSPGK

SEQ ID NO: 99
KKVVLGKKGDTVELTCTASQKKNIQFHWKNSNQIKILGNQGSFLT

KGPSKLNDRVDSRRSLWDQGNFPLIIKNLKIEDSDTYICEVEDQK

EEVQLVVFGLTANSDTHLLQGQSLTLTLESPPGSSPSVQCRSPRG

KNIQGGKTLSVSQLELQDSGTWTCTVLQNQKKVEFKIDIVVLAFG

GGGSGGGGSGGGGSQPQLQESGPTLVEASETLSLTCAVSGDSTAA

CNSFWGWVRQPPGKGLEWVGSLSHCASYWNRGWTYHNPSLKSRLT

LALDTPKNLVFLKLNSVTAADTATYYCARFGGEVLRYTDWPKPAW

VDLWGRGTLVTVSSASTKGPSVFPLAPSSKSTSGGTAALGCLVKD

YFPEPVTVSWNSGALTSGVHTFPAVLQSSGLYSLSSVVTVPSSSL

GTQTYICNVNHKPSNTKVDKKVEPKSCDKTHTCPPCPAPELLGGP

SVFLFPPKPKDTLMISRTPEVTCVVVDVSHEDPEVKFNWYVDGVE

VHNAKTKPREEQYNSTYRVVSVLTVLHQDWLNGKEYKCKVSNKAL

PAPIEKTISKAKGQPREPQVYTLPPSRDELTKNQVSLTCLVKGFY

PSDIAVEWESNGQPENNYKTTPPVLDSDGSFFLYSKLTVDKSRWQ

QGNVFSCSVLHEALHSHYTQKSLSLSPGK

SEQ ID NO: 100
KKVVLGKKGDTVELTCTASQKKNIQFHWKNSNQIKILGNQGSFLT

KGPSKLNDRVDSRRSLWDQGNFPLIIKNLKIEDSDTYICEVEDQK

EEVQLVVFGLTANSDTHLLQGQSLTLTLESPPGSSPSVQCRSPRG

KNIQGGKTLSVSQLELQDSGTWTCTVLQNQKKVEFKIDIVVLAFG

GGGSGGGGSGGGGSGGGGSQPQLQESGPTLVEASETLSLTCAVSG

DSTAACNSFWGWVRQPPGKGLEWVGSLSHCASYWNRGWTYHNPSL

KSRLTLALDTPKNLVFLKLNSVTAADTATYYCARFGGEVLRYTDW

PKPAWVDLWGRGTLVTVSSASTKGPSVFPLAPSSKSTSGGTAALG

CLVKDYFPEPVTVSWNSGALTSGVHTFPAVLQSSGLYSLSSVVTV

PSSSLGTQTYICNVNHKPSNTKVDKKVEPKSCDKTHTCPPCPAPE

LLGGPSVFLFPPKPKDTLMISRTPEVTCVVVDVSHEDPEVKFNWY

VDGVEVHNAKTKPREEQYNSTYRVVSVLTVLHQDWLNGKEYKCKV

SNKALPAPIEKTISKAKGQPREPQVYTLPPSRDELTKNQVSLTCL

VKGFYPSDIAVEWESNGQPENNYKTTPPVLDSDGSFFLYSKLTVD

KSRWQQGNVFSCSVLHEALHSHYTQKSLSLSPGK

SEQ ID NO: 101
KKVVYGKKGDTVELTCTASQKKNIQFHWKNSNQIKILGNQGSFLT

KGPSKLNDRVDSRRSLWDQGNFPLIIKNLKPEDSDTYICEVEDQK

EEVQLVVVGQPQLQESGPTLVEASETLSLTCAVSGDSTAACNSFW

GWVRQPPGKGLEWVGSLSHCASYWNRGWTYHNPSLKSRLTLALDT

PKNLVFLKLNSVTAADTATYYCARFGGEVLRYTDWPKPAWVDLWG

RGTLVTVSSASTKGPSVFPLAPSSKSTSGGTAALGCLVKDYFPEP

VTVSWNSGALTSGVHTFPAVLQSSGLYSLSSVVTVPSSSLGTQTY

ICNVNHKPSNTKVDKKVEPKSCDKTHTCPPCPAPELLGGPSVFLF

PPKPKDTLMISRTPEVTCVVVDVSHEDPEVKFNWYVDGVEVHNAK

TKPREEQYNSTYRVVSVLTVLHQDWLNGKEYKCKVSNKALPAPIE

KTISKAKGQPREPQVYTLPPSRDELTKNQVSLTCLVKGFYPSDIA

VEWESNGQPENNYKTTPPVLDSDGSFFLYSKLTVDKSRWQQGNVF

SCSVLHEALHSHYTQKSLSLSPGK

SEQ ID NO: 102
KKVVYGKKGDTVELTCTASQKKNIQFHWKNSNQIKILGNQGSFLT

KGPSKLNDRVDSRRSLWDQGNFPLIIKNLKPEDSDTYICEVEDQK

EEVQLVVVGGGGGSQPQLQESGPTLVEASETLSLTCAVSGDSTAA

CNSFWGWVRQPPGKGLEWVGSLSHCASYWNRGWTYHNPSLKSRLT

LALDTPKNLVFLKLNSVTAADTATYYCARFGGEVLRYTDWPKPAW

VDLWGRGTLVTVSSASTKGPSVFPLAPSSKSTSGGTAALGCLVKD

YFPEPVTVSWNSGALTSGVHTFPAVLQSSGLYSLSSVVTVPSSSL

GTQTYICNVNHKPSNTKVDKKVEPKSCDKTHTCPPCPAPELLGGP

SVFLFPPKPKDTLMISRTPEVTCVVVDVSHEDPEVKFNWYVDGVE

VHNAKTKPREEQYNSTYRVVSVLTVLHQDWLNGKEYKCKVSNKAL

PAPIEKTISKAKGQPREPQVYTLPPSRDELTKNQVSLTCLVKGFY

PSDIAVEWESNGQPENNYKTTPPVLDSDGSFFLYSKLTVDKSRWQ

QGNVFSCSVLHEALHSHYTQKSLSLSPGK

SEQ ID NO: 103
KKVVYGKKGDTVELTCTASQKKNIQFHWKNSNQIKILGNQGSFLT

KGPSKLNDRVDSRRSLWDQGNFPLIIKNLKPEDSDTYICEVEDQK

EEVQLVVVGGGGGSGGGGSQPQLQESGPTLVEASETLSLTCAVSG

DSTAACNSFWGWVRQPPGKGLEWVGSLSHCASYWNRGWTYHNPSL

KSRLTLALDTPKNLVFLKLNSVTAADTATYYCARFGGEVLRYTDW

PKPAWVDLWGRGTLVTVSSASTKGPSVFPLAPSSKSTSGGTAALG

CLVKDYFPEPVTVSWNSGALTSGVHTFPAVLQSSGLYSLSSVVTV

PSSSLGTQTYICNVNHKPSNTKVDKKVEPKSCDKTHTCPPCPAPE

LLGGPSVFLFPPKPKDTLMISRTPEVTCVVVDVSHEDPEVKFNWY

VDGVEVHNAKTKPREEQYNSTYRVVSVLTVLHQDWLNGKEYKCKV

SNKALPAPIEKTISKAKGQPREPQVYTLPPSRDELTKNQVSLTCL

VKGFYPSDIAVEWESNGQPENNYKTTPPVLDSDGSFFLYSKLTVD

KSRWQQGNVFSCSVLHEALHSHYTQKSLSLSPGK

SEQ ID NO: 104
KKVVYGKKGDTVELTCTASQKKNIQFHWKNSNQIKILGNQGSFLT

KGPSKLNDRVDSRRSLWDQGNFPLIIKNLKPEDSDTYICEVEDQK

EEVQLVVVGGGGGSGGGGSGGGGSQPQLQESGPTLVEASETLSLT

CAVSGDSTAACNSFWGWVRQPPGKGLEWVGSLSHCASYWNRGWTY

HNPSLKSRLTLALDTPKNLVFLKLNSVTAADTATYYCARFGGEVL

RYTDWPKPAWVDLWGRGTLVTVSSASTKGPSVFPLAPSSKSTSGG

TAALGCLVKDYFPEPVTVSWNSGALTSGVHTFPAVLQSSGLYSLS

SVVTVPSSSLGTQTYICNVNHKPSNTKVDKKVEPKSCDKTHTCPP

CPAPELLGGPSVFLFPPKPKDTLMISRTPEVTCVVVDVSHEDPEV

KFNWYVDGVEVHNAKTKPREEQYNSTYRVVSVLTVLHQDWLNGKE

YKCKVSNKALPAPIEKTISKAKGQPREPQVYTLPPSRDELTKNQV

SLTCLVKGFYPSDIAVEWESNGQPENNYKTTPPVLDSDGSFFLYS

KLTVDKSRWQQGNVFSCSVLHEALHSHYTQKSLSLSPGK

SEQ ID NO: 105
KKVVYGKKGDTVELTCTASQKKNIQFHWKNSNQIKILGNQGSFLT

KGPSKLNDRVDSRRSLWDQGNFPLIIKNLKPEDSDTYICEVEDQK

EEVQLVVVGGGGGSGGGGSGGGGSGGGGSQPQLQESGPTLVEASE

TLSLTCAVSGDSTAACNSFWGWVRQPPGKGLEWVGSLSHCASYWN

RGWTYHNPSLKSRLTLALDTPKNLVFLKLNSVTAADTATYYCARF

GGEVLRYTDWPKPAWVDLWGRGTLVTVSSASTKGPSVFPLAPSSK

STSGGTAALGCLVKDYFPEPVTVSWNSGALTSGVHTFPAVLQSSG

LYSLSSVVTVPSSSLGTQTYICNVNHKPSNTKVDKKVEPKSCDKT

HTCPPCPAPELLGGPSVFLFPPKPKDTLMISRTPEVTCVVVDVSH

EDPEVKFNWYVDGVEVHNAKTKPREEQYNSTYRVVSVLTVLHQDW

LNGKEYKCKVSNKALPAPIEKTISKAKGQPREPQVYTLPPSRDEL

TKNQVSLTCLVKGFYPSDIAVEWESNGQPENNYKTTPPVLDSDGS

FFLYSKLTVDKSRWQQGNVFSCSVLHEALHSHYTQKSLSLSPGK

SEQ ID NO: 106
KKVVYGKKGDTVELTCTASQKKNIQFHWKNSNQIKILGNQGSFLT

KGPSKLNDRVDSRRSLWDQGNFPLIIKNLKPEDSDTYICEVEDQK

EEVQLVVVGGGGGSGGGGSGGGGSGGGGSGGGGSQPQLQESGPTL

VEASETLSLTCAVSGDSTAACNSFWGWVRQPPGKGLEWVGSLSHC

ASYWNRGWTYHNPSLKSRLTLALDTPKNLVFLKLNSVTAADTATY

YCARFGGEVLRYTDWPKPAWVDLWGRGTLVTVSSASTKGPSVFPL

APSSKSTSGGTAALGCLVKDYFPEPVTVSWNSGALTSGVHTFPAV

LQSSGLYSLSSVVTVPSSSLGTQTYICNVNHKPSNTKVDKKVEPK

SCDKTHTCPPCPAPELLGGPSVFLEPPKPKDTLMISRTPEVTCVV

DVSHEDPEVKFNWYVDGVEVHNAKTKPREEQYNSTYRVVSVLTVL

HQDWLNGKEYKCKVSNKALPAPIEKTISKAKGQPREPQVYTLPPS

-continued

RDELTKNQVSLTCLVKGFYPSDIAVEWESNGQPENNYKTTPPVLD

SDGSFFLYSKLTVDKSRWQQGNVFSCSVLHEALHSHYTQKSLSLS

PGK

SEQ ID NO: 107
KKVVYGKKGDTVELTCTASQKKNIQFHWKNSNQIKILGNQGSFLT

KGPSKLNDRVDSRRSLWDQGNFPLIIKNLKPEDSDTYICEVEDQK

EEVQLVVVGGGGGSGGGGSGGGGSGGGGSGGGGSGGGGSQPQLQE

SGPTLVEASETLSLTCAVSGDSTAACNSFWGWVRQPPGKGLEWVG

SLSHCASYWNRGWTYHNPSLKSRLTLALDTPKNLVFLKLNSVTAA

DTATYYCARFGGEVLRYTDWPKPAWVDLWGRGTLVTVSSASTKGP

SVFPLAPSSKSTSGGTAALGCLVKDYFPEPVTVSWNSGALTSGVH

TFPAVLQSSGLYSLSSVVTVPSSSLGTQTYICNVNHKPSNTKVDK

KVEPKSCDKTHTCPPCPAPELLGGPSVFLFPPKPKDTLMISRTPE

VTCVVVDVSHEDPEVKFNWYVDGVEVHNAKTKPREEQYNSTYRVV

SVLTVLHQDWLNGKEYKCKVSNKALPAPIEKTISKAKGQPREPQV

YTLPPSRDELTKNQVSLTCLVKGFYPSDIAVEWESNGQPENNYKT

TPPVLDSDGSFFLYSKLTVDKSRWQQGNVFSCSVLHEALHSHYTQ

KSLSLSPGK

SEQ ID NO: 108
KKVVYGKKGDTVELTCTASQKKNIQFHWKNSNQIKILGNQGSFLT

KGPSKLNDRVDSRRSLWDQGNFPLIIKNLKPEDSDTYICEVEDQK

EEVQLVVVGQSALTQPPSASGSPGQSITISCTGTSNNFVSWYQQH

AGKAPKLVIYDVNKRPSGVPDRFSGSKSGNTASLTVSGLQTDDEA

VYYCGSLVGNWDVIFGGGTKLTVLGQPKAAPSVTLFPPSSEELQA

NKATLVCLISDFYPGAVTVAWKADSSPVKAGVETTTPSKQSNNKY

AASSYLSLTPEQWKSHRSYSCQVTHEGSTVEKTVAPTECS

SEQ ID NO: 109
KKVVYGKKGDTVELTCTASQKKNIQFHWKNSNQIKILGNQGSFLT

KGPSKLNDRVDSRRSLWDQGNFPLIIKNLKPEDSDTYICEVEDQK

EEVQLVVVGGGGGSQSALTQPPSASGSPGQSITISCTGTSNNFVS

WYQQHAGKAPKLVIYDVNKRPSGVPDRFSGSKSGNTASLTVSGLQ

TDDEAVYYCGSLVGNWDVIFGGGTKLTVLGQPKAAPSVTLFPPSS

EELQANKATLVCLISDFYPGAVTVAWKADSSPVKAGVETTTPSKQ

SNNKYAASSYLSLTPEQWKSHRSYSCQVTHEGSTVEKTVAPTECS

SEQ ID NO: 110
KKVVYGKKGDTVELTCTASQKKNIQFHWKNSNQIKILGNQGSFLT

KGPSKLNDRVDSRRSLWDQGNFPLIIKNLKPEDSDTYICEVEDQK

EEVQLVVVGGGGGSGGGGSQSALTQPPSASGSPGQSITISCTGTS

NNFVSWYQQHAGKAPKLVIYDVNKRPSGVPDRFSGSKSGNTASLT

VSGLQTDDEAVYYCGSLVGNWDVIFGGGTKLTVLGQPKAAPSVTL

-continued

FPPPSSEELQANKATLVCLISDFYPGAVTVAWKADSSPVKAGVETT

TPSKQSNNKYAASSYLSLTPEQWKSHRSYSCQVTHEGSTVEKTVA

PTECS

SEQ ID NO: 111
KKVVYGKKGDTVELTCTASQKKNIQFHWKNSNQIKILGNQGSFLT

KGPSKLNDRVDSRRSLWDQGNFPLIIKNLKPEDSDTYICEVEDQK

EEVQLVVVGGGGGSGGGGSGGGGSQSALTQPPSASGSPGQSITIS

CTGTSNNFVSWYQQHAGKAPKLVIYDVNKRPSGVPDRFSGSKSGN

TASLTVSGLQTDDEAVYYCGSLVGNWDVIFGGGTKLTVLGQPKAA

PSVTLFPPSSEELQANKATLVCLISDFYPGAVTVAWKADSSPVKA

GVETTTPSKQSNNKYAASSYLSLTPEQWKSHRSYSCQVTHEGSTV

EKTVAPTECS

SEQ ID NO: 112
KKVVYGKKGDTVELTCTASQKKNIQFHWKNSNQIKILGNQGSFLT

KGPSKLNDRVDSRRSLWDQGNFPLIIKNLKPEDSDTYICEVEDQK

EEVQLVVVGGGGGSGGGGSGGGGSGGGGSQSALTQPPSASGSPGQ

SITISCTGTSNNFVSWYQQHAGKAPKLVIYDVNKRPSGVPDRFSG

SKSGNTASLTVSGLQTDDEAVYYCGSLVGNWDVIFGGGTKLTVLG

QPKAAPSVTLFPPSSEELQANKATLVCLISDFYPGAVTVAWKADS

SPVKAGVETTTPSKQSNNKYAASSYLSLTPEQWKSHRSYSCQVTH

EGSTVEKTVAPTECS

SEQ ID NO: 113
KKVVYGKKGDTVELTCTASQKKNIQFHWKNSNQIKILGNQGSFLT

KGPSKLNDRVDSRRSLWDQGNFPLIIKNLKPEDSDTYICEVEDQK

EEVQLVVVGGGGGSGGGGSGGGGSGGGGSGGGGSQSALTQPPSAS

GSPGQSITISCTGTSNNFVSWYQQHAGKAPKLVIYDVNKRPSGVP

DRFSGSKSGNTASLTVSGLQTDDEAVYYCGSLVGNWDVIFGGGTK

LTVLGQPKAAPSVTLFPPSSEELQANKATLVCLISDFYPGAVTVA

WKADSSPVKAGVETTTPSKQSNNKYAASSYLSLTPEQWKSHRSYS

CQVTHEGSTVEKTVAPTECS

SEQ ID NO: 114
KKVVYGKKGDTVELTCTASQKKNIQFHWKNSNQIKILGNQGSFLT

KGPSKLNDRVDSRRSLWDQGNFPLIIKNLKPEDSDTYICEVEDQK

EEVQLVVVGGGGGSGGGGSGGGGSGGGGSGGGGSGGGGSQSALTQ

PPSASGSPGQSITISCTGTSNNFVSWYQQHAGKAPKLVIYDVNKR

PSGVPDRFSGSKSGNTASLTVSGLQTDDEAVYYCGSLVGNWDVIF

GGGTKLTVLGQPKAAPSVTLFPPSSEELQANKATLVCLISDFYPG

AVTVAWKADSSPVKAGVETTTPSKQSNNKYAASSYLSLTPEQWKS

HRSYSCQVTHEGSTVEKTVAPTECS

SEQ ID NO: 115
KKVVYGKCGDTVELTCTASQKKNIQFHWKNSNQIKILGNQGSFLT

KGPSKLNDRVDSRRSLWDQGNFPLIIKNLKPEDSDTYICEVEDQK

EEVQLVVVCGGGGSQSALTQPPSASGSPGQSITISCTGTSNNFVS

WYQQHAGKAPKLVIYDVNKRPSGVPDRFSGSKSGNTASLTVSGLQ

TDDEAVYYCGSLVGNWDVIFGGGTKLTVLGQPKAAPSVTLFPPSS

EELQANKATLVCLISDFYPGAVTVAWKADSSPVKAGVETTTPSKQ

SNNKYAASSYLSLTPEQWKSHRSYSCQVTHEGSTVEKTVAPTECS

SEQ ID NO: 116
QPQLQESGPTLVEASETLSLTCAVSGDSTAACNSFWGWVRQPPGK

GLEWVGSLSHCASYWNRGWTYHNPSLKSRLTLALDTPKNLVFLKL

NSVTAADTATYYCARFGGEVLRYTDWPKPAWVDLWGRGTLVTVSS

ASTKGPSVFPLAPSSKSTSGGTAALGCLVKDYFPEPVTVSWNSGA

LTSGVHTFPAVLQSSGLYSLSSVVTVPSSSLGTQTYICNVNHKPS

NTKVDKKVEPKSCGGGGSKKVVYGKCGDTVELTCTASQKKNIQFH

WKNSNQIKILGNQGSFLTKGPSKLNDRVDSRRSLWDQGNFPLIIK

NLKPEDSDTYICEVEDQKEEVQLVVVCGGGGSDKTHTCPPCPAPE

LLGGPSVFLFPPKPKDTLMISRTPEVTCVVVDVSHEDPEVKFNWY

VDGVEVHNAKTKPREEQYNSTYRVVSVLTVLHQDWLNGKEYKCKV

SNKALPAPIEKTISKAKGQPREPQVYTLPPSRDELTKNQVSLTCL

VKGFYPSDIAVEWESNGQPENNYKTTPPVLDSDGSFFLYSKLTVD

KSRWQQGNVFSCSVLHEALHSHYTQKSLSLSPGK

SEQ ID NO: 117
QPQLQESGPTLVEASETLSLTCAVSGDSTAACNSFWGWVRQPPGK

GLEWVGSLSHCASYWNRGWTYHNPSLKSRLTLALDTPKNLVFLKL

NSVTAADTATYYCARFGGEVLRYTDWPKPAWVDLWGRGTLVTVSS

ASTKGPSVFPLAPSSKSTSGGTAALGCLVKDYFPEPVTVSWNSGA

LTSGVHTFPAVLQSSGLYSLSSVVTVPSSSLGTQTYICNVNHKPS

NTKVDKKVEPKSCDKTHTCPPCPAPELLGGPSVFLFPPKPKDTLM

ISRTPEVTCVVVDVSHEDPEVKFNWYVDGVEVHNAKTKPREEQYN

STYRVVSVLTVLHQDWLNGKEYKCKVSNKALPAPIEKTISKAKGQ

PREPQVYTLPPSRDELTKNQVSLTCLVKGFYPSDIAVEWESNGQP

ENNYKTTPPVLDSDGSFFLYSKLTVDKSRWQQGNVFSCSVLHEAL

HSHYTQKSLSLSPGGGGGSKKVVYGKCGDTVELTCTASQKKNIQF

HWKNSNQIKILGNQGSFLTKGPSKLNDRVDSRRSLWDQGNFPLII

KNLKPEDSDTYICEVEDQKEEVQLVVVC

SEQ ID NO: 118
QSALTQPPSASGSPGQSITISCTGTSNNFVSWYQQHAGKAPKLVI

YDVNKRPSGVPDRFSGSKSGNTASLTVSGLQTDDEAVYYCGSLVG

NWDVIFGGGTKLTVLGQPKAAPSVTLFPPSSEELQANKATLVCLI

SDFYPGAVTVAWKADSSPVKAGVETTTPSKQSNNKYAASSYLSLT

PEQWKSHRSYSCQVTHEGSTVEKTVAPTECSGGGGSKKVVYGKCG

DTVELTCTASQKKNIQFHWKNSNQIKILGNQGSFLTKGPSKLNDR

VDSRRSLWDQGNFPLIIKNLKPEDSDTYICEVEDQKEEVQLVVVC

SEQ ID NO: 119
KKVVYGKIGDTVELTCTASQKKNIQFHWKNSNQIKILGNQGSFLT

KGPSKLNDRVDSRRSLWDQGNFPLIIKNLKPEDSDTYICEVEDQK

EEVQLVVVGGGGGSQPQLQESGPTLVEASETLSLTCAVSGDSTAA

CNSFWGWVRQPPGKGLEWVGSLSHCASYWNRGWTYHNPSLKSRLT

LALDTPKNLVFLKLNSVTAADTATYYCARFGGEVLRYTDWPKPAW

VDLWGRGTLVTVSSASTKGPSVFPLAPSSKSTSGGTAALGCLVKD

YFPEPVTVSWNSGALTSGVHTFPAVLQSSGLYSLSSVVTVPSSSL

GTQTYICNVNHKPSNTKVDKKVEPKSCDKTHTCPPCPAPELLGGP

SVFLFPPKPKDTLMISRTPEVTCVVVDVSHEDPEVKFNWYVDGVE

VHNAKTKPREEQYNSTYRVVSVLTVLHQDWLNGKEYKCKVSNKAL

PAPIEKTISKAKGQPREPQVYTLPPSRDELTKNQVSLTCLVKGFY

PSDIAVEWESNGQPENNYKTTPPVLDSDGSFFLYSKLTVDKSRWQ

QGNVFSCSVLHEALHSHYTQKSLSLSPGK

SEQ ID NO: 120
KKVVYGKVGDTVELTCTASQKKNIQFHWKNSNQIKILGNQGSFLT

KGPSKLNDRVDSRRSLWDQGNFPLIIKNLKPEDSDTYICEVEDQK

EEVQLVVVGGGGGSQPQLQESGPTLVEASETLSLTCAVSGDSTAA

CNSFWGWVRQPPGKGLEWVGSLSHCASYWNRGWTYHNPSLKSRLT

LALDTPKNLVFLKLNSVTAADTATYYCARFGGEVLRYTDWPKPAW

VDLWGRGTLVTVSSASTKGPSVFPLAPSSKSTSGGTAALGCLVKD

YFPEPVTVSWNSGALTSGVHTFPAVLQSSGLYSLSSWVTVPSSSL

GTQTYICNVNHKPSNTKVDKKVEPKSCDKTHTCPPCPAPELLGGP

SVFLFPPKPKDTLMISRTPEVTCVVVDVSHEDPEVKFNWYVDGVE

VHNAKTKPREEQYNSTYRVVSVLTVLHQDWLNGKEYKCKVSNKAL

PAPIEKTISKAKGQPREPQVYTLPPSRDELTKNQVSLTCLVKGFY

PSDIAVEWESNGQPENNYKTTPPVLDSDGSFFLYSKLTVDKSRWQ

QGNVFSCSVLHEALHSHYTQKSLSLSPGK

SEQ ID NO: 121
KKVVYGKCGDTVELTCTASQKKNIQFHWKNSNQIKILGNQGSFLT

KGPSKLNDRVDSRRSLWDQGNFPLIIKNLKPEDSDTYICEVEDQK

EEVQLVVVCGGGGSQPQLQESGPTLVEASETLSLTCAVSGDSTAA

CNSFWGWVRQPPGKGLEWVGSLSHCASYWNRGWTYHNPSLKSRLT

LALDTPKNLVFLKLNSVTAADTATYYCARFGGEVLRYTDWPKPAW

VDLWGRGTLVTVSSASTKGPSVFPLAPSSKSTSGGTAALGCLVKD

YFPEPVTVSWNSGALTSGVHTFPAVLQSSGLYSLSSWVTVPSSSL

GTQTYICNVNHKPSNTKVDKKVEPKSCDKTHTCPPCPAPELLGGP

SVFLFPPKPKDTLMISRTPEVTCVVVDVSHEDPEVKFNWYVDGVE

VHNAKTKPREEQYNSTYRVVSVLTVLHQDWLNGKEYKCKVSNKAL

PAPIEKTISKAKGQPREPQVYTLPPSRDELTKNQVSLTCLVKGFY

PSDIAVEWESNGQPENNYKTTPPVLDSDGSFFLYSKLTVDKSRWQ

QGNVFSCSVLHEALHSHYTQKSLSLSPGK 5 10 15 20 25 30 35 40 45 50 55 60 65

SEQ ID NO: 122
KKVVYGKKGDCVELTCTASQKKNIQFHWKNSNQIKILGNQGSFLT

KGPSKLNDRVDSRRSLWDQGNFPLIICNLKPEDSDTYICEVEDQK

EEVQLVVVGGGGGSQPQLQESGPTLVEASETLSLTCAVSGDSTAA

CNSFWGWVRQPPGKGLEWVGSLSHCASYWNRGWTYHNPSLKSRLT

LALDTPKNLVFLKLNSVTAADTATYYCARFGGEVLRYTDWPKPAW

VDLWGRGTLVTVSSASTKGPSVFPLAPSSKSTSGGTAALGCLVKD

YFPEPVTVSWNSGALTSGVHTFPAVLQSSGLYSLSSVVTVPSSSL

GTQTYICNVNHKPSNTKVDKKVEPKSCDKTHTCPPCPAPELLGGP

SVFLFPPKPKDTLMISRTPEVTCVVVDVSHEDPEVKFNWYVDGVE

VHNAKTKPREEQYNSTYRVVSVLTVLHQDWLNGKEYKCKVSNKAL

PAPIEKTISKAKGQPREPQVYTLPPSRDELTKNQVSLTCLVKGFY

PSDIAVEWESNGQPENNYKTTPPVLDSDGSFFLYSKLTVDKSRWQ

QGNVFSCSVLHEALHSHYTQKSLSLSPGK

SEQ ID NO: 123
KKVVYGKKGDTVELTCTASQKKNIQFHWKNSNQIKILGNQGSFLT

KGPSKLNDRVDSRRSLWDQGNFPLIIKNLKPEDSDTYICEVEDQK

QEVQLVVVGGGGGSQPQLQESGPTLVEASETLSLTCAVSGDSTAA

CNSFWGWVRQPPGKGLEWVGSLSHCASYWNRGWTYHNPSLKSRLT

LALDTPKNLVFLKLNSVTAADTATYYCARFGGEVLRYTDWPKPAW

VDLWGRGTLVTVSSASTKGPSVFPLAPSSKSTSGGTAALGCLVKD

YFPEPVTVSWNSGALTSGVHTFPAVLQSSGLYSLSSVVTVPSSSL

GTQTYICNVNHKPSNTKVDKKVEPKSCDKTHTCPPCPAPELLGGP

SVFLFPPKPKDTLMISRTPEVTCVVVDVSHEDPEVKFNWYVDGVE

VHNAKTKPREEQYNSTYRVVSVLTVLHQDWLNGKEYKCKVSNKAL

PAPIEKTISKAKGQPREPQVYTLPPSRDELTKNQVSLTCLVKGFY

PSDIAVEWESNGQPENNYKTTPPVLDSDGSFFLYSKLTVDKSRWQ

QGNVFSCSVLHEALHSHYTQKSLSLSPGK

SEQ ID NO: 124
KKVVYGKKGDTVELTCTASQKKNIQFHWKNSNQIKILGNQGSFLT

KGPSKLNDRVDSRRSLWDQGNFPLIIKNLKPEDSDTYICEVEDQK

HEVQLVVVGGGGGSQPQLQESGPTLVEASETLSLTCAVSGDSTAA

CNSFWGWVRQPPGKGLEWVGSLSHCASYWNRGWTYHNPSLKSRLT

LALDTPKNLVFLKLNSVTAADTATYYCARFGGEVLRYTDWPKPAW

VDLWGRGTLVTVSSASTKGPSVFPLAPSSKSTSGGTAALGCLVKD

YFPEPVTVSWNSGALTSGVHTFPAVLQSSGLYSLSSVVTVPSSSL

GTQTYICNVNHKPSNTKVDKKVEPKSCDKTHTCPPCPAPELLGGP

SVFLFPPKPKDTLMISRTPEVTCVVVDVSHEDPEVKFNWYVDGVE

VHNAKTKPREEQYNSTYRVVSVLTVLHQDWLNGKEYKCKVSNKAL

PAPIEKTISKAKGQPREPQVYTLPPSRDELTKNQVSLTCLVKGFY

PSDIAVEWESNGQPENNYKTTPPVLDSDGSFFLYSKLTVDKSRWQ

QGNVFSCSVLHEALHSHYTQKSLSLSPGK

SEQ ID NO: 125
KKVVYGKKGDTVELTCTASQKKNIEFHWKNSNQIKILGNQGSFLT

KGPSKLNDRVDSRRSLWDQGNFPLIIKNLKPEDSDTYICEVEDQK

EEVQLVVVGGGGGSQPQLQESGPTLVEASETLSLTCAVSGDSTAA

CNSFWGWVRQPPGKGLEWVGSLSHCASYWNRGWTYHNPSLKSRLT

LALDTPKNLVFLKLNSVTAADTATYYCARFGGEVLRYTDWPKPAW

VDLWGRGTLVTVSSASTKGPSVFPLAPSSKSTSGGTAALGCLVKD

YFPEPVTVSWNSGALTSGVHTFPAVLQSSGLYSLSSVVTVPSSSL

GTQTYICNVNHKPSNTKVDKKVEPKSCDKTHTCPPCPAPELLGGP

SVFLFPPKPKDTLMISRTPEVTCVVVDVSHEDPEVKFNWYVDGVE

VHNAKTKPREEQYNSTYRVVSVLTVLHQDWLNGKEYKCKVSNKAL

PAPIEKTISKAKGQPREPQVYTLPPSRDELTKNQVSLTCLVKGFY

PSDIAVEWESNGQPENNYKTTPPVLDSDGSFFLYSKLTVDKSRWQ

QGNVFSCSVLHEALHSHYTQKSLSLSPGK

SEQ ID NO: 126
KKVVYGKKGDTVELTCTASQKKNIQFDWKNSNQIKILGNQGSFLT

KGPSKLNDRVDSRRSLWDQGNFPLIIKNLKPEDSDTYICEVEDQK

EEVQLVVVGGGGGSQPQLQESGPTLVEASETLSLTCAVSGDSTAA

CNSFWGWVRQPPGKGLEWVGSLSHCASYWNRGWTYHNPSLKSRLT

LALDTPKNLVFLKLNSVTAADTATYYCARFGGEVLRYTDWPKPAW

VDLWGRGTLVTVSSASTKGPSVFPLAPSSKSTSGGTAALGCLVKD

YFPEPVTVSWNSGALTSGVHTFPAVLQSSGLYSLSSVVTVPSSSL

GTQTYICNVNHKPSNTKVDKKVEPKSCDKTHTCPPCPAPELLGGP

SVFLFPPKPKDTLMISRTPEVTCVVVDVSHEDPEVKFNWYVDGVE

VHNAKTKPREEQYNSTYRVVSVLTVLHQDWLNGKEYKCKVSNKAL

PAPIEKTISKAKGQPREPQVYTLPPSRDELTKNQVSLTCLVKGFY

PSDIAVEWESNGQPENNYKTTPPVLDSDGSFFLYSKLTVDKSRWQ

QGNVFSCSVLHEALHSHYTQKSLSLSPGK

SEQ ID NO: 127
KKVVYGKKGDTVELTCTASQKKNIQFHWKNSNQIKILGNQGSFLT

KGPSKLNDRVDSVRSLWDQGNFPLIIKNLKPEDSDTYICEVEDQK

EEVQLVVVGGGGGSQPQLQESGPTLVEASETLSLTCAVSGDSTAA

CNSFWGWVRQPPGKGLEWVGSLSHCASYWNRGWTYHNPSLKSRLT

LALDTPKNLVFLKLNSVTAADTATYYCARFGGEVLRYTDWPKPAW

VDLWGRGTLVTVSSASTKGPSVFPLAPSSKSTSGGTAALGCLVKD

YFPEPVTVSWNSGALTSGVHTFPAVLQSSGLYSLSSVVTVPSSSL

GTQTYICNVNHKPSNTKVDKKVEPKSCDKTHTCPPCPAPELLGGP

SVFLFPPKPKDTLMISRTPEVTCVVVDVSHEDPEVKFNWYVDGVE

VHNAKTKPREEQYNSTYRVVSVLTVLHQDWLNGKEYKCKVSNKAL

PAPIEKTISKAKGQPREPQVYTLPPSRDELTKNQVSLTCLVKGFY

PSDIAVEWESNGQPENNYKTTPPVLDSDGSFFLYSKLTVDKSRWQ

QGNVFSCSVLHEALHSHYTQKSLSLSPGK

-continued

SEQ ID NO: 128
KKVVYGKKGDTVELTCTASQKKNIQFHWKNSNQIKILGNQGSFLT

KGPSKLNDRVDSNRSLWDQGNFPLIIKNLKPEDSDTYICEVEDQK

EEVQLVVVGGGGGSQPQLQESGPTLVEASETLSLTCAVSGDSTAA

CNSFWGWVRQPPGKGLEWVGSLSHCASYWNRGWTYHNPSLKSRLT

LALDTPKNLVFLKLNSVTAADTATYYCARFGGEVLRYTDWPKPAW

VDLWGRGTLVTVSSASTKGPSVFPLAPSSKSTSGGTAALGCLVKD

YFPEPVTVSWNSGALTSGVHTFPAVLQSSGLYSLSSVVTVPSSSL

GTQTYICNVNHKPSNTKVDKKVEPKSCDKTHTCPPCPAPELLGGP

SVFLFPPKPKDTLMISRTPEVTCVVVDVSHEDPEVKFNWYVDGVE

VHNAKTKPREEQYNSTYRVVSVLTVLHQDWLNGKEYKCKVSNKAL

PAPIEKTISKAKGQPREPQVYTLPPSRDELTKNQVSLTCLVKGFY

PSDIAVEWESNGQPENNYKTTPPVLDSDGSFFLYSKLTVDKSRWQ

QGNVFSCSVLHEALHSHYTQKSLSLSPGK

SEQ ID NO: 129
KKVVYGKKGDTVELTCTASQKKNIQFHWKNSNQIKILGNQGSFLT

KGPSKLNDRVDSTRSLWDQGNFPLIIKNLKPEDSDTYICEVEDQK

EEVQLVVVGGGGGSQPQLQESGPTLVEASETLSLTCAVSGDSTAA

CNSFWGWVRQPPGKGLEWVGSLSHCASYWNRGWTYHNPSLKSRLT

LALDTPKNLVFLKLNSVTAADTATYYCARFGGEVLRYTDWPKPAW

VDLWGRGTLVTVSSASTKGPSVFPLAPSSKSTSGGTAALGCLVKD

YFPEPVTVSWNSGALTSGVHTFPAVLQSSGLYSLSSVVTVPSSSL

GTQTYICNVNHKPSNTKVDKKVEPKSCDKTHTCPPCPAPELLGGP

SVFLFPPKPKDTLMISRTPEVTCVVVDVSHEDPEVKFNWYVDGVE

VHNAKTKPREEQYNSTYRVVSVLTVLHQDWLNGKEYKCKVSNKAL

PAPIEKTISKAKGQPREPQVYTLPPSRDELTKNQVSLTCLVKGFY

PSDIAVEWESNGQPENNYKTTPPVLDSDGSFFLYSKLTVDKSRWQ

QGNVFSCSVLHEALHSHYTQKSLSLSPGK

SEQ ID NO: 130
KKVVYGKKGDTVELTCTASQKKNIQFHWKNSNQIKILGNQGSFLT

KGPSKLNDRVDSRRSMWDQGNFPLIIKNLKPEDSDTYICEVEDQK

EEVQLVVVGGGGGSQPQLQESGPTLVEASETLSLTCAVSGDSTAA

CNSFWGWVRQPPGKGLEWVGSLSHCASYWNRGWTYHNPSLKSRLT

LALDTPKNLVFLKLNSVTAADTATYYCARFGGEVLRYTDWPKPAW

VDLWGRGTLVTVSSASTKGPSVFPLAPSSKSTSGGTAALGCLVKD

YFPEPVTVSWNSGALTSGVHTFPAVLQSSGLYSLSSVVTVPSSSL

GTQTYICNVNHKPSNTKVDKKVEPKSCDKTHTCPPCPAPELLGGP

SVFLFPPKPKDTLMISRTPEVTCVVVDVSHEDPEVKFNWYVDGVE

VHNAKTKPREEQYNSTYRVVSVLTVLHQDWLNGKEYKCKVSNKAL

PAPIEKTISKAKGQPREPQVYTLPPSRDELTKNQVSLTCLVKGFY

PSDIAVEWESNGQPENNYKTTPPVLDSDGSFFLYSKLTVDKSRWQ

QGNVFSCSVLHEALHSHYTQKSLSLSPGK

-continued

SEQ ID NO: 131
KKVVYGKKGDTVCLTCTASQKKNIQFHWKNSNQIKILGNQGSFLT

KGPSKLNDRVDSRRSLWDQGNFPLCIKNLKPEDSDTYICEVEDQK

EEVQLVVVGGGGGSQPQLQESGPTLVEASETLSLTCAVSGDSTAA

CNSFWGWVRQPPGKGLEWVGSLSHCASYWNRGWTYHNPSLKSRLT

LALDTPKNLVFLKLNSVTAADTATYYCARFGGEVLRYTDWPKPAW

VDLWGRGTLVTVSSASTKGPSVFPLAPSSKSTSGGTAALGCLVKD

YFPEPVTVSWNSGALTSGVHTFPAVLQSSGLYSLSSVVTVPSSSL

GTQTYICNVNHKPSNTKVDKKVEPKSCDKTHTCPPCPAPELLGGP

SVFLFPPKPKDTLMISRTPEVTCVVVDVSHEDPEVKFNWYVDGVE

VHNAKTKPREEQYNSTYRVVSVLTVLHQDWLNGKEYKCKVSNKAL

PAPIEKTISKAKGQPREPQVYTLPPSRDELTKNQVSLTCLVKGFY

PSDIAVEWESNGQPENNYKTTPPVLDSDGSFFLYSKLTVDKSRWQ

QGNVFSCSVLHEALHSHYTQKSLSLSPGK

SEQ ID NO: 132
KKVVYGKKGDTVELTCTASQKKNIQFCWKNSNQIKILCNQGSFLT

KGPSKLNDRVDSRRSLWDQGNFPLIIKNLKPEDSDTYICEVEDQK

EEVQLVVVGGGGGSQPQLQESGPTLVEASETLSLTCAVSGDSTAA

CNSFWGWVRQPPGKGLEWVGSLSHCASYWNRGWTYHNPSLKSRLT

LALDTPKNLVFLKLNSVTAADTATYYCARFGGEVLRYTDWPKPAW

VDLWGRGTLVTVSSASTKGPSVFPLAPSSKSTSGGTAALGCLVKD

YFPEPVTVSWNSGALTSGVHTFPAVLQSSGLYSLSSVVTVPSSSL

GTQTYICNVNHKPSNTKVDKKVEPKSCDKTHTCPPCPAPELLGGP

SVFLFPPKPKDTLMISRTPEVTCVVVDVSHEDPEVKFNWYVDGVE

VHNAKTKPREEQYNSTYRVVSVLTVLHQDWLNGKEYKCKVSNKAL

PAPIEKTISKAKGQPREPQVYTLPPSRDELTKNQVSLTCLVKGFY

PSDIAVEWESNGQPENNYKTTPPVLDSDGSFFLYSKLTVDKSRWQ

QGNVFSCSVLHEALHSHYTQKSLSLSPGK

SEQ ID NO: 133
KKVVYGKKGDTVELTCTASQCKNIQFHWKNSNQIKILGNQGSFLT

KGPSKLNDRVDSRRSLWDQCNFPLIIKNLKPEDSDTYICEVEDQK

EEVQLVVVGGGGGSQPQLQESGPTLVEASETLSLTCAVSGDSTAA

CNSFWGWVRQPPGKGLEWVGSLSHCASYWNRGWTYHNPSLKSRLT

LALDTPKNLVFLKLNSVTAADTATYYCARFGGEVLRYTDWPKPAW

VDLWGRGTLVTVSSASTKGPSVFPLAPSSKSTSGGTAALGCLVKD

YFPEPVTVSWNSGALTSGVHTFPAVLQSSGLYSLSSVVTVPSSSL

GTQTYICNVNHKPSNTKVDKKVEPKSCDKTHTCPPCPAPELLGGP

SVFLFPPKPKDTLMISRTPEVTCVVVDVSHEDPEVKFNWYVDGVE

VHNAKTKPREEQYNSTYRVVSVLTVLHQDWLNGKEYKCKVSNKAL

PAPIEKTISKAKGQPREPQVYTLPPSRDELTKNQVSLTCLVKGFY

PSDIAVEWESNGQPENNYKTTPPVLDSDGSFFLYSKLTVDKSRWQ

QGNVFSCSVLHEALHSHYTQKSLSLSPGK

SEQ ID NO: 134

```
KKVVYGKKGDTVELTCTASQKKNIQFHWKNSNQIKILGNQGSFLT

KGPSKLNDRVDSRRSLWDQGNFPLIIKNLKPEDSDTYICEVGDQK

EEVQLVVVGGGGGSQPQLQESGPTLVEASETLSLTCAVSGDSTAA

CNSFWGWVRQPPGKGLEWVGSLSHCASYWNRGWTYHNPSLKSRLT

LALDTPKNLVFLKLNSVTAADTATYYCARFGGEVLRYTDWPKPAW

VDLWGRGTLVTVSSASTKGPSVFPLAPSSKSTSGGTAALGCLVKD

YFPEPVTVSWNSGALTSGVHTFPAVLQSSGLYSLSSVVTVPSSSL

GTQTYICNVNHKPSNTKVDKKVEPKSCDKTHTCPPCPAPELLGGP

SVFLFPPKPKDTLMISRTPEVTCVVVDVSHEDPEVKFNWYVDGVE

VHNAKTKPREEQYNSTYRVVSVLTVLHQDWLNGKEYKCKVSNKAL

PAPIEKTISKAKGQPREPQVYTLPPSRDELTKNQVSLTCLVKGFY

PSDIAVEWESNGQPENNYKTTPPVLDSDGSFFLYSKLTVDKSRWQ

QGNVFSCSVLHEALHSHYTQKSLSLSPGK
```

SEQ ID NO: 135

```
KKVVYGKKGDTVELTCTASQKKNIQFHWKNSNQIKILGNQGSFLT

KGPSKLWDRVDSRRSLWDQGNFPLIIKNLKPEDSDTYICEVEDQK

EEVQLVVVGGGGGSQPQLQESGPTLVEASETLSLTCAVSGDSTAA

CNSFWGWVRQPPGKGLEWVGSLSHCASYWNRGWTYHNPSLKSRLT

LALDTPKNLVFLKLNSVTAADTATYYCARFGGEVLRYTDWPKPAW

VDLWGRGTLVTVSSASTKGPSVFPLAPSSKSTSGGTAALGCLVKD

YFPEPVTVSWNSGALTSGVHTFPAVLQSSGLYSLSSVVTVPSSSL

GTQTYICNVNHKPSNTKVDKKVEPKSCDKTHTCPPCPAPELLGGP

SVFLFPPKPKDTLMISRTPEVTCVVVDVSHEDPEVKFNWYVDGVE

VHNAKTKPREEQYNSTYRVVSVLTVLHQDWLNGKEYKCKVSNKAL

PAPIEKTISKAKGQPREPQVYTLPPSRDELTKNQVSLTCLVKGFY

PSDIAVEWESNGQPENNYKTTPPVLDSDGSFFLYSKLTVDKSRWQ

QGNVFSCSVLHEALHSHYTQKSLSLSPGK
```

SEQ ID NO: 136

```
KKVVYGKCGDTVELTCTASQKKNIQFHWKNSNQIKILGNQGSFLT

KGPSKLNDRVDSRRSLWDQGNFPLIIKNLKPEDSDTYICEVEDQK

EEVQLVVVCGGGGSQMQLQESGPGLVKPSETLSLTCSVSGASISD

SYWSWIRRSPGKGLEWIGYVHKSGDTNYSPSLKSRVNLSLDTSKN

QVSLSLVAATAADSGKYYCARTLHGRRIYGIVAFNEWFTYFYMDV

WGNGTQVTVSSASTKGPSVFPLAPSSKSTSGGTAALGCLVKDYFP

EPVTVSWNSGALTSGVHTFPAVLQSSGLYSLSSVVTVPSSSLGTQ

TYICNVNHKPSNTKVDKRVEPKSCDKTHTCPPCPAPELLGGPSVF

LFPPKPKDTLMISRTPEVTCVVVDVSHEDPEVKFNWYVDGVEVHN

AKTKPREEQYNSTYRVVSVLTVLHQDWLNGKEYKCKVSNKALPAP

IEKTISKAKGQPREPQVYTLPPSRDELTKNQVSLTCLVKGFYPSD

IAVEWESNGQPENNYKTTPPVLDSDGSFFLYSKLTVDKSRWQQGN

VFSCSVLHEALHSHYTQKSLSLSPGK
```

SEQ ID NO: 137

```
KKVVYGKCGDTVELTCTASQKKNIQFHWKNSNQIKILGNQGSFLT

KGPSKLNDRVDSRRSLWDQGNFPLIIKNLKPEDSDTYICEVEDQK

EEVQLVVVCGGGGSGGGGSQMQLQESGPGLVKPSETLSLTCSVSG

ASISDSYWSWIRRSPGKGLEWIGYVHKSGDTNYSPSLKSRVNLSL

DTSKNQVSLSLVAATAADSGKYYCARTLHGRRIYGIVAFNEWFTY

FYMDVWGNGTQVTVSSASTKGPSVFPLAPSSKSTSGGTAALGCLV

KDYFPEPVTVSWNSGALTSGVHTFPAVLQSSGLYSLSSVVTVPSS

SLGTQTYICNVNHKPSNTKVDKRVEPKSCDKTHTCPPCPAPELLG

GPSVFLFPPKPKDTLMISRTPEVTCVVVDVSHEDPEVKFNWYVDG

VEVHNAKTKPREEQYNSTYRVVSVLTVLHQDWLNGKEYKCKVSNK

ALPAPIEKTISKAKGQPREPQVYTLPPSRDELTKNQVSLTCLVKG

FYPSDIAVEWESNGQPENNYKTTPPVLDSDGSFFLYSKLTVDKSR

WQQGNVFSCSVLHEALHSHYTQKSLSLSPGK
```

SEQ ID NO: 138

```
KKVVYGKCGDTVELTCTASQKKNIQFHWKNSNQIKILGNQGSFLT

KGPSKLNDRVDSRRSLWDQGNFPLIIKNLKPEDSDTYICEVEDQK

EEVQLVVVCGGGGSGGGGSGGGGSQMQLQESGPGLVKPSETLSLT

CSVSGASISDSYWSWIRRSPGKGLEWIGYVHKSGDTNYSPSLKSR

VNLSLDTSKNQVSLSLVAATAADSGKYYCARTLHGRRIYGIVAFN

EWFTYFYMDVWGNGTQVTVSSASTKGPSVFPLAPSSKSTSGGTAA

LGCLVKDYFPEPVTVSWNSGALTSGVHTFPAVLQSSGLYSLSSVV

TVPSSSLGTQTYICNVNHKPSNTKVDKRVEPKSCDKTHTCPPCPA

PELLGGPSVFLFPPKPKDTLMISRTPEVTCVVVDVSHEDPEVKFN

WYVDGVEVHNAKTKPREEQYNSTYRVVSVLTVLHQDWLNGKEYKC

KVSNKALPAPIEKTISKAKGQPREPQVYTLPPSRDELTKNQVSLT

CLVKGFYPSDIAVEWESNGQPENNYKTTPPVLDSDGSFFLYSKLT

VDKSRWQQGNVFSCSVLHEALHSHYTQKSLSLSPGK
```

SEQ ID NO: 139

```
KKVVYGKCGDTVELTCTASQKKNIQFHWKNSNQIKILGNQGSFLT

KGPSKLNDRVDSRRSLWDQGNFPLIIKNLKPEDSDTYICEVEDQK

EEVQLVVVCGGGGSGGGGSGGGGSGGGGSQMQLQESGPGLVKPSE

TLSLTCSVSGASISDSYWSWIRRSPGKGLEWIGYVHKSGDTNYSP

SLKSRVNLSLDTSKNQVSLSLVAATAADSGKYYCARTLHGRRIYG

IVAFNEWFTYFYMDVWGNGTQVTVSSASTKGPSVFPLAPSSKSTS

GGTAALGCLVKDYFPEPVTVSWNSGALTSGVHTFPAVLQSSGLYS

LSSVVTVPSSSLGTQTYICNVNHKPSNTKVDKRVEPKSCDKTHTC

PPCPAPELLGGPSVFLFPPKPKDTLMISRTPEVTCVVVDVSHEDP

EVKFNWYVDGVEVHNAKTKPREEQYNSTYRVVSVLTVLHQDWLNG

KEYKCKVSNKALPAPIEKTISKAKGQPREPQVYTLPPSRDELTKN

QVSLTCLVKGFYPSDIAVEWESNGQPENNYKTTPPVLDSDGSFFL

YSKLTVDKSRWQQGNVFSCSVLHEALHSHYTQKSLSLSPGK
```

-continued

QMQLQESGPGLVKPSETLSLTCSVSGASISDSYWSWIRRSPGKGL

EWIGYVHKSGDTNYSPSLKSRVNLSLDTSKNQVSLSLVAATAADS

GKYYCARTLHGRRIYGIVAFNEWFTYFYMDVWGNGTQVTVSSAST

KGPSVFPLAPSSKSTSGGTAALGCLVKDYFPEPVTVSWNSGALTS

GVHTFPAVLQSSGLYSLSSVVTVPSSSLGTQTYICNVNHKPSNTK

VDKRVEPKSCGGGGSKKVVYGKCGDTVELTCTASQKKNIQFHWKN

SNQIKILGNQGSFLTKGPSKLNDRVDSRRSLWDQGNFPLIIKNLK

PEDSDTYICEVEDQKEEVQLVVVCGGGGSDKTHTCPPCPAPELLG

GPSVFLFPPKPKDTLMISRTPEVTCVVVDVSHEDPEVKFNWYVDG

VEVHNAKTKPREEQYNSTYRVVSVLTVLHQDWLNGKEYKCKVSNK

ALPAPIEKTISKAKGQPREPQVYTLPPSRDELTKNQVSLTCLVKG

FYPSDIAVEWESNGQPENNYKTTPPVLDSDGSFFLYSKLTVDKSR

WQQGNVFSCSVLHEALHSHYTQKSLSLSPGK

SEQ ID NO: 141
QMQLQESGPGLVKPSETLSLTCSVSGASISDSYWSWIRRSPGKGL

EWIGYVHKSGDTNYSPSLKSRVNLSLDTSKNQVSLSLVAATAADS

GKYYCARTLHGRRIYGIVAFNEWFTYFYMDVWGNGTQVTVSSAST

KGPSVFPLAPSSKSTSGGTAALGCLVKDYFPEPVTVSWNSGALTS

GVHTFPAVLQSSGLYSLSSVVTVPSSSLGTQTYICNVNHKPSNTK

VDKRVEPKSCDKTHTCPPCPAPELLGGPSVFLFPPKPKDTLMISR

TPEVTCVVVDVSHEDPEVKFNWYVDGVEVHNAKTKPREEQYNSTY

RVVSVLTVLHQDWLNGKEYKCKVSNKALPAPIEKTISKAKGQPRE

PQVYTLPPSRDELTKNQVSLTCLVKGFYPSDIAVEWESNGQPENN

YKTTPPVLDSDGSFFLYSKLTVDKSRWQQGNVFSCSVLHEALHSH

YTQKSLSLSPGGGGGSKKVVYGKCGDTVELTCTASQKKNIQFHWK

NSNQIKILGNQGSFLTKGPSKLNDRVDSRRSLWDQGNFPLIIKNL

KPEDSDTYICEVEDQKEEVQLVVVC

SEQ ID NO: 142
KKVVYGKCGDTVELTCTASQKKNIQFHWKNSNQIKILGNQGSFLT

KGPSKLNDRVDSRRSLWDQGNFPLIIKNLKPEDSDTYICEVEDQK

EEVQLVVVCGGGGSSDISVAPGETARISCGEKSLGSRAVQWYQHR

AGQAPSLIIYNNQDRPSGIPERFSGSPDSPFGTTATLTITSVEAG

DEADYYCHIWDSRVPTKWVFGGGTTLTVLGQPKAAPSVTLFPPSS

EELQANKATLVCLISDFYPGAVTVAWKADSSPVKAGVETTTPSKQ

SNNKYAASSYLSLTPEQWKSHKSYSCQVTHEGSTVEKTVAPTECS

SEQ ID NO: 143
SDISVAPGETARISCGEKSLGSRAVQWYQHRAGQAPSLIIYNNQD

RPSGIPERFSGSPDSPFGTTATLTITSVEAGDEADYYCHIWDSRV

PTKWVFGGGTTLTVLGQPKAAPSVTLFPPSSEELQANKATLVCLI

SDFYPGAVTVAWKADSSPVKAGVETTTPSKQSNNKYAASSYLSLT

PEQWKSHKSYSCQVTHEGSTVEKTVAPTECSGGGGSKKVVYGKCG

-continued

DTVELTCTASQKKNIQFHWKNSNQIKILGNQGSFLTKGPSKLNDR

VDSRRSLWDQGNFPLIIKNLKPEDSDTYICEVEDQKEEVQLVVVC

SEQ ID NO: 144
KKVVYGKCGDTVELTCTASQKKNIQFHWKNSNQIKILGNQGSFLT

KGPSKLNDRVDSRRSLWDQGNFPLIIKNLKPEDSDTYICEVEDQK

EEVQLVVVCGGGGSQVQLRESGPGLVKPSETLSLSCTVSNDSRPS

DHSWTWVRQSPGKALEWIGDIHYNGATTYNPSLRSRVRIELDQSI

PRFSLKMTSMTAADTGMYYCARNAIRIYGVVALGEWFHYGMDVWG

QGTAVTVSSASTKGPSVFPLAPSSKSTSGGTAALGCLVKDYFPEP

VTVSWNSGALTSGVHTFPAVLQSSGLYSLSSVVTVPSSSLGTQTY

ICNVNHKPSNTKVDKRVEPKSCDKTHTCPPCPAPELLGGPSVFLF

PPKPKDTLMISRTPEVTCVVVDVSHEDPEVKFNWYVDGVEVHNAK

TKPREEQYNSTYRVVSVLTVLHQDWLNGKEYKCKVSNKALPAPIE

KTISKAKGQPREPQVYTLPPSRDELTKNQVSLTCLVKGFYPSDIA

VEWESNGQPENNYKTTPPVLDSDGSFFLYSKLTVDKSRWQQGNVF

SCSVLHEALHSHYTQKSLSLSPGK

SEQ ID NO: 145
KKVVYGKCGDTVELTCTASQKKNIQFHWKNSNQIKILGNQGSFLT

KGPSKLNDRVDSRRSLWDQGNFPLIIKNLKPEDSDTYICEVEDQK

EEVQLVVVCGGGGSGGGGSGGGGSGGGGSGGGGSQVQLRESGPGLVKPSE

TLSLSCTVSNDSRPSDHSWTWVRQSPGKALEWIGDIHYNGATTYN

PSLRSRVRIELDQSIPRFSLKMTSMTAADTGMYYCARNAIRIYGV

VALGEWFHYGMDVWGQGTAVTVSSASTKGPSVFPLAPSSKSTSGG

TAALGCLVKDYFPEPVTVSWNSGALTSGVHTFPAVLQSSGLYSLS

SVVTVPSSSLGTQTYICNVNHKPSNTKVDKRVEPKSCDKTHTCPP

CPAPELLGGPSVFLFPPKPKDTLMISRTPEVTCVVVDVSHEDPEV

KFNWYVDGVEVHNAKTKPREEQYNSTYRVVSVLTVLHQDWLNGKE

YKCKVSNKALPAPIEKTISKAKGQPREPQVYTLPPSRDELTKNQV

SLTCLVKGFYPSDIAVEWESNGQPENNYKTTPPVLDSDGSFFLYS

KLTVDKSRWQQGNVFSCSVLHEALHSHYTQKSLSLSPGK

SEQ ID NO: 146
KKVVYGKCGDTVELTCTASQKKNIQFHWKNSNQIKILGNQGSFLT

KGPSKLNDRVDSRRSLWDQGNFPLIIKNLKPEDSDTYICEVEDQK

EEVQLVVVCGGGGSQVQLQESGPGLVKPSETLSVTCSVSGDSMNN

YYWTWIRQSPGKGLEWIGYISDRESATYNPSLNSRVVISRDTSKN

QLSLKLNSVTPADTAVYYCATARRGQRIYGVVSFGEFFYYYSMDV

WGKGTTVTVSSASTKGPSVFPLAPSSKSTSGGTAALGCLVKDYFP

EPVTVSWNSGALTSGVHTFPAVLQSSGLYSLSSVVTVPSSSLGTQ

TYICNVNHKPSNTKVDKRVEPKSCDKTHTCPPCPAPELLGGPSVF

LFPPKPKDTLMISRTPEVTCVVVDVSHEDPEVKFNWYVDGVEVHN

AKTKPREEQYNSTYRVVSVLTVLHQDWLNGKEYKCKVSNKALPAP

IEKTISKAKGQPREPQVYTLPPSRDELTKNQVSLTCLVKGFYPSD

IAVEWESNGQPENNYKTTPPVLDSDGSFFLYSKLTVDKSRWQQGN

VFSCSVLHEALHSHYTQKSLSLSPGK

SEQ ID NO: 147

KKVVYGKCGDTVELTCTASQKKNIQFHWKNSNQIKILGNQGSFLT

KGPSKLNDRVDSRRSLWDQGNFPLIIKNLKPEDSDTYICEVEDQK

EEVQLVVVCGGGGGGGGSGGGGSGGGGSQVQLQESGPGLVKPSET

LSVTCSVSGDSMNNYYWTWIRQSPGKGLEWIGYISDRESATYNPS

LNSRVVISRDTSKNQLSLKLNSVTPADTAVYYCATARRGQRIYGV

VSFGEFFYYYSMDVWGKGTTVTVSSASTKGPSVFPLAPSSKSTSG

GTAALGCLVKDYFPEPVTVSWNSGALTSGVHTFPAVLQSSGLYSL

SSVVTVPSSSLGTQTYICNVNHKPSNTKVDKRVEPKSCDKTHTCP

PCPAPELLGGPSVFLFPPKPKDTLMISRTPEVTCVVVDVSHEDPE

VKFNWYVDGVEVHNAKTKPREEQYNSTYRVVSVLTVLHQDWLNGK

EYKCKVSNKALPAPIEKTISKAKGQPREPQVYTLPPSRDELTKNQ

VSLTCLVKGFYPSDIAVEWESNGQPENNYKTTPPVLDSDGSFFLY

SKLTVDKSRWQQGNVFSCSVLHEALHSHYTQKSLSLSPGK

SEQ ID NO: 148

KKVVYGKCGDTVELTCTASQKKNIQFHWKNSNQIKILGNQGSFLT

KGPSKLNDRVDSRRSLWDQGNFPLIIKNLKPEDSDTYICEVEDQK

EEVQLVVVCGGGGSQLQMQESGPGLVKPSETLSLSCTVSGDSIRG

GEWGDKDYHWGWVRHSAGKGLEWIGSIHWRGTTHYKESLRRRVSM

SIDTSRNWFSLRLASVTAADTAVYFCARHRHHDVFMLVPIAGWFD

VWGPGVQVTVSSASTKGPSVFPLAPSSKSTSGGTAALGCLVKDYF

PEPVTVSWNSGALTSGVHTFPAVLQSSGLYSLSSVVTVPSSSLGT

QTYICNVNHKPSNTKVDKRVEPKSCDKTHTCPPCPAPELLGGPSV

FLFPPKPKDTLMISRTPEVTCVVVDVSHEDPEVKFNWYVDGVEVH

NAKTKPREEQYNSTYRVVSVLTVLHQDWLNGKEYKCKVSNKALPA

PIEKTISKAKGQPREPQVYTLPPSRDELTKNQVSLTCLVKGFYPS

DIAVEWESNGQPENNYKTTPPVLDSDGSFFLYSKLTVDKSRWQQG

NVFSCSVLHEALHSHYTQKSLSLSPGK

SEQ ID NO: 149

KKVVYGKCGDTVELTCTASQKKNIQFHWKNSNQIKILGNQGSFLT

KGPSKLNDRVDSRRSLWDQGNFPLIIKNLKPEDSDTYICEVEDQK

EEVQLVVVCGGGGSGGGGSGGGGSGGGGSQLQMQESGPGLVKPSE

TLSLSCTVSGDSIRGGEWGDKDYHWGWVRHSAGKGLEWIGSIHWR

GTTHYKESLRRRVSMSIDTSRNWFSLRLASVTAADTAVYFCARHR

HHDVFMLVPIAGWFDVWGPGVQVTVSSASTKGPSVFPLAPSSKST

SGGTAALGCLVKDYFPEPVTVSWNSGALTSGVHTFPAVLQSSGLY

SLSSWVTVPSSSLGTQTYICNVNHKPSNTKVDKRVEPKSCDKTHT

CPPCPAPELLGGPSVFLFPPKPKDTLMISRTPEVTCVVVDVSHED

PEVKFNWYVDGVEVHNAKTKPREEQYNSTYRVVSVLTVLHQDWLN

GKEYKCKVSNKALPAPIEKTISKAKGQPREPQVYTLPPSRDELTK

NQVSLTCLVKGFYPSDIAVEWESNGQPENNYKTTPPVLDSDGSFF

LYSKLTVDKSRWQQGNVFSCSVLHEALHSHYTQKSLSLSPGK

SEQ ID NO: 150

KKVVLGKKGDTVELTCTASQKKNIQFHWKNSNQIKILGNQGSFLT

KGPSKLNDRVDSRRSLWDQGNFPLIIKNLKIEDSDTYICEVEDQK

EEVQLVVFGLTANSDTHLLQGQSLTLTLESPPGSSPSVQCRSPRG

KNIQGGKTLSVSQLELQDSGTWTCTVLQNQKKVEFKIDIVVLAFG

GGGSGGGGSGGGGSGGGGSQVQLVQSGAQMKNPGASVKVSCAPSG

YTFTDFYIHWLRQAPGQGLQWMGWMNPQTGRTNTARNFQGRVTMT

RDTSIGTAYMELRSLTSDDTAIYYCTTGGWISLYYDSSYYPNFDH

WGQGTLLTVSSASTKGPSVFPLAPSSKSTSGGTAALGCLVKDYFP

EPVTVSWNSGALTSGVHTFPAVLQSSGLYSLSSVVTVPSSSLGTQ

TYICNVNHKPSNTKVDKKVEPKSCDKTHTCPPCPAPELLGGPSVF

LFPPKPKDTLMISRTPEVTCVVVDVSHEDPEVKFNWYVDGVEVHN

AKTKPREEQYNSTYRVVSVLTVLHQDWLNGKEYKCKVSNKALPAP

IEKTISKAKGQPREPQVYTLPPSRDELTKNQVSLTCLVKGFYPSD

IAVEWESNGQPENNYKTTPPVLDSDGSFFLYSKLTVDKSRWQQGN

VFSCSVLHEALHSHYTQKSLSLSPGK

SEQ ID NO: 151

KKVVYGKKGDTVELTCTASQKKNIQFHWKNSNQIKILGNQGSFLT

KGPSKLNDRVDSRRSLWDQGNFPLIIKNLKPEDSDTYICEVEDQK

EEVQLVVVGGGGGSGGGGSGGGGSGGGGSQVQLVQSGAQMKNPGA

SVKVSCAPSGYTFTDFYIHWLRQAPGQGLQWMGWMNPQTGRTNTA

RNFQGRVTMTRDTSIGTAYMELRSLTSDDTAIYYCTTGGWISLYY

DSSYYPNFDHWGQGTLLTVSSASTKGPSVFPLAPSSKSTSGGTAA

LGCLVKDYFPEPVTVSWNSGALTSGVHTFPAVLQSSGLYSLSSWV

TVPSSSLGTQTYICNVNHKPSNTKVDKKVEPKSCDKTHTCPPCPA

PELLGGPSVFLFPPKPKDTLMISRTPEVTCVVVDVSHEDPEVKFN

WYVDGVEVHNAKTKPREEQYNSTYRVVSVLTVLHQDWLNGKEYKC

KVSNKALPAPIEKTISKAKGQPREPQVYTLPPSRDELTKNQVSLT

CLVKGFYPSDIAVEWESNGQPENNYKTTPPVLDSDGSFFLYSKLT

VDKSRWQQGNVFSCSVLHEALHSHYTQKSLSLSPGK

SEQ ID NO: 152

KKVVYGKKGDTVELTCTASQKKNIQFHWKNSNQIKILGNQGSFLT

KGPSKLNDRVDSRRSLWDQGNFPLIIKNLKPEDSDTYICEVEDQK

EEVQLVVVGGGGSGGGGSGGGGSGGGGSQPQLQESGPTLVEASE

TLSLTCAVSGDSTAACNSFWGWVRQPPGKCLEWVGSLSHCASYWN

RGWTYHNPSLKSRLTLALDTPKNLVFLKLNSVTAADTATYYCARF

GGEVLRYTDWPKPAWVDLWGRGTLVTVSSGGGGSGGGGSGGGGSG

GGGSQSALTQPPSASGSPGQSITISCTGTSNNFVSWYQQHAGKAP

KLVIYDVNKRPSGVPDRFSGSKSGNTASLTVSGLQTDDEAVYYCG

SLVGNWDVIFGCGTKLTVLGGGGSGGGGSGGGGSDKTHTCPPCPAPELLG

-continued　　　　　　　　　　　　　　　-continued

GPSVFLFPPKPKDTLMISRTPEVTCVVVDVSHEDPEVKFNWYVDG

VEVHNAKTKPREEQYNSTYRVVSVLTVLHQDWLNGKEYKCKVSNK

ALPAPIEKTISKAKGQPREPQVYTLPPSRDELTKNQVSLTCLVKG

FYPSDIAVEWESNGQPENNYKTTPPVLDSDGSFFLYSKLTVDKSR

WQQGNVFSCSVLHEALHSHYTQKSLSLSPGK

SEQ ID NO: 153
KKVVYGKKGDTVELTCTASQKKNIQFHWKNSNQIKILGNQGSFLT

KGPSKLNDRVDSRRSLWDQGNFPLIIKNLKPEDSDTYICEVEDQK

EEVQLVVVGGGGGSGGGGSGGGGSQPQLQESGPTLVEASETLSLT

CAVSGDSTAACNSFWGWVRQPPGKCLEWVGSLSHCASYWNRGWTY

HNPSLKSRLTLALDTPKNLVFLKLNSVTAADTATYYCARFGGEVL

RYTDWPKPAWVDLWGRGTLVTVSSGGGGSGGGGSGGGGSGGGGSQ

SALTQPPSASGSPGQSITISCTGTSNNFVSWYQQHAGKAPKLVIY

DVNKRPSGVPDRFSGSKSGNTASLTVSGLQTDDEAVYYCGSLVGN

WDVIFGCGTKLTVLGGGGSGGGGSDKTHTCPPCPAPELLGGPSVF

LFPPKPKDTLMISRTPEVTCVVVDVSHEDPEVKFNWYVDGVEVHN

AKTKPREEQYNSTYRVVSVLTVLHQDWLNGKEYKCKVSNKALPAP

IEKTISKAKGQPREPQVYTLPPSRDELTKNQVSLTCLVKGFYPSD

IAVEWESNGQPENNYKTTPPVLDSDGSFFLYSKLTVDKSRWQQGN

VFSCSVLHEALHSHYTQKSLSLSPGK

SEQ ID NO: 154
KKVVYGKKGDTVELTCTASQKKNIQFHWKNSNQIKILGNQGSFLT

KGPSKLNDRVDSRRSLWDQGNFPLIIKNLKPEDSDTYICEVEDQK

EEVQLVVVGGGGGSGGGGSQPQLQESGPTLVEASETLSLTCAVSG

DSTAACNSFWGWVRQPPGKCLEWVGSLSHCASYWNRGWTYHNPSL

KSRLTLALDTPKNLVFLKLNSVTAADTATYYCARFGGEVLRYTDW

PKPAWVDLWGRGTLVTVSSGGGGSGGGGSGGGGSGGGGSQSALTQ

PPSASGSPGQSITISCTGTSNNFVSWYQQHAGKAPKLVIYDVNKR

PSGVPDRFSGSKSGNTASLTVSGLQTDDEAVYYCGSLVGNWDVIF

GCGTKLTVLGGGGSGGGGSDKTHTCPPCPAPELLGGPSVFLFPPK

PKDTLMISRTPEVTCVVVDVSHEDPEVKFNWYVDGVEVHNAKTKP

REEQYNSTYRVVSVLTVLHQDWLNGKEYKCKVSNKALPAPIEKTI

SKAKGQPREPQVYTLPPSRDELTKNQVSLTCLVKGFYPSDIAVEW

ESNGQPENNYKTTPPVLDSDGSFFLYSKLTVDKSRWQQGNVFSCS

VLHEALHSHYTQKSLSLSPGK

SEQ ID NO: 155
KKVVYGKKGDTVELTCTASQKKNIQFHWKNSNQIKILGNQGSFLT

KGPSKLNDRVDSRRSLWDQGNFPLIIKNLKPEDSDTYICEVEDQK

EEVQLVVVGGGGGSQPQLQESGPTLVEASETLSLTCAVSGDSTAA

CNSFWGWVRQPPGKCLEWVGSLSHCASYWNRGWTYHNPSLKSRLT

LALDTPKNLVFLKLNSVTAADTATYYCARFGGEVLRYTDWPKPAW

VDLWGRGTLVTVSSGGGGSGGGGSGGGGSGGGGSGGGGSQSALTQPPSAS

SEQ ID NO: 156
GSPGQSITISCTGTSNNFVSWYQQHAGKAPKLVIYDVNKRPSGVP

DRFSGSKSGNTASLTVSGLQTDDEAVYYCGSLVGNWDVIFGCGTK

LTVLGGGGSGGGGSDKTHTCPPCPAPELLGGPSVFLFPPKPKDTL

MISRTPEVTCVVVDVSHEDPEVKFNWYVDGVEVHNAKTKPREEQY

NSTYRVVSVLTVLHQDWLNGKEYKCKVSNKALPAPIEKTISKAKG

QPREPQVYTLPPSRDELTKNQVSLTCLVKGFYPSDIAVEWESNGQ

PENNYKTTPPVLDSDGSFFLYSKLTVDKSRWQQGNVFSCSVLHEA

LHSHYTQKSLSLSPGK

SEQ ID NO: 156
DKTHTCPPCPAPELLGGPSVFLFPPKPKDTLMISRTPEVTCVVVD

VSHEDPEVKFNWYVDGVEVHNAKTKPREEQYNSTYRVVSVLTVLH

QDWLNGKEYKCKVSNKALPAPIEKTISKAKGQPREPQVYTLPPSR

DELTKNQVSLTCLVKGFYPSDIAVEWESNGQPENNYKTTPPVLDS

DGSFFLYSKLTVDKSRWQQGNVFSCSVLHEALHSHYTQKSLSLSP

GKGGGGSGGGGSGGGGSGGGGSKKVVYGKKGDTVELTCTASQKKN

IQFHWKNSNQIKILGNQGSFLTKGPSKLNDRVDSRRSLWDQGNFP

LIIKNLKPEDSDTYICEVEDQKEEVQLVVVGGGGGSGGGGSGGGG

SQPQLQESGPTLVEASETLSLTCAVSGDSTAACNSFWGWVRQPPG

KCLEWVGSLSHCASYWNRGWTYHNPSLKSRLTLALDTPKNLVFLK

LNSVTAADTATYYCARFGGEVLRYTDWPKPAWVDLWGRGTLVTVS

SGGGGSGGGGSGGGGSGGGGSQSALTQPPSASGSPGQSITISCTG

TSNNFVSWYQQHAGKAPKLVIYDVNKRPSGVPDRFSGSKSGNTAS

LTVSGLQTDDEAVYYCGSLVGNWDVIFGCGTKLTVL

SEQ ID NO: 157
QSALTQPPSASGSPGQSITISCTGTSNNFVSWYQQHAGKAPKLVI

YDVNKRPSGVPDRFSGSKSGNTASLTVSGLQTDDEAVYYCGSLVG

NWDVIFGCGTKLTVLGGGGSGGGGSGGGGSGGGGSQPQLQESGPT

LVEASETLSLTCAVSGDSTAACNSFWGWVRQPPGKCLEWVGSLSH

CASYWNRGWTYHNPSLKSRLTLALDTPKNLVFLKLNSVTAADTAT

YYCARFGGEVLRYTDWPKPAWVDLWGRGTLVTVSSGGGGGGGGS

GGGGSGGGGSKKVVYGKKGDTVELTCTASQKKNIQFHWKNSNQIKI

LGNQGSFLTKGPSKLNDRVDSRRSLWDQGNFPLIIKNLKPEDSDT

YICEVEDQKEEVQLVVVGGGGGSGGGGSGGGGSDKTHTCPPCPAP

ELLGGPSVFLFPPKPKDTLMISRTPEVTCVVVDVSHEDPEVKFNW

YVDGVEVHNAKTKPREEQYNSTYRVVSVLTVLHQDWLNGKEYKCK

VSNKALPAPIEKTISKAKGQPREPQVYTLPPSRDELTKNQVSLTC

LVKGFYPSDIAVEWESNGQPENNYKTTPPVLDSDGSFFLYSKLTV

DKSRWQQGNVFSCSVLHEALHSHYTQKSLSLSPGK

SEQ ID NO: 158
KKVVYGKCGDTVELTCTASQKKNIQFHWKNSNQIKILGNQGSFLT

KGPSKLNDRVDSRRSLWDQGNFPLIIKNLKPEDSDTYICEVEDQK

EEVQLVVVCGGGGSGGGGSGGGGSGGGGSDKTHTCPPCPAPELLG

-continued

GPSVFLFPPKPKDTLMISRTPEVTCVVVDVSHEDPEVKFNWYVDG

VEVHNAKTKPREEQYNSTYRVVSVLTVLHQDWLNGKEYKCKVSNK

ALPAPIEKTISKAKGQPREPQVYTLPPSRDELTKNQVSLTCLVKG

FYPSDIAVEWESNGQPENNYKTTPPVLDSDGSFFLYSKLTVDKSR

WQQGNVFSCSVLHEALHSHYTQKSLSLSPGK

SEQ ID NO: 159

DNYWS

SEQ ID NO: 160

YVHDSGDTNYNPSLKS

SEQ ID NO: 161

TKHGRRIYGVVAFKEWFTYFYMDV

SEQ ID NO: 162

GEESLGSRSVI

SEQ ID NO: 163

NNNDRPS

SEQ ID NO: 164

HIWDSRRPTNWV

SEQ ID NO: 165

DAYWS

SEQ ID NO: 166

YVHHSGDTNYNPSLKR

SEQ ID NO: 167

ALHGKRIYGIVALGELFTYFYMDV

SEQ ID NO: 168

GKESIGSRAVQ

SEQ ID NO: 169

NNQDRPA

SEQ ID NO: 170

HIYDARGGTNWV

SEQ ID NO: 171

ACTYFWG

SEQ ID NO: 172

SLSHCQSFWGSGWTFHNPSLKS

SEQ ID NO: 173

FDGEVLVYNHWPKPAWVDL

SEQ ID NO: 174

NGTATNFVS

SEQ ID NO: 175

GVDKRPP

SEQ ID NO: 176

GSLVGNWDVI

SEQ ID NO: 177

ACDYFWG

SEQ ID NO: 178

GLSHCAGYYNTGWTYHNPSLKS

SEQ ID NO: 179

FDGEVLVYHDWPKPAWVDL

SEQ ID NO: 180

TGTSNRFVS

SEQ ID NO: 181

GVNKRPS

-continued

SEQ ID NO: 182

SSLVGNWDVI

SEQ ID NO: 183

RCNYFWG

SEQ ID NO: 184

SLSHCRSYYNTDWTYHNPSLKS

SEQ ID NO: 185

FGGEVLVYRDWPKPAWVDL

SEQ ID NO: 186

TGTSNNFVS

SEQ ID NO: 187

EVNKRPS

SEQ ID NO: 188

SSLVGNWDVI

SEQ ID NO: 189

TGHYYWG

SEQ ID NO: 190

HIHYTTAVLHNPSLKS

SEQ ID NO: 191

SGGDILYYYEWQKPHWFSP

SEQ ID NO: 192

NGTSSDIGGWNFVS

SEQ ID NO: 193

EVNKRPS

SEQ ID NO: 194

SSLFGRWDVV

SEQ ID NO: 185

TGHHYWG

SEQ ID NO: 196

HIHYNTAVLHNPALKS

SEQ ID NO: 197

SGGDILYYIEWQKPHWFYP

SEQ ID NO: 198

SGTGSDIGSWNFVS

SEQ ID NO: 199

EVNRRRS

SEQ ID NO: 200

SSLSGRWDIV

SEQ ID NO: 201

GTDWGENDFHYG

SEQ ID NO: 202

SIHWRGRTTHYKTSFRS

SEQ ID NO: 203

HKYHDIFRVVPVAGWFDP

SEQ ID NO: 204

RASQNVKNNLA

SEQ ID NO: 205

DASSRAG

SEQ ID NO: 206

QQYEEWPRT

SEQ ID NO: 207

GGEWGDSDYHWG

SEQ ID NO: 208

SIHWRGTTHYNAPFRG

-continued

SEQ ID NO: 209
HKYHDIVMVVPIAGWFDP

SEQ ID NO: 210
RASQSVKNNLA

SEQ ID NO: 211
DTSSRAS

SEQ ID NO: 212
QQYEEWPRT

SEQ ID NO: 213
DVWLN

SEQ ID NO: 214
RIKSRTDGGTTDYAASVKG

SEQ ID NO: 215
DGFIMIRGVSEDYYYYYMDV

SEQ ID NO: 216
SGSSSNIGNNYVL

SEQ ID NO: 217
GNNKRPS

SEQ ID NO: 218
ATWDSGLSADWV

SEQ ID NO: 219
SYVMH

SEQ ID NO: 220
AISSDGETTYHANSVKG

SEQ ID NO: 221
DRYYETSGSNAFDV

SEQ ID NO: 222
QASQDISNYLN

SEQ ID NO: 223
TASNLET

SEQ ID NO: 224
QQYDNLGDLS

SEQ ID NO: 225
NFAIH

SEQ ID NO: 226
GRVPVVGIYKYGKKFHD

SEQ ID NO: 227
WRGCGMCPYDTSSYYNDASDV

SEQ ID NO: 228
RASQNISSSWIA

SEQ ID NO: 229
AASARAA

SEQ ID NO: 230
QYYGGSFFT

SEQ ID NO: 231
AHTMN

SEQ ID NO: 232
SISTSSTYRDYADAVKG

SEQ ID NO: 233
KGSDRLSDNDPFDA

SEQ ID NO: 234
RASQSIETWLA

SEQ ID NO: 235
KASTLKT

-continued

SEQ ID NO: 236
QHYAGYSAT

SEQ ID NO: 237
SSYWS

SEQ ID NO: 238
YTHHSGDTNYAPSLKS

SEQ ID NO: 239
TLHGRRIYGVVAFNEFFTYFYWEV

SEQ ID NO: 240
GGESIGSRAVQ

SEQ ID NO: 241
NNQDRPP

SEQ ID NO: 242
HIWDSRRPTNWV

SEQ ID NO: 243
SSYWS

SEQ ID NO: 244
YTHHSGDTNYAPSLKS

SEQ ID NO: 245
TLHGRRIYGVVAFNEYYTYFYWPT

SEQ ID NO: 246
GGESIGSRAVQ

SEQ ID NO: 247
NNQDRPP

SEQ ID NO: 248
HIWDSRRPTNWE

SEQ ID NO: 249
SSYWS

SEQ ID NO: 250
YTHHSGDTNYAPSLKS

SEQ ID NO: 251
TLHGRRIYGVVAFNEYYTYFYWPT

SEQ ID NO: 252
TGTSSDIGASDYVS

SEQ ID NO: 253
DVTKRPS

SEQ ID NO: 254
SSDAGRHTLL

SEQ ID NO: 255
QVHLQESGPGLVKPSETLSLTCNVSGTLVRDNYWSWIRQPLGKQP
EWIGYVHDSGDTNYNPSLKSRVHLSLDKSKNLVSLRLTGVTAADS
AIYYCATTKHGRRIYGVVAFKEWFTYFYMDVWGKGTSVTVSS

SEQ ID NO: 256
TFVSVAPGQTARITCGEESLGSRSVIWYQQRPGQAPSLIIYNNND
RPSGIPDRFSGSPGSTFGTTATLTITSVEAGDEADYYCHIWDSRR
PTNWVFGEGTTLIVL

SEQ ID NO: 257
QVHLQESGPGLVKPSETLSLTCNVSGTLVRDNYWSWIRQPLGKQP
EWIGYVHDSGDTNYNPSLKSRVHLSLDKSKNLVSLRLTGVTAADS
AIYYCATTKHGRRIYGVVAFKEWFTYFYMDVWGKGTSVTVSSAST
KGPSVFPLAPSSKSTSGGTAALGCLVKDYFPEPVTVSWNSGALTS
GVHTFPAVLQSSGLYSLSSVVTVPSSSLGTQTYICNVNHKPSNTK

VDKKVEPKSCDKTHTCPPCPAPELLGGPSVFLFPPKPKDTLMISR

TPEVTCVVVDVSHEDPEVKFNWYVDGVEVHNAKTKPREEQYNSTY

RVVSVLTVLHQDWLNGKEYKCKVSNKALPAPIEKTISKAKGQPRE

PQVYTLPPSRDELTKNQVSLTCLVKGFYPSDIAVEWESNGQPENN

YKTTPPVLDSDGSFFLYSKLTVDKSRWQQGNVFSCSVMHEALHNH

YTQKSLSLSPGK

```
                                   SEQ ID NO: 258
```
QVHLQESGPGLVKPSETLSLTCNVSGTLVRDNYWSWIRQPLGKQP

EWIGYVHDSGDTNYNPSLKSRVHLSLDKSKNLVSLRLTGVTAADS

AIYYCATTKHGRRIYGVVAFKEWFTYFYMDVWGKGTSVTVSSAST

KGPSVFPLAPSSKSTSGGTAALGCLVKDYFPEPVTVSWNSGALTS

GVHTFPAVLQSSGLYSLSSVVTVPSSSLGTQTYICNVNHKPSNTK

VDKKVEPKSCDKTHTCPPCPAPELLGGPSVFLFPPKPKDTLMISR

TPEVTCVVVDVSHEDPEVKFNWYVDGVEVHNAKTKPREEQYNSTY

RVVSVLTVLHQDWLNGKEYKCKVSNKALPAPIEKTISKAKGQPRE

PQVYTLPPSRDELTKNQVSLTCLVKGFYPSDIAVEWESNGQPENN

YKTTPPVLDSDGSFFLYSKLTVDKSRWQQGNVFSCSVLHEALHSH

YTQKSLSLSPGK

```
                                   SEQ ID NO: 259
```
TFVSVAPGQTARITCGEESLGSRSVIWYQQRPGQAPSLIIYNNND

RPSGIPDRFSGSPGSTFGTTATLTITSVEAGDEADYYCHIWDSRR

PTNWVFGEGTTLIVLGQPKAAPSVTLFPPSSEELQANKATLVCLI

SDFYPGAVTVAWKADSSPVKAGVETTTPSKQSNNKYAASSYLSLT

PEQWKSHRSYSCQVTHEGSTVEKTVAPTECS

```
                                   SEQ ID NO: 260
```
QLHLQESGPGLVKPPETLSLTCSVSGASINDAYWSWIRQSPGKRP

EWVGYVHHSGDTNYNPSLKRRVTFSLDTAKNEVSLKLVDLTAADS

ATYFCARALHGKRIYGIVALGELFTYFYMDVWGKGTAVTVSS

```
                                   SEQ ID NO: 261
```
SSMSVSPGETAKISCGKESIGSRAVQWYQQKPGQPPSLIIYNNQD

RPAGVPERFSASPDFRPGTTATLTITNVDAEDEADYYCHIYDARG

GTNWVFDRGTTLTVL

```
                                   SEQ ID NO: 262
```
QLHLQESGPGLVKPPETLSLTCSVSGASINDAYWSWIRQSPGKRP

EWVGYVHHSGDTNYNPSLKRRVTFSLDTAKNEVSLKLVDLTAADS

ATYFCARALHGKRIYGIVALGELFTYFYMDVWGKGTAVTVSSAST

KGPSVFPLAPSSKSTSGGTAALGCLVKDYFPEPVTVSWNSGALTS

GVHTFPAVLQSSGLYSLSSVVTVPSSSLGTQTYICNVNHKPSNTK

VDKKVEPKSCDKTHTCPPCPAPELLGGPSVFLFPPKPKDTLMISR

TPEVTCVVVDVSHEDPEVKFNWYVDGVEVHNAKTKPREEQYNSTY

RVVSVLTVLHQDWLNGKEYKCKVSNKALPAPIEKTISKAKGQPRE

PQVYTLPPSRDELTKNQVSLTCLVKGFYPSDIAVEWESNGQPENN

YKTTPPVLDSDGSFFLYSKLTVDKSRWQQGNVFSCSVMHEALHNH

YTQKSLSLSPGK

```
                                   SEQ ID NO: 263
```
QLHLQESGPGLVKPPETLSLTCSVSGASINDAYWSWIRQSPGKRP

EWVGYVHHSGDTNYNPSLKRRVTFSLDTAKNEVSLKLVDLTAADS

ATYFCARALHGKRIYGIVALGELFTYFYMDVWGKGTAVTVSSAST

KGPSVFPLAPSSKSTSGGTAALGCLVKDYFPEPVTVSWNSGALTS

GVHTFPAVLQSSGLYSLSSVVTVPSSSLGTQTYICNVNHKPSNTK

VDKKVEPKSCDKTHTCPPCPAPELLGGPSVFLFPPKPKDTLMISR

TPEVTCVVVDVSHEDPEVKFNWYVDGVEVHNAKTKPREEQYNSTY

RVVSVLTVLHQDWLNGKEYKCKVSNKALPAPIEKTISKAKGQPRE

PQVYTLPPSRDELTKNQVSLTCLVKGFYPSDIAVEWESNGQPENN

YKTTPPVLDSDGSFFLYSKLTVDKSRWQQGNVFSCSVLHEALHSH

YTQKSLSLSPGK

```
                                   SEQ ID NO: 264
```
SSMSVSPGETAKISCGKESIGSRAVQWYQQKPGQPPSLIIYNNQD

RPAGVPERFSASPDFRPGTTATLTITNVDAEDEADYYCHIYDARG

GTNWVFDRGTTLTVLGQPKAAPSVTLFPPSSEELQANKATLVCLI

SDFYPGAVTVAWKADSSPVKAGVETTTPSKQSNNKYAASSYLSLT

PEQWKSHRSYSCQVTHEGSTVEKTVAPTECS

```
                                   SEQ ID NO: 265
```
QSQLQESGPRLVEASETLSLTCNVSGESTGACTYFWGWVRQAPGK

GLEWIGSLSHCQSFWGSGWTFHNPSLKSRLTISLDTPKNQVFLKL

TSLTAADTATYYCARFDGEVLVYNHWPKPAWVDLWGRGIPVTVTV

SS

```
                                   SEQ ID NO: 266
```
QSALTQPPSASGSPGQSITISCNGTATNFVSWYQQFPDKAPKLII

FGVDKRPPGVPDRFSGSRSGTTASLTVSRLQTDDEAVYYCGSLVG

NWDVIFGGGTTLTVL

```
                                   SEQ ID NO: 267
```
QSQLQESGPRLVEASETLSLTCNVSGESTGACTYFWGWVRQAPGK

GLEWIGSLSHCQSFWGSGWTFHNPSLKSRLTISLDTPKNQVFLKL

TSLTAADTATYYCARFDGEVLVYNHWPKPAWVDLWGRGIPVTVTV

SSASTKGPSVFPLAPSSKSTSGGTAALGCLVKDYFPEPVTVSWNS

GALTSGVHTFPAVLQSSGLYSLSSVVTVPSSSLGTQTYICNVNHK

PSNTKVDKKVEPKSCDKTHTCPPCPAPELLGGPSVFLFPPKPKDT

LMISRTPEVTCVVVDVSHEDPEVKFNWYVDGVEVHNAKTKPREEQ

YNSTYRVVSVLTVLHQDWLNGKEYKCKVSNKALPAPIEKTISKAK

GQPREPQVYTLPPSRDELTKNQVSLTCLVKGFYPSDIAVEWESNG

QPENNYKTTPPVLDSDGSFFLYSKLTVDKSRWQQGNVFSCSVMHE

ALHNHYTQKSLSLSPGK

```
                                   SEQ ID NO: 268
QSQLQESGPRLVEASETLSLTCNVSGESTGACTYFWGWVRQAPGK

GLEWIGSLSHCQSFWGSGWTFHNPSLKSRLTISLDTPKNQVFLKL

TSLTAADTATYYCARFDGEVLVYNHWPKPAWVDLWGRGIPVTVTV

SSASTKGPSVFPLAPSSKSTSGGTAALGCLVKDYFPEPVTVSWNS

GALTSGVHTFPAVLQSSGLYSLSSVVTVPSSSLGTQTYICNVNHK

PSNTKVDKKVEPKSCDKTHTCPPCPAPELLGGPSVFLFPPKPKDT

LMISRTPEVTCVVVDVSHEDPEVKFNWYVDGVEVHNAKTKPREEQ

YNSTYRVVSVLTVLHQDWLNGKEYKCKVSNKALPAPIEKTISKAK

GQPREPQVYTLPPSRDELTKNQVSLTCLVKGFYPSDIAVEWESNG

QPENNYKTTPPVLDSDGSFFLYSKLTVDKSRWQQGNVFSCSVLHE

ALHSHYTQKSLSLSPGK

SEQ ID NO: 269
QSALTQPPSASGSPGQSITISCNGTATNFVSWYQQFPDKAPKLII

FGVDKRPPGVPDRFSGSRSGTTASLTVSRLQTDDEAVYYCGSLVG

NWDVIFGGGTTLTVLGQPKAAPSVTLFPPSSEELQANKATLVCLI

SDFYPGAVTVAWKADSSPVKAGVETTTPSKQSNNKYAASSYLSLT

PEQWKSHRSYSCQVTHEGSTVEKTVAPTECS

SEQ ID NO: 270
QPQLQESGPGLVEASETLSLTCTVSGDSTAACDYFWGWVRQPPGK

GLEWIGGLSHCAGYYNTGWTYHNPSLKSRLTISLDTPKNQVFLKL

NSVTAADTAIYYCARFDGEVLVYHDWPKPAWVDLWGRGTLVTVTV

SS

SEQ ID NO: 271
QSALTQPPSASGSPGQSISISCTGTSNRFVSWYQQHPGKAPKLVI

YGVNKRPSGVPDRFSGSKSGNTASLTVSGLQTDDEAVYYCSSLVG

NWDVIFGGGTKLTVL

SEQ ID NO: 272
QPQLQESGPGLVEASETLSLTCTVSGDSTAACDYFWGWVRQPPGK

GLEWIGGLSHCAGYYNTGWTYHNPSLKSRLTISLDTPKNQVFLKL

NSVTAADTAIYYCARFDGEVLVYHDWPKPAWVDLWGRGTLVTVTV

SSASTKGPSVFPLAPSSKSTSGGTAALGCLVKDYFPEPVTVSWNS

GALTSGVHTFPAVLQSSGLYSLSSVVTVPSSSLGTQTYICNVNHK

PSNTKVDKKVEPKSCDKTHTCPPCPAPELLGGPSVFLFPPKPKDT

LMISRTPEVTCVVVDVSHEDPEVKFNWYVDGVEVHNAKTKPREEQ

YNSTYRVVSVLTVLHQDWLNGKEYKCKVSNKALPAPIEKTISKAK

GQPREPQVYTLPPSRDELTKNQVSLTCLVKGFYPSDIAVEWESNG

QPENNYKTTPPVLDSDGSFFLYSKLTVDKSRWQQGNVFSCSVMHE

ALHNHYTQKSLSLSPGK

SEQ ID NO: 273
QPQLQESGPGLVEASETLSLTCTVSGDSTAACDYFWGWVRQPPGK

GLEWIGGLSHCAGYYNTGWTYHNPSLKSRLTISLDTPKNQVFLKL

NSVTAADTAIYYCARFDGEVLVYHDWPKPAWVDLWGRGTLVTVTV
```

```
SSASTKGPSVFPLAPSSKSTSGGTAALGCLVKDYFPEPVTVSWNS

GALTSGVHTFPAVLQSSGLYSLSSVVTVPSSSLGTQTYICNVNHK

PSNTKVDKKVEPKSCDKTHTCPPCPAPELLGGPSVFLFPPKPKDT

LMISRTPEVTCVVVDVSHEDPEVKFNWYVDGVEVHNAKTKPREEQ

YNSTYRVVSVLTVLHQDWLNGKEYKCKVSNKALPAPIEKTISKAK

GQPREPQVYTLPPSRDELTKNQVSLTCLVKGFYPSDIAVEWESNG

QPENNYKTTPPVLDSDGSFFLYSKLTVDKSRWQQGNVFSCSVLHE

ALHSHYTQKSLSLSPGK

SEQ ID NO: 274
QSALTQPPSASGSPGQSISISCTGTSNRFVSWYQQHPGKAPKLVI

YGVNKRPSGVPDRFSGSKSGNTASLTVSGLQTDDEAVYYCSSLVG

NWDVIFGGGTKLTVLGQPKAAPSVTLFPPSSEELQANKATLVCLI

SDFYPGAVTVAWKADSSPVKAGVETTTPSKQSNNKYAASSYLSLT

PEQWKSHRSYSCQVTHEGSTVEKTVAPTECS

SEQ ID NO: 275
QPQLQESGPGLVEASETLSLTCTVSGDSTGRCNYFWGWVRQPPGK

GLEWIGSLSHCRSYYNTDWTYHNPSLKSRLTISLDTPKNQVFLRL

TSVTAADTATYYCARFGGEVLVYRDWPKPAWVDLWGRGTLVTVSS

SEQ ID NO: 276
QSALTQPPSASGSPGQSITISCTGTSNNFVSWYQQYPGKAPKLVI

YEVNKRPSGVPDRFSGSKSGSTASLTVSGLQADDEGVYYCSSLVG

NWDVIFGGGTKLTVL

SEQ ID NO: 277
QPQLQESGPGLVEASETLSLTCTVSGDSTGRCNYFWGWVRQPPGK

GLEWIGSLSHCRSYYNTDWTYHNPSLKSRLTISLDTPKNQVFLRL

TSVTAADTATYYCARFGGEVLVYRDWPKPAWVDLWGRGTLVTVSS

ASTKGPSVFPLAPSSKSTSGGTAALGCLVKDYFPEPVTVSWNSGA

LTSGVHTFPAVLQSSGLYSLSSVVTVPSSSLGTQTYICNVNHKPS

NTKVDKKVEPKSCDKTHTCPPCPAPELLGGPSVFLFPPKPKDTLM

ISRTPEVTCVVVDVSHEDPEVKFNWYVDGVEVHNAKTKPREEQYN

STYRVVSVLTVLHQDWLNGKEYKCKVSNKALPAPIEKTISKAKGQ

PREPQVYTLPPSRDELTKNQVSLTCLVKGFYPSDIAVEWESNGQP

ENNYKTTPPVLDSDGSFFLYSKLTVDKSRWQQGNVFSCSVMHEAL

HNHYTQKSLSLSPGK

SEQ ID NO: 278
QPQLQESGPGLVEASETLSLTCTVSGDSTGRCNYFWGWVRQPPGK

GLEWIGSLSHCRSYYNTDWTYHNPSLKSRLTISLDTPKNQVFLRL

TSVTAADTATYYCARFGGEVLVYRDWPKPAWVDLWGRGTLVTVSS

ASTKGPSVFPLAPSSKSTSGGTAALGCLVKDYFPEPVTVSWNSGA

LTSGVHTFPAVLQSSGLYSLSSVVTVPSSSLGTQTYICNVNHKPS

NTKVDKKVEPKSCDKTHTCPPCPAPELLGGPSVFLFPPKPKDTLM

ISRTPEVTCVVVDVSHEDPEVKFNWYVDGVEVHNAKTKPREEQYN

STYRVVSVLTVLHQDWLNGKEYKCKVSNKALPAPIEKTISKAKGQ
```

-continued

PREPQVYTLPPSRDELTKNQVSLTCLVKGFYPSDIAVEWESNGQP

ENNYKTTPPVLDSDGSFFLYSKLTVDKSRWQQGNVFSCSVLHEAL

HSHYTQKSLSLSPGK

SEQ ID NO: 279
QSALTQPPSASGSPGQSITISCTGTSNNFVSWYQQYPGKAPKLVI

YEVNKRPSGVPDRFSGSKSGSTASLTVSGLQADDEGVYYCSSLVG

NWDVIFGGGTKLTVLGQPKAAPSVTLFPPSSEELQANKATLVCLI

SDFYPGAVTVAWKADSSPVKAGVETTTPSKQSNNKYAASSYLSLT

PEQWKSHRSYSCQVTHEGSTVEKTVAPTECS

SEQ ID NO: 280
QVQLQESGPGLVKPAETLSLTCSVSGESINTGHYYWGWVRQVPGK

GLEWIGHIHYTTAVLHNPSLKSRLTIKIYTLRNQITLRLSNVTAA

DTAVYHCVRSGGDILYYYEWQKPHWFSPWGPGIHVTVSS

SEQ ID NO: 281
QSALTQPPSASGSLGQSVTISCNGTSSDIGGWNFVSWYQQFPGRA

PRLIIFEVNKRPSGVPGRFSGSKSGNSASLTVSGLQSDDEGQYFC

SSLFGRWDVVFGGGTKLTVL

SEQ ID NO: 282
QVQLQESGPGLVKPAETLSLTCSVSGESINTGHYYWGWVRQVPGK

GLEWIGHIHYTTAVLHNPSLKSRLTIKIYTLRNQITLRLSNVTAA

DTAVYHCVRSGGDILYYYEWQKPHWFSPWGPGIHVTVSSASTKGP

SVFPLAPSSKSTSGGTAALGCLVKDYFPEPVTVSWNSGALTSGVH

TFPAVLQSSGLYSLSSVVTVPSSSLGTQTYICNVNHKPSNTKVDK

KVEPKSCDKTHTCPPCPAPELLGGPSVFLFPPKPKDTLMISRTPE

VTCVVVDVSHEDPEVKFNWYVDGVEVHNAKTKPREEQYNSTYRVV

SVLTVLHQDWLNGKEYKCKVSNKALPAPIEKTISKAKGQPREPQV

YTLPPSRDELTKNQVSLTCLVKGFYPSDIAVEWESNGQPENNYKT

TPPVLDSDGSFFLYSKLTVDKSRWQQGNVFSCSVMHEALHNHYTQ

KSLSLSPGK

SEQ ID NO: 283
QVQLQESGPGLVKPAETLSLTCSVSGESINTGHYYWGWVRQVPGK

GLEWIGHIHYTTAVLHNPSLKSRLTIKIYTLRNQITLRLSNVTAA

DTAVYHCVRSGGDILYYYEWQKPHWFSPWGPGIHVTVSSASTKGP

SVFPLAPSSKSTSGGTAALGCLVKDYFPEPVTVSWNSGALTSGVH

TFPAVLQSSGLYSLSSVVTVPSSSLGTQTYICNVNHKPSNTKVDK

KVEPKSCDKTHTCPPCPAPELLGGPSVFLFPPKPKDTLMISRTPE

VTCVVVDVSHEDPEVKFNWYVDGVEVHNAKTKPREEQYNSTYRVV

SVLTVLHQDWLNGKEYKCKVSNKALPAPIEKTISKAKGQPREPQV

YTLPPSRDELTKNQVSLTCLVKGFYPSDIAVEWESNGQPENNYKT

TPPVLDSDGSFFLYSKLTVDKSRWQQGNVFSCSVLHEALHSHYTQ

KSLSLSPGK

-continued

SEQ ID NO: 284
QSALTQPPSASGSLGQSVTISCNGTSSDIGGWNFVSWYQQFPGRA

PRLIIFEVNKRPSGVPGRFSGSKSGNSASLTVSGLQSDDEGQYFC

SSLFGRWDVVFGGGTKLTVLGQPKAAPSVTLFPPSSEELQANKAT

LVCLISDFYPGAVTVAWKADSSPVKAGVETTTPSKQSNNKYAASS

YLSLTPEQWKSHRSYSCQVTHEGSTVEKTVAPTECS

SEQ ID NO: 285
QVQLQESGPGLVKPSETLSLTCTVSGDSINTGHHYWGWVRQVPGK

GPEWIAHIHYNTAVLHNPALKSRVTISIFTLKNLITLSLSNVTAA

DTAVYFCVRSGGDILYYIEWQKPHWFYPWGPGILVTVSS

SEQ ID NO: 286
QSALTQPPSASGSLGQSLTISCSGTGSDIGSWNFVSWYQQFPGRA

PNLIIFEVNRRRSGVPDRFSGSKSGNTASLTVSGLRSEDEAEYFC

SSLSGRWDIVFGGGTKVTVL

SEQ ID NO: 287
QVQLQESGPGLVKPSETLSLTCTVSGDSINTGHHYWGWVRQVPGK

GPEWIAHIHYNTAVLHNPALKSRVTISIFTLKNLITLSLSNVTAA

DTAVYFCVRSGGDILYYIEWQKPHWFYPWGPGILVTVSSASTKGP

SVFPLAPSSKSTSGGTAALGCLVKDYFPEPVTVSWNSGALTSGVH

TFPAVLQSSGLYSLSSVVTVPSSSLGTQTYICNVNHKPSNTKVDK

KVEPKSCDKTHTCPPCPAPELLGGPSVFLFPPKPKDTLMISRTPE

VTCVVVDVSHEDPEVKFNWYVDGVEVHNAKTKPREEQYNSTYRVV

SVLTVLHQDWLNGKEYKCKVSNKALPAPIEKTISKAKGQPREPQV

YTLPPSRDELTKNQVSLTCLVKGFYPSDIAVEWESNGQPENNYKT

TPPVLDSDGSFFLYSKLTVDKSRWQQGNVFSCSVMHEALHNHYTQ

KSLSLSPGK

SEQ ID NO: 288
QVQLQESGPGLVKPSETLSLTCTVSGDSINTGHHYWGWVRQVPGK

GPEWIAHIHYNTAVLHNPALKSRVTISIFTLKNLITLSLSNVTAA

DTAVYFCVRSGGDILYYIEWQKPHWFYPWGPGILVTVSSASTKGP

SVFPLAPSSKSTSGGTAALGCLVKDYFPEPVTVSWNSGALTSGVH

TFPAVLQSSGLYSLSSVVTVPSSSLGTQTYICNVNHKPSNTKVDK

KVEPKSCDKTHTCPPCPAPELLGGPSVFLFPPKPKDTLMISRTPE

VTCVVVDVSHEDPEVKFNWYVDGVEVHNAKTKPREEQYNSTYRVV

SVLTVLHQDWLNGKEYKCKVSNKALPAPIEKTISKAKGQPREPQV

YTLPPSRDELTKNQVSLTCLVKGFYPSDIAVEWESNGQPENNYKT

TPPVLDSDGSFFLYSKLTVDKSRWQQGNVFSCSVLHEALHSHYTQ

KSLSLSPGK

SEQ ID NO: 289
QSALTQPPSASGSLGQSLTISCSGTGSDIGSWNFVSWYQQFPGRA

PNLIIFEVNRRRSGVPDRFSGSKSGNTASLTVSGLRSEDEAEYFC

SSLSGRWDIVFGGGTKVTVLGQPKAAPSVTLFPPSSEELQANKAT

-continued

LVCLISDFYPGAVTVAWKADSSPVKAGVETTTPSKQSNNKYAASS

YLSLTPEQWKSHRSYSCQVTHEGSTVEKTVAPTECS

SEQ ID NO: 290
QLQLQESGPGLVKPSETLSLTCTVSGGSMRGTDWGENDFHYGWIR

QSSAKGLEWIGSIHWRGRTTHYKTSFRSRATLSIDTSNNRFSLTF

SFVTAADTAVYYCARHKYHDIFRVVPVAGWFDPWGQGLLVTVSS

SEQ ID NO: 291
EIVMTQSPPTLSVSPGETATLSCRASQNVKNNLAWYQLKPGQAPR

LLIFDASSRAGGIPDRFSGSGYGTDFTLTVNSVQSEDFGDYFCQQ

YEEWPRTFGQGTKVDIK

SEQ ID NO: 292
QLQLQESGPGLVKPSETLSLTCTVSGGSMRGTDWGENDFHYGWIR

QSSAKGLEWIGSIHWRGRTTHYKTSFRSRATLSIDTSNNRFSLTF

SFVTAADTAVYYCARHKYHDIFRVVPVAGWFDPWGQGLLVTVSSA

STKGPSVFPLAPSSKSTSGGTAALGCLVKDYFPEPVTVSWNSGAL

TSGVHTFPAVLQSSGLYSLSSVVTVPSSSLGTQTYICNVNHKPSN

TKVDKKVEPKSCDKTHTCPPCPAPELLGGPSVFLFPPKPKDTLMI

SRTPEVTCVVVDVSHEDPEVKFNWYVDGVEVHNAKTKPREEQYNS

TYRVVSVLTVLHQDWLNGKEYKCKVSNKALPAPIEKTISKAKGQP

REPQVYTLPPSRDELTKNQVSLTCLVKGFYPSDIAVEWESNGQPE

NNYKTTPPVLDSDGSFFLYSKLTVDKSRWQQGNVFSCSVMHEALH

NHYTQKSLSLSPGK

SEQ ID NO: 293
QLQLQESGPGLVKPSETLSLTCTVSGGSMRGTDWGENDFHYGWIR

QSSAKGLEWIGSIHWRGRTTHYKTSFRSRATLSIDTSNNRFSLTF

SFVTAADTAVYYCARHKYHDIFRVVPVAGWFDPWGQGLLVTVSSA

STKGPSVFPLAPSSKSTSGGTAALGCLVKDYFPEPVTVSWNSGAL

TSGVHTFPAVLQSSGLYSLSSVVTVPSSSLGTQTYICNVNHKPSN

TKVDKKVEPKSCDKTHTCPPCPAPELLGGPSVFLFPPKPKDTLMI

SRTPEVTCVVVDVSHEDPEVKFNWYVDGVEVHNAKTKPREEQYNS

TYRVVSVLTVLHQDWLNGKEYKCKVSNKALPAPIEKTISKAKGQP

REPQVYTLPPSRDELTKNQVSLTCLVKGFYPSDIAVEWESNGQPE

NNYKTTPPVLDSDGSFFLYSKLTVDKSRWQQGNVFSCSVLHEALH

SHYTQKSLSLSPGK

SEQ ID NO: 294
EIVMTQSPPTLSVSPGETATLSCRASQNVKNNLAWYQLKPGQAPR

LLIFDASSRAGGIPDRFSGSGYGTDFTLTVNSVQSEDFGDYFCQQ

YEEWPRTFGQGTKVDIKRTVAAPSVFIFPPSDEQLKSGTASVVCL

LNNFYPREAKVQWKVDNALQSGNSQESVTEQDSKDSTYSLSSTLT

LSKADYEKHKVYACEVTHQGLSSPVTKSFNRGEC

-continued

SEQ ID NO: 295
EVHLEESGPGLVRPSETLSLTCTASGGSIRGGEWGDSDYHWGWVR

HSPEKGLEWIGSIHWRGTTHYNAPFRGRGRLSIDLSRNQFSLRLT

SVTAEDTAVYYCVKHKYHDIVMVVPIAGWFDPWGQGLQVTVSS

SEQ ID NO: 296
EIMMTQSPAILSVSPGDRATLSCRASQSVKNNLAWYQKRPGQAPR

LLIFDTSSRASGIPARFSGGGSGTEFTLTVNSMQSEDFATYYCQQ

YEEWPRTFGQGTKVEIK

SEQ ID NO: 297
EVHLEESGPGLVRPSETLSLTCTASGGSIRGGEWGDSDYHWGWVR

HSPEKGLEWIGSIHWRGTTHYNAPFRGRGRLSIDLSRNQFSLRLT

SVTAEDTAVYYCVKHKYHDIVMVVPIAGWFDPWGQGLQVTVSSAS

TKGPSVFPLAPSSKSTSGGTAALGCLVKDYFPEPVTVSWNSGALT

SGVHTFPAVLQSSGLYSLSSVVTVPSSSLGTQTYICNVNHKPSNT

KVDKKVEPKSCDKTHTCPPCPAPELLGGPSVFLFPPKPKDTLMIS

RTPEVTCVVVDVSHEDPEVKFNWYVDGVEVHNAKTKPREEQYNST

YRVVSVLTVLHQDWLNGKEYKCKVSNKALPAPIEKTISKAKGQPR

EPQVYTLPPSRDELTKNQVSLTCLVKGFYPSDIAVEWESNGQPEN

NYKTTPPVLDSDGSFFLYSKLTVDKSRWQQGNVFSCSVMHEALHN

HYTQKSLSLSPGK

SEQ ID NO: 298
EVHLEESGPGLVRPSETLSLTCTASGGSIRGGEWGDSDYHWGWVR

HSPEKGLEWIGSIHWRGTTHYNAPFRGRGRLSIDLSRNQFSLRLT

SVTAEDTAVYYCVKHKYHDIVMVVPIAGWFDPWGQGLQVTVSSAS

TKGPSVFPLAPSSKSTSGGTAALGCLVKDYFPEPVTVSWNSGALT

SGVHTFPAVLQSSGLYSLSSVVTVPSSSLGTQTYICNVNHKPSNT

KVDKKVEPKSCDKTHTCPPCPAPELLGGPSVFLFPPKPKDTLMIS

RTPEVTCVWDVSHEDPEVKFNWYVDGVEVHNAKTKPREEQYNSTY

RVVSVLTVLHQDWLNGKEYKCKVSNKALPAPIEKTISKAKGQPRE

PQVYTLPPSRDELTKNQVSLTCLVKGFYPSDIAVEWESNGQPENN

YKTTPPVLDSDGSFFLYSKLTVDKSRWQQGNVFSCSVLHEALHSH

YTQKSLSLSPGK

SEQ ID NO: 299
EIMMTQSPAILSVSPGDRATLSCRASQSVKNNLAWYQKRPGQAPR

LLIFDTSSRASGIPARFSGGGSGTEFTLTVNSMQSEDFATYYCQQ

YEEWPRTFGQGTKVEIKRTVAAPSVFIFPPSDEQLKSGTASVVCL

LNNFYPREAKVQWKVDNALQSGNSQESVTEQDSKDSTYSLSSTLT

LSKADYEKHKVYACEVTHQGLSSPVTKSFNRGEC

SEQ ID NO: 300
EVQLVESGGGLVKPGGSLRLTCVASGFTFSDVWLNWVRQAPGKGL

EWVGRIKSRTDGGTTDYAASVKGRFTISRDDSKNTLYLQMNSLKT

EDTAVYSCTTDGFIMIRGVSEDYYYYYMDVWGKGTTVTVSS

-continued

SEQ ID NO: 301
QSVLTQPPSVSAAPGQKVTISCSGSSSNIGNNYVLWYQQFPGTAP

KLLIYGNNKRPSGIPDRFSGSKSGTSATLGITGLQTGDEADYFCA

TWDSGLSADWVFGGGTKLTVL

SEQ ID NO: 302
EVQLVESGGGLVKPGGSLRLTCVASGFTFSDVWLNWVRQAPGKGL

EWVGRIKSRTDGGTTDYAASVKGRFTISRDDSKNTLYLQMNSLKT

EDTAVYSCTTDGFIMIRGVSEDYYYYYMDVWGKGTTVTVSSASTK

GPSVFPLAPSSKSTSGGTAALGCLVKDYFPEPVTVSWNSGALTSG

VHTFPAVLQSSGLYSLSSVVTVPSSSLGTQTYICNVNHKPSNTKV

DKKVEPKSCDKTHTCPPCPAPELLGGPSVFLFPPKPKDTLMISRT

PEVTCVVVDVSHEDPEVKFNWYVDGVEVHNAKTKPREEQYNSTYR

VVSVLTVLHQDWLNGKEYKCKVSNKALPAPIEKTISKAKGQPREP

QVYTLPPSRDELTKNQVSLTCLVKGFYPSDIAVEWESNGQPENNY

KTTPPVLDSDGSFFLYSKLTVDKSRWQQGNVFSCSVMHEALHNHY

TQKSLSLSPGK

SEQ ID NO: 303
EVQLVESGGGLVKPGGSLRLTCVASGFTFSDVWLNWVRQAPGKGL

EWVGRIKSRTDGGTTDYAASVKGRFTISRDDSKNTLYLQMNSLKT

EDTAVYSCTTDGFIMIRGVSEDYYYYYMDVWGKGTTVTVSSASTK

GPSVFPLAPSSKSTSGGTAALGCLVKDYFPEPVTVSWNSGALTSG

VHTFPAVLQSSGLYSLSSVVTVPSSSLGTQTYICNVNHKPSNTKV

DKKVEPKSCDKTHTCPPCPAPELLGGPSVFLFPPKPKDTLMISRT

PEVTCVVVDVSHEDPEVKFNWYVDGVEVHNAKTKPREEQYNSTYR

VVSVLTVLHQDWLNGKEYKCKVSNKALPAPIEKTISKAKGQPREP

QVYTLPPSRDELTKNQVSLTCLVKGFYPSDIAVEWESNGQPENNY

KTTPPVLDSDGSFFLYSKLTVDKSRWQQGNVFSCSVLHEALHSHY

TQKSLSLSPGK

SEQ ID NO: 304
QSVLTQPPSVSAAPGQKVTISCSGSSSNIGNNYVLWYQQFPGTAP

KLLIYGNNKRPSGIPDRFSGSKSGTSATLGITGLQTGDEADYFCA

TWDSGLSADWVFGGGTKLTVLGQPKAAPSVTLFPPSSEELQANKA

TLVCLISDFYPGAVTVAWKADSSPVKAGVETTTPSKQSNNKYAAS

SYLSLTPEQWKSHRSYSCQVTHEGSTVEKTVAPTECS

SEQ ID NO: 305
QVQLVQSGGGLVQPGGSLRLSCAAFGFNFSSYVMHWVRQAPGQGL

EYLSAISSDGETTYHANSVKGRFTSSRDNSKNTLFLQMGSLRTED

VAVYYCARDRYYETSGSNAFDVWGQGTMVVVSS

SEQ ID NO: 306
NSVLTQSPSSLSASVGDRVTITCQASQDISNYLNWYQHKPGKAPK

LLIYTASNLETGVPSRFSGGGSGTHFSFTITSLQPEDAATYFCQQ

YDNLGDLSFGGGTKVEIK

-continued

SEQ ID NO: 307
QVQLVQSGGGLVQPGGSLRLSCAAFGFNFSSYVMHWVRQAPGQGL

EYLSAISSDGETTYHANSVKGRFTSSRDNSKNTLFLQMGSLRTED

VAVYYCARDRYYETSGSNAFDVWGQGTMVVVSSASTKGPSVFPLA

PSSKSTSGGTAALGCLVKDYFPEPVTVSWNSGALTSGVHTFPAVL

QSSGLYSLSSVVTVPSSSLGTQTYICNVNHKPSNTKVDKKVEPKS

CDKTHTCPPCPAPELLGGPSVFLFPPKPKDTLMISRTPEVTCVVV

DVSHEDPEVKFNWYVDGVEVHNAKTKPREEQYNSTYRVVSVLTVL

HQDWLNGKEYKCKVSNKALPAPIEKTISKAKGQPREPQVYTLPPS

RDELTKNQVSLTCLVKGFYPSDIAVEWESNGQPENNYKTTPPVLD

SDGSFFLYSKLTVDKSRWQQGNVFSCSVMHEALHNHYTQKSLSLS

PGK

SEQ ID NO: 308
QVQLVQSGGGLVQPGGSLRLSCAAFGFNFSSYVMHWVRQAPGQGL

EYLSAISSDGETTYHANSVKGRFTSSRDNSKNTLFLQMGSLRTED

VAVYYCARDRYYETSGSNAFDVWGQGTMVVVSSASTKGPSVFPLA

PSSKSTSGGTAALGCLVKDYFPEPVTVSWNSGALTSGVHTFPAVL

QSSGLYSLSSVVTVPSSSLGTQTYICNVNHKPSNTKVDKKVEPKS

CDKTHTCPPCPAPELLGGPSVFLFPPKPKDTLMISRTPEVTCVVV

DVSHEDPEVKFNWYVDGVEVHNAKTKPREEQYNSTYRVVSVLTVL

HQDWLNGKEYKCKVSNKALPAPIEKTISKAKGQPREPQVYTLPPS

RDELTKNQVSLTCLVKGFYPSDIAVEWESNGQPENNYKTTPPVLD

SDGSFFLYSKLTVDKSRWQQGNVFSCSVLHEALHSHYTQKSLSLS

PGK

SEQ ID NO: 309
NSVLTQSPSSLSASVGDRVTITCQASQDISNYLNWYQHKPGKAPK

LLIYTASNLETGVPSRFSGGGSGTHFSFTITSLQPEDAATYFCQQ

YDNLGDLSFGGGTKVEIKRTVAAPSVFIFPPSDEQLKSGTASVVC

LLNNFYPREAKVQWKVDNALQSGNSQESVTEQDSKDSTYSLSSTL

TLSKADYEKHKVYACEVTHQGLSSPVTKSFNRGEC

SEQ ID NO: 310
QVQLVQSGAEVRKPGSSVTISCKPVGGTFTNFAIHWVRQAPGQGL

EWVGGRVPVVGIYKYGKKFHDRLRLYEDDPMKTVFLELRSLTSDD

TGVYYCTRWRGCGMCPYDTSSYYNDASDVWGPGTKVIVSA

SEQ ID NO: 311
EIVLTQSPVTLSLSSGETGTLSCRASQNISSSWIAWYQQRRGQVP

RLLISAASARAAGIPDRFTGRGSGTDFTLTITRLEPEDFGVYSCQ

YYGGSFFTFGPGTQVDVK

SEQ ID NO: 312
QVQLVQSGAEVRKPGSSVTISCKPVGGTFTNFAIHWVRQAPGQGL

EWVGGRVPVVGIYKYGKKFHDRLRLYEDDPMKTVFLELRSLTSDD

TGVYYCTRWRGCGMCPYDTSSYYNDASDVWGPGTKVIVSAASTKG

PSVFPLAPSSKSTSGGTAALGCLVKDYFPEPVTVSWNSGALTSGV

HTFPAVLQSSGLYSLSSVVTVPSSSLGTQTYICNVNHKPSNTKVD

KKVEPKSCDKTHTCPPCPAPELLGGPSVFLFPPKPKDTLMISRTP

EVTCVVVDVSHEDPEVKFNWYVDGVEVHNAKTKPREEQYNSTYRV

VSVLTVLHQDWLNGKEYKCKVSNKALPAPIEKTISKAKGQPREPQ

VYTLPPSRDELTKNQVSLTCLVKGFYPSDIAVEWESNGQPENNYK

TTPPVLDSDGSFFLYSKLTVDKSRWQQGNVFSCSVMHEALHNHYT

QKSLSLSPGK

SEQ ID NO: 313

QVQLVQSGAEVRKPGSSVTISCKPVGGTFTNFAIHWVRQAPGQGL

EWVGGRVPVVGIYKYGKKFHDRLRLYEDDPMKTVFLELRSLTSDD

TGVYYCTRWRGCGMCPYDTSSYYNDASDVWGPGTKVIVSAASTKG

PSVFPLAPSSKSTSGGTAALGCLVKDYFPEPVTVSWNSGALTSGV

HTFPAVLQSSGLYSLSSVVTVPSSSLGTQTYICNVNHKPSNTKVD

KKVEPKSCDKTHTCPPCPAPELLGGPSVFLFPPKPKDTLMISRTP

EVTCVVVDVSHEDPEVKFNWYVDGVEVHNAKTKPREEQYNSTYRV

VSVLTVLHQDWLNGKEYKCKVSNKALPAPIEKTISKAKGQPREPQ

VYTLPPSRDELTKNQVSLTCLVKGFYPSDIAVEWESNGQPENNYK

TTPPVLDSDGSFFLYSKLTVDKSRWQQGNVFSCSVLHEALHSHYT

QKSLSLSPGK

SEQ ID NO: 314

EIVLTQSPVTLSLSSGETGTLSCRASQNISSSWIAWYQQRGQVP

RLLISAASARAAGIPDRFTGRGSGTDFTLTITRLEPEDFGVYSCQ

YYGGSFFTFGPGTQVDVKRTVAAPSVFIFPPSDEQLKSGTASVVC

LLNNFYPREAKVQWKVDNALQSGNSQESVTEQDSKDSTYSLSSTL

TLSKADYEKHKVYACEVTHQGLSSPVTKSFNRGEC

SEQ ID NO: 315

EVQLVESGGGLVKAGGSLILSCGVSNFRISAHTMNWVRRVPGGGL

EWVASISTSSTYRDYADAVKGRFTVSRDDLEDFVYLQMHKMRVED

TAIYYCARKGSDRLSDNDPFDAWGPGTVVTVSP

SEQ ID NO: 316

DVVMTQSPSTLSASVGDTITITCRASQSIETWLAWYQQKPGKAPK

LLIYKASTLKTGVPSRFSGSGSGTEFTLTISGLQFDDFATYHCQH

YAGYSATFGQGTRVEIK

SEQ ID NO: 317

EVQLVESGGGLVKAGGSLILSCGVSNFRISAHTMNWVRRVPGGGL

EWVASISTSSTYRDYADAVKGRFTVSRDDLEDFVYLQMHKMRVED

TAIYYCARKGSDRLSDNDPFDAWGPGTVVTVSPASTKGPSVFPLA

PSSKSTSGGTAALGCLVKDYFPEPVTVSWNSGALTSGVHTFPAVL

QSSGLYSLSSVVTVPSSSLGTQTYICNVNHKPSNTKVDKKVEPKS

CDKTHTCPPCPAPELLGGPSVFLFPPKPKDTLMISRTPEVTCVVV

DVSHEDPEVKFNWYVDGVEVHNAKTKPREEQYNSTYRVVSVLTVL

HQDWLNGKEYKCKVSNKALPAPIEKTISKAKGQPREPQVYTLPPS

RDELTKNQVSLTCLVKGFYPSDIAVEWESNGQPENNYKTTPPVLD

SDGSFFLYSKLTVDKSRWQQGNVFSCSVMHEALHNHYTQKSLSLS

PGK

SEQ ID NO: 318

EVQLVESGGGLVKAGGSLILSCGVSNFRISAHTMNWVRRVPGGGL

EWVASISTSSTYRDYADAVKGRFTVSRDDLEDFVYLQMHKMRVED

TAIYYCARKGSDRLSDNDPFDAWGPGTVVTVSPASTKGPSVFPLA

PSSKSTSGGTAALGCLVKDYFPEPVTVSWNSGALTSGVHTFPAVL

QSSGLYSLSSVVTVPSSSLGTQTYICNVNHKPSNTKVDKKVEPKS

CDKTHTCPPCPAPELLGGPSVFLFPPKPKDTLMISRTPEVTCVVV

DVSHEDPEVKFNWYVDGVEVHNAKTKPREEQYNSTYRVVSVLTVL

HQDWLNGKEYKCKVSNKALPAPIEKTISKAKGQPREPQVYTLPPS

RDELTKNQVSLTCLVKGFYPSDIAVEWESNGQPENNYKTTPPVLD

SDGSFFLYSKLTVDKSRWQQGNVFSCSVLHEALHSHYTQKSLSLS

PGK

SEQ ID NO: 319

DVVMTQSPSTLSASVGDTITITCRASQSIETWLAWYQQKPGKAPK

LLIYKASTLKTGVPSRFSGSGSGTEFTLTISGLQFDDFATYHCQH

YAGYSATFGQGTRVEIKRTVAAPSVFIFPPSDEQLKSGTASWVCL

LNNFYPREAKVQWKVDNALQSGNSQESVTEQDSKDSTYSLSSTLT

LSKADYEKHKVYACEVTHQGLSSPVTKSFNRGEC

SEQ ID NO: 320

QMQLQESGPGLVKPGETLSLTCSVSGASISSSYWSWLRETPGKGL

EWIGYTHHSGDTNYAPSLKSRVHLGLHPSKNQVSLSLTSVTAADT

AVYYCARTLHGRRIYGVVAFNEFFTYFYWEVWGKGTQVTVSS

SEQ ID NO: 321

SDISVAPGETVRISCGGESIGSRAVQWYQHRAGQAPKLIIYNNQD

RPPGIPERFSGSPDIDFGTTATLTITNVEAGDEATYYCHIWDSRR

PTNWVFGGGTTLTVL

SEQ ID NO: 322

QMQLQESGPGLVKPGETLSLTCSVSGASISSSYWSWLRETPGKGL

EWIGYTHHSGDTNYAPSLKSRVHLGLHPSKNQVSLSLTSVTAADT

AVYYCARTLHGRRIYGVVAFNEFFTYFYWEVWGKGTQVTVSSAST

KGPSVFPLAPSSKSTSGGTAALGCLVKDYFPEPVTVSWNSGALTS

GVHTFPAVLQSSGLYSLSSVVTVPSSSLGTQTYICNVNHKPSNTK

VDKKVEPKSCDKTHTCPPCPAPELLGGPSVFLFPPKPKDTLMISR

TPEVTCVVVDVSHEDPEVKFNWYVDGVEVHNAKTKPREEQYNSTY

RVVSVLTVLHQDWLNGKEYKCKVSNKALPAPIEKTISKAKGQPRE

PQVYTLPPSRDELTKNQVSLTCLVKGFYPSDIAVEWESNGQPENN

YKTTPPVLDSDGSFFLYSKLTVDKSRWQQGNVFSCSVMHEALHNH

YTQKSLSLSPGK

SEQ ID NO: 323
QMQLQESGPGLVKPGETLSLTCSVSGASISSSYWSWLRETPGKGL

EWIGYTHHSGDTNYAPSLKSRVHLGLHPSKNQVSLSLTSVTAADT

AVYYCARTLHGRRIYGVVAFNEFFTYFYWEVWGKGTQVTVSSAST

KGPSVFPLAPSSKSTSGGTAALGCLVKDYFPEPVTVSWNSGALTS

GVHTFPAVLQSSGLYSLSSVVTVPSSSLGTQTYICNVNHKPSNTK

VDKKVEPKSCDKTHTCPPCPAPELLGGPSVFLFPPKPKDTLMISR

TPEVTCVVVDVSHEDPEVKFNWYVDGVEVHNAKTKPREEQYNSTY

RVVSVLTVLHQDWLNGKEYKCKVSNKALPAPIEKTISKAKGQPRE

PQVYTLPPSRDELTKNQVSLTCLVKGFYPSDIAVEWESNGQPENN

YKTTPPVLDSDGSFFLYSKLTVDKSRWQQGNVFSCSVLHEALHSH

YTQKSLSLSPGK

SEQ ID NO: 324
SDISVAPGETVRISCGGESIGSRAVQWYQHRAGQAPKLIIYNNQD

RPPGIPERFSGSPDIDFGTTATLTITNVEAGDEATYYCHIWDSRR

PTNWVFGGGTTLTVLGQPKAAPSVTLFPPSSEELQANKATLVCLI

SDFYPGAVTVAWKADSSPVKAGVETTTPSKQSNNKYAASSYLSLT

PEQWKSHRSYSCQVTHEGSTVEKTVAPTECS

SEQ ID NO: 325
QMQLQESGPGLVKPGETLSLTCSVSGASISSSYWSWLRETPGKGL

EWIGYTHHSGDTNYAPSLKSRVHLGLHPSKNQVSLSLTSVTAADT

AVYYCARTLHGRRIYGVVAFNEYYTYFYWPTWGKGTQVTVSS

SEQ ID NO: 326
SDISVAPGETVRITCGGESIGSRAVQWYQHRPGQAPRLIIYNNQD

RPPGIPERFSGSPDIDFGTTATLTISNVEAGDEATYYCHIWDSRR

PTNWELGPGTTLTVL

SEQ ID NO: 327
QMQLQESGPGLVKPGETLSLTCSVSGASISSSYWSWLRETPGKGL

EWIGYTHHSGDTNYAPSLKSRVHLGLHPSKNQVSLSLTSVTAADT

AVYYCARTLHGRRIYGVVAFNEYYTYFYWPTWGKGTQVTVSSAST

KGPSVFPLAPSSKSTSGGTAALGCLVKDYFPEPVTVSWNSGALTS

GVHTFPAVLQSSGLYSLSSVVTVPSSSLGTQTYICNVNHKPSNTK

VDKKVEPKSCDKTHTCPPCPAPELLGGPSVFLFPPKPKDTLMISR

TPEVTCVVVDVSHEDPEVKFNWYVDGVEVHNAKTKPREEQYNSTY

RVVSVLTVLHQDWLNGKEYKCKVSNKALPAPIEKTISKAKGQPRE

PQVYTLPPSRDELTKNQVSLTCLVKGFYPSDIAVEWESNGQPENN

YKTTPPVLDSDGSFFLYSKLTVDKSRWQQGNVFSCSVMHEALHNH

YTQKSLSLSPGK

SEQ ID NO: 328
QMQLQESGPGLVKPGETLSLTCSVSGASISSSYWSWLRETPGKGL

EWIGYTHHSGDTNYAPSLKSRVHLGLHPSKNQVSLSLTSVTAADT

AVYYCARTLHGRRIYGVVAFNEYYTYFYWPTWGKGTQVTVSSAST

KGPSVFPLAPSSKSTSGGTAALGCLVKDYFPEPVTVSWNSGALTS

GVHTFPAVLQSSGLYSLSSVVTVPSSSLGTQTYICNVNHKPSNTK

VDKKVEPKSCDKTHTCPPCPAPELLGGPSVFLFPPKPKDTLMISR

TPEVTCVVVDVSHEDPEVKFNWYVDGVEVHNAKTKPREEQYNSTY

RVVSVLTVLHQDWLNGKEYKCKVSNKALPAPIEKTISKAKGQPRE

PQVYTLPPSRDELTKNQVSLTCLVKGFYPSDIAVEWESNGQPENN

YKTTPPVLDSDGSFFLYSKLTVDKSRWQQGNVFSCSVLHEALHSH

YTQKSLSLSPGK

SEQ ID NO: 329
SDISVAPGETVRITCGGESIGSRAVQWYQHRPGQAPRLIIYNNQD

RPPGIPERFSGSPDIDFGTTATLTISNVEAGDEATYYCHIWDSRR

PTNWELGPGTTLTVLGQPKAAPSVTLFPPSSEELQANKATLVCLI

SDFYPGAVTVAWKADSSPVKAGVETTTPSKQSNNKYAASSYLSLT

PEQWKSHRSYSCQVTHEGSTVEKTVAPTECS

SEQ ID NO: 330
QMQLQESGPGLVKPGETLSLTCSVSGASISSSYWSWLRETPGKGL

EWIGYTHHSGDTNYAPSLKSRVTIGLDPSKNQVSLSLTSVTAADT

AVYYCARTLHGRRIYGVVAFNEYYTYFYWPTWGKGTQVTVSS

SEQ ID NO: 331
QMQLQESGPGLVKPGETLSLTCSVSGASISSSYWSWLRETPGKGL

EWIGYTHHSGDTNYAPSLKSRVTIGLDPSKNQVSLSLTSVTAADT

AVYYCARTLHGRRIYGVVAFNEYYTYFYWPTWGKGTQVTVSSAST

KGPSVFPLAPSSKSTSGGTAALGCLVKDYFPEPVTVSWNSGALTS

GVHTFPAVLQSSGLYSLSSVVTVPSSSLGTQTYICNVNHKPSNTK

VDKKVEPKSCDKTHTCPPCPAPELLGGPSVFLFPPKPKDTLMISR

TPEVTCVVVDVSHEDPEVKFNWYVDGVEVHNAKTKPREEQYNSTY

RVVSVLTVLHQDWLNGKEYKCKVSNKALPAPIEKTISKAKGQPRE

PQVYTLPPSRDELTKNQVSLTCLVKGFYPSDIAVEWESNGQPENN

YKTTPPVLDSDGSFFLYSKLTVDKSRWQQGNVFSCSVMHEALHNH

YTQKSLSLSPGK

SEQ ID NO: 332
QMQLQESGPGLVKPGETLSLTCSVSGASISSSYWSWLRETPGKGL

EWIGYTHHSGDTNYAPSLKSRVTIGLDPSKNQVSLSLTSVTAADT

AVYYCARTLHGRRIYGVVAFNEYYTYFYWPTWGKGTQVTVSSAST

KGPSVFPLAPSSKSTSGGTAALGCLVKDYFPEPVTVSWNSGALTS

GVHTFPAVLQSSGLYSLSSVVTVPSSSLGTQTYICNVNHKPSNTK

VDKKVEPKSCDKTHTCPPCPAPELLGGPSVFLFPPKPKDTLMISR

TPEVTCVVVDVSHEDPEVKFNWYVDGVEVHNAKTKPREEQYNSTY

RVVSVLTVLHQDWLNGKEYKCKVSNKALPAPIEKTISKAKGQPRE

PQVYTLPPSRDELTKNQVSLTCLVKGFYPSDIAVEWESNGQPENN

YKTTPPVLDSDGSFFLYSKLTVDKSRWQQGNVFSCSVLHEALHSH

YTQKSLSLSPGK

-continued

SEQ ID NO: 333
QMQLQESGPGLVKPGETLSLTCSVSGASISSSYWSWLRETPGKGL

EWIGYTHHSGDTNYAPSLKSRVTIGLDPSKNQVSLSLTSVTAADT

AVYYCARTLHGRRIYGVVAFNEYYTYFYWPTWGKGTQVTVSS

SEQ ID NO: 334
QSVLTQPPSASGSPGQSVTISCTGTSSDIGASDYVSWYQQYPGEA

PKVIIYDVTKRPSGVPDRFSGSKSGTTASLTVSGLQAEDEADYYC

SSDAGRHTLLFGGGTKVTVL

SEQ ID NO: 335
QVQLLESGPGLVRPSETLTLTCSVFNSRVSGYYYSWIRQPPGRGL

EWIASTHFSLRPSRNPSLLSRVTTSIDTERYQVFLNMRSVTAADT

AVYFCARGDASGWRADYFPHWGQGTLVVVSSASTKGPSVFPLAPS

SKSTSGGTAALGCLVKDYFPEPVTVSWNSGALTSGVHTFPAVLQS

SGLYSLSSVVTVPSSSLGTQTYICNVNHKPSNTKVDKKVEPKSCD

KTHTCPPCPAPELLGGPSVFLFPPKPKDTLMISRTPEVTCVVVDV

SHEDPEVKFNWYVDGVEVHNAKTKPREEQYNSTYRVVSVLTVLHQ

DWLNGKEYKCKVSNKALPAPIEKTISKAKGQPREPQVYTLPPSRD

ELTKNQVSLTCLVKGFYPSDIAVEWESNGQPENNYKTTPPVLDSD

GSFFLYSKLTVDKSRWQQGNVFSCSVMHEALHNHYTQKSLSLSPG

K

SEQ ID NO: 336
QVQLLESGPGLVRPSETLTLTCSVFNSRVSGYYYSWIRQPPGRGL

EWIASTHFSLRPSRNPSLLSRVTTSIDTERYQVFLNMRSVTAADT

AVYFCARGDASGWRADYFPHWGQGTLVVVSSASTKGPSVFPLAPS

SKSTSGGTAALGCLVKDYFPEPVTVSWNSGALTSGVHTFPAVLQS

SGLYSLSSVVTVPSSSLGTQTYICNVNHKPSNTKVDKKVEPKSCD

KTHTCPPCPAPELLGGPSVFLFPPKPKDTLMISRTPEVTCVVVDV

SHEDPEVKFNWYVDGVEVHNAKTKPREEQYNSTYRVVSVLTVLHQ

DWLNGKEYKCKVSNKALPAPIEKTISKAKGQPREPQVYTLPPSRD

ELTKNQVSLTCLVKGFYPSDIAVEWESNGQPENNYKTTPPVLDSD

GSFFLYSKLTVDKSRWQQGNVFSCSVLHEALHSHYTQKSLSLSPG

K

SEQ ID NO: 337
QSVLTQPPSASGSPGQSVTISCTGTSSDIGASDYVSWYQQYPGEA

PKVIIYDVTKRPSGVPDRFSGSKSGTTASLTVSGLQAEDEADYYC

SSDAGRHTLLFGGGTKVTVLGQPKAAPSVTLFPPSSEELQANKAT

LVCLISDFYPGAVTVAWKADSSPVKAGVETTTPSKQSNNKYAASS

YLSLTPEQWKSHRSYSCQVTHEGSTVEKTVAPTECS

SEQ ID NO: 338
KKVVYGKCGDTVELTCTASQKKNIQFHWKNSNQIKILGNQGSFLT

KGPSKLNDRVDSRRSLWDQGNFPLIIKNLKPEDSDTYICEVEDQK

EEVQLVVVCGGGGSQVHLQESGPGLVKPSETLSLTCNVSGTLVRD

NYWSWIRQPLGKQPEWIGYVHDSGDTNYNPSLKSRVHLSLDKSKN

-continued

LVSLRLTGVTAADSAIYYCATTKHGRRIYGVVAFKEWFTYFYMDV

WGKGTSVTVSSASTKGPSVFPLAPSSKSTSGGTAALGCLVKDYFP

EPVTVSWNSGALTSGVHTFPAVLQSSGLYSLSSVVTVPSSSLGTQ

TYICNVNHKPSNTKVDKKVEPKSCDKTHTCPPCPAPELLGGPSVF

LFPPKPKDTLMISRTPEVTCVVVDVSHEDPEVKFNWYVDGVEVHN

AKTKPREEQYNSTYRVVSVLTVLHQDWLNGKEYKCKVSNKALPAP

IEKTISKAKGQPREPQVYTLPPSRDELTKNQVSLTCLVKGFYPSD

IAVEWESNGQPENNYKTTPPVLDSDGSFFLYSKLTVDKSRWQQGN

VFSCSVLHEALHSHYTQKSLSLSPGK

SEQ ID NO: 339
KKVVYGKCGDTVELTCTASQKKNIQFHWKNSNQIKILGNQGSFLT

KGPSKLNDRVDSRRSLWDQGNFPLIIKNLKPEDSDTYICEVEDQK

EEVQLVVVCGGGGSQLHLQESGPGLVKPPETLSLTCSVSGASIND

AYWSWIRQSPGKRPEWVGYVHHSGDTNYNPSLKRRVTFSLDTAKN

EVSLKLVDLTAADSATYFCARALHGKRIYGIVALGELFTYFYMDV

WGKGTAVTVSSASTKGPSVFPLAPSSKSTSGGTAALGCLVKDYFP

EPVTVSWNSGALTSGVHTFPAVLQSSGLYSLSSVVTVPSSSLGTQ

TYICNVNHKPSNTKVDKKVEPKSCDKTHTCPPCPAPELLGGPSVF

LFPPKPKDTLMISRTPEVTCVVVDVSHEDPEVKFNWYVDGVEVHN

AKTKPREEQYNSTYRVVSVLTVLHQDWLNGKEYKCKVSNKALPAP

IEKTISKAKGQPREPQVYTLPPSRDELTKNQVSLTCLVKGFYPSD

IAVEWESNGQPENNYKTTPPVLDSDGSFFLYSKLTVDKSRWQQGN

VFSCSVLHEALHSHYTQKSLSLSPGK

SEQ ID NO: 340
KKVVYGKCGDTVELTCTASQKKNIQFHWKNSNQIKILGNQGSFLT

KGPSKLNDRVDSRRSLWDQGNFPLIIKNLKPEDSDTYICEVEDQK

EEVQLVVVCGGGGSQSQLQESGPRLVEASETLSLTCNVSGESTGA

CTYFWGWVRQAPGKGLEWIGSLSHCQSFWGSGWTFHNPSLKSRLT

ISLDTPKNQVFLKLTSLTAADTATYYCARFDGEVLVYNHWPKPAW

VDLWGRGIPVTVTVSSASTKGPSVFPLAPSSKSTSGGTAALGCLV

KDYFPEPVTVSWNSGALTSGVHTFPAVLQSSGLYSLSSVVTVPSS

SLGTQTYICNVNHKPSNTKVDKKVEPKSCDKTHTCPPCPAPELLG

GPSVFLFPPKPKDTLMISRTPEVTCVVVDVSHEDPEVKFNWYVDG

VEVHNAKTKPREEQYNSTYRVVSVLTVLHQDWLNGKEYKCKVSNK

ALPAPIEKTISKAKGQPREPQVYTLPPSRDELTKNQVSLTCLVKG

FYPSDIAVEWESNGQPENNYKTTPPVLDSDGSFFLYSKLTVDKSR

WQQGNVFSCSVLHEALHSHYTQKSLSLSPGK

SEQ ID NO: 341
KKVVYGKCGDTVELTCTASQKKNIQFHWKNSNQIKILGNQGSFLT

KGPSKLNDRVDSRRSLWDQGNFPLIIKNLKPEDSDTYICEVEDQK

EEVQLVVVCGGGGSQPQLQESGPGLVEASETLSLTCTVSGDSTAA

CDYFWGWVRQPPGKGLEWIGGLSHCAGYYNTGWTYHNPSLKSRLT

-continued

ISLDTPKNQVFLKLNSVTAADTAIYYCARFDGEVLVYHDWPKPAW

VDLWGRGTLVTVTVSSASTKGPSVFPLAPSSKSTSGGTAALGCLV

KDYFPEPVTVSWNSGALTSGVHTFPAVLQSSGLYSLSSVVTVPSS

SLGTQTYICNVNHKPSNTKVDKKVEPKSCDKTHTCPPCPAPELLG

GPSVFLFPPKPKDTLMISRTPEVTCVVVDVSHEDPEVKFNWYVDG

VEVHNAKTKPREEQYNSTYRVVSVLTVLHQDWLNGKEYKCKVSNK

ALPAPIEKTISKAKGQPREPQVYTLPPSRDELTKNQVSLTCLVKG

FYPSDIAVEWESNGQPENNYKTTPPVLDSDGSFFLYSKLTVDKSR

WQQGNVFSCSVLHEALHSHYTQKSLSLSPGK

SEQ ID NO: 342

KKVVYGKCGDTVELTCTASQKKNIQFHWKNSNQIKILGNQGSFLT

KGPSKLNDRVDSRRSLWDQGNFPLIIKNLKPEDSDTYICEVEDQK

EEVQLVVVCGGGGSQPQLQESGPGLVEASETLSLTCTVSGDSTGR

CNYFWGWVRQPPGKGLEWIGSLSHCRSYYNTDWTYHNPSLKSRLT

ISLDTPKNQVFLRLTSVTAADTATYYCARFGGEVLVYRDWPKPAW

VDLWGRGTLVTVSSASTKGPSVFPLAPSSKSTSGGTAALGCLVKD

YFPEPVTVSWNSGALTSGVHTFPAVLQSSGLYSLSSVVTVPSSSL

GTQTYICNVNHKPSNTKVDKKVEPKSCDKTHTCPPCPAPELLGGP

SVFLFPPKPKDTLMISRTPEVTCVVVDVSHEDPEVKFNWYVDGVE

VHNAKTKPREEQYNSTYRVVSVLTVLHQDWLNGKEYKCKVSNKAL

PAPIEKTISKAKGQPREPQVYTLPPSRDELTKNQVSLTCLVKGFY

PSDIAVEWESNGQPENNYKTTPPVLDSDGSFFLYSKLTVDKSRWQ

QGNVFSCSVLHEALHSHYTQKSLSLSPGK

SEQ ID NO: 343

KKVVYGKCGDTVELTCTASQKKNIQFHWKNSNQIKILGNQGSFLT

KGPSKLNDRVDSRRSLWDQGNFPLIIKNLKPEDSDTYICEVEDQK

EEVQLVVVCGGGGSQVQLQESGPGLVKPAETLSLTCSVSGESINT

GHYYWGWVRQVPGKGLEWIGHIHYTTAVLHNPSLKSRLTIKIYTL

RNQITLRLSNVTAADTAVYHCVRSGGDILYYYEWQKPHWFSPWGP

GIHVTVSSASTKGPSVFPLAPSSKSTSGGTAALGCLVKDYFPEPV

TVSWNSGALTSGVHTFPAVLQSSGLYSLSSVVTVPSSSLGTQTYI

CNVNHKPSNTKVDKKVEPKSCDKTHTCPPCPAPELLGGPSVFLFP

PKPKDTLMISRTPEVTCVVVDVSHEDPEVKFNWYVDGVEVHNAKT

KPREEQYNSTYRVVSVLTVLHQDWLNGKEYKCKVSNKALPAPIEK

TISKAKGQPREPQVYTLPPSRDELTKNQVSLTCLVKGFYPSDIAV

EWESNGQPENNYKTTPPVLDSDGSFFLYSKLTVDKSRWQQGNVFS

CSVLHEALHSHYTQKSLSLSPGK

SEQ ID NO: 344

QVQLQESGPGLVKPAETLSLTCSVSGESINTGHYYWGWVRQVPGK

GLEWIGHIHYTTAVLHNPSLKSRLTIKIYTLRNQITLRLSNVTAA

DTAVYHCVRSGGDILYYYEWQKPHWFSPWGPGIHVTVSSASTKGP

SVFPLAPSSKSTSGGTAALGCLVKDYFPEPVTVSWNSGALTSGVH

-continued

TFPAVLQSSGLYSLSSVVTVPSSSLGTQTYICNVNHKPSNTKVDK

KVEPKSCDKTHTCPPCPAPELLGGPSVFLFPPKPKDTLMISRTPE

VTCVVVDVSHEDPEVKFNWYVDGVEVHNAKTKPREEQYNSTYRVV

SVLTVLHQDWLNGKEYKCKVSNKALPAPIEKTISKAKGQPREPQV

YTLPPSRDELTKNQVSLTCLVKGFYPSDIAVEWESNGQPENNYKT

TPPVLDSDGSFFLYSKLTVDKSRWQQGNVFSCSVLHEALHSHYTQ

KSLSLSPGKGGGGSKKVVYGKCGDTVELTCTASQKKNIQFHWKNS

NQIKILGNQGSFLTKGPSKLNDRVDSRRSLWDQGNFPLIIKNLKP

EDSDTYICEVEDQKEEVQLVVVC

SEQ ID NO: 345

KKVVYGKCGDTVELTCTASQKKNIQFHWKNSNQIKILGNQGSFLT

KGPSKLNDRVDSRRSLWDQGNFPLIIKNLKPEDSDTYICEVEDQK

EEVQLVVVCGGGGSQSALTQPPSASGSLGQSVTISCNGTSSDIGG

WNFVSWYQQFPGRAPRLIIFEVNKRPSGVPGRFSGSKSGNSASLT

VSGLQSDDEGQYFCSSLFGRWDVVFGGGTKLTVLGQPKAAPSVTL

FPPSSEELQANKATLVCLISDFYPGAVTVAWKADSSPVKAGVETT

TPSKQSNNKYAASSYLSLTPEQWKSHRSYSCQVTHEGSTVEKTVA

PTECS

SEQ ID NO: 346

QSALTQPPSASGSLGQSVTISCNGTSSDIGGWNFVSWYQQFPGRA

PRLIIFEVNKRPSGVPGRFSGSKSGNSASLTVSGLQSDDEGQYFC

SSLFGRWDVVFGGGTKLTVLGQPKAAPSVTLFPPSSEELQANKAT

LVCLISDFYPGAVTVAWKADSSPVKAGVETTTPSKQSNNKYAASS

YLSLTPEQWKSHRSYSCQVTHEGSTVEKTVAPTECSGGGGSKKVV

YGKCGDTVELTCTASQKKNIQFHWKNSNQIKILGNQGSFLTKGPS

KLNDRVDSRRSLWDQGNFPLIIKNLKPEDSDTYICEVEDQKEEVQ

LVVVC

SEQ ID NO: 347

KKVVYGKCGDTVELTCTASQKKNIQFHWKNSNQIKILGNQGSFLT

KGPSKLNDRVDSRRSLWDQGNFPLIIKNLKPEDSDTYICEVEDQK

EEVQLVVVCGGGGSQVQLQESGPGLVKPSETLSLTCTVSGDSINT

GHHYWGWVRQVPGKGPEWIAHIHYNTAVLHNPALKSRVTISIFTL

KNLITLSLSNVTAADTAVYFCVRSGGDILYYIEWQKPHWFYPWGP

GILVTVSSASTKGPSVFPLAPSSKSTSGGTAALGCLVKDYFPEPV

TVSWNSGALTSGVHTFPAVLQSSGLYSLSSVVTVPSSSLGTQTYI

CNVNHKPSNTKVDKKVEPKSCDKTHTCPPCPAPELLGGPSVFLFP

PKPKDTLMISRTPEVTCVVVDVSHEDPEVKFNWYVDGVEVHNAKT

KPREEQYNSTYRVVSVLTVLHQDWLNGKEYKCKVSNKALPAPIEK

TISKAKGQPREPQVYTLPPSRDELTKNQVSLTCLVKGFYPSDIAV

EWESNGQPENNYKTTPPVLDSDGSFFLYSKLTVDKSRWQQGNVFS

CSVLHEALHSHYTQKSLSLSPGK

-continued

SEQ ID NO: 348
KKVVYGKCGDTVELTCTASQKKNIQFHWKNSNQIKILGNQGSFLT

KGPSKLNDRVDSRRSLWDQGNFPLIIKNLKPEDSDTYICEVEDQK

EEVQLVVVCGGGGSQLQLQESGPGLVKPSETLSLTCTVSGGSMRG

TDWGENDFHYGWIRQSSAKGLEWIGSIHWRGRTTHYKTSFRSRAT

LSIDTSNNRFSLTFSFVTAADTAVYYCARHKYHDIFRVVPVAGWF

DPWGQGLLVTVSSASTKGPSVFPLAPSSKSTSGGTAALGCLVKDY

FPEPVTVSWNSGALTSGVHTFPAVLQSSGLYSLSSVVTVPSSSLG

TQTYICNVNHKPSNTKVDKKVEPKSCDKTHTCPPCPAPELLGGPS

VFLFPPKPKDTLMISRTPEVTCVVVDVSHEDPEVKFNWYVDGVEV

HNAKTKPREEQYNSTYRVVSVLTVLHQDWLNGKEYKCKVSNKALP

APIEKTISKAKGQPREPQVYTLPPSRDELTKNQVSLTCLVKGFYP

SDIAVEWESNGQPENNYKTTPPVLDSDGSFFLYSKLTVDKSRWQQ

GNVFSCSVLHEALHSHYTQKSLSLSPGK

SEQ ID NO: 349
KKVVYGKCGDTVELTCTASQKKNIQFHWKNSNQIKILGNQGSFLT

KGPSKLNDRVDSRRSLWDQGNFPLIIKNLKPEDSDTYICEVEDQK

EEVQLVVVCGGGGSEVHLEESGPGLVRPSETLSLTCTASGGSIRG

GEWGDSDYHWGWVRHSPEKGLEWIGSIHWRGTTHYNAPFRGRGRL

SIDLSRNQFSLRLTSVTAEDTAVYYCVKHKYHDIVMVVPIAGWFD

PWGQGLQVTVSSASTKGPSVFPLAPSSKSTSGGTAALGCLVKDYF

PEPVTVSWNSGALTSGVHTFPAVLQSSGLYSLSSVVTVPSSSLGT

QTYICNVNHKPSNTKVDKKVEPKSCDKTHTCPPCPAPELLGGPSV

FLFPPKPKDTLMISRTPEVTCVVVDVSHEDPEVKFNWYVDGVEVH

NAKTKPREEQYNSTYRVVSVLTVLHQDWLNGKEYKCKVSNKALPA

PIEKTISKAKGQPREPQVYTLPPSRDELTKNQVSLTCLVKGFYPS

DIAVEWESNGQPENNYKTTPPVLDSDGSFFLYSKLTVDKSRWQQG

NVFSCSVLHEALHSHYTQKSLSLSPGK

SEQ ID NO: 350
KKVVYGKCGDTVELTCTASQKKNIQFHWKNSNQIKILGNQGSFLT

KGPSKLNDRVDSRRSLWDQGNFPLIIKNLKPEDSDTYICEVEDQK

EEVQLVVVCGGGGSEVQLVESGGGLVKPGGSLRLTCVASGFTFSD

VWLNWVRQAPGKGLEWVGRIKSRTDGGTTDYAASVKGRFTISRDD

SKNTLYLQMNSLKTEDTAVYSCTTDGFIMIRGVSEDYYYYYMDVW

GKGTTVTVSSASTKGPSVFPLAPSSKSTSGGTAALGCLVKDYFPE

PVTVSWNSGALTSGVHTFPAVLQSSGLYSLSSVVTVPSSSLGTQT

YICNVNHKPSNTKVDKKVEPKSCDKTHTCPPCPAPELLGGPSVFL

FPPKPKDTLMISRTPEVTCVVVDVSHEDPEVKFNWYVDGVEVHNA

KTKPREEQYNSTYRVVSVLTVLHQDWLNGKEYKCKVSNKALPAPI

EKTISKAKGQPREPQVYTLPPSRDELTKNQVSLTCLVKGFYPSDI

AVEWESNGQPENNYKTTPPVLDSDGSFFLYSKLTVDKSRWQQGNV

FSCSVLHEALHSHYTQKSLSLSPGK

-continued

SEQ ID NO: 351
KKVVYGKCGDTVELTCTASQKKNIQFHWKNSNQIKILGNQGSFLT

KGPSKLNDRVDSRRSLWDQGNFPLIIKNLKPEDSDTYICEVEDQK

EEVQLVVVCGGGGSQVQLVQSGGGLVQPGGSLRLSCAAFGFNFSS

YVMHWVRQAPGQGLEYLSAISSDGETTYHANSVKGRFTSSRDNSK

NTLFLQMGSLRTEDVAVYYCARDRYYETSGSNAFDVWGQGTMVVV

SSASTKGPSVFPLAPSSKSTSGGTAALGCLVKDYFPEPVTVSWNS

GALTSGVHTFPAVLQSSGLYSLSSVVTVPSSSLGTQTYICNVNHK

PSNTKVDKKVEPKSCDKTHTCPPCPAPELLGGPSVFLFPPKPKDT

LMISRTPEVTCVVVDVSHEDPEVKFNWYVDGVEVHNAKTKPREEQ

YNSTYRVVSVLTVLHQDWLNGKEYKCKVSNKALPAPIEKTISKAK

GQPREPQVYTLPPSRDELTKNQVSLTCLVKGFYPSDIAVEWESNG

QPENNYKTTPPVLDSDGSFFLYSKLTVDKSRWQQGNVFSCSVLHE

ALHSHYTQKSLSLSPGK

SEQ ID NO: 352
KKVVYGKCGDTVELTCTASQKKNIQFHWKNSNQIKILGNQGSFLT

KGPSKLNDRVDSRRSLWDQGNFPLIIKNLKPEDSDTYICEVEDQK

EEVQLVVVCGGGGSQVQLVQSGAEVRKPGSSVTISCKPVGGTFTN

FAIHWVRQAPGQGLEWVGGRVPVVGIYKYGKKFHDRLRLYEDDPM

KTVFLELRSLTSDDTGVYYCTRWRGCGMCPYDTSSYYNDASDVWG

PGTKVIVSAASTKGPSVFPLAPSSKSTSGGTAALGCLVKDYFPEP

VTVSWNSGALTSGVHTFPAVLQSSGLYSLSSVVTVPSSSLGTQTY

ICNVNHKPSNTKVDKKVEPKSCDKTHTCPPCPAPELLGGPSVFLF

PPKPKDTLMISRTPEVTCVVVDVSHEDPEVKFNWYVDGVEVHNAK

TKPREEQYNSTYRVVSVLTVLHQDWLNGKEYKCKVSNKALPAPIE

KTISKAKGQPREPQVYTLPPSRDELTKNQVSLTCLVKGFYPSDIA

VEWESNGQPENNYKTTPPVLDSDGSFFLYSKLTVDKSRWQQGNVF

SCSVLHEALHSHYTQKSLSLSPGK

SEQ ID NO: 353
KKVVYGKCGDTVELTCTASQKKNIQFHWKNSNQIKILGNQGSFLT

KGPSKLNDRVDSRRSLWDQGNFPLIIKNLKPEDSDTYICEVEDQK

EEVQLVVVCGGGGSEVQLVESGGGLVKAGGSLILSCGVSNFRISA

HTMNWVRRVPGGGLEWVASISTSSTYRDYADAVKGRFTVSRDDLE

DFVYLQMHKMRVEDTAIYYCARKGSDRLSDNDPFDAWGPGTVVTV

SPASTKGPSVFPLAPSSKSTSGGTAALGCLVKDYFPEPVTVSWNS

GALTSGVHTFPAVLQSSGLYSLSSVVTVPSSSLGTQTYICNVNHK

PSNTKVDKKVEPKSCDKTHTCPPCPAPELLGGPSVFLFPPKPKDT

LMISRTPEVTCVVVDVSHEDPEVKFNWYVDGVEVHNAKTKPREEQ

YNSTYRVVSVLTVLHQDWLNGKEYKCKVSNKALPAPIEKTISKAK

GQPREPQVYTLPPSRDELTKNQVSLTCLVKGFYPSDIAVEWESNG

QPENNYKTTPPVLDSDGSFFLYSKLTVDKSRWQQGNVFSCSVLHE

ALHSHYTQKSLSLSPGK

-continued

SEQ ID NO: 354
KKVVYGKCGDTVELTCTASQKKNIQFHWKNSNQIKILGNQGSFLT

KGPSKLNDRVDSRRSLWDQGNFPLIIKNLKPEDSDTYICEVEDQK

EEVQLVVVCGGGGSQMQLQESGPGLVKPGETLSLTCSVSGASISS

SYWSWLRETPGKGLEWIGYTHHSGDTNYAPSLKSRVHLGLHPSKN

QVSLSLTSVTAADTAVYYCARTLHGRRIYGVVAFNEFFTYFYWEV

WGKGTQVTVSSASTKGPSVFPLAPSSKSTSGGTAALGCLVKDYFP

EPVTVSWNSGALTSGVHTFPAVLQSSGLYSLSSVVTVPSSSLGTQ

TYICNVNHKPSNTKVDKKVEPKSCDKTHTCPPCPAPELLGGPSVF

LFPPKPKDTLMISRTPEVTCVVVDVSHEDPEVKFNWYVDGVEVHN

AKTKPREEQYNSTYRVVSVLTVLHQDWLNGKEYKCKVSNKALPAP

IEKTISKAKGQPREPQVYTLPPSRDELTKNQVSLTCLVKGFYPSD

IAVEWESNGQPENNYKTTPPVLDSDGSFFLYSKLTVDKSRWQQGN

VFSCSVLHEALHSHYTQKSLSLSPGK

SEQ ID NO: 355
KKVVYGKCGDTVELTCTASQKKNIQFHWKNSNQIKILGNQGSFLT

KGPSKLNDRVDSRRSLWDQGNFPLIIKNLKPEDSDTYICEVEDQK

EEVQLVVVCGGGGSQMQLQESGPGLVKPGETLSLTCSVSGASISS

SYWSWLRETPGKGLEWIGYTHHSGDTNYAPSLKSRVHLGLHPSKN

QVSLSLTSVTAADTAVYYCARTLHGRRIYGVVAFNEYYTYFYWPT

WGKGTQVTVSSASTKGPSVFPLAPSSKSTSGGTAALGCLVKDYFP

EPVTVSWNSGALTSGVHTFPAVLQSSGLYSLSSVVTVPSSSLGTQ

TYICNVNHKPSNTKVDKKVEPKSCDKTHTCPPCPAPELLGGPSVF

LFPPKPKDTLMISRTPEVTCVVVDVSHEDPEVKFNWYVDGVEVHN

AKTKPREEQYNSTYRVVSVLTVLHQDWLNGKEYKCKVSNKALPAP

IEKTISKAKGQPREPQVYTLPPSRDELTKNQVSLTCLVKGFYPSD

IAVEWESNGQPENNYKTTPPVLDSDGSFFLYSKLTVDKSRWQQGN

VFSCSVLHEALHSHYTQKSLSLSPGK

SEQ ID NO: 356
KKVVYGKCGDTVELTCTASQKKNIQFHWKNSNQIKILGNQGSFLT

KGPSKLNDRVDSRRSLWDQGNFPLIIKNLKPEDSDTYICEVEDQK

EEVQLVVVCGGGGSQMQLQESGPGLVKPGETLSLTCSVSGASISS

SYWSWLRETPGKGLEWIGYTHHSGDTNYAPSLKSRVTIGLDPSKN

QVSLSLTSVTAADTAVYYCARTLHGRRIYGVVAFNEYYTYFYWPT

WGKGTQVTVSSASTKGPSVFPLAPSSKSTSGGTAALGCLVKDYFP

EPVTVSWNSGALTSGVHTFPAVLQSSGLYSLSSVVTVPSSSLGTQ

TYICNVNHKPSNTKVDKKVEPKSCDKTHTCPPCPAPELLGGPSVF

LFPPKPKDTLMISRTPEVTCVVVDVSHEDPEVKFNWYVDGVEVHN

AKTKPREEQYNSTYRVVSVLTVLHQDWLNGKEYKCKVSNKALPAP

IEKTISKAKGQPREPQVYTLPPSRDELTKNQVSLTCLVKGFYPSD

IAVEWESNGQPENNYKTTPPVLDSDGSFFLYSKLTVDKSRWQQGN

VFSCSVLHEALHSHYTQKSLSLSPGK

-continued

SEQ ID NO: 357
KKVVYGKCGDTVELTCTASQKKNIQFHWKNSNQIKILGNQGSFLT

KGPSKLNDRVDSRRSLWDQGNFPLIIKNLKPEDSDTYICEVEDQK

EEVQLVVVCGGGGSQVQLLESGPGLVRPSETLTLTCSVFNSRVSG

YYYSWIRQPPGRGLEWIASTHFSLRPSRNPSLLSRVTTSIDTERY

QVFLNMRSVTAADTAVYFCARGDASGWRADYFPHWGQGTLVVVSS

ASTKGPSVFPLAPSSKSTSGGTAALGCLVKDYFPEPVTVSWNSGA

LTSGVHTFPAVLQSSGLYSLSSVVTVPSSSLGTQTYICNVNHKPS

NTKVDKKVEPKSCDKTHTCPPCPAPELLGGPSVFLFPPKPKDTLM

ISRTPEVTCVVVDVSHEDPEVKFNWYVDGVEVHNAKTKPREEQYN

STYRVVSVLTVLHQDWLNGKEYKCKVSNKALPAPIEKTISKAKGQ

PREPQVYTLPPSRDELTKNQVSLTCLVKGFYPSDIAVEWESNGQP

ENNYKTTPPVLDSDGSFFLYSKLTVDKSRWQQGNVFSCSVLHEAL

HSHYTQKSLSLSPGK

SEQ ID NO: 358
KKVVYGKCGDTVELTCTASQKKNIQFHWKNSNQIKILGNQGSFLT

KGPSKLNDRVDSRRSLWDQGNFPLIIKNLKPEDSDTYICEVEDQK

EEVQLVVVCGGGGSQSVLTQPPSASGSPGQSVTISCTGTSSDIGA

SDYVSWYQQYPGEAPKVIIYDVTKRPSGVPDRFSGSKSGTTASLT

VSGLQAEDEADYYCSSDAGRHTLLFGGGTKVTVLGQPKAAPSVTL

FPPSSEELQANKATLVCLISDFYPGAVTVAWKADSSPVKAGVETT

TPSKQSNNKYAASSYLSLTPEQWKSHRSYSCQVTHEGSTVEKTVA

PTECS

SEQ ID NO: 359
QVQLLESGPGLVRPSETLTLTCSVFNSRVSGYYYSWIRQPPGRGL

EWIASTHFSLRPSRNPSLLSRVTTSIDTERYQVFLNMRSVTAADT

AVYFCARGDASGWRADYFPHWGQGTLVVVSSASTKGPSVFPLAPS

SKSTSGGTAALGCLVKDYFPEPVTVSWNSGALTSGVHTFPAVLQS

SGLYSLSSWVTVPSSSLGTQTYICNVNHKPSNTKVDKKVEPKSCD

KTHTCPPCPAPELLGGPSVFLFPPKPKDTLMISRTPEVTCVVVDV

SHEDPEVKFNWYVDGVEVHNAKTKPREEQYNSTYRVVSVLTVLHQ

DWLNGKEYKCKVSNKALPAPIEKTISKAKGQPREPQVYTLPPSRD

ELTKNQVSLTCLVKGFYPSDIAVEWESNGQPENNYKTTPPVLDSD

GSFFLYSKLTVDKSRWQQGNVFSCSVLHEALHSHYTQKSLSLSPG

KGGGGSKKVVYGKCGDTVELTCTASQKKNIQFHWKNSNQIKILGN

QGSFLTKGPSKLNDRVDSRRSLWDQGNFPLIIKNLKPEDSDTYIC

EVEDQKEEVQLVVVC

SEQ ID NO: 360
QSVLTQPPSASGSPGQSVTISCTGTSSDIGASDYVSWYQQYPGEA

PKVIIYDVTKRPSGVPDRFSGSKSGTTASLTVSGLQAEDEADYYC

SSDAGRHTLLFGGGTKVTVLGQPKAAPSVTLFPPSSEELQANKAT

LVCLISDFYPGAVTVAWKADSSPVKAGVETTTPSKQSNNKYAASS

-continued

YLSLTPEQWKSHRSYSCQVTHEGSTVEKTVAPTECSGGGGSKKVV

YGKCGDTVELTCTASQKKNIQFHWKNSNQIKILGNQGSFLTKGPS

KLNDRVDSRRSLWDQGNFPLIIKNLKPEDSDTYICEVEDQKEEVQ

LVVVC

SEQ ID NO: 361
CTRPNNNTRKSIHIGPGRAFYTTGEIIGDIRQAHC

SEQ ID NO: 362
KKVVYGKCGDTVELTCTASQKKNIQFHWKNSNQIKILGNQGSFLT

KGPSKLNDRVDSRRSLWDQGNFPLIIKNLKPEDSDTYICEVEDQK

EEVQLVVVCGGGGSQVQLVQSGAQMKNPGASVKVSCAPSGYTFTD

FYIHWLRQAPGQGLQWMGWMNPQTGRTNTARNFQGRVTMTRDTSI

GTAYMELRSLTSDDTAIYYCTTGGWISLYYDSSYYPNFDHWGQGT

LLTVSSASTKGPSVFPLAPSSKSTSGGTAALGCLVKDYFPEPVTV

SWNSGALTSGVHTFPAVLQSSGLYSLSSVVTVPSSSLGTQTYICN

VNHKPSNTKVDKKVEPKSCDKTHTCPPCPAPELLGGPSVFLFPPK

PKDTLMISRTPEVTCVVVDVSHEDPEVKFNWYVDGVEVHNAKTKP

REEQYNSTYRVVSVLTVLHQDWLNGKEYKCKVSNKALPAPIEKTI

SKAKGQPREPQVYTLPPSRDELTKNQVSLTCLVKGFYPSDIAVEW

ESNGQPENNYKTTPPVLDSDGSFFLYSKLTVDKSRWQQGNVFSCS

VLHEALHSHYTQKSLSLSPGK

SEQ ID NO: 363
MKVVMGTKKNYQHLWRWGIMLLGMLMMSSAAEQLWVTVYYGVPVWR

EANTTLFCASDAKAYDTEVHNVWATHACVPTDPNPQEVVMGNVTE

DFNMWKNNMVEQMHEDIISLWDQSLKPCVKLTPLCVTLHCTNVTI

SSTNGSTANVTMREEMKNCSFNTTTVIRDKIQKEYALFYKLDIVP

IEGKNTNTSYRLINCNTSVITQACPKVSFEPIPIHYCAPAGFAIL

KCNNKTFNGKGPCRNVSTVQCTHGIKPVVSTQLLLNGSLAEEDII

IRSENFTNNGKNIIVQLKEPVKINCTRPGNNTRRSINIGPGRAFY

ATGAIIGDIRKAHCNISTEQWNNTLTQIVDKLREQFGNKTIIFNQ

SSGGDPEVVMHTFNCGGEFFYCNSTQLFNSTWFNNGTSTWNSTAD

NITLPCRIKQVINMWQEVGKAMYAPPIRGQIDCSSNITGLILTRD

GGSNSSQNETFRPGGGNMKDNWRSELYKYKVVKIEPLGIAPTRAK

RRVVQREKRAVTLGAVFLGFLGAAGSTMGAASLTLTVQARLLLSG

IVQQQSNLLRAIEAQQHMLQLTVWGIKQLQARVLAIERYLKDQQL

LGIWGCSGKLICTTTVPWNTSWSNKSYDYIWNNMTWMQWEREIDN

YTGFIYTLIEESQNQQEKNELELLELDKWASLWNWFNITNWLWYI

KLFIMIIGGLVGLRIVCAVLSIVNRVRQGYSPLSFQTRLPNPRGP

DRPEETEGEGGERDRDRSARLVNGFLAIIWDDLRSLCLFSYHRLR

DLLLIVARVVEILGRRGWEILKYWWNLLKYWSQELKNSAVSLLNV

TAIAVAEGTDRVIEIVQRAVRAILHIPTRIRQGFERALL

SEQ ID NO: 364
AEQLWVIVYYGVPVWREANTTLFCASDAKAYDTEVHNVWATHACV

PTDPNPQEVVMGNVTEDFNMWKNNMVEQMHEDIISLWDQSLKPCV

KLTPLCVTLHCTNVTISSTNGSTANVTMREEMKNCSFNTTTVIRD

KIQKEYALFYKLDIVPIEGKNTNTSYRLINCNTSVITQACPKVSF

EPIPIHYCAPAGFAILKCNNKTFNGKGPCRNVSTVQCTHGIKPVV

STQLLLNGSLAEEDIIIRSENFTNNGKNIIVQLKEPVKINCTRPG

NNTRRSINIGPGRAFYATGAIIGDIRKAHCNISTEQWNNTLTQIV

DKLREQFGNKTIIFNQSSGGDPEVVMHTFNCGGEFFYCNSTQLFN

STWENNGTSTWNSTADNITLPCRIKQVINMWQEVGKAMYAPPIRG

QIDCSSNITGLILTRDGGSNSSQNETFRPGGGNMKDNWRSELYKY

KVVKIEPLGIAPTRAKRRVVQREKR

SEQ ID NO: 365
SDISVAPGETVRITCGGESIGSRAVQWYQHRPGQAPRLIIYNNQD

RPPGIPERFSGSPDIDFGTTATLTISNVEAGDEATYYCHIWDSRR

PTNWELGPGTTLTVL

SEQ ID NO: 366
SDISVAPGETVRITCGGESIGSRAVQWYQHRPGQAPRLIIYNNQD

RPPGIPERFSGSPDIDFGTTATLTISNVEAGDEATYYCHIWDSRR

PTNWELGPGTTLTVLGQPKAAPSVTLFPPSSEELQANKATLVCLI

SDFYPGAVTVAWKADSSPVKAGVETTTPSKQSNNKYAASSYLSLT

PEQWKSHRSYSCQVTHEGSTVEKTVAPTECS

40

What is claimed is:

1. A nucleic acid sequence that encodes an anti-HIV gp120-binding protein having two identical heavy chains and two identical light chains, comprising or consisting of:
   a heavy chain that is at least 95% identical to SEQ ID NO: 121 and
   a light chain that is at least 95% identical to SEQ ID NO:63,
   wherein the two heavy chains comprise a CDRH1 of SEQ ID NO:22, a CDRH2 of SEQ ID NO: 23, a CDRH3 of SEQ ID NO:24, and the two light chains comprise a CDRL1 of SEQ ID NO:25, a CDRL2 of SEQ ID NO:26 and a CDRL3 of SEQ ID NO:27.

2. An expression vector that comprises the nucleic acid sequence of claim 1.

3. A host cell that comprises the nucleic acid sequence of claim 1.

4. A host cell that comprises two expression vectors:
   a first expression vector comprising a first nucleic acid sequence encoding a heavy chain of SEQ ID NO: 121; and
   a second expression vector comprising a second nucleic acid sequence encoding a light chain of SEQ ID NO:63.

5. A method of producing an anti-HIV gp120-binding protein, comprising culturing the host cell as defined in claim 3 under conditions suitable for expression of said nucleic acid sequence, whereby the anti-HIV gp120-binding protein is produced.

6. The host cell of claim 3, wherein the host cell is a mammalian host cell.

7. The host cell of claim 6, wherein the mammalian host cell is a Chinese Hamster Ovary (CHO) cell, an NS0 cell, a PER.C6 cell, a HEK293 cell, or a HeLa cell.

8. A method of producing an anti-HIV gp120-binding protein, comprising culturing the host cell as defined in claim 4 under conditions suitable for expression of said expression vectors whereby the anti-HIV gp120-binding protein is produced.

9. The host cell of claim 4, wherein the host cell is a mammalian host cell.

10. The host cell of claim 9, wherein the mammalian host cell is a Chinese Hamster Ovary (CHO) cell, an NS0 cell, a PER.C6 cell, a HEK293 cell, or a HeLa cell.

* * * * *

SEQUENCE LISTING

Sequence total quantity: 366
SEQ ID NO: 1          moltype = AA  length = 178
FEATURE               Location/Qualifiers
source                1..178
                      mol_type = protein
                      organism = Homo sapiens
SEQUENCE: 1
KKVVLGKKGD TVELTCTASQ KKSIQFHWKN SNQIKILGNQ GSFLTKGPSK LNDRADSRRS  60
LWDQGNFPLI IKNLKIEDSD TYICEVEDQK EEVQLLVFGL TANSDTHLLQ GQSLTLTLES  120
PPGSSPSVQC RSPRGKNIQG GKTLSVSQLE LQDSGTWTCT VLQNQKKVEF KIDIVVLA    178

SEQ ID NO: 2          moltype = AA  length = 179
FEATURE               Location/Qualifiers
source                1..179
                      mol_type = protein -continued

```
                             organism = synthetic construct
SEQUENCE: 2
KKVVLGKKGD TVELTCTASQ KKNIQFHWKN SNQIKILGNQ GSFLTKGPSK LNDRVDSRRS  60
LWDQGNFPLI IKNLKIEDSD TYICEVEDQK EEVQLVVFGL TANSDTHLLQ GQSLTLTLES  120
PPGSSPSVQC RSPRGKNIQG GKTLSVSQLE LQDSGTWTCT VLQNQKKVEF KIDIVVLAF   179

SEQ ID NO: 3              moltype = AA   length = 99
FEATURE                  Location/Qualifiers
source                   1..99
                         mol_type = protein
                         organism = Homo sapiens
SEQUENCE: 3
KKVVLGKKGD TVELTCTASQ KKSIQFHWKN SNQIKILGNQ GSFLTKGPSK LNDRADSRRS  60
LWDQGNFPLI IKNLKIEDSD TYICEVEDQK EEVQLLVFG                          99

SEQ ID NO: 4              moltype = AA   length = 99
FEATURE                  Location/Qualifiers
source                   1..99
                         mol_type = protein
                         organism = synthetic construct
SEQUENCE: 4
KKVVYGKKGD TVELTCTASQ KKNIQFHWKN SNQIKILGNQ GSFLTKGPSK LNDRVDSRRS  60
LWDQGNFPLI IKNLKPEDSD TYICEVEDQK EEVQLVVG                           99

SEQ ID NO: 5              moltype = AA   length = 99
FEATURE                  Location/Qualifiers
source                   1..99
                         mol_type = protein
                         organism = synthetic construct
SEQUENCE: 5
KKVVYGKVGD TVELTCTASQ KKNIQFHWKN SNQIKILGNQ GSFLTKGPSK LNDRVDSRRS  60
LWDQGNFPLI IKNLKPEDSD TYICEVEDQK EEVQLVVG                           99

SEQ ID NO: 6              moltype = AA   length = 99
FEATURE                  Location/Qualifiers
source                   1..99
                         mol_type = protein
                         organism = synthetic construct
SEQUENCE: 6
KKVVYGKKGD TVELTCTASQ KKNIQFHWKN SNQIKILGNQ GSFLTKGPSK LNDRVDSRRS  60
LWDQGNFPLI IKNLKPEDSD TYICEVEDQK QEVQLVVG                           99

SEQ ID NO: 7              moltype = AA   length = 99
FEATURE                  Location/Qualifiers
source                   1..99
                         mol_type = protein
                         organism = synthetic construct
SEQUENCE: 7
KKVVYGKKGD TVELTCTASQ KKNIQFHWKN SNQIKILGNQ GSFLTKGPSK LNDRVDSRRS  60
LWDQGNFPLI IKNLKPEDSD TYICEVEDQK HEVQLVVG                           99

SEQ ID NO: 8              moltype = AA   length = 99
FEATURE                  Location/Qualifiers
source                   1..99
                         mol_type = protein
                         organism = synthetic construct
SEQUENCE: 8
KKVVYGKKGD TVELTCTASQ KKNIQFHWKN SNQIKILGNQ GSFLTKGPSK LNDRVDSRRS  60
LWDQGNFPLI IKNLKPEDSD TYICEVGDQK EEVQLVVG                           99

SEQ ID NO: 9              moltype = AA   length = 99
FEATURE                  Location/Qualifiers
source                   1..99
                         mol_type = protein
                         organism = synthetic construct
SEQUENCE: 9
KKVVYGKKGD TVELTCTASQ KKNIQFHWKN SNQIKILGNQ GSFLTKGPSK LWDRVDSRRS  60
LWDQGNFPLI IKNLKPEDSD TYICEVEDQK EEVQLVVG                           99

SEQ ID NO: 10             moltype = AA   length = 99
FEATURE                  Location/Qualifiers
source                   1..99
                         mol_type = protein
                         organism = synthetic construct
SEQUENCE: 10
KKVVYGKIGD TVELTCTASQ KKNIQFHWKN SNQIKILGNQ GSFLTKGPSK LNDRVDSRRS  60
LWDQGNFPLI IKNLKPEDSD TYICEVEDQK EEVQLVVG                           99

SEQ ID NO: 11             moltype = AA   length = 99
```

-continued

```
FEATURE               Location/Qualifiers
source                1..99
                      mol_type = protein
                      organism = synthetic construct
SEQUENCE: 11
KKVVYGKCGD TVELTCTASQ KKNIQFHWKN SNQIKILGNQ GSFLTKGPSK LNDRVDSRRS   60
LWDQGNFPLI IKNLKPEDSD TYICEVEDQK EEVQLVVVC                           99

SEQ ID NO: 12         moltype = AA   length = 99
FEATURE               Location/Qualifiers
source                1..99
                      mol_type = protein
                      organism = synthetic construct
SEQUENCE: 12
KKVVYGKKGD CVELTCTASQ KKNIQFHWKN SNQIKILGNQ GSFLTKGPSK LNDRVDSRRS   60
LWDQGNFPLI ICNLKPEDSD TYICEVEDQK EEVQLVVVG                           99

SEQ ID NO: 13         moltype = AA   length = 99
FEATURE               Location/Qualifiers
source                1..99
                      mol_type = protein
                      organism = synthetic construct
SEQUENCE: 13
KKVVYGKKGD TVCLTCTASQ KKNIQFHWKN SNQIKILGNQ GSFLTKGPSK LNDRVDSRRS   60
LWDQGNFPLC IKNLKPEDSD TYICEVEDQK EEVQLVVVG                           99

SEQ ID NO: 14         moltype = AA   length = 99
FEATURE               Location/Qualifiers
source                1..99
                      mol_type = protein
                      organism = synthetic construct
SEQUENCE: 14
KKVVYGKKGD TVELTCTASQ KKNIQFCWKN SNQIKILCNQ GSFLTKGPSK LNDRVDSRRS   60
LWDQGNFPLI IKNLKPEDSD TYICEVEDQK EEVQLVVVG                           99

SEQ ID NO: 15         moltype = AA   length = 99
FEATURE               Location/Qualifiers
source                1..99
                      mol_type = protein
                      organism = synthetic construct
SEQUENCE: 15
KKVVYGKKGD TVELTCTASQ CKNIQFHWKN SNQIKILGNQ GSFLTKGPSK LNDRVDSRRS   60
LWDQCNFPLI IKNLKPEDSD TYICEVEDQK EEVQLVVVG                           99

SEQ ID NO: 16         moltype = AA   length = 99
FEATURE               Location/Qualifiers
source                1..99
                      mol_type = protein
                      organism = synthetic construct
SEQUENCE: 16
KKVVYGKKGD TVELTCTASQ KKNIEFHWKN SNQIKILGNQ GSFLTKGPSK LNDRVDSRRS   60
LWDQGNFPLI IKNLKPEDSD TYICEVEDQK EEVQLVVVG                           99

SEQ ID NO: 17         moltype = AA   length = 99
FEATURE               Location/Qualifiers
source                1..99
                      mol_type = protein
                      organism = synthetic construct
SEQUENCE: 17
KKVVYGKKGD TVELTCTASQ KKNIQFDWKN SNQIKILGNQ GSFLTKGPSK LNDRVDSRRS   60
LWDQGNFPLI IKNLKPEDSD TYICEVEDQK EEVQLVVVG                           99

SEQ ID NO: 18         moltype = AA   length = 99
FEATURE               Location/Qualifiers
source                1..99
                      mol_type = protein
                      organism = synthetic construct
SEQUENCE: 18
KKVVYGKKGD TVELTCTASQ KKNIQFHWKN SNQIKILGNQ GSFLTKGPSK LNDRVDSVRS   60
LWDQGNFPLI IKNLKPEDSD TYICEVEDQK EEVQLVVVG                           99

SEQ ID NO: 19         moltype = AA   length = 99
FEATURE               Location/Qualifiers
source                1..99
                      mol_type = protein
                      organism = synthetic construct
SEQUENCE: 19
KKVVYGKKGD TVELTCTASQ KKNIQFHWKN SNQIKILGNQ GSFLTKGPSK LNDRVDSNRS   60
LWDQGNFPLI IKNLKPEDSD TYICEVEDQK EEVQLVVVG                           99
```

-continued

```
SEQ ID NO: 20            moltype = AA  length = 99
FEATURE                  Location/Qualifiers
source                   1..99
                         mol_type = protein
                         organism = synthetic construct
SEQUENCE: 20
KKVVYGKKGD TVELTCTASQ KKNIQFHWKN SNQIKILGNQ GSFLTKGPSK LNDRVDSTRS   60
LWDQGNFPLI IKNLKPEDSD TYICEVEDQK EEVQLVVVG                           99

SEQ ID NO: 21            moltype = AA  length = 99
FEATURE                  Location/Qualifiers
source                   1..99
                         mol_type = protein
                         organism = synthetic construct
SEQUENCE: 21
KKVVYGKKGD TVELTCTASQ KKNIQFHWKN SNQIKILGNQ GSFLTKGPSK LNDRVDSRRS   60
MWDQGNFPLI IKNLKPEDSD TYICEVEDQK EEVQLVVVG                           99

SEQ ID NO: 22            moltype = AA  length = 7
FEATURE                  Location/Qualifiers
source                   1..7
                         mol_type = protein
                         organism = synthetic construct
SEQUENCE: 22
ACNSFWG                                                               7

SEQ ID NO: 23            moltype = AA  length = 22
FEATURE                  Location/Qualifiers
source                   1..22
                         mol_type = protein
                         organism = synthetic construct
SEQUENCE: 23
SLSHCASYWN RGWTYHNPSL KS                                             22

SEQ ID NO: 24            moltype = AA  length = 19
FEATURE                  Location/Qualifiers
source                   1..19
                         mol_type = protein
                         organism = synthetic construct
SEQUENCE: 24
FGGEVLRYTD WPKPAWVDL                                                 19

SEQ ID NO: 25            moltype = AA  length = 9
FEATURE                  Location/Qualifiers
source                   1..9
                         mol_type = protein
                         organism = synthetic construct
SEQUENCE: 25
TGTSNNFVS                                                             9

SEQ ID NO: 26            moltype = AA  length = 7
FEATURE                  Location/Qualifiers
source                   1..7
                         mol_type = protein
                         organism = synthetic construct
SEQUENCE: 26
DVNKRPS                                                               7

SEQ ID NO: 27            moltype = AA  length = 10
FEATURE                  Location/Qualifiers
source                   1..10
                         mol_type = protein
                         organism = synthetic construct
SEQUENCE: 27
GSLVGNWDVI                                                           10

SEQ ID NO: 28            moltype = AA  length = 5
FEATURE                  Location/Qualifiers
source                   1..5
                         mol_type = protein
                         organism = synthetic construct
SEQUENCE: 28
DSYWS                                                                 5

SEQ ID NO: 29            moltype = AA  length = 16
FEATURE                  Location/Qualifiers
source                   1..16
                         mol_type = protein
```

-continued

```
                        organism = synthetic construct
SEQUENCE: 29
YVHKSGDTNY SPSLKS                                                        16

SEQ ID NO: 30          moltype = AA   length = 24
FEATURE                Location/Qualifiers
source                 1..24
                       mol_type = protein
                       organism = synthetic construct
SEQUENCE: 30
TLHGRRIYGI VAFNEWFTYF YMDV                                               24

SEQ ID NO: 31          moltype = AA   length = 11
FEATURE                Location/Qualifiers
source                 1..11
                       mol_type = protein
                       organism = synthetic construct
SEQUENCE: 31
GEKSLGSRAV Q                                                             11

SEQ ID NO: 32          moltype = AA   length = 7
FEATURE                Location/Qualifiers
source                 1..7
                       mol_type = protein
                       organism = synthetic construct
SEQUENCE: 32
NNQDRPS                                                                   7

SEQ ID NO: 33          moltype = AA   length = 12
FEATURE                Location/Qualifiers
source                 1..12
                       mol_type = protein
                       organism = synthetic construct
SEQUENCE: 33
HIWDSRVPTK WV                                                            12

SEQ ID NO: 34          moltype = AA   length = 6
FEATURE                Location/Qualifiers
source                 1..6
                       mol_type = protein
                       organism = synthetic construct
SEQUENCE: 34
SDHSWT                                                                    6

SEQ ID NO: 35          moltype = AA   length = 16
FEATURE                Location/Qualifiers
source                 1..16
                       mol_type = protein
                       organism = synthetic construct
SEQUENCE: 35
DIHYNGATTY NPSLRS                                                        16

SEQ ID NO: 36          moltype = AA   length = 21
FEATURE                Location/Qualifiers
source                 1..21
                       mol_type = protein
                       organism = synthetic construct
SEQUENCE: 36
NAIRIYGVVA LGEWFHYGMD V                                                  21

SEQ ID NO: 37          moltype = AA   length = 11
FEATURE                Location/Qualifiers
source                 1..11
                       mol_type = protein
                       organism = synthetic construct
SEQUENCE: 37
SGAPLTSRFT Y                                                             11

SEQ ID NO: 38          moltype = AA   length = 7
FEATURE                Location/Qualifiers
source                 1..7
                       mol_type = protein
                       organism = synthetic construct
SEQUENCE: 38
RSSQRSS                                                                   7

SEQ ID NO: 39          moltype = AA   length = 11
FEATURE                Location/Qualifiers
source                 1..11
```

-continued

```
                         mol_type = protein
                         organism = synthetic construct
SEQUENCE: 39
QSSDTSDSYK M                                                    11

SEQ ID NO: 40           moltype = AA   length = 5
FEATURE                 Location/Qualifiers
source                  1..5
                        mol_type = protein
                        organism = synthetic construct
SEQUENCE: 40
NYYWT                                                          5

SEQ ID NO: 41           moltype = AA   length = 16
FEATURE                 Location/Qualifiers
source                  1..16
                        mol_type = protein
                        organism = synthetic construct
SEQUENCE: 41
YISDRESATY NPSLNS                                              16

SEQ ID NO: 42           moltype = AA   length = 24
FEATURE                 Location/Qualifiers
source                  1..24
                        mol_type = protein
                        organism = synthetic construct
SEQUENCE: 42
ARRGQRIYGV VSFGEFFYYY SMDV                                     24

SEQ ID NO: 43           moltype = AA   length = 11
FEATURE                 Location/Qualifiers
source                  1..11
                        mol_type = protein
                        organism = synthetic construct
SEQUENCE: 43
GRQALGSRAV Q                                                   11

SEQ ID NO: 44           moltype = AA   length = 7
FEATURE                 Location/Qualifiers
source                  1..7
                        mol_type = protein
                        organism = synthetic construct
SEQUENCE: 44
NNQDRPS                                                        7

SEQ ID NO: 45           moltype = AA   length = 12
FEATURE                 Location/Qualifiers
source                  1..12
                        mol_type = protein
                        organism = synthetic construct
SEQUENCE: 45
HMWDSRSGFS WS                                                  12

SEQ ID NO: 46           moltype = AA   length = 12
FEATURE                 Location/Qualifiers
source                  1..12
                        mol_type = protein
                        organism = synthetic construct
SEQUENCE: 46
GGEWGDKDYH WG                                                  12

SEQ ID NO: 47           moltype = AA   length = 16
FEATURE                 Location/Qualifiers
source                  1..16
                        mol_type = protein
                        organism = synthetic construct
SEQUENCE: 47
SIHWRGTTHY KESLRR                                              16

SEQ ID NO: 48           moltype = AA   length = 18
FEATURE                 Location/Qualifiers
source                  1..18
                        mol_type = protein
                        organism = synthetic construct
SEQUENCE: 48
HRHHDVFMLV PIAGWFDV                                            18

SEQ ID NO: 49           moltype = AA   length = 11
FEATURE                 Location/Qualifiers
```

```
source                    1..11
                          mol_type = protein
                          organism = synthetic construct
SEQUENCE: 49
RASQNINKNL A                                                        11

SEQ ID NO: 50             moltype = AA   length = 7
FEATURE                   Location/Qualifiers
source                    1..7
                          mol_type = protein
                          organism = synthetic construct
SEQUENCE: 50
ETYSKIA                                                             7

SEQ ID NO: 51             moltype = AA   length = 9
FEATURE                   Location/Qualifiers
source                    1..9
                          mol_type = protein
                          organism = synthetic construct
SEQUENCE: 51
QQYEEWPRT                                                           9

SEQ ID NO: 52             moltype = AA   length = 5
FEATURE                   Location/Qualifiers
source                    1..5
                          mol_type = protein
                          organism = synthetic construct
SEQUENCE: 52
DFYIH                                                               5

SEQ ID NO: 53             moltype = AA   length = 17
FEATURE                   Location/Qualifiers
source                    1..17
                          mol_type = protein
                          organism = synthetic construct
SEQUENCE: 53
WMNPQTGRTN TARNFQG                                                  17

SEQ ID NO: 54             moltype = AA   length = 18
FEATURE                   Location/Qualifiers
source                    1..18
                          mol_type = protein
                          organism = synthetic construct
SEQUENCE: 54
GGWISLYYDS SYYPNFDH                                                 18

SEQ ID NO: 55             moltype = AA   length = 14
FEATURE                   Location/Qualifiers
source                    1..14
                          mol_type = protein
                          organism = synthetic construct
SEQUENCE: 55
TGTKYDVGSH DLVS                                                     14

SEQ ID NO: 56             moltype = AA   length = 7
FEATURE                   Location/Qualifiers
source                    1..7
                          mol_type = protein
                          organism = synthetic construct
SEQUENCE: 56
EVNKRPS                                                             7

SEQ ID NO: 57             moltype = AA   length = 10
FEATURE                   Location/Qualifiers
source                    1..10
                          mol_type = protein
                          organism = synthetic construct
SEQUENCE: 57
CSFGGSATVV                                                          10

SEQ ID NO: 58             moltype = AA   length = 135
FEATURE                   Location/Qualifiers
source                    1..135
                          mol_type = protein
                          organism = synthetic construct
SEQUENCE: 58
QPQLQESGPT LVEASETLSL TCAVSGDSTA ACNSFWGWVR QPPGKGLEWV GSLSHCASYW   60
NRGWTYHNPS LKSRLTLALD TPKNLVFLKL NSVTAADTAT YYCARFGGEV LRYTDWPKPA  120
WVDLWGRGTL VTVSS                                                   135
```

-continued

```
SEQ ID NO: 59              moltype = AA  length = 105
FEATURE                    Location/Qualifiers
source                     1..105
                           mol_type = protein
                           organism = synthetic construct
SEQUENCE: 59
QSALTQPPSA SGSPGQSITI SCTGTSNNFV SWYQQHAGKA PKLVIYDVNK RPSGVPDRFS    60
GSKSGNTASL TVSGLQTDDE AVYYCGSLVG NWDVIFGGGT KLTVL                   105

SEQ ID NO: 60              moltype = AA  length = 105
FEATURE                    Location/Qualifiers
source                     1..105
                           mol_type = protein
                           organism = synthetic construct
SEQUENCE: 60
QSALTQPPSA SGSPGQSITI SCTGTSNNYV SWYQQHAGKA PKLVIYDVNK RPSGVPDRFS    60
GSKSGNTASL TVSGLQTDDE AVYYCGSLVG NWDVIFGGGT KLTVL                   105

SEQ ID NO: 61              moltype = AA  length = 465
FEATURE                    Location/Qualifiers
source                     1..465
                           mol_type = protein
                           organism = synthetic construct
SEQUENCE: 61
QPQLQESGPT LVEASETLSL TCAVSGDSTA ACNSFWGWVR QPPGKGLEWV GSLSHCASYW    60
NRGWTYHNPS LKSRLTLALD TPKNLVFLKL NSVTAADTAT YYCARFGGEV LRYTDWPKPA   120
WVDLWGRGTL VTVSSASTKG PSVFPLAPSS KSTSGGTAAL GCLVKDYFPE PVTVSWNSGA   180
LTSGVHTFPA VLQSSGLYSL SSVVTVPSSS LGTQTYICNV NHKPSNTKVD KKVEPKSCDK   240
THTCPPCPAP ELLGGPSVFL FPPKPKDTLM ISRTPEVTCV VVDVSHEDPE VKFNWYVDGV   300
EVHNAKTKPR EEQYNSTYRV VSVLTVLHQD WLNGKEYKCK VSNKALPAPI EKTISKAKGQ   360
PREPQVYTLP PSRDELTKNQ VSLTCLVKGF YPSDIAVEWE SNGQPENNYK TTPPVLDSDG   420
SFFLYSKLTV DKSRWQQGNV FSCSVMHEAL HNHYTQKSLS LSPGK                   465

SEQ ID NO: 62              moltype = AA  length = 465
FEATURE                    Location/Qualifiers
source                     1..465
                           mol_type = protein
                           organism = synthetic construct
SEQUENCE: 62
QPQLQESGPT LVEASETLSL TCAVSGDSTA ACNSFWGWVR QPPGKGLEWV GSLSHCASYW    60
NRGWTYHNPS LKSRLTLALD TPKNLVFLKL NSVTAADTAT YYCARFGGEV LRYTDWPKPA   120
WVDLWGRGTL VTVSSASTKG PSVFPLAPSS KSTSGGTAAL GCLVKDYFPE PVTVSWNSGA   180
LTSGVHTFPA VLQSSGLYSL SSVVTVPSSS LGTQTYICNV NHKPSNTKVD KKVEPKSCDK   240
THTCPPCPAP ELLGGPSVFL FPPKPKDTLM ISRTPEVTCV VVDVSHEDPE VKFNWYVDGV   300
EVHNAKTKPR EEQYNSTYRV VSVLTVLHQD WLNGKEYKCK VSNKALPAPI EKTISKAKGQ   360
PREPQVYTLP PSRDELTKNQ VSLTCLVKGF YPSDIAVEWE SNGQPENNYK TTPPVLDSDG   420
SFFLYSKLTV DKSRWQQGNV FSCSVLHEAL HSHYTQKSLS LSPGK                   465

SEQ ID NO: 63              moltype = AA  length = 211
FEATURE                    Location/Qualifiers
source                     1..211
                           mol_type = protein
                           organism = synthetic construct
SEQUENCE: 63
QSALTQPPSA SGSPGQSITI SCTGTSNNFV SWYQQHAGKA PKLVIYDVNK RPSGVPDRFS    60
GSKSGNTASL TVSGLQTDDE AVYYCGSLVG NWDVIFGGGT KLTVLGQPKA APSVTLFPPS   120
SEELQANKAT LVCLISDFYP GAVTVAWKAD SSPVKAGVET TTPSKQSNNK YAASSYLSLT   180
PEQWKSHRSY SCQVTHEGST VEKTVAPTEC S                                 211

SEQ ID NO: 64              moltype = AA  length = 211
FEATURE                    Location/Qualifiers
source                     1..211
                           mol_type = protein
                           organism = synthetic construct
SEQUENCE: 64
QSALTQPPSA SGSPGQSITI SCTGTSNNYV SWYQQHAGKA PKLVIYDVNK RPSGVPDRFS    60
GSKSGNTASL TVSGLQTDDE AVYYCGSLVG NWDVIFGGGT KLTVLGQPKA APSVTLFPPS   120
SEELQANKAT LVCLISDFYP GAVTVAWKAD SSPVKAGVET TTPSKQSNNK YAASSYLSLT   180
PEQWKSHRSY SCQVTHEGST VEKTVAPTEC S                                 211

SEQ ID NO: 65              moltype = AA  length = 132
FEATURE                    Location/Qualifiers
source                     1..132
                           mol_type = protein
                           organism = synthetic construct
SEQUENCE: 65
QMQLQESGPG LVKPSETLSL TCSVSGASIS DSYWSWIRRS PGKGLEWIGY VHKSGDTNYS    60
PSLKSRVNLS LDTSKNQVSL SLVAATAADS GKYYCARTLH GRRIYGIVAF NEWFTYFYMD   120
```

```
VWGNGTQVTV SS                                                                       132

SEQ ID NO: 66              moltype = AA   length = 105
FEATURE                    Location/Qualifiers
source                     1..105
                           mol_type = protein
                           organism = synthetic construct
SEQUENCE: 66
SDISVAPGET ARISCGEKSL GSRAVQWYQH RAGQAPSLII YNNQDRPSGI PERFSGSPDS   60
PFGTTATLTI TSVEAGDEAD YYCHIWDSRV PTKWVFGGGT TLTVL                   105

SEQ ID NO: 67              moltype = AA   length = 462
FEATURE                    Location/Qualifiers
source                     1..462
                           mol_type = protein
                           organism = synthetic construct
SEQUENCE: 67
QMQLQESGPG LVKPSETLSL TCSVSGASIS DSYWSWIRRS PGKGLEWIGY VHKSGDTNYS   60
PSLKSRVNLS LDTSKNQVSL SLVAATAADS GKYYCARTLH GRRIYGIVAF NEWFTYFYMD   120
VWGNGTQVTV SSASTKGPSV FPLAPSSKST SGGTAALGCL VKDYFPEPVT VSWNSGALTS   180
GVHTFPAVLQ SSGLYSLSSV VTVPSSSLGT QTYICNVNHK PSNTKVDKRV EPKSCDKTHT   240
CPPCPAPELL GGPSVFLFPP KPKDTLMISR TPEVTCVVVD VSHEDPEVKF NWYVDGVEVH   300
NAKTKPREEQ YNSTYRVVSV LTVLHQDWLN GKEYKCKVSN KALPAPIEKT ISKAKGQPRE   360
PQVYTLPPSR DELTKNQVSL TCLVKGFYPS DIAVEWESNG QPENNYKTTP PVLDSDGSFF   420
LYSKLTVDKS RWQQGNVFSC SVMHEALHNH YTQKSLSLSP GK                      462

SEQ ID NO: 68              moltype = AA   length = 462
FEATURE                    Location/Qualifiers
source                     1..462
                           mol_type = protein
                           organism = synthetic construct
SEQUENCE: 68
QMQLQESGPG LVKPSETLSL TCSVSGASIS DSYWSWIRRS PGKGLEWIGY VHKSGDTNYS   60
PSLKSRVNLS LDTSKNQVSL SLVAATAADS GKYYCARTLH GRRIYGIVAF NEWFTYFYMD   120
VWGNGTQVTV SSASTKGPSV FPLAPSSKST SGGTAALGCL VKDYFPEPVT VSWNSGALTS   180
GVHTFPAVLQ SSGLYSLSSV VTVPSSSLGT QTYICNVNHK PSNTKVDKRV EPKSCDKTHT   240
CPPCPAPELL GGPSVFLFPP KPKDTLMISR TPEVTCVVVD VSHEDPEVKF NWYVDGVEVH   300
NAKTKPREEQ YNSTYRVVSV LTVLHQDWLN GKEYKCKVSN KALPAPIEKT ISKAKGQPRE   360
PQVYTLPPSR DELTKNQVSL TCLVKGFYPS DIAVEWESNG QPENNYKTTP PVLDSDGSFF   420
LYSKLTVDKS RWQQGNVFSC SVLHEALHSH YTQKSLSLSP GK                      462

SEQ ID NO: 69              moltype = AA   length = 211
FEATURE                    Location/Qualifiers
source                     1..211
                           mol_type = protein
                           organism = synthetic construct
SEQUENCE: 69
SDISVAPGET ARISCGEKSL GSRAVQWYQH RAGQAPSLII YNNQDRPSGI PERFSGSPDS   60
PFGTTATLTI TSVEAGDEAD YYCHIWDSRV PTKWVFGGGT TLTVLGQPKA APSVTLFPPS   120
SEELQANKAT LVCLISDFYP GAVTVAWKAD SSPVKAGVET TTPSKQSNNK YAASSYLSLT   180
PEQWKSHKSY SCQVTHEGST VEKTVAPTEC S                                  211

SEQ ID NO: 70              moltype = AA   length = 130
FEATURE                    Location/Qualifiers
source                     1..130
                           mol_type = protein
                           organism = synthetic construct
SEQUENCE: 70
QVQLRESGPG LVKPSETLSL SCTVSNDSRP SDHSWTWVRQ SPGKALEWIG DIHYNGATTY   60
NPSLRSRVRI ELDQSIPRFS LKMTSMTAAD TGMYYCARNA IRIYGVVALG EWFHYGMDVW   120
GQGTAVTVSS                                                          130

SEQ ID NO: 71              moltype = AA   length = 108
FEATURE                    Location/Qualifiers
source                     1..108
                           mol_type = protein
                           organism = synthetic construct
SEQUENCE: 71
SSELTQPPSV SVSPGQTARI TCSGAPLTSR FTYWYRQKPG QAPVLIISRS SQRSSGWSGR   60
FSASWSGTTV TLTIRGVQAD DEADYYCQSS DTSDSYKMFG GGTKLTVL                108

SEQ ID NO: 72              moltype = AA   length = 460
FEATURE                    Location/Qualifiers
source                     1..460
                           mol_type = protein
                           organism = synthetic construct
SEQUENCE: 72
QVQLRESGPG LVKPSETLSL SCTVSNDSRP SDHSWTWVRQ SPGKALEWIG DIHYNGATTY   60
NPSLRSRVRI ELDQSIPRFS LKMTSMTAAD TGMYYCARNA IRIYGVVALG EWFHYGMDVW   120
```

```
GGQGTAVTVSS ASTKGPSVFP LAPSSKSTSG GTAALGCLVK DYFPEPVTVS WNSGALTSGV    180
HTFPAVLQSS GLYSLSSVVT VPSSSLGTQT YICNVNHKPS NTKVDKRVEP KSCDKTHTCP    240
PCPAPELLGG PSVFLFPPKP KDTLMISRTP EVTCVVVDVS HEDPEVKFNW YVDGVEVHNA    300
KTKPREEQYN STYRVVSVLT VLHQDWLNGK EYKCKVSNKA LPAPIEKTIS KAKGQPREPQ    360
VYTLPPSRDE LTKNQVSLTC LVKGFYPSDI AVEWESNGQP ENNYKTTPPV LDSDGSFFLY    420
SKLTVDKSRW QQGNVFSCSV MHEALHNHYT QKSLSLSPGK                         460

SEQ ID NO: 73            moltype = AA  length = 460
FEATURE                  Location/Qualifiers
source                   1..460
                         mol_type = protein
                         organism = synthetic construct
SEQUENCE: 73
QVQLRESGPG LVKPSETLSL SCTVSNDSRP SDHSWTWVRQ SPGKALEWIG DIHYNGATTY     60
NPSLRSRVRI ELDQSIPRFS LKMTSMTAAD TGMYYCARNA IRIYGVVALG EWFHYGMDVW    120
GGQGTAVTVSS ASTKGPSVFP LAPSSKSTSG GTAALGCLVK DYFPEPVTVS WNSGALTSGV   180
HTFPAVLQSS GLYSLSSVVT VPSSSLGTQT YICNVNHKPS NTKVDKRVEP KSCDKTHTCP    240
PCPAPELLGG PSVFLFPPKP KDTLMISRTP EVTCVVVDVS HEDPEVKFNW YVDGVEVHNA    300
KTKPREEQYN STYRVVSVLT VLHQDWLNGK EYKCKVSNKA LPAPIEKTIS KAKGQPREPQ    360
VYTLPPSRDE LTKNQVSLTC LVKGFYPSDI AVEWESNGQP ENNYKTTPPV LDSDGSFFLY    420
SKLTVDKSRW QQGNVFSCSV LHEALHSHYT QKSLSLSPGK                         460

SEQ ID NO: 74            moltype = AA  length = 213
FEATURE                  Location/Qualifiers
source                   1..213
                         mol_type = protein
                         organism = synthetic construct
SEQUENCE: 74
SSELTQPPSV SVSPGQTARI TCSGAPLTSR FTYWYRQKPG QAPVLIISRS SQRSSGWSGR     60
FSASWSGTTV TLTIRGVQAD DEADYYCQSS DTSDSYKMFG GGTKLTVLGQ PAAAPSVTLF    120
PPSSEELQAN KATLVCLISD FYPGAVTVAW KADSSPVKAG VETTTPSKQS NNKYAASSYL    180
SLTPEQWKSH KSYSCQVTHE GSTVEKTVAP TEC                               213

SEQ ID NO: 75            moltype = AA  length = 132
FEATURE                  Location/Qualifiers
source                   1..132
                         mol_type = protein
                         organism = synthetic construct
SEQUENCE: 75
QVQLQESGPG LVKPSETLSV TCSVSGDSMN NYYWTWIRQS PGKGLEWIGY ISDRESATYN     60
PSLNSRVVIS RDTSKNQLSL KLNSVTPADT AVYYCATARR GQRIYGVVSF GEFFYYYSMD    120
VWGKGTTVTV SS                                                      132

SEQ ID NO: 76            moltype = AA  length = 108
FEATURE                  Location/Qualifiers
source                   1..108
                         mol_type = protein
                         organism = synthetic construct
SEQUENCE: 76
SYVRPLSVAL GETARISCGR QALGSRAVQW YQHRPGQAPI LLIYNNQDRP SGIPERFSGT     60
PDINFGTRAT LTISGVEAGD EADYYCHMWD SRSGFSWSFG GATRLTVL                108

SEQ ID NO: 77            moltype = AA  length = 462
FEATURE                  Location/Qualifiers
source                   1..462
                         mol_type = protein
                         organism = synthetic construct
SEQUENCE: 77
QVQLQESGPG LVKPSETLSV TCSVSGDSMN NYYWTWIRQS PGKGLEWIGY ISDRESATYN     60
PSLNSRVVIS RDTSKNQLSL KLNSVTPADT AVYYCATARR GQRIYGVVSF GEFFYYYSMD    120
VWGKGTTVTV SSASTKGPSV FPLAPSSKST SGGTAALGCL VKDYFPEPVT VSWNSGALTS    180
GVHTFPAVLQ SSGLYSLSSV VTVPSSSLGT QTYICNVNHK PSNTKVDKRV EPKSCDKTHT    240
CPPCPAPELL GGPSVFLFPP KPKDTLMISR TPEVTCVVVD VSHEDPEVKF NWYVDGVEVH    300
NAKTKPREEQ YNSTYRVVSV LTVLHQDWLN GKEYKCKVSN KALPAPIEKT ISKAKGQPRE    360
PQVYTLPPSR DELTKNQVSL TCLVKGFYPS DIAVEWESNG QPENNYKTTP PVLDSDGSFF    420
LYSKLTVDKS RWQQGNVFSC SVMHEALHNH YTQKSLSLSP GK                      462

SEQ ID NO: 78            moltype = AA  length = 462
FEATURE                  Location/Qualifiers
source                   1..462
                         mol_type = protein
                         organism = synthetic construct
SEQUENCE: 78
QVQLQESGPG LVKPSETLSV TCSVSGDSMN NYYWTWIRQS PGKGLEWIGY ISDRESATYN     60
PSLNSRVVIS RDTSKNQLSL KLNSVTPADT AVYYCATARR GQRIYGVVSF GEFFYYYSMD    120
VWGKGTTVTV SSASTKGPSV FPLAPSSKST SGGTAALGCL VKDYFPEPVT VSWNSGALTS    180
GVHTFPAVLQ SSGLYSLSSV VTVPSSSLGT QTYICNVNHK PSNTKVDKRV EPKSCDKTHT    240
CPPCPAPELL GGPSVFLFPP KPKDTLMISR TPEVTCVVVD VSHEDPEVKF NWYVDGVEVH    300
NAKTKPREEQ YNSTYRVVSV LTVLHQDWLN GKEYKCKVSN KALPAPIEKT ISKAKGQPRE    360
```

```
PQVYTLPPSR DELTKNQVSL TCLVKGFYPS DIAVEWESNG QPENNYKTTP PVLDSDGSFF   420
LYSKLTVDKS RWQQGNVFSC SVLHEALHSH YTQKSLSLSP GK                       462

SEQ ID NO: 79            moltype = AA   length = 214
FEATURE                  Location/Qualifiers
source                   1..214
                         mol_type = protein
                         organism = synthetic construct
SEQUENCE: 79
SYVRPLSVAL GETARISCGR QALGSRAVQW YQHRPGQAPI LLIYNNQDRP SGIPERFSGT    60
PDINFGTRAT LTISGVEAGD EADYYCHMWD SRSGFSWSFG GATRLTVLGQ PKAAPSVTLF   120
PPSSEELQAN KATLVCLISD FYPGAVTVAW KADSSPVKAG VETTTPSKQS NNKYAASSYL   180
SLTPEQWKSH RSYSCQVTHE GSTVEKTVAP TECS                               214

SEQ ID NO: 80            moltype = AA   length = 133
FEATURE                  Location/Qualifiers
source                   1..133
                         mol_type = protein
                         organism = synthetic construct
SEQUENCE: 80
QLQMQESGPG LVKPSETLSL SCTVSGDSIR GGEWGDKDYH WGWVRHSAGK GLEWIGSIHW    60
RGTTHYKESL RRRVSMSIDT SRNWFSLRLA SVTAADTAVY FCARHRHHDV FMLVPIAGWF   120
DVWGPGVQVT VSS                                                      133

SEQ ID NO: 81            moltype = AA   length = 107
FEATURE                  Location/Qualifiers
source                   1..107
                         mol_type = protein
                         organism = synthetic construct
SEQUENCE: 81
EIVMTQSPDT LSVSPGETVT LSCRASQNIN KNLAWYQYKP GQSPRLVIFE TYSKIAAFPA    60
RFVASGSGTE FTLTINNMQS EDVAVYYCQQ YEEWPRTFGQ GTKVDIK                 107

SEQ ID NO: 82            moltype = AA   length = 463
FEATURE                  Location/Qualifiers
source                   1..463
                         mol_type = protein
                         organism = synthetic construct
SEQUENCE: 82
QLQMQESGPG LVKPSETLSL SCTVSGDSIR GGEWGDKDYH WGWVRHSAGK GLEWIGSIHW    60
RGTTHYKESL RRRVSMSIDT SRNWFSLRLA SVTAADTAVY FCARHRHHDV FMLVPIAGWF   120
DVWGPGVQVT VSSASTKGPS VFPLAPSSKS TSGGTAALGC LVKDYFPEPV TVSWNSGALT   180
SGVHTFPAVL QSSGLYSLSS VVTVPSSSLG TQTYICNVNH KPSNTKVDKR VEPKSCDKTH   240
TCPPCPAPEL LGGPSVFLFP PKPKDTLMIS RTPEVTCVVV DVSHEDPEVK FNWYVDGVEV   300
HNAKTKPREE QYNSTYRVVS VLTVLHQDWL NGKEYKCKVS NKALPAPIEK TISKAKGQPR   360
EPQVYTLPPS RDELTKNQVS LTCLVKGFYP SDIAVEWESN GQPENNYKTT PPVLDSDGSF   420
FLYSKLTVDK SRWQQGNVFS CSVMHEALHN HYTQKSLSLS PGK                     463

SEQ ID NO: 83            moltype = AA   length = 463
FEATURE                  Location/Qualifiers
source                   1..463
                         mol_type = protein
                         organism = synthetic construct
SEQUENCE: 83
QLQMQESGPG LVKPSETLSL SCTVSGDSIR GGEWGDKDYH WGWVRHSAGK GLEWIGSIHW    60
RGTTHYKESL RRRVSMSIDT SRNWFSLRLA SVTAADTAVY FCARHRHHDV FMLVPIAGWF   120
DVWGPGVQVT VSSASTKGPS VFPLAPSSKS TSGGTAALGC LVKDYFPEPV TVSWNSGALT   180
SGVHTFPAVL QSSGLYSLSS VVTVPSSSLG TQTYICNVNH KPSNTKVDKR VEPKSCDKTH   240
TCPPCPAPEL LGGPSVFLFP PKPKDTLMIS RTPEVTCVVV DVSHEDPEVK FNWYVDGVEV   300
HNAKTKPREE QYNSTYRVVS VLTVLHQDWL NGKEYKCKVS NKALPAPIEK TISKAKGQPR   360
EPQVYTLPPS RDELTKNQVS LTCLVKGFYP SDIAVEWESN GQPENNYKTT PPVLDSDGSF   420
FLYSKLTVDK SRWQQGNVFS CSVLHEALHS HYTQKSLSLS PGK                     463

SEQ ID NO: 84            moltype = AA   length = 214
FEATURE                  Location/Qualifiers
source                   1..214
                         mol_type = protein
                         organism = synthetic construct
SEQUENCE: 84
EIVMTQSPDT LSVSPGETVT LSCRASQNIN KNLAWYQYKP GQSPRLVIFE TYSKIAAFPA    60
RFVASGSGTE FTLTINNMQS EDVAVYYCQQ YEEWPRTFGQ GTKVDIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 85            moltype = AA   length = 127
FEATURE                  Location/Qualifiers
source                   1..127
                         mol_type = protein
                         organism = synthetic construct
```

-continued

```
SEQUENCE: 85
QVQLVQSGAQ MKNPGASVKV SCAPSGYTFT DFYIHWLRQA PGQGLQWMGW MNPQTGRTNT    60
ARNFQGRVTM TRDTSIGTAY MELRSLTSDD TAIYYCTTGG WISLYYDSSY YPNFDHWGQG   120
TLLTVSS                                                            127

SEQ ID NO: 86            moltype = AA   length = 110
FEATURE                  Location/Qualifiers
source                   1..110
                         mol_type = protein
                         organism = synthetic construct
SEQUENCE: 86
QSALTQPASV SGSPGQSITI SCTGTKYDVG SHDLVSWYQQ YPGKVPKYMI YEVNKRPSGV    60
SNRFSGSKSG NTASLTISGL RAEDEADYYC CSFGGSATVV CGGGTKVTVL             110

SEQ ID NO: 87            moltype = AA   length = 457
FEATURE                  Location/Qualifiers
source                   1..457
                         mol_type = protein
                         organism = synthetic construct
SEQUENCE: 87
QVQLVQSGAQ MKNPGASVKV SCAPSGYTFT DFYIHWLRQA PGQGLQWMGW MNPQTGRTNT    60
ARNFQGRVTM TRDTSIGTAY MELRSLTSDD TAIYYCTTGG WISLYYDSSY YPNFDHWGQG   120
TLLTVSSAST KGPSVFPLAP SSKSTSGGTA ALGCLVKDYF PEPVTVSWNS GALTSGVHTF   180
PAVLQSSGLY SLSSVVTVPS SSLGTQTYIC NVNHKPSNTK VDKKVEPKSC DKTHTCPPCP   240
APELLGGPSV FLFPPKPKDT LMISRTPEVT CVVVDVSHED PEVKFNWYVD GVEVHNAKTK   300
PREEQYNSTY RVVSVLTVLH QDWLNGKEYK CKVSNKALPA PIEKTISKAK GQPREPQVYT   360
LPPSRDELTK NQVSLTCLVK GFYPSDIAVE WESNGQPENN YKTTPPVLDS DGSFFLYSKL   420
TVDKSRWQQG NVFSCSVMHE ALHNHYTQKS LSLSPGK                           457

SEQ ID NO: 88            moltype = AA   length = 457
FEATURE                  Location/Qualifiers
source                   1..457
                         mol_type = protein
                         organism = synthetic construct
SEQUENCE: 88
QVQLVQSGAQ MKNPGASVKV SCAPSGYTFT DFYIHWLRQA PGQGLQWMGW MNPQTGRTNT    60
ARNFQGRVTM TRDTSIGTAY MELRSLTSDD TAIYYCTTGG WISLYYDSSY YPNFDHWGQG   120
TLLTVSSAST KGPSVFPLAP SSKSTSGGTA ALGCLVKDYF PEPVTVSWNS GALTSGVHTF   180
PAVLQSSGLY SLSSVVTVPS SSLGTQTYIC NVNHKPSNTK VDKKVEPKSC DKTHTCPPCP   240
APELLGGPSV FLFPPKPKDT LMISRTPEVT CVVVDVSHED PEVKFNWYVD GVEVHNAKTK   300
PREEQYNSTY RVVSVLTVLH QDWLNGKEYK CKVSNKALPA PIEKTISKAK GQPREPQVYT   360
LPPSRDELTK NQVSLTCLVK GFYPSDIAVE WESNGQPENN YKTTPPVLDS DGSFFLYSKL   420
TVDKSRWQQG NVFSCSVLHE ALHSHYTQKS LSLSPGK                           457

SEQ ID NO: 89            moltype = AA   length = 216
FEATURE                  Location/Qualifiers
source                   1..216
                         mol_type = protein
                         organism = synthetic construct
SEQUENCE: 89
QSALTQPASV SGSPGQSITI SCTGTKYDVG SHDLVSWYQQ YPGKVPKYMI YEVNKRPSGV    60
SNRFSGSKSG NTASLTISGL RAEDEADYYC CSFGGSATVV CGGGTKVTVL GQPKAAPSVT   120
LFPPSSEELQ ANKATLVCLI SDFYPGAVTV AWKADSSPVK AGVETTTPSK QSNNKYAASS   180
YLSLTPEQWK SHRSYSCQVT HEGSTVEKTV APTECS                           216

SEQ ID NO: 90            moltype = AA   length = 5
FEATURE                  Location/Qualifiers
source                   1..5
                         mol_type = protein
                         organism = synthetic construct
SEQUENCE: 90
GGGGS                                                               5

SEQ ID NO: 91            moltype = AA   length = 10
FEATURE                  Location/Qualifiers
source                   1..10
                         mol_type = protein
                         organism = synthetic construct
SEQUENCE: 91
GGGGSGGGGS                                                         10

SEQ ID NO: 92            moltype = AA   length = 15
FEATURE                  Location/Qualifiers
source                   1..15
                         mol_type = protein
                         organism = synthetic construct
SEQUENCE: 92
GGGGSGGGGS GGGGS                                                   15
```

-continued

```
SEQ ID NO: 93              moltype = AA   length = 20
FEATURE                    Location/Qualifiers
source                     1..20
                           mol_type = protein
                           organism = synthetic construct
SEQUENCE: 93
GGGGSGGGGS GGGGSGGGGS                                                    20

SEQ ID NO: 94              moltype = AA   length = 25
FEATURE                    Location/Qualifiers
source                     1..25
                           mol_type = protein
                           organism = synthetic construct
SEQUENCE: 94
GGGGSGGGGS GGGGSGGGGS GGGGS                                              25

SEQ ID NO: 95              moltype = AA   length = 30
FEATURE                    Location/Qualifiers
source                     1..30
                           mol_type = protein
                           organism = synthetic construct
SEQUENCE: 95
GGGGSGGGGS GGGGSGGGGS GGGGSGGGGS                                         30

SEQ ID NO: 96              moltype = AA   length = 644
FEATURE                    Location/Qualifiers
source                     1..644
                           mol_type = protein
                           organism = synthetic construct
SEQUENCE: 96
KKVVLGKKGD TVELTCTASQ KKNIQFHWKN SNQIKILGNQ GSFLTKGPSK LNDRVDSRRS    60
LWDQGNFPLI IKNLKIEDSD TYICEVEDQK EEVQLVVFGL TANSDTHLLQ GQSLTLTLES   120
PPGSSPSVQC RSPRGKNIQG GKTLSVSQLE LQDSGTWTCT VLQNQKKVEF KIDIVVLAFQ   180
PQLQESGPTL VEASETLSLT CAVSGDSTAA CNSFWGWVRQ PPGKGLEWVG SLSHCASYWN   240
RGWTYHNPSL KSRLTLALDT PKNLVFLKLN SVTAADTATY YCARFGGEVL RYTDWPKPAW   300
VDLWGRGTLV TVSSASTKGP SVFPLAPSSK STSGGTAALG CLVKDYFPEP VTVSWNSGAL   360
TSGVHTFPAV LQSSGLYSLS SVVTVPSSSL GTQTYICNVN HKPSNTKVDK KVEPKSCDKT   420
HTCPPCPAPE LLGGPSVFLF PPKPKDTLMI SRTPEVTCVV VDVSHEDPEV KFNWYVDGVE   480
VHNAKTKPRE EQYNSTYRVV SVLTVLHQDW LNGKEYKCKV SNKALPAPIE KTISKAKGQP   540
REPQVYTLPP SRDELTKNQV SLTCLVKGFY PSDIAVEWES NGQPENNYKT TPPVLDSDGS   600
FFLYSKLTVD KSRWQQGNVF SCSVLHEALH SHYTQKSLSL SPGK                     644

SEQ ID NO: 97              moltype = AA   length = 649
FEATURE                    Location/Qualifiers
source                     1..649
                           mol_type = protein
                           organism = synthetic construct
SEQUENCE: 97
KKVVLGKKGD TVELTCTASQ KKNIQFHWKN SNQIKILGNQ GSFLTKGPSK LNDRVDSRRS    60
LWDQGNFPLI IKNLKIEDSD TYICEVEDQK EEVQLVVFGL TANSDTHLLQ GQSLTLTLES   120
PPGSSPSVQC RSPRGKNIQG GKTLSVSQLE LQDSGTWTCT VLQNQKKVEF KIDIVVLAFG   180
GGGSQPQLQE SGPTLVEASE TLSLTCAVSG DSTAACNSFW GWVRQPPGKG LEWVGSLSHC   240
ASYWNRGWTY HNPSLKSRLT LALDTPKNLV FLKLNSVTAA DTATYYCARF GGEVLRYTDW   300
PKPAWVDLWG RGTLVTVSSA STKGPSVFPL APSSKSTSGG TAALGCLVKD YFPEPVTVSW   360
NSGALTSGVH TFPAVLQSSG LYSLSSVVTV PSSSLGTQTY ICNVNHKPSN TKVDKKVEPK   420
SCDKTHTCPP CPAPELLGGP SVFLFPPKPK DTLMISRTPE VTCVVVDVSH EDPEVKFNWY   480
VDGVEVHNAK TKPREEQYNS TYRVVSVLTV LHQDWLNGKE YKCKVSNKAL PAPIEKTISK   540
AKGQPREPQV YTLPPSRDEL TKNQVSLTCL VKGFYPSDIA VEWESNGQPE NNYKTTPPVL   600
DSDGSFFLYS KLTVDKSRWQ QGNVFSCSVL HEALHSHYTQ KSLSLSPGK               649

SEQ ID NO: 98              moltype = AA   length = 654
FEATURE                    Location/Qualifiers
source                     1..654
                           mol_type = protein
                           organism = synthetic construct
SEQUENCE: 98
KKVVLGKKGD TVELTCTASQ KKNIQFHWKN SNQIKILGNQ GSFLTKGPSK LNDRVDSRRS    60
LWDQGNFPLI IKNLKIEDSD TYICEVEDQK EEVQLVVFGL TANSDTHLLQ GQSLTLTLES   120
PPGSSPSVQC RSPRGKNIQG GKTLSVSQLE LQDSGTWTCT VLQNQKKVEF KIDIVVLAFG   180
GGGSGGGGSQ PQLQESGPTL VEASETLSLT CAVSGDSTAA CNSFWGWVRQ PPGKGLEWVG   240
SLSHCASYWN RGWTYHNPSL KSRLTLALDT PKNLVFLKLN SVTAADTATY YCARFGGEVL   300
RYTDWPKPAW VDLWGRGTLV TVSSASTKGP SVFPLAPSSK STSGGTAALG CLVKDYFPEP   360
VTVSWNSGAL TSGVHTFPAV LQSSGLYSLS SVVTVPSSSL GTQTYICNVN HKPSNTKVDK   420
KVEPKSCDKT HTCPPCPAPE LLGGPSVFLF PPKPKDTLMI SRTPEVTCVV VDVSHEDPEV   480
KFNWYVDGVE VHNAKTKPRE EQYNSTYRVV SVLTVLHQDW LNGKEYKCKV SNKALPAPIE   540
KTISKAKGQP REPQVYTLPP SRDELTKNQV SLTCLVKGFY PSDIAVEWES NGQPENNYKT   600
TPPVLDSDGS FFLYSKLTVD KSRWQQGNVF SCSVLHEALH SHYTQKSLSL SPGK         654

SEQ ID NO: 99              moltype = AA   length = 659
```

-continued

```
FEATURE            Location/Qualifiers
source             1..659
                   mol_type = protein
                   organism = synthetic construct
SEQUENCE: 99
KKVVLGKKGD TVELTCTASQ KKNIQFHWKN SNQIKILGNQ GSFLTKGPSK LNDRVDSRRS    60
LWDQGNFPLI IKNLKIEDSD TYICEVEDQK EEVQLVVFGL TANSDTHLLQ GQSLTLTLES   120
PPGSSPSVQC RSPRGKNIQG GKTLSVSQLE LQDSGTWTCT VLQNQKKVEF KIDIVVLAFG   180
GGGSGGGGSG GGGSQPQLQE SGPTLVEASE TLSLTCAVSG DSTAACNSFW GWVRQPPGKG   240
LEWVGSLSHC ASYWNRGWTY HNPSLKSRLT LALDTPKNLV FLKLNSVTAA DTATYYCARF   300
GGEVLRYTDW PKPAWVDLWG RGTLVTVSSA STKGPSVFPL APSSKSTSGG TAALGCLVKD   360
YFPEPVTVSW NSGALTSGVH TFPAVLQSSG LYSLSSVVTV PSSSLGTQTY ICNVNHKPSN   420
TKVDKKVEPK SCDKTHTCPP CPAPELLGGP SVFLFPPKPK DTLMISRTPE VTCVVVDVSH   480
EDPEVKFNWY VDGVEVHNAK TKPREEQYNS TYRVVSVLTV LHQDWLNGKE YKCKVSNKAL   540
PAPIEKTISK AKGQPREPQV YTLPPSRDEL TKNQVSLTCL VKGFYPSDIA VEWESNGQPE   600
NNYKTTPPVL DSDGSFFLYS KLTVDKSRWQ QGNVFSCSVL HEALHSHYTQ KSLSLSPGK    659

SEQ ID NO: 100         moltype = AA  length = 664
FEATURE            Location/Qualifiers
source             1..664
                   mol_type = protein
                   organism = synthetic construct
SEQUENCE: 100
KKVVLGKKGD TVELTCTASQ KKNIQFHWKN SNQIKILGNQ GSFLTKGPSK LNDRVDSRRS    60
LWDQGNFPLI IKNLKIEDSD TYICEVEDQK EEVQLVVFGL TANSDTHLLQ GQSLTLTLES   120
PPGSSPSVQC RSPRGKNIQG GKTLSVSQLE LQDSGTWTCT VLQNQKKVEF KIDIVVLAFG   180
GGGSGGGGSG GGGSGGGGSQ PQLQESGPTL VEASETLSLT CAVSGDSTAA CNSFWGWVRQ   240
PPGKGLEWVG SLSHCASYWN RGWTYHNPSL KSRLTLALDT PKNLVFLKLN SVTAADTATY   300
YCARFGGEVL RYTDWPKPAW VDLWGRGTLV TVSSASTKGP SVFPLAPSSK STSGGTAALG   360
CLVKDYFPEP VTVSWNSGAL TSGVHTFPAV LQSSGLYSLS SVVTVPSSSL GTQTYICNVN   420
HKPSNTKVDK KVEPKSCDKT HTCPPCPAPE LLGGPSVFLF PPKPKDTLMI SRTPEVTCVV   480
VDVSHEDPEV KFNWYVDGVE VHNAKTKPRE EQYNSTYRVV SVLTVLHQDW LNGKEYKCKV   540
SNKALPAPIE KTISKAKGQP REPQVYTLPP SRDELTKNQV SLTCLVKGFY PSDIAVEWES   600
NGQPENNYKT TPPVLDSDGS FFLYSKLTVD KSRWQQGNVF SCSVLHEALH SHYTQKSLSL   660
SPGK                                                               664

SEQ ID NO: 101         moltype = AA  length = 564
FEATURE            Location/Qualifiers
source             1..564
                   mol_type = protein
                   organism = synthetic construct
SEQUENCE: 101
KKVVYGKKGD TVELTCTASQ KKNIQFHWKN SNQIKILGNQ GSFLTKGPSK LNDRVDSRRS    60
LWDQGNFPLI IKNLKPEDSD TYICEVEDQK EEVQLVVVGQ PQLQESGPTL VEASETLSLT   120
CAVSGDSTAA CNSFWGWVRQ PPGKGLEWVG SLSHCASYWN RGWTYHNPSL KSRLTLALDT   180
PKNLVFLKLN SVTAADTATY YCARFGGEVL RYTDWPKPAW VDLWGRGTLV TVSSASTKGP   240
SVFPLAPSSK STSGGTAALG CLVKDYFPEP VTVSWNSGAL TSGVHTFPAV LQSSGLYSLS   300
SVVTVPSSSL GTQTYICNVN HKPSNTKVDK KVEPKSCDKT HTCPPCPAPE LLGGPSVFLF   360
PPKPKDTLMI SRTPEVTCVV VDVSHEDPEV KFNWYVDGVE VHNAKTKPRE EQYNSTYRVV   420
SVLTVLHQDW LNGKEYKCKV SNKALPAPIE KTISKAKGQP REPQVYTLPP SRDELTKNQV   480
SLTCLVKGFY PSDIAVEWES NGQPENNYKT TPPVLDSDGS FFLYSKLTVD KSRWQQGNVF   540
SCSVLHEALH SHYTQKSLSL SPGK                                         564

SEQ ID NO: 102         moltype = AA  length = 569
FEATURE            Location/Qualifiers
source             1..569
                   mol_type = protein
                   organism = synthetic construct
SEQUENCE: 102
KKVVYGKKGD TVELTCTASQ KKNIQFHWKN SNQIKILGNQ GSFLTKGPSK LNDRVDSRRS    60
LWDQGNFPLI IKNLKPEDSD TYICEVEDQK EEVQLVVVGG GGSQPQLQE SGPTLVEASE   120
TLSLTCAVSG DSTAACNSFW GWVRQPPGKG LEWVGSLSHC ASYWNRGWTY HNPSLKSRLT   180
LALDTPKNLV FLKLNSVTAA DTATYYCARF GGEVLRYTDW PKPAWVDLWG RGTLVTVSSA   240
STKGPSVFPL APSSKSTSGG TAALGCLVKD YFPEPVTVSW NSGALTSGVH TFPAVLQSSG   300
LYSLSSVVTV PSSSLGTQTY ICNVNHKPSN TKVDKKVEPK SCDKTHTCPP CPAPELLGGP   360
SVFLFPPKPK DTLMISRTPE VTCVVVDVSH EDPEVKFNWY VDGVEVHNAK TKPREEQYNS   420
TYRVVSVLTV LHQDWLNGKE YKCKVSNKAL PAPIEKTISK AKGQPREPQV YTLPPSRDEL   480
TKNQVSLTCL VKGFYPSDIA VEWESNGQPE NNYKTTPPVL DSDGSFFLYS KLTVDKSRWQ   540
QGNVFSCSVL HEALHSHYTQ KSLSLSPGK                                    569

SEQ ID NO: 103         moltype = AA  length = 574
FEATURE            Location/Qualifiers
source             1..574
                   mol_type = protein
                   organism = synthetic construct
SEQUENCE: 103
KKVVYGKKGD TVELTCTASQ KKNIQFHWKN SNQIKILGNQ GSFLTKGPSK LNDRVDSRRS    60
LWDQGNFPLI IKNLKPEDSD TYICEVEDQK EEVQLVVVGG GGSGGGGSQ PQLQESGPTL   120
VEASETLSLT CAVSGDSTAA CNSFWGWVRQ PPGKGLEWVG SLSHCASYWN RGWTYHNPSL   180
```

```
KSRLTLALDT PKNLVFLKLN SVTAADTATY YCARFGGEVL RYTDWPKPAW VDLWGRGTLV    240
TVSSASTKGP SVFPLAPSSK STSGGTAALG CLVKDYFPEP VTVSWNSGAL TSGVHTFPAV    300
LQSSGLYSLS SVVTVPSSSL GTQTYICNVN HKPSNTKVDK KVEPKSCDKT HTCPPCPAPE    360
LLGGPSVFLF PPKPKDTLMI SRTPEVTCVV VDVSHEDPEV KFNWYVDGVE VHNAKTKPRE    420
EQYNSTYRVV SVLTVLHQDW LNGKEYKCKV SNKALPAPIE KTISKAKGQP REPQVYTLPP    480
SRDELTKNQV SLTCLVKGFY PSDIAVEWES NGQPENNYKT TPPVLDSDGS FFLYSKLTVD    540
KSRWQQGNVF SCSVLHEALH SHYTQKSLSL SPGK    574

SEQ ID NO: 104        moltype = AA  length = 579
FEATURE               Location/Qualifiers
source                1..579
                      mol_type = protein
                      organism = synthetic construct
SEQUENCE: 104
KKVVYGKKGD TVELTCTASQ KKNIQFHWKN SNQIKILGNQ GSFLTKGPSK LNDRVDSRRS    60
LWDQGNFPLI IKNLKPEDSD TYICEVEDQK EEVQLVVVGG GGGSGGGGSG GGGSQPQLQE    120
SGPTLVEASE TLSLTCAVSG DSTAACNSFW GWVRQPPGKG LEWVGSLSHC ASYWNRGWTY    180
HNPSLKSRLT LALDTPKNLV FLKLNSVTAA DTATYYCARF GGEVLRYTDW PKPAWVDLWG    240
RGTLVTVSSA STKGPSVFPL APSSKSTSGG TAALGCLVKD YFPEPVTVSW NSGALTSGVH    300
TFPAVLQSSG LYSLSSVVTV PSSSLGTQTY ICNVNHKPSN TKVDKKVEPK SCDKTHTCPP    360
CPAPELLGGP SVFLFPPKPK DTLMISRTPE VTCVVVDVSH EDPEVKFNWY VDGVEVHNAK    420
TKPREEQYNS TYRVVSVLTV LHQDWLNGKE YKCKVSNKAL PAPIEKTISK AKGQPREPQV    480
YTLPPSRDEL TKNQVSLTCL VKGFYPSDIA VEWESNGQPE NNYKTTPPVL DSDGSFFLYS    540
KLTVDKSRWQ QGNVFSCSVL HEALHSHYTQ KSLSLSPGK    579

SEQ ID NO: 105        moltype = AA  length = 584
FEATURE               Location/Qualifiers
source                1..584
                      mol_type = protein
                      organism = synthetic construct
SEQUENCE: 105
KKVVYGKKGD TVELTCTASQ KKNIQFHWKN SNQIKILGNQ GSFLTKGPSK LNDRVDSRRS    60
LWDQGNFPLI IKNLKPEDSD TYICEVEDQK EEVQLVVVGG GGGSGGGGSG GGGSGGGGSQ    120
PQLQESGPTL VEASETLSLT CAVSGDSTAA CNSFWGWVRQ PPGKGLEWVG SLSHCASYWN    180
RGWTYHNPSL KSRLTLALDT PKNLVFLKLN SVTAADTATY YCARFGGEVL RYTDWPKPAW    240
VDLWGRGTLV TVSSASTKGP SVFPLAPSSK STSGGTAALG CLVKDYFPEP VTVSWNSGAL    300
TSGVHTFPAV LQSSGLYSLS SVVTVPSSSL GTQTYICNVN HKPSNTKVDK KVEPKSCDKT    360
HTCPPCPAPE LLGGPSVFLF PPKPKDTLMI SRTPEVTCVV VDVSHEDPEV KFNWYVDGVE    420
VHNAKTKPRE EQYNSTYRVV SVLTVLHQDW LNGKEYKCKV SNKALPAPIE KTISKAKGQP    480
REPQVYTLPP SRDELTKNQV SLTCLVKGFY PSDIAVEWES NGQPENNYKT TPPVLDSDGS    540
FFLYSKLTVD KSRWQQGNVF SCSVLHEALH SHYTQKSLSL SPGK    584

SEQ ID NO: 106        moltype = AA  length = 589
FEATURE               Location/Qualifiers
source                1..589
                      mol_type = protein
                      organism = synthetic construct
SEQUENCE: 106
KKVVYGKKGD TVELTCTASQ KKNIQFHWKN SNQIKILGNQ GSFLTKGPSK LNDRVDSRRS    60
LWDQGNFPLI IKNLKPEDSD TYICEVEDQK EEVQLVVVGG GGGSGGGGSG GGGSGGGGSQ    120
GGGSQPQLQE SGPTLVEASE TLSLTCAVSG DSTAACNSFW GWVRQPPGKG LEWVGSLSHC    180
ASYWNRGWTY HNPSLKSRLT LALDTPKNLV FLKLNSVTAA DTATYYCARF GGEVLRYTDW    240
PKPAWVDLWG RGTLVTVSSA STKGPSVFPL APSSKSTSGG TAALGCLVKD YFPEPVTVSW    300
NSGALTSGVH TFPAVLQSSG LYSLSSVVTV PSSSLGTQTY ICNVNHKPSN TKVDKKVEPK    360
SCDKTHTCPP CPAPELLGGP SVFLFPPKPK DTLMISRTPE VTCVVVDVSH EDPEVKFNWY    420
VDGVEVHNAK TKPREEQYNS TYRVVSVLTV LHQDWLNGKE YKCKVSNKAL PAPIEKTISK    480
AKGQPREPQV YTLPPSRDEL TKNQVSLTCL VKGFYPSDIA VEWESNGQPE NNYKTTPPVL    540
DSDGSFFLYS KLTVDKSRWQ QGNVFSCSVL HEALHSHYTQ KSLSLSPGK    589

SEQ ID NO: 107        moltype = AA  length = 594
FEATURE               Location/Qualifiers
source                1..594
                      mol_type = protein
                      organism = synthetic construct
SEQUENCE: 107
KKVVYGKKGD TVELTCTASQ KKNIQFHWKN SNQIKILGNQ GSFLTKGPSK LNDRVDSRRS    60
LWDQGNFPLI IKNLKPEDSD TYICEVEDQK EEVQLVVVGG GGGSGGGGSG GGGSGGGGSQ    120
GGGSGGGGSQ PQLQESGPTL VEASETLSLT CAVSGDSTAA CNSFWGWVRQ PPGKGLEWVG    180
SLSHCASYWN RGWTYHNPSL KSRLTLALDT PKNLVFLKLN SVTAADTATY YCARFGGEVL    240
RYTDWPKPAW VDLWGRGTLV TVSSASTKGP SVFPLAPSSK STSGGTAALG CLVKDYFPEP    300
VTVSWNSGAL TSGVHTFPAV LQSSGLYSLS SVVTVPSSSL GTQTYICNVN HKPSNTKVDK    360
KVEPKSCDKT HTCPPCPAPE LLGGPSVFLF PPKPKDTLMI SRTPEVTCVV VDVSHEDPEV    420
KFNWYVDGVE VHNAKTKPRE EQYNSTYRVV SVLTVLHQDW LNGKEYKCKV SNKALPAPIE    480
KTISKAKGQP REPQVYTLPP SRDELTKNQV SLTCLVKGFY PSDIAVEWES NGQPENNYKT    540
TPPVLDSDGS FFLYSKLTVD KSRWQQGNVF SCSVLHEALH SHYTQKSLSL SPGK    594

SEQ ID NO: 108        moltype = AA  length = 310
FEATURE               Location/Qualifiers
source                1..310
```

```
                          mol_type = protein
                          organism = synthetic construct
SEQUENCE: 108
KKVVYGKKGD TVELTCTASQ KKNIQFHWKN SNQIKILGNQ GSFLTKGPSK LNDRVDSRRS     60
LWDQGNFPLI IKNLKPEDSD TYICEVEDQK EEVQLVVVGQ SALTQPPSAS GSPGQSITIS     120
CTGTSNNFVS WYQQHAGKAP KLVIYDVNKR PSGVPDRFSG SKSGNTASLT VSGLQTDDEA     180
VYYCGSLVGN WDVIFGGGTK LTVLGQPKAA PSVTLFPPSS EELQANKATL VCLISDFYPG     240
AVTVAWKADS SPVKAGVETT TPSKQSNNKY AASSYLSLTP EQWKSHRSYS CQVTHEGSTV     300
EKTVAPTECS                                                           310

SEQ ID NO: 109           moltype = AA   length = 315
FEATURE                  Location/Qualifiers
source                   1..315
                         mol_type = protein
                         organism = synthetic construct
SEQUENCE: 109
KKVVYGKKGD TVELTCTASQ KKNIQFHWKN SNQIKILGNQ GSFLTKGPSK LNDRVDSRRS     60
LWDQGNFPLI IKNLKPEDSD TYICEVEDQK EEVQLVVVGG GGGSQSALTQ PPSASGSPGQ     120
SITISCTGTS NNFVSWYQQH AGKAPKLVIY DVNKRPSGVP DRFSGSKSGN TASLTVSGLQ     180
TDDEAVYYCG SLVGNWDVIF GGGTKLTVLG QPKAAPSVTL FPPSSEELQA NKATLVCLIS     240
DFYPGAVTVA WKADSSPVKA GVETTTPSKQ SNNKYAASSY LSLTPEQWKS HRSYSCQVTH     300
EGSTVEKTVA PTECS                                                     315

SEQ ID NO: 110           moltype = AA   length = 320
FEATURE                  Location/Qualifiers
source                   1..320
                         mol_type = protein
                         organism = synthetic construct
SEQUENCE: 110
KKVVYGKKGD TVELTCTASQ KKNIQFHWKN SNQIKILGNQ GSFLTKGPSK LNDRVDSRRS     60
LWDQGNFPLI IKNLKPEDSD TYICEVEDQK EEVQLVVVGG GGGSGGGGSQ SALTQPPSAS     120
GSPGQSITIS CTGTSNNFVS WYQQHAGKAP KLVIYDVNKR PSGVPDRFSG SKSGNTASLT     180
VSGLQTDDEA VYYCGSLVGN WDVIFGGGTK LTVLGQPKAA PSVTLFPPSS EELQANKATL     240
VCLISDFYPG AVTVAWKADS SPVKAGVETT TPSKQSNNKY AASSYLSLTP EQWKSHRSYS     300
CQVTHEGSTV EKTVAPTECS                                                 320

SEQ ID NO: 111           moltype = AA   length = 325
FEATURE                  Location/Qualifiers
source                   1..325
                         mol_type = protein
                         organism = synthetic construct
SEQUENCE: 111
KKVVYGKKGD TVELTCTASQ KKNIQFHWKN SNQIKILGNQ GSFLTKGPSK LNDRVDSRRS     60
LWDQGNFPLI IKNLKPEDSD TYICEVEDQK EEVQLVVVGG GGGSGGGGSG GGGSQSALTQ     120
PPSASGSPGQ SITISCTGTS NNFVSWYQQH AGKAPKLVIY DVNKRPSGVP DRFSGSKSGN     180
TASLTVSGLQ TDDEAVYYCG SLVGNWDVIF GGGTKLTVLG QPKAAPSVTL FPPSSEELQA     240
NKATLVCLIS DFYPGAVTVA WKADSSPVKA GVETTTPSKQ SNNKYAASSY LSLTPEQWKS     300
HRSYSCQVTH EGSTVEKTVA PTECS                                           325

SEQ ID NO: 112           moltype = AA   length = 330
FEATURE                  Location/Qualifiers
source                   1..330
                         mol_type = protein
                         organism = synthetic construct
SEQUENCE: 112
KKVVYGKKGD TVELTCTASQ KKNIQFHWKN SNQIKILGNQ GSFLTKGPSK LNDRVDSRRS     60
LWDQGNFPLI IKNLKPEDSD TYICEVEDQK EEVQLVVVGG GGGSGGGGSG GGGSGGGGSQ     120
SALTQPPSAS GSPGQSITIS CTGTSNNFVS WYQQHAGKAP KLVIYDVNKR PSGVPDRFSG     180
SKSGNTASLT VSGLQTDDEA VYYCGSLVGN WDVIFGGGTK LTVLGQPKAA PSVTLFPPSS     240
EELQANKATL VCLISDFYPG AVTVAWKADS SPVKAGVETT TPSKQSNNKY AASSYLSLTP     300
EQWKSHRSYS CQVTHEGSTV EKTVAPTECS                                      330

SEQ ID NO: 113           moltype = AA   length = 335
FEATURE                  Location/Qualifiers
source                   1..335
                         mol_type = protein
                         organism = synthetic construct
SEQUENCE: 113
KKVVYGKKGD TVELTCTASQ KKNIQFHWKN SNQIKILGNQ GSFLTKGPSK LNDRVDSRRS     60
LWDQGNFPLI IKNLKPEDSD TYICEVEDQK EEVQLVVVGG GGGSGGGGSG GGGSGGGGSG     120
GGGSQSALTQ PPSASGSPGQ SITISCTGTS NNFVSWYQQH AGKAPKLVIY DVNKRPSGVP     180
DRFSGSKSGN TASLTVSGLQ TDDEAVYYCG SLVGNWDVIF GGGTKLTVLG QPKAAPSVTL     240
FPPSSEELQA NKATLVCLIS DFYPGAVTVA WKADSSPVKA GVETTTPSKQ SNNKYAASSY     300
LSLTPEQWKS HRSYSCQVTH EGSTVEKTVA PTECS                                335

SEQ ID NO: 114           moltype = AA   length = 340
FEATURE                  Location/Qualifiers
source                   1..340
                         mol_type = protein
```

```
                                organism = synthetic construct
SEQUENCE: 114
KKVVYGKKGD TVELTCTASQ KKNIQFHWKN SNQIKILGNQ GSFLTKGPSK LNDRVDSRRS  60
LWDQGNFPLI IKNLKPEDSD TYICEVEDQK EEVQLVVVGG GGGSGGGGSG GGGSGGGGSG  120
GGGSGGGGSQ SALTQPPSAS GSPGQSITIS CTGTSNNFVS WYQQHAGKAP KLVIYDVNKR  180
PSGVPDRFSG SKSGNTASLT VSGLQTDDEA VYYCGSLVGN WDVIFGGGTK LTVLGQPKAA  240
PSVTLFPPSS EELQANKATL VCLISDFYPG AVTVAWKADS SPVKAGVETT TPSKQSNNKY  300
AASSYLSLTP EQWKSHRSYS CQVTHEGSTV EKTVAPTECS                        340

SEQ ID NO: 115           moltype = AA  length = 315
FEATURE                  Location/Qualifiers
source                   1..315
                         mol_type = protein
                         organism = synthetic construct
SEQUENCE: 115
KKVVYGKCGD TVELTCTASQ KKNIQFHWKN SNQIKILGNQ GSFLTKGPSK LNDRVDSRRS  60
LWDQGNFPLI IKNLKPEDSD TYICEVEDQK EEVQLVVSVG GGGSQSALTQ PPSASGSPGQ  120
SITISCTGTS NNFVSWYQQH AGKAPKLVIY DVNKRPSGVP DRFSGSKSGN TASLTVSGLQ  180
TDDEAVYYCG SLVGNWDVIF GGGTKLTVLG QPKAAPSVTL FPPSSEELQA NKATLVCLIS  240
DFYPGAVTVA WKADSSPVKA GVETTTPSKQ SNNKYAASSY LSLTPEQWKS HRSYSCQVTH  300
EGSTVEKTVA PTECS                                                  315

SEQ ID NO: 116           moltype = AA  length = 574
FEATURE                  Location/Qualifiers
source                   1..574
                         mol_type = protein
                         organism = synthetic construct
SEQUENCE: 116
QPQLQESGPT LVEASETLSL TCAVSGDSTA ACNSFWGWVR QPPGKGLEWV GSLSHCASYW  60
NRGWTYHNPS LKSRLTLALD TPKNLVFLKL NSVTAADTAT YYCARFGGEV LRYTDWPKPA  120
WVDLWGRGTL VTVSSASTKG PSVFPLAPSS KSTSGGTAAL GCLVKDYFPE PVTVSWNSGA  180
LTSGVHTFPA VLQSSGLYSL SSVVTVPSSS LGTQTYICNV NHKPSNTKVD KKVEPKSCGG  240
GGSKKVVYGK CGDTVELTCT ASQKKNIQFH WKNSNQIKIL GNQGSFLTKG PSKLNDRVDS  300
RRSLWDQGNF PLIIKNLKPE DSDTYICEVE DQKEEVQLVV VCGGGGSDKT HTCPPCPAPE  360
LLGGPSVFLF PPKPKDTLMI SRTPEVTCVV VDVSHEDPEV KFNWYVDGVE VHNAKTKPRE  420
EQYNSTYRVV SVLTVLHQDW LNGKEYKCKV SNKALPAPIE KTISKAKGQP REPQVYTLPP  480
SRDELTKNQV SLTCLVKGFY PSDIAVEWES NGQPENNYKT TPPVLDSDGS FFLYSKLTVD  540
KSRWQQGNVF SCSVLHEALH SHYTQKSLSL SPGK                             574

SEQ ID NO: 117           moltype = AA  length = 568
FEATURE                  Location/Qualifiers
source                   1..568
                         mol_type = protein
                         organism = synthetic construct
SEQUENCE: 117
QPQLQESGPT LVEASETLSL TCAVSGDSTA ACNSFWGWVR QPPGKGLEWV GSLSHCASYW  60
NRGWTYHNPS LKSRLTLALD TPKNLVFLKL NSVTAADTAT YYCARFGGEV LRYTDWPKPA  120
WVDLWGRGTL VTVSSASTKG PSVFPLAPSS KSTSGGTAAL GCLVKDYFPE PVTVSWNSGA  180
LTSGVHTFPA VLQSSGLYSL SSVVTVPSSS LGTQTYICNV NHKPSNTKVD KKVEPKSCDK  240
THTCPPCPAP ELLGGPSVFL FPPKPKDTLM ISRTPEVTCV VVDVSHEDPE VKFNWYVDGV  300
EVHNAKTKPR EEQYNSTYRV VSVLTVLHQD WLNGKEYKCK VSNKALPAPI EKTISKAKGQ  360
PREPQVYTLP PSRDELTKNQ VSLTCLVKGF YPSDIAVEWE SNGQPENNYK TTPPVLDSDG  420
SFFLYSKLTV DKSRWQQGNV FSCSVLHEAL HSHYTQKSLS LSPGGGGGSK VVVYGKCGDT  480
VELTCTASQK KNIQFHWKNS NQIKILGNQG SFLTKGPSKL NDRVDSRRSL WDQGNFPLII  540
KNLKPEDSDT YICEVEDQKE EVQLVVVC                                    568

SEQ ID NO: 118           moltype = AA  length = 315
FEATURE                  Location/Qualifiers
source                   1..315
                         mol_type = protein
                         organism = synthetic construct
SEQUENCE: 118
QSALTQPPSA SGSPGQSITI SCTGTSNNFV SWYQQHAGKA PKLVIYDVNK RPSGVPDRFS  60
GSKSGNTASL TVSGLQTDDE AVYYCGSLVG NWDVIFGGGT KLTVLGQPKA APSVTLFPPS  120
SEELQANKAT LVCLISDFYP GAVTVAWKAD SSPVKAGVET TTPSKQSNNK YAASSYLSLT  180
PEQWKSHRSY SCQVTHEGST VEKTVAPTEC SGGGGSKKVV YGKCGDTVEL TCTASQKKNI  240
QFHWKNSNQI KILGNQGSFL TKGPSKLNDR VDSRRSLWDQ GNFPLIIKNL KPEDSDTYIC  300
EVEDQKEEVQ LVVVC                                                  315

SEQ ID NO: 119           moltype = AA  length = 569
FEATURE                  Location/Qualifiers
source                   1..569
                         mol_type = protein
                         organism = synthetic construct
SEQUENCE: 119
KKVVYGKIGD TVELTCTASQ KKNIQFHWKN SNQIKILGNQ GSFLTKGPSK LNDRVDSRRS  60
LWDQGNFPLI IKNLKPEDSD TYICEVEDQK EEVQLVVVGG GGGSQPQLQE SGPTLVEASE  120
TLSLTCAVSG DSTAACNSFW GWVRQPPGKG LEWVGSLSHC ASYWNRGWTY HNPSLKSRLT  180
LALDTPKNLV FLKLNSVTAA DTATYYCARF GGEVLRYTDW PKPAWVDLWG RGTLVTVSSA  240
```

```
STKGPSVFPL APSSKSTSGG TAALGCLVKD YFPEPVTVSW NSGALTSGVH TFPAVLQSSG  300
LYSLSSVVTV PSSSLGTQTY ICNVNHKPSN TKVDKKVEPK SCDKTHTCPP CPAPELLGGP  360
SVFLFPPKPK DTLMISRTPE VTCVVVDVSH EDPEVKFNWY VDGVEVHNAK TKPREEQYNS  420
TYRVVSVLTV LHQDWLNGKE YKCKVSNKAL PAPIEKTISK AKGQPREPQV YTLPPSRDEL  480
TKNQVSLTCL VKGFYPSDIA VEWESNGQPE NNYKTTPPVL DSDGSFFLYS KLTVDKSRWQ  540
QGNVFSCSVL HEALHSHYTQ KSLSLSPGK                                   569

SEQ ID NO: 120          moltype = AA  length = 569
FEATURE                 Location/Qualifiers
source                  1..569
                        mol_type = protein
                        organism = synthetic construct
SEQUENCE: 120
KKVVYGKVGD TVELTCTASQ KKNIQFHWKN SNQIKILGNQ GSFLTKGPSK LNDRVDSRRS  60
LWDQGNFPLI IKNLKPEDSD TYICEVEDQK EEVQLVVVGG GGGSQPQLQE SGPTLVEASE  120
TLSLTCAVSG DSTAACNSFW GWVRQPPGKG LEWVGSLSHC ASYWNRGWTY HNPSLKSRLT  180
LALDTPKNLV FLKLNSVTAA DTATYYCARF GGEVLRYTDW PKPAWVDLWG RGTLVTVSSA  240
STKGPSVFPL APSSKSTSGG TAALGCLVKD YFPEPVTVSW NSGALTSGVH TFPAVLQSSG  300
LYSLSSVVTV PSSSLGTQTY ICNVNHKPSN TKVDKKVEPK SCDKTHTCPP CPAPELLGGP  360
SVFLFPPKPK DTLMISRTPE VTCVVVDVSH EDPEVKFNWY VDGVEVHNAK TKPREEQYNS  420
TYRVVSVLTV LHQDWLNGKE YKCKVSNKAL PAPIEKTISK AKGQPREPQV YTLPPSRDEL  480
TKNQVSLTCL VKGFYPSDIA VEWESNGQPE NNYKTTPPVL DSDGSFFLYS KLTVDKSRWQ  540
QGNVFSCSVL HEALHSHYTQ KSLSLSPGK                                   569

SEQ ID NO: 121          moltype = AA  length = 569
FEATURE                 Location/Qualifiers
source                  1..569
                        mol_type = protein
                        organism = synthetic construct
SEQUENCE: 121
KKVVYGKCGD TVELTCTASQ KKNIQFHWKN SNQIKILGNQ GSFLTKGPSK LNDRVDSRRS  60
LWDQGNFPLI IKNLKPEDSD TYICEVEDQK EEVQLVVVCG GGGSQPQLQE SGPTLVEASE  120
TLSLTCAVSG DSTAACNSFW GWVRQPPGKG LEWVGSLSHC ASYWNRGWTY HNPSLKSRLT  180
LALDTPKNLV FLKLNSVTAA DTATYYCARF GGEVLRYTDW PKPAWVDLWG RGTLVTVSSA  240
STKGPSVFPL APSSKSTSGG TAALGCLVKD YFPEPVTVSW NSGALTSGVH TFPAVLQSSG  300
LYSLSSVVTV PSSSLGTQTY ICNVNHKPSN TKVDKKVEPK SCDKTHTCPP CPAPELLGGP  360
SVFLFPPKPK DTLMISRTPE VTCVVVDVSH EDPEVKFNWY VDGVEVHNAK TKPREEQYNS  420
TYRVVSVLTV LHQDWLNGKE YKCKVSNKAL PAPIEKTISK AKGQPREPQV YTLPPSRDEL  480
TKNQVSLTCL VKGFYPSDIA VEWESNGQPE NNYKTTPPVL DSDGSFFLYS KLTVDKSRWQ  540
QGNVFSCSVL HEALHSHYTQ KSLSLSPGK                                   569

SEQ ID NO: 122          moltype = AA  length = 569
FEATURE                 Location/Qualifiers
source                  1..569
                        mol_type = protein
                        organism = synthetic construct
SEQUENCE: 122
KKVVYGKKGD CVELTCTASQ KKNIQFHWKN SNQIKILGNQ GSFLTKGPSK LNDRVDSRRS  60
LWDQGNFPLI ICNLKPEDSD TYICEVEDQK EEVQLVVVGG GGGSQPQLQE SGPTLVEASE  120
TLSLTCAVSG DSTAACNSFW GWVRQPPGKG LEWVGSLSHC ASYWNRGWTY HNPSLKSRLT  180
LALDTPKNLV FLKLNSVTAA DTATYYCARF GGEVLRYTDW PKPAWVDLWG RGTLVTVSSA  240
STKGPSVFPL APSSKSTSGG TAALGCLVKD YFPEPVTVSW NSGALTSGVH TFPAVLQSSG  300
LYSLSSVVTV PSSSLGTQTY ICNVNHKPSN TKVDKKVEPK SCDKTHTCPP CPAPELLGGP  360
SVFLFPPKPK DTLMISRTPE VTCVVVDVSH EDPEVKFNWY VDGVEVHNAK TKPREEQYNS  420
TYRVVSVLTV LHQDWLNGKE YKCKVSNKAL PAPIEKTISK AKGQPREPQV YTLPPSRDEL  480
TKNQVSLTCL VKGFYPSDIA VEWESNGQPE NNYKTTPPVL DSDGSFFLYS KLTVDKSRWQ  540
QGNVFSCSVL HEALHSHYTQ KSLSLSPGK                                   569

SEQ ID NO: 123          moltype = AA  length = 569
FEATURE                 Location/Qualifiers
source                  1..569
                        mol_type = protein
                        organism = synthetic construct
SEQUENCE: 123
KKVVYGKKGD TVELTCTASQ KKNIQFHWKN SNQIKILGNQ GSFLTKGPSK LNDRVDSRRS  60
LWDQGNFPLI IKNLKPEDSD TYICEVEDQK QEVQLVVVGG GGGSQPQLQE SGPTLVEASE  120
TLSLTCAVSG DSTAACNSFW GWVRQPPGKG LEWVGSLSHC ASYWNRGWTY HNPSLKSRLT  180
LALDTPKNLV FLKLNSVTAA DTATYYCARF GGEVLRYTDW PKPAWVDLWG RGTLVTVSSA  240
STKGPSVFPL APSSKSTSGG TAALGCLVKD YFPEPVTVSW NSGALTSGVH TFPAVLQSSG  300
LYSLSSVVTV PSSSLGTQTY ICNVNHKPSN TKVDKKVEPK SCDKTHTCPP CPAPELLGGP  360
SVFLFPPKPK DTLMISRTPE VTCVVVDVSH EDPEVKFNWY VDGVEVHNAK TKPREEQYNS  420
TYRVVSVLTV LHQDWLNGKE YKCKVSNKAL PAPIEKTISK AKGQPREPQV YTLPPSRDEL  480
TKNQVSLTCL VKGFYPSDIA VEWESNGQPE NNYKTTPPVL DSDGSFFLYS KLTVDKSRWQ  540
QGNVFSCSVL HEALHSHYTQ KSLSLSPGK                                   569

SEQ ID NO: 124          moltype = AA  length = 569
FEATURE                 Location/Qualifiers
source                  1..569
                        mol_type = protein
```

```
                           organism = synthetic construct
SEQUENCE: 124
KKVVYGKKGD TVELTCTASQ KKNIQFHWKN SNQIKILGNQ GSFLTKGPSK LNDRVDSRRS  60
LWDQGNFPLI IKNLKPEDSD TYICEVEDQK HEVQLVVGG GGGSQPQLQE SGPTLVEASE  120
TLSLTCAVSG DSTAACNSFW GWVRQPPGKG LEWVGSLSHC ASYWNRGWTY HNPSLKSRLT  180
LALDTPKNLV FLKLNSVTAA DTATYYCARF GGEVLRYTDW PKPAWVDLWG RGTLVTVSSA  240
STKGPSVFPL APSSKSTSGG TAALGCLVKD YFPEPVTVSW NSGALTSGVH TFPAVLQSSG  300
LYSLSSVVTV PSSSLGTQTY ICNVNHKPSN TKVDKKVEPK SCDKTHTCPP CPAPELLGGP  360
SVFLFPPKPK DTLMISRTPE VTCVVVDVSH EDPEVKFNWY VDGVEVHNAK TKPREEQYNS  420
TYRVVSVLTV LHQDWLNGKE YKCKVSNKAL PAPIEKTISK AKGQPREPQV YTLPPSRDEL  480
TKNQVSLTCL VKGFYPSDIA VEWESNGQPE NNYKTTPPVL DSDGSFFLYS KLTVDKSRWQ  540
QGNVFSCSVL HEALHSHYTQ KSLSLSPGK                                   569

SEQ ID NO: 125          moltype = AA  length = 569
FEATURE                 Location/Qualifiers
source                  1..569
                        mol_type = protein
                        organism = synthetic construct
SEQUENCE: 125
KKVVYGKKGD TVELTCTASQ KKNIEFHWKN SNQIKILGNQ GSFLTKGPSK LNDRVDSRRS  60
LWDQGNFPLI IKNLKPEDSD TYICEVEDQK EEVQLVVGG GGGSQPQLQE SGPTLVEASE  120
TLSLTCAVSG DSTAACNSFW GWVRQPPGKG LEWVGSLSHC ASYWNRGWTY HNPSLKSRLT  180
LALDTPKNLV FLKLNSVTAA DTATYYCARF GGEVLRYTDW PKPAWVDLWG RGTLVTVSSA  240
STKGPSVFPL APSSKSTSGG TAALGCLVKD YFPEPVTVSW NSGALTSGVH TFPAVLQSSG  300
LYSLSSVVTV PSSSLGTQTY ICNVNHKPSN TKVDKKVEPK SCDKTHTCPP CPAPELLGGP  360
SVFLFPPKPK DTLMISRTPE VTCVVVDVSH EDPEVKFNWY VDGVEVHNAK TKPREEQYNS  420
TYRVVSVLTV LHQDWLNGKE YKCKVSNKAL PAPIEKTISK AKGQPREPQV YTLPPSRDEL  480
TKNQVSLTCL VKGFYPSDIA VEWESNGQPE NNYKTTPPVL DSDGSFFLYS KLTVDKSRWQ  540
QGNVFSCSVL HEALHSHYTQ KSLSLSPGK                                   569

SEQ ID NO: 126          moltype = AA  length = 569
FEATURE                 Location/Qualifiers
source                  1..569
                        mol_type = protein
                        organism = synthetic construct
SEQUENCE: 126
KKVVYGKKGD TVELTCTASQ KKNIQFDWKN SNQIKILGNQ GSFLTKGPSK LNDRVDSRRS  60
LWDQGNFPLI IKNLKPEDSD TYICEVEDQK EEVQLVVGG GGGSQPQLQE SGPTLVEASE  120
TLSLTCAVSG DSTAACNSFW GWVRQPPGKG LEWVGSLSHC ASYWNRGWTY HNPSLKSRLT  180
LALDTPKNLV FLKLNSVTAA DTATYYCARF GGEVLRYTDW PKPAWVDLWG RGTLVTVSSA  240
STKGPSVFPL APSSKSTSGG TAALGCLVKD YFPEPVTVSW NSGALTSGVH TFPAVLQSSG  300
LYSLSSVVTV PSSSLGTQTY ICNVNHKPSN TKVDKKVEPK SCDKTHTCPP CPAPELLGGP  360
SVFLFPPKPK DTLMISRTPE VTCVVVDVSH EDPEVKFNWY VDGVEVHNAK TKPREEQYNS  420
TYRVVSVLTV LHQDWLNGKE YKCKVSNKAL PAPIEKTISK AKGQPREPQV YTLPPSRDEL  480
TKNQVSLTCL VKGFYPSDIA VEWESNGQPE NNYKTTPPVL DSDGSFFLYS KLTVDKSRWQ  540
QGNVFSCSVL HEALHSHYTQ KSLSLSPGK                                   569

SEQ ID NO: 127          moltype = AA  length = 569
FEATURE                 Location/Qualifiers
source                  1..569
                        mol_type = protein
                        organism = synthetic construct
SEQUENCE: 127
KKVVYGKKGD TVELTCTASQ KKNIQFHWKN SNQIKILGNQ GSFLTKGPSK LNDRVDSVRS  60
LWDQGNFPLI IKNLKPEDSD TYICEVEDQK EEVQLVVGG GGGSQPQLQE SGPTLVEASE  120
TLSLTCAVSG DSTAACNSFW GWVRQPPGKG LEWVGSLSHC ASYWNRGWTY HNPSLKSRLT  180
LALDTPKNLV FLKLNSVTAA DTATYYCARF GGEVLRYTDW PKPAWVDLWG RGTLVTVSSA  240
STKGPSVFPL APSSKSTSGG TAALGCLVKD YFPEPVTVSW NSGALTSGVH TFPAVLQSSG  300
LYSLSSVVTV PSSSLGTQTY ICNVNHKPSN TKVDKKVEPK SCDKTHTCPP CPAPELLGGP  360
SVFLFPPKPK DTLMISRTPE VTCVVVDVSH EDPEVKFNWY VDGVEVHNAK TKPREEQYNS  420
TYRVVSVLTV LHQDWLNGKE YKCKVSNKAL PAPIEKTISK AKGQPREPQV YTLPPSRDEL  480
TKNQVSLTCL VKGFYPSDIA VEWESNGQPE NNYKTTPPVL DSDGSFFLYS KLTVDKSRWQ  540
QGNVFSCSVL HEALHSHYTQ KSLSLSPGK                                   569

SEQ ID NO: 128          moltype = AA  length = 569
FEATURE                 Location/Qualifiers
source                  1..569
                        mol_type = protein
                        organism = synthetic construct
SEQUENCE: 128
KKVVYGKKGD TVELTCTASQ KKNIQFHWKN SNQIKILGNQ GSFLTKGPSK LNDRVDSNRS  60
LWDQGNFPLI IKNLKPEDSD TYICEVEDQK EEVQLVVGG GGGSQPQLQE SGPTLVEASE  120
TLSLTCAVSG DSTAACNSFW GWVRQPPGKG LEWVGSLSHC ASYWNRGWTY HNPSLKSRLT  180
LALDTPKNLV FLKLNSVTAA DTATYYCARF GGEVLRYTDW PKPAWVDLWG RGTLVTVSSA  240
STKGPSVFPL APSSKSTSGG TAALGCLVKD YFPEPVTVSW NSGALTSGVH TFPAVLQSSG  300
LYSLSSVVTV PSSSLGTQTY ICNVNHKPSN TKVDKKVEPK SCDKTHTCPP CPAPELLGGP  360
SVFLFPPKPK DTLMISRTPE VTCVVVDVSH EDPEVKFNWY VDGVEVHNAK TKPREEQYNS  420
TYRVVSVLTV LHQDWLNGKE YKCKVSNKAL PAPIEKTISK AKGQPREPQV YTLPPSRDEL  480
TKNQVSLTCL VKGFYPSDIA VEWESNGQPE NNYKTTPPVL DSDGSFFLYS KLTVDKSRWQ  540
```

```
QGNVFSCSVL HEALHSHYTQ KSLSLSPGK                                             569

SEQ ID NO: 129           moltype = AA  length = 569
FEATURE                  Location/Qualifiers
source                   1..569
                         mol_type = protein
                         organism = synthetic construct
SEQUENCE: 129
KKVVYGKKGD TVELTCTASQ KKNIQFHWKN SNQIKILGNQ GSFLTKGPSK LNDRVDSTRS    60
LWDQGNFPLI IKNLKPEDSD TYICEVEDQK EEVQLVVVGG GGGSQPQLQE SGPTLVEASE    120
TLSLTCAVSG DSTAACNSFW GWVRQPPGKG LEWVGSLSHC ASYWNRGWTY HNPSLKSRLT    180
LALDTPKNLV FLKLNSVTAA DTATYYCARF GGEVLRYTDW PKPAWVDLWG RGTLVTVSSA    240
STKGPSVFPL APSSKSTSGG TAALGCLVKD YFPEPVTVSW NSGALTSGVH TFPAVLQSSG    300
LYSLSSVVTV PSSSLGTQTY ICNVNHKPSN TKVDKKVEPK SCDKTHTCPP CPAPELLGGP    360
SVFLFPPKPK DTLMISRTPE VTCVVVDVSH EDPEVKFNWY VDGVEVHNAK TKPREEQYNS    420
TYRVVSVLTV LHQDWLNGKE YKCKVSNKAL PAPIEKTISK AKGQPREPQV YTLPPSRDEL    480
TKNQVSLTCL VKGFYPSDIA VEWESNGQPE NNYKTTPPVL DSDGSFFLYS KLTVDKSRWQ    540
QGNVFSCSVL HEALHSHYTQ KSLSLSPGK                                             569

SEQ ID NO: 130           moltype = AA  length = 569
FEATURE                  Location/Qualifiers
source                   1..569
                         mol_type = protein
                         organism = synthetic construct
SEQUENCE: 130
KKVVYGKKGD TVELTCTASQ KKNIQFHWKN SNQIKILGNQ GSFLTKGPSK LNDRVDSRRS    60
MWDQGNFPLI IKNLKPEDSD TYICEVEDQK EEVQLVVVGG GGGSQPQLQE SGPTLVEASE    120
TLSLTCAVSG DSTAACNSFW GWVRQPPGKG LEWVGSLSHC ASYWNRGWTY HNPSLKSRLT    180
LALDTPKNLV FLKLNSVTAA DTATYYCARF GGEVLRYTDW PKPAWVDLWG RGTLVTVSSA    240
STKGPSVFPL APSSKSTSGG TAALGCLVKD YFPEPVTVSW NSGALTSGVH TFPAVLQSSG    300
LYSLSSVVTV PSSSLGTQTY ICNVNHKPSN TKVDKKVEPK SCDKTHTCPP CPAPELLGGP    360
SVFLFPPKPK DTLMISRTPE VTCVVVDVSH EDPEVKFNWY VDGVEVHNAK TKPREEQYNS    420
TYRVVSVLTV LHQDWLNGKE YKCKVSNKAL PAPIEKTISK AKGQPREPQV YTLPPSRDEL    480
TKNQVSLTCL VKGFYPSDIA VEWESNGQPE NNYKTTPPVL DSDGSFFLYS KLTVDKSRWQ    540
QGNVFSCSVL HEALHSHYTQ KSLSLSPGK                                             569

SEQ ID NO: 131           moltype = AA  length = 569
FEATURE                  Location/Qualifiers
source                   1..569
                         mol_type = protein
                         organism = synthetic construct
SEQUENCE: 131
KKVVYGKKGD TVCLTCTASQ KKNIQFHWKN SNQIKILGNQ GSFLTKGPSK LNDRVDSRRS    60
LWDQGNFPLC IKNLKPEDSD TYICEVEDQK EEVQLVVVGG GGGSQPQLQE SGPTLVEASE    120
TLSLTCAVSG DSTAACNSFW GWVRQPPGKG LEWVGSLSHC ASYWNRGWTY HNPSLKSRLT    180
LALDTPKNLV FLKLNSVTAA DTATYYCARF GGEVLRYTDW PKPAWVDLWG RGTLVTVSSA    240
STKGPSVFPL APSSKSTSGG TAALGCLVKD YFPEPVTVSW NSGALTSGVH TFPAVLQSSG    300
LYSLSSVVTV PSSSLGTQTY ICNVNHKPSN TKVDKKVEPK SCDKTHTCPP CPAPELLGGP    360
SVFLFPPKPK DTLMISRTPE VTCVVVDVSH EDPEVKFNWY VDGVEVHNAK TKPREEQYNS    420
TYRVVSVLTV LHQDWLNGKE YKCKVSNKAL PAPIEKTISK AKGQPREPQV YTLPPSRDEL    480
TKNQVSLTCL VKGFYPSDIA VEWESNGQPE NNYKTTPPVL DSDGSFFLYS KLTVDKSRWQ    540
QGNVFSCSVL HEALHSHYTQ KSLSLSPGK                                             569

SEQ ID NO: 132           moltype = AA  length = 569
FEATURE                  Location/Qualifiers
source                   1..569
                         mol_type = protein
                         organism = synthetic construct
SEQUENCE: 132
KKVVYGKKGD TVELTCTASQ KKNIQFCWKN SNQIKILCNQ GSFLTKGPSK LNDRVDSRRS    60
LWDQGNFPLI IKNLKPEDSD TYICEVEDQK EEVQLVVVGG GGGSQPQLQE SGPTLVEASE    120
TLSLTCAVSG DSTAACNSFW GWVRQPPGKG LEWVGSLSHC ASYWNRGWTY HNPSLKSRLT    180
LALDTPKNLV FLKLNSVTAA DTATYYCARF GGEVLRYTDW PKPAWVDLWG RGTLVTVSSA    240
STKGPSVFPL APSSKSTSGG TAALGCLVKD YFPEPVTVSW NSGALTSGVH TFPAVLQSSG    300
LYSLSSVVTV PSSSLGTQTY ICNVNHKPSN TKVDKKVEPK SCDKTHTCPP CPAPELLGGP    360
SVFLFPPKPK DTLMISRTPE VTCVVVDVSH EDPEVKFNWY VDGVEVHNAK TKPREEQYNS    420
TYRVVSVLTV LHQDWLNGKE YKCKVSNKAL PAPIEKTISK AKGQPREPQV YTLPPSRDEL    480
TKNQVSLTCL VKGFYPSDIA VEWESNGQPE NNYKTTPPVL DSDGSFFLYS KLTVDKSRWQ    540
QGNVFSCSVL HEALHSHYTQ KSLSLSPGK                                             569

SEQ ID NO: 133           moltype = AA  length = 569
FEATURE                  Location/Qualifiers
source                   1..569
                         mol_type = protein
                         organism = synthetic construct
SEQUENCE: 133
KKVVYGKKGD TVELTCTASQ CKNIQFHWKN SNQIKILGNQ GSFLTKGPSK LNDRVDSRRS    60
LWDQCNFPLI IKNLKPEDSD TYICEVEDQK EEVQLVVVGG GGGSQPQLQE SGPTLVEASE    120
TLSLTCAVSG DSTAACNSFW GWVRQPPGKG LEWVGSLSHC ASYWNRGWTY HNPSLKSRLT    180
```

```
LALDTPKNLV FLKLNSVTAA DTATYYCARF GGEVLRYTDW PKPAWVDLWG RGTLVTVSSA   240
STKGPSVFPL APSSKSTSGG TAALGCLVKD YFPEPVTVSW NSGALTSGVH TFPAVLQSSG   300
LYSLSSVVTV PSSSLGTQTY ICNVNHKPSN TKVDKKVEPK SCDKTHTCPP CPAPELLGGP   360
SVFLFPPKPK DTLMISRTPE VTCVVVDVSH EDPEVKFNWY VDGVEVHNAK TKPREEQYNS   420
TYRVVSVLTV LHQDWLNGKE YKCKVSNKAL PAPIEKTISK AKGQPREPQV YTLPPSRDEL   480
TKNQVSLTCL VKGFYPSDIA VEWESNGQPE NNYKTTPPVL DSDGSFFLYS KLTVDKSRWQ   540
QGNVFSCSVL HEALHSHYTQ KSLSLSPGK                                      569

SEQ ID NO: 134          moltype = AA  length = 569
FEATURE                 Location/Qualifiers
source                  1..569
                        mol_type = protein
                        organism = synthetic construct
SEQUENCE: 134
KKVVYGKKGD TVELTCTASQ KKNIQFHWKN SNQIKILGNQ GSFLTKGPSK LNDRVDSRRS    60
LWDQGNFPLI IKNLKPEDSD TYICEVGDQK EEVQLVVVGG GGGSQPQLQE SGPTLVEASE   120
TLSLTCAVSG DSTAACNSFW GWVRQPPGKG LEWVGSLSHC ASYWNRGWTY HNPSLKSRLT   180
LALDTPKNLV FLKLNSVTAA DTATYYCARF GGEVLRYTDW PKPAWVDLWG RGTLVTVSSA   240
STKGPSVFPL APSSKSTSGG TAALGCLVKD YFPEPVTVSW NSGALTSGVH TFPAVLQSSG   300
LYSLSSVVTV PSSSLGTQTY ICNVNHKPSN TKVDKKVEPK SCDKTHTCPP CPAPELLGGP   360
SVFLFPPKPK DTLMISRTPE VTCVVVDVSH EDPEVKFNWY VDGVEVHNAK TKPREEQYNS   420
TYRVVSVLTV LHQDWLNGKE YKCKVSNKAL PAPIEKTISK AKGQPREPQV YTLPPSRDEL   480
TKNQVSLTCL VKGFYPSDIA VEWESNGQPE NNYKTTPPVL DSDGSFFLYS KLTVDKSRWQ   540
QGNVFSCSVL HEALHSHYTQ KSLSLSPGK                                      569

SEQ ID NO: 135          moltype = AA  length = 569
FEATURE                 Location/Qualifiers
source                  1..569
                        mol_type = protein
                        organism = synthetic construct
SEQUENCE: 135
KKVVYGKKGD TVELTCTASQ KKNIQFHWKN SNQIKILGNQ GSFLTKGPSK LWDRVDSRRS    60
LWDQGNFPLI IKNLKPEDSD TYICEVEDQK EEVQLVVVGG GGGSQPQLQE SGPTLVEASE   120
TLSLTCAVSG DSTAACNSFW GWVRQPPGKG LEWVGSLSHC ASYWNRGWTY HNPSLKSRLT   180
LALDTPKNLV FLKLNSVTAA DTATYYCARF GGEVLRYTDW PKPAWVDLWG RGTLVTVSSA   240
STKGPSVFPL APSSKSTSGG TAALGCLVKD YFPEPVTVSW NSGALTSGVH TFPAVLQSSG   300
LYSLSSVVTV PSSSLGTQTY ICNVNHKPSN TKVDKKVEPK SCDKTHTCPP CPAPELLGGP   360
SVFLFPPKPK DTLMISRTPE VTCVVVDVSH EDPEVKFNWY VDGVEVHNAK TKPREEQYNS   420
TYRVVSVLTV LHQDWLNGKE YKCKVSNKAL PAPIEKTISK AKGQPREPQV YTLPPSRDEL   480
TKNQVSLTCL VKGFYPSDIA VEWESNGQPE NNYKTTPPVL DSDGSFFLYS KLTVDKSRWQ   540
QGNVFSCSVL HEALHSHYTQ KSLSLSPGK                                      569

SEQ ID NO: 136          moltype = AA  length = 566
FEATURE                 Location/Qualifiers
source                  1..566
                        mol_type = protein
                        organism = synthetic construct
SEQUENCE: 136
KKVVYGKCGD TVELTCTASQ KKNIQFHWKN SNQIKILGNQ GSFLTKGPSK LNDRVDSRRS    60
LWDQGNFPLI IKNLKPEDSD TYICEVEDQK EEVQLVVVCG GGGSQMQLQE SGPGLVKPSE   120
TLSLTCSVSG ASISDSYWSW IRRSPGKGLE WIGYVHKSGD TNYSPSLKSR VNLSLDTSKN   180
QVSLSLVAAT AADSGKYYCA RTLHGRRIYG IVAFNEWFTY FYMDVWGNGT QVTVSSASTK   240
GPSVFPLAPS SKSTSGGTAA LGCLVKDYFP EPVTVSWNSG ALTSGVHTFP AVLQSSGLYS   300
LSSVVTVPSS SLGTQYICN VNHKPSNTKV DKRVEPKSCD KTHTCPPCPA PELLGGPSVF   360
LFPPKPKDTL MISRTPEVTC VVVDVSHEDP EVKFNWYVDG VEVHNAKTKP REEQYNSTYR   420
VVSVLTVLHQ DWLNGKEYKC KVSNKALPAP IEKTISKAKG QPREPQVYTL PPSRDELTKN   480
QVSLTCLVKG FYPSDIAVEW ESNGQPENNY KTTPPVLDSD GSFFLYSKLT VDKSRWQQGN   540
VFSCSVLHEA LHSHYTQKSL SLSPGK                                         566

SEQ ID NO: 137          moltype = AA  length = 571
FEATURE                 Location/Qualifiers
source                  1..571
                        mol_type = protein
                        organism = synthetic construct
SEQUENCE: 137
KKVVYGKCGD TVELTCTASQ KKNIQFHWKN SNQIKILGNQ GSFLTKGPSK LNDRVDSRRS    60
LWDQGNFPLI IKNLKPEDSD TYICEVEDQK EEVQLVVVCG GGGSGGGGSQ MQLQESGPGL   120
VKPSETLSLT CSVSGASISD SYWSWIRRSP GKGLEWIGYV HKSGDTNYSP SLKSRVNLSL   180
DTSKNQVSLS LVAATAADSG KYYCARTLHG RRIYGIVAFN EWFTYFYMDV WGNGTQVTVS   240
SASTKGPSVF PLAPSSKSTS GGTAALGCLV KDYFPEPVTV SWNSGALTSG VHTFPAVLQS   300
SGLYSLSSVV TVPSSSLGTQ TYICNVNHKP SNTKVDKRVE PKSCDKTHTC PPCPAPELLG   360
GPSVFLFPPK PKDTLMISRT PEVTCVVVDV SHEDPEVKFN WYVDGVEVHN AKTKPREEQY   420
NSTYRVVSVL TVLHQDWLNG KEYKCKVSNK ALPAPIEKTI SKAKGQPREP QVYTLPPSRD   480
ELTKNQVSLT CLVKGFYPSD IAVEWESNGQ PENNYKTTPP VLDSDGSFFL YSKLTVDKSR   540
WQQGNVFSCS VLHEALHSHY TQKSLSLSPG K                                   571

SEQ ID NO: 138          moltype = AA  length = 576
FEATURE                 Location/Qualifiers
source                  1..576
```

```
                         mol_type = protein
                         organism = synthetic construct
SEQUENCE: 138
KKVVYGKCGD TVELTCTASQ KKNIQFHWKN SNQIKILGNQ GSFLTKGPSK LNDRVDSRRS    60
LWDQGNFPLI IKNLKPEDSD TYICEVEDQK EEVQLVVVCG GGGSGGGGSG GGGSQMQLQE   120
SGPGLVKPSE TLSLTCSVSG ASISDSYWSW IRRSPGKGLE WIGYVHKSGD TNYSPSLKSR   180
VNLSLDTSKN QVSLSLVAAT AADSGKYYCA RTLHGRRIYG IVAFNEWFTY FYMDVWGNGT   240
QVTVSSASTK GPSVFPLAPS SKSTSGGTAA LGCLVKDYFP EPVTVSWNSG ALTSGVHTFP   300
AVLQSSGGLYS LSSVVTVPSS SLGTQTYICN VNHKPSNTKV DKRVEPKSCD KTHTCPPCSC   360
PELLGGPSVF LFPPKPKDTL MISRTPEVTC VVVDVSHEDP EVKFNWYVDG VEVHNAKTKP   420
REEQYNSTYR VVSVLTVLHQ DWLNGKEYKC KVSNKALPAP IEKTISKAKG QPREPQVYTL   480
PPSRDELTKN QVSLTCLVKG FYPSDIAVEW ESNGQPENNY KTTPPVLDSD GSFFLYSKLT   540
VDKSRWQQGN VFSCSVLHEA LHSHYTQKSL SLSPGK                            576

SEQ ID NO: 139          moltype = AA  length = 581
FEATURE                 Location/Qualifiers
source                  1..581
                        mol_type = protein
                        organism = synthetic construct
SEQUENCE: 139
KKVVYGKCGD TVELTCTASQ KKNIQFHWKN SNQIKILGNQ GSFLTKGPSK LNDRVDSRRS    60
LWDQGNFPLI IKNLKPEDSD TYICEVEDQK EEVQLVVVCG GGGSGGGGSG GGGSGGGGSQ   120
MQLQESGPGL VKPSETLSLT CSVSGASISD SYWSWIRRSP GKGLEWIGYV HKSGDTNYSP   180
SLKSRVNLSL DTSKNQVSLS LVAATAADSG KYYCARTLHG RRIYGIVAFN EWFTYFYMDV   240
WGNGTQVTVS SASTKGPSVF PLAPSSKSTS GGTAALGCLV KDYFPEPVTV SWNSGALTSG   300
VHTFPAVLQS SGGLYSLSSVV TVPSSSLGTQ TYICNVNHKP SNTKVDKRVE PKSCDKTHTC   360
PPCPAPELLG GPSVFLFPPK PKDTLMISRT PEVTCVVVDV SHEDPEVKFN WYVDGVEVHN   420
AKTKPREEQY NSTYRVVSVL TVLHQDWLNG KEYKCKVSNK ALPAPIEKTI SKAKGQPREP   480
QVYTLPPSRD ELTKNQVSLT CLVKGFYPSD IAVEWESNGQ PENNYKTTPP VLDSDGSFFL   540
YSKLTVDKSR WQQGNVFSCS VLHEALHSHY TQKSLSLSPG K                      581

SEQ ID NO: 140          moltype = AA  length = 571
FEATURE                 Location/Qualifiers
source                  1..571
                        mol_type = protein
                        organism = synthetic construct
SEQUENCE: 140
QMQLQESGPG LVKPSETLSL TCSVSGASIS DSYWSWIRRS PGKGLEWIGY VHKSGDTNYS    60
PSLKSRVNLS LDTSKNQVSL SLVAATAADS GKYYCARTLH GRRIYGIVAF NEWFTYFYMD   120
VWGNGTQVTV SSASTKGPSV FPLAPSSKST SGGTAALGCL VKDYFPEPVT VSWNSGALTS   180
GVHTFPAVLQ SSGLYSLSSV VTVPSSSLGT QTYICNVNHK PSNTKVDKRV EPKSCGGGGS   240
KKVVYGKCGD TVELTCTASQ KKNIQFHWKN SNQIKILGNQ GSFLTKGPSK LNDRVDSRRS   300
LWDQGNFPLI IKNLKPEDSD TYICEVEDQK EEVQLVVVCG GGGSDKTHTC PPCPAPELLG   360
GPSVFLFPPK PKDTLMISRT PEVTCVVVDV SHEDPEVKFN WYVDGVEVHN AKTKPREEQY   420
NSTYRVVSVL TVLHQDWLNG KEYKCKVSNK ALPAPIEKTI SKAKGQPREP QVYTLPPSRD   480
ELTKNQVSLT CLVKGFYPSD IAVEWESNGQ PENNYKTTPP VLDSDGSFFL YSKLTVDKSR   540
WQQGNVFSCS VLHEALHSHY TQKSLSLSPG K                                 571

SEQ ID NO: 141          moltype = AA  length = 565
FEATURE                 Location/Qualifiers
source                  1..565
                        mol_type = protein
                        organism = synthetic construct
SEQUENCE: 141
QMQLQESGPG LVKPSETLSL TCSVSGASIS DSYWSWIRRS PGKGLEWIGY VHKSGDTNYS    60
PSLKSRVNLS LDTSKNQVSL SLVAATAADS GKYYCARTLH GRRIYGIVAF NEWFTYFYMD   120
VWGNGTQVTV SSASTKGPSV FPLAPSSKST SGGTAALGCL VKDYFPEPVT VSWNSGALTS   180
GVHTFPAVLQ SSGLYSLSSV VTVPSSSLGT QTYICNVNHK PSNTKVDKRV EPKSCDKTHT   240
CPPCPAPELL GGPSVFLFPP KPKDTLMISR TPEVTCVVVD VSHEDPEVKF NWYVDGVEVH   300
NAKTKPREEQ YNSTYRVVSV LTVLHQDWLN GKEYKCKVSN KALPAPIEKT ISKAKGQPRE   360
PQVYTLPPSR DELTKNQVSL TCLVKGFYPS DIAVEWESNG QPENNYKTTP PVLDSDGSFF   420
LYSKLTVDKS RWQQGNVFSC SVLHEALHSH YTQKSLSLSP GGGGGSKKVV YGKCGDTVEL   480
TCTASQKKNI QFHWKNSNQI KILGNQGSFL TKGPSKLNDR VDSRRSLWDQ GNFPLIIKNL   540
KPEDSDTYIC EVEDQKEEVQ LVVVC                                        565

SEQ ID NO: 142          moltype = AA  length = 315
FEATURE                 Location/Qualifiers
source                  1..315
                        mol_type = protein
                        organism = synthetic construct
SEQUENCE: 142
KKVVYGKCGD TVELTCTASQ KKNIQFHWKN SNQIKILGNQ GSFLTKGPSK LNDRVDSRRS    60
LWDQGNFPLI IKNLKPEDSD TYICEVEDQK EEVQLVVVCG GGGSSDISVA PGETARISCG   120
EKSLGSRAVQ WYQHRAGQAP SLIIYNNQDR PSGIPERFSG SPDSPFGTTA TLTITSVEAG   180
DEADYYCHIW DSRVPTKWVF GGGTTLTVLG QPKAAPSVTL FPPSSEELQA NKATLVCLIS   240
DFYPGAVTVA WKADSSPVKA GVETTTPSKQ SNNKYAASSY LSLTPEQWKS HKSYSCQVTH   300
EGSTVEKTVA PTECS                                                  315

SEQ ID NO: 143          moltype = AA  length = 315
```

```
FEATURE              Location/Qualifiers
source               1..315
                     mol_type = protein
                     organism = synthetic construct
SEQUENCE: 143
SDISVAPGET ARISCGEKSL GSRAVQWYQH RAGQAPSLII YNNQDRPSGI PERFSGSPDS     60
PPGTTATLTI TSVEAGDEAD YYCHIWDSRV PTKWVFGGGT TLTVLGQPKA APSVTLFPPS    120
SEELQANKAT LVCLISDFYP GAVTVAWKAD SSPVKAGVET TTPSKQSNNK YAASSYLSLT    180
PEQWKSHKSY SCQVTHEGST VEKTVAPTEC SGGGGSKKVV YGKCGDTVEL TCTASQKKNI    240
QFHWKNSNQI KILGNQGSFL TKGPSKLNDR VDSRRSLWDQ GNFPLIIKNL KPEDSDTYIC    300
EVEDQKEEVQ LVVVC                                                     315

SEQ ID NO: 144          moltype = AA  length = 564
FEATURE              Location/Qualifiers
source               1..564
                     mol_type = protein
                     organism = synthetic construct
SEQUENCE: 144
KKVVYGKCGD TVELTCTASQ KKNIQFHWKN SNQIKILGNQ GSFLTKGPSK LNDRVDSRRS     60
LWDQGNFPLI IKNLKPEDSD TYICEVEDQK EEVQLVVVCG GGGSQVQLRE SGPGLVKPSE    120
TLSLSCTVSN DSRPSDHSWT WVRQSPGKAL EWIGDIHYNG ATTYNPSLRS RVRIELDQSI    180
PRFSLKMTSM TAADTGMYYC ARNAIRIYGV VALGEWFHYG MDVWGQGTAV TVSSASTKGP    240
SVFPLAPSSK STSGGTAALG CLVKDYFPEP VTVSWNSGAL TSGVHTFPAV LQSSGLYSLS    300
SVVTVPSSSL GTQTYICNVN HKPSNTKVDK RVEPKSCDKT HTCPPCPAPE LLGGPSVFLF    360
PPKPKDTLMI SRTPEVTCVV VDVSHEDPEV KFNWYVDGVE VHNAKTKPRE EQYNSTYRVV    420
SVLTVLHQDW LNGKEYKCKV SNKALPAPIE KTISKAKGQP REPQVYTLPP SRDELTKNQV    480
SLTCLVKGFY PSDIAVEWES NGQPENNYKT TPPVLDSDGS FFLYSKLTVD KSRWQQGNVF    540
SCSVLHEALH SHYTQKSLSL SPGK                                          564

SEQ ID NO: 145          moltype = AA  length = 579
FEATURE              Location/Qualifiers
source               1..579
                     mol_type = protein
                     organism = synthetic construct
SEQUENCE: 145
KKVVYGKCGD TVELTCTASQ KKNIQFHWKN SNQIKILGNQ GSFLTKGPSK LNDRVDSRRS     60
LWDQGNFPLI IKNLKPEDSD TYICEVEDQK EEVQLVVVCG GGGSGGGGSG GGGSGGGGSQ    120
VQLRESGPGL VKPSETLSLS CTVSNDSRPS DHSWTWVRQS PGKALEWIGD IHYNGATTYN    180
PSLRSRVRIE LDQSIPRFSL KMTSMTAADT GMYYCARNAI RIYGVVALGE WFHYGMDVWG    240
QGTAVTVSSA STKGPSVFPL APSSKSTSGG TAALGCLVKD YFPEPVTVSW NSGALTSGVH    300
TFPAVLQSSG LYSLSSVVTV PSSSLGTQTY ICNVNHKPSN TKVDKRVEPK SCDKTHTCPP    360
CPAPELLGGP SVFLFPPKPK DTLMISRTPE VTCVVVDVSH EDPEVKFNWY VDGVEVHNAK    420
TKPREEQYNS TYRVVSVLTV LHQDWLNGKE YKCKVSNKAL PAPIEKTISK AKGQPREPQV    480
YTLPPSRDEL TKNQVSLTCL VKGFYPSDIA VEWESNGQPE NNYKTTPPVL DSDGSFFLYS    540
KLTVDKSRWQ QGNVFSCSVL HEALHSHYTQ KSLSLSPGK                          579

SEQ ID NO: 146          moltype = AA  length = 566
FEATURE              Location/Qualifiers
source               1..566
                     mol_type = protein
                     organism = synthetic construct
SEQUENCE: 146
KKVVYGKCGD TVELTCTASQ KKNIQFHWKN SNQIKILGNQ GSFLTKGPSK LNDRVDSRRS     60
LWDQGNFPLI IKNLKPEDSD TYICEVEDQK EEVQLVVVCG GGGSQVQLQE SGPGLVKPSE    120
TLSVTCSVSG DSMNNYYWTW IRQSPGKGLE WIGYISDRES ATYNPSLNSR VVISRDTSKN    180
QLSLKLNSVT PADTAVYYCA TARRGQRIYG VVSFGEFFYY YSMDVWGKGT TVTVSSASTK    240
GPSVFPLAPS SKSTSGGTAA LGCLVKDYFP EPVTVSWNSG ALTSGVHTFP AVLQSSGLYS    300
LSSVVTVPSS SLGTQTYICN VNHKPSNTKV DKRVEPKSCD KTHTCPPCPA PELLGGPSVF    360
LFPPKPKDTL MISRTPEVTC VVVDVSHEDP EVKFNWYVDG VEVHNAKTKP REEQYNSTYR    420
VVSVLTVLHQ DWLNGKEYKC KVSNKALPAP IEKTISKAKG QPREPQVYTL PPSRDELTKN    480
QVSLTCLVKG FYPSDIAVEW ESNGQPENNY KTTPPVLDSD GSFFLYSKLT VDKSRWQQGN    540
VFSCSVLHEA LHSHYTQKSL SLSPGK                                        566

SEQ ID NO: 147          moltype = AA  length = 581
FEATURE              Location/Qualifiers
source               1..581
                     mol_type = protein
                     organism = synthetic construct
SEQUENCE: 147
KKVVYGKCGD TVELTCTASQ KKNIQFHWKN SNQIKILGNQ GSFLTKGPSK LNDRVDSRRS     60
LWDQGNFPLI IKNLKPEDSD TYICEVEDQK EEVQLVVVCG GGGSGGGGSG GGGSGGGGSQ    120
VQLQESGPGL VKPSETLSVT CSVSGDSMNN YYWTWIRQSP GKGLEWIGYI SDRESATYNP    180
SLNSRVVISR DTSKNQLSLK LNSVTPADTA VYYCATARRG QRIYGVVSFG EFFYYYSMDV    240
WGKGTTVTVS SASTKGPSVF PLAPSSKSTS GGTAALGCLV KDYFPEPVTV SWNSGALTSG    300
VHTFPAVLQS SGLYSLSSVV TVPSSSLGTQ TYICNVNHKP SNTKVDKRVE PKSCDKTHTC    360
PPCPAPELLG GPSVFLFPPK PKDTLMISRT PEVTCVVVDV SHEDPEVKFN WYVDGVEVHN    420
AKTKPREEQY NSTYRVVSVL TVLHQDWLNG KEYKCKVSNK ALPAPIEKTI SKAKGQPREP    480
QVYTLPPSRD ELTKNQVSLT CLVKGFYPSD IAVEWESNGQ PENNYKTTPP VLDSDGSFFL    540
YSKLTVDKSR WQQGNVFSCS VLHEALHSHY TQKSLSLSPG K                       581
```

```
SEQ ID NO: 148          moltype = AA  length = 567
FEATURE                 Location/Qualifiers
source                  1..567
                        mol_type = protein
                        organism = synthetic construct
SEQUENCE: 148
KKVVYGKCGD TVELTCTASQ KKNIQFHWKN SNQIKILGNQ GSFLTKGPSK LNDRVDSRRS   60
LWDQGNFPLI IKNLKPEDSD TYICEVEDQK EEVQLVVVCG GGGSQLQMQE SGPGLVKPSE  120
TLSLSCTVSG DSIRGGEWGD KDYHWGVVRH SAGKGLEWIG SIHWRGTTHY KESLRRRVSM  180
SIDTSRNWFS LRLASVTAAD TAVYFCARHR HHDVFMLVPI AGWFDVWGPG VQVTVSSAST  240
KGPSVFPLAP SSKSTSGGTA ALGCLVKDYF PEPVTVSWNS GALTSGVHTF PAVLQSSGLY  300
SLSSVVTVPS SSLGTQTYIC NVNHKPSNTK VDKRVEPKSC DKTHTCPPCP APELLGGPSV  360
FLFPPKPKDT LMISRTPEVT CVVVDVSHED PEVKFNWYVD GVEVHNAKTK PREEQYNSTY  420
RVVSVLTVLH QDWLNGKEYK CKVSNKALPA PIEKTISKAK GQPREPQVYT LPPSRDELTK  480
NQVSLTCLVK GFYPSDIAVE WESNGQPENN YKTTPPVLDS DGSFFLYSKL TVDKSRWQQG  540
NVFSCSVLHE ALHSHYTQKS LSLSPGK                                     567

SEQ ID NO: 149          moltype = AA  length = 582
FEATURE                 Location/Qualifiers
source                  1..582
                        mol_type = protein
                        organism = synthetic construct
SEQUENCE: 149
KKVVYGKCGD TVELTCTASQ KKNIQFHWKN SNQIKILGNQ GSFLTKGPSK LNDRVDSRRS   60
LWDQGNFPLI IKNLKPEDSD TYICEVEDQK EEVQLVVVCG GGGSGGGGSG GGGSGGGGSQ  120
LQMQESGPGL VKPSETLSLS CTVSGDSIRG GEWGDKDYHW GWVRHSAGKG LEWIGSIHWR  180
GTTHYKESLR RRVSMSIDTS RNWFSLRLAS VTAADTAVYF CARHRHHDVF MLVPIAGWFD  240
VWGPGVQVTV SSASTKGPSV FPLAPSSKST SGGTAALGCL VKDYFPEPVT VSWNSGALTS  300
GVHTFPAVLQ SSGLYSLSSV VTVPSSSLGT QTYICNVNHK PSNTKVDKRV EPKSCDKTHT  360
CPPCPAPELL GGPSVFLFPP KPKDTLMISR TPEVTCVVVD VSHEDPEVKF NWYVDGVEVH  420
NAKTKPREEQ YNSTYRVVSV LTVLHQDWLN GKEYKCKVSN KALPAPIEKT ISKAKGQPRE  480
PQVYTLPPSR DELTKNQVSL TCLVKGFYPS DIAVEWESNG QPENNYKTTP PVLDSDGSFF  540
LYSKLTVDKS RWQQGNVFSC SVLHEALHSH YTQKSLSLSP GK                     582

SEQ ID NO: 150          moltype = AA  length = 656
FEATURE                 Location/Qualifiers
source                  1..656
                        mol_type = protein
                        organism = synthetic construct
SEQUENCE: 150
KKVVLGKKGD TVELTCTASQ KKNIQFHWKN SNQIKILGNQ GSFLTKGPSK LNDRVDSRRS   60
LWDQGNFPLI IKNLKIEDSD TYICEVEDQK EEVQLVVFGL TANSDTHLLQ GQSLTLTLES  120
PPGSSPSVQC RSPRGKNIQG GKTLSVSQLE LQDSGTWTCT VLQNQKKVEF KIDIVVLAFG  180
GGGSGGGGSG GGGSGGGGSQ VQLVQSGAQM KNPGASVKVS CAPSGYTFTD FYIHWLRQAP  240
GQGLQWMGWM NPQTGRTNTA RNFQGRVTMT RDTSIGTAYM ELRSLTSDDT AIYYCTTGGW  300
ISLYYDSSYY PNFDHWGQGT LLTVSSASTK GPSVFPLAPS SKSTSGGTAA LGCLVKDYFP  360
EPVTVSWNSG ALTSGVHTFP AVLQSSGLYS LSSVVTVPSS SLGTQTYICN VNHKPSNTKV  420
DKKVEPKSCD KTHTCPPCPA PELLGGPSVF LFPPKPKDTL MISRTPEVTC VVVDVSHEDP  480
EVKFNWYVDG VEVHNAKTKP REEQYNSTYR VVSVLTVLHQ DWLNGKEYKC KVSNKALPAP  540
IEKTISKAKG QPREPQVYTL PPSRDELTKN QVSLTCLVKG FYPSDIAVEW ESNGQPENNY  600
KTTPPVLDSD GSFFLYSKLT VDKSRWQQGN VFSCSVLHEA LHSHYTQKSL SLSPGK       656

SEQ ID NO: 151          moltype = AA  length = 576
FEATURE                 Location/Qualifiers
source                  1..576
                        mol_type = protein
                        organism = synthetic construct
SEQUENCE: 151
KKVVYGKKGD TVELTCTASQ KKNIQFHWKN SNQIKILGNQ GSFLTKGPSK LNDRVDSRRS   60
LWDQGNFPLI IKNLKPEDSD TYICEVEDQK EEVQLVVVGG GGGSGGGGSG GGGSGGGGSQ  120
VQLVQSGAQM KNPGASVKVS CAPSGYTFTD FYIHWLRQAP GQGLQWMGWM NPQTGRTNTA  180
RNFQGRVTMT RDTSIGTAYM ELRSLTSDDT AIYYCTTGGW ISLYYDSSYY PNFDHWGQGT  240
LLTVSSASTK GPSVFPLAPS SKSTSGGTAA LGCLVKDYFP EPVTVSWNSG ALTSGVHTFP  300
AVLQSSGLYS LSSVVTVPSS SLGTQTYICN VNHKPSNTKV DKKVEPKSCD KTHTCPPCPA  360
PELLGGPSVF LFPPKPKDTL MISRTPEVTC VVVDVSHEDP EVKFNWYVDG VEVHNAKTKP  420
REEQYNSTYR VVSVLTVLHQ DWLNGKEYKC KVSNKALPAP IEKTISKAKG QPREPQVYTL  480
PPSRDELTKN QVSLTCLVKG FYPSDIAVEW ESNGQPENNY KTTPPVLDSD GSFFLYSKLT  540
VDKSRWQQGN VFSCSVLHEA LHSHYTQKSL SLSPGK                            576

SEQ ID NO: 152          moltype = AA  length = 616
FEATURE                 Location/Qualifiers
source                  1..616
                        mol_type = protein
                        organism = synthetic construct
SEQUENCE: 152
KKVVYGKKGD TVELTCTASQ KKNIQFHWKN SNQIKILGNQ GSFLTKGPSK LNDRVDSRRS   60
LWDQGNFPLI IKNLKPEDSD TYICEVEDQK EEVQLVVVGG GGGSGGGGSG GGGSGGGGSQ  120
PQLQESGPTL VEASETLSLT CAVSGDSTAA CNSFWGWVRQ PPGKCLEWVG SLSHCASYWN  180
```

-continued

```
RGWTYHNPSL KSRLTLALDT PKNLVFLKLN SVTAADTATY YCARFGGEVL RYTDWPKPAW  240
VDLWGRGTLV TVSSGGGGSG GGGSGGGGSG GGGSQSALTQ PPSASGSPGQ SITISCTGTS  300
NNFVSWYQQH AGKAPKLVIY DVNKRPSGVP DRFSGSKSGN TASLTVSGLQ TDDEAVYYCG  360
SLVGNWDVIF GCGTKLTVLG GGGSGGGGSD KTHTCPPCPA PELLGGPSVF LFPPKPKDTL  420
MISRTPEVTC VVVDVSHEDP EVKFNWYVDG VEVHNAKTKP REEQYNSTYR VVSVLTVLHQ  480
DWLNGKEYKC KVSNKALPAP IEKTISKAKG QPREPQVYTL PPSRDELTKN QVSLTCLVKG  540
FYPSDIAVEW ESNGQPENNY KTTPPVLDSD GSFFLYSKLT VDKSRWQQGN VFSCSVLHEA  600
LHSHYTQKSL SLSPGK                                                    616
```

```
SEQ ID NO: 153              moltype = AA   length = 611
FEATURE                     Location/Qualifiers
source                      1..611
                            mol_type = protein
                            organism = synthetic construct
SEQUENCE: 153
KKVVYGKKGD TVELTCTASQ KKNIQFHWKN SNQIKILGNQ GSFLTKGPSK LNDRVDSRRS  60
LWDQGNFPLI IKNLKPEDSD TYICEVEDQK EEVQLVVGG GGGSGGGGSG GGGSQPQLQE  120
SGPTLVEASE TLSLTCAVSG DSTAACNSFW GWVRQPPGKC LEWVGSLSHC ASYWNRGWTY  180
HNPSLKSRLT LALDTPKNLV FLKLNSVTAA DTATYYCARF GGEVLRYTDW PKPAWVDLWG  240
RGTLVTVSSG GGGSGGGGSG GGGSGGGGSQ SALTQPPSAS GSPGQSITIS CTGTSNNFVS  300
WYQQHAGKAP KLVIYDVNKR PSGVPDRFSG SKSGNTASLT VSGLQTDDEA VYYCGSLVGN  360
WDVIFGCGTK LTVLGGGGSG GGGSDKTHTC PPCPAPELLG GPSVFLFPPK PKDTLMISRT  420
PEVTCVVVDV SHEDPEVKFN WYVDGVEVHN AKTKPREEQY NSTYRVVSVL TVLHQDWLNG  480
KEYKCKVSNK ALPAPIEKTI SKAKGQPREP QVYTLPPSRD ELTKNQVSLT CLVKGFYPSD  540
IAVEWESNGQ PENNYKTTPP VLDSDGSFFL YSKLTVDKSR WQQGNVFSCS VLHEALHSHY  600
TQKSLSLSPG K                                                        611
```

```
SEQ ID NO: 154              moltype = AA   length = 606
FEATURE                     Location/Qualifiers
source                      1..606
                            mol_type = protein
                            organism = synthetic construct
SEQUENCE: 154
KKVVYGKKGD TVELTCTASQ KKNIQFHWKN SNQIKILGNQ GSFLTKGPSK LNDRVDSRRS  60
LWDQGNFPLI IKNLKPEDSD TYICEVEDQK EEVQLVVGG GGGSGGGGSQ PQLQESGPTL  120
VEASETLSLT CAVSGDSTAA CNSFWGWVRQ PPGKCLEWVG SLSHCASYWN RGWTYHNPSL  180
KSRLTLALDT PKNLVFLKLN SVTAADTATY YCARFGGEVL RYTDWPKPAW VDLWGRGTLV  240
TVSSGGGGSG GGGSGGGGSG GGGSQSALTQ PPSASGSPGQ SITISCTGTS NNFVSWYQQH  300
AGKAPKLVIY DVNKRPSGVP DRFSGSKSGN TASLTVSGLQ TDDEAVYYCG SLVGNWDVIF  360
GCGTKLTVLG GGGSGGGGSD KTHTCPPCPA PELLGGPSVF LFPPKPKDTL MISRTPEVTC  420
VVVDVSHEDP EVKFNWYVDG VEVHNAKTKP REEQYNSTYR VVSVLTVLHQ DWLNGKEYKC  480
KVSNKALPAP IEKTISKAKG QPREPQVYTL PPSRDELTKN QVSLTCLVKG FYPSDIAVEW  540
ESNGQPENNY KTTPPVLDSD GSFFLYSKLT VDKSRWQQGN VFSCSVLHEA LHSHYTQKSL  600
SLSPGK                                                              606
```

```
SEQ ID NO: 155              moltype = AA   length = 601
FEATURE                     Location/Qualifiers
source                      1..601
                            mol_type = protein
                            organism = synthetic construct
SEQUENCE: 155
KKVVYGKKGD TVELTCTASQ KKNIQFHWKN SNQIKILGNQ GSFLTKGPSK LNDRVDSRRS  60
LWDQGNFPLI IKNLKPEDSD TYICEVEDQK EEVQLVVGG GGGSQPQLQE SGPTLVEASE  120
TLSLTCAVSG DSTAACNSFW GWVRQPPGKC LEWVGSLSHC ASYWNRGWTY HNPSLKSRLT  180
LALDTPKNLV FLKLNSVTAA DTATYYCARF GGEVLRYTDW PKPAWVDLWG RGTLVTVSSG  240
GGGSGGGGSG GGGSGGGGSQ SALTQPPSAS GSPGQSITIS CTGTSNNFVS WYQQHAGKAP  300
KLVIYDVNKR PSGVPDRFSG SKSGNTASLT VSGLQTDDEA VYYCGSLVGN WDVIFGCGTK  360
LTVLGGGGSG GGGSDKTHTC PPCPAPELLG GPSVFLFPPK PKDTLMISRT PEVTCVVVDV  420
SHEDPEVKFN WYVDGVEVHN AKTKPREEQY NSTYRVVSVL TVLHQDWLNG KEYKCKVSNK  480
ALPAPIEKTI SKAKGQPREP QVYTLPPSRD ELTKNQVSLT CLVKGFYPSD IAVEWESNGQ  540
PENNYKTTPP VLDSDGSFFL YSKLTVDKSR WQQGNVFSCS VLHEALHSHY TQKSLSLSPG  600
K                                                                   601
```

```
SEQ ID NO: 156              moltype = AA   length = 621
FEATURE                     Location/Qualifiers
source                      1..621
                            mol_type = protein
                            organism = synthetic construct
SEQUENCE: 156
DKTHTCPPCP APELLGGPSV FLFPPKPKDT LMISRTPEVT CVVVDVSHED PEVKFNWYVD  60
GVEVHNAKTK PREEQYNSTY RVVSVLTVLH QDWLNGKEYK CKVSNKALPA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVLHE ALHSHYTQKS LSLSPGKGGG GSGGGGSGGG  240
GSGGGGSKKV VYGKKGDTVE LTCTASQKKN IQFHWKNSNQ IKILGNQGSF LTKGPSKLND  300
RVDSRRSLWD QGNFPLIIKN LKPEDSDTYI CEVEDQKEEV QLVVGGGGG SGGGGSGGGG  360
SQPQLQESGP TLVEASETLS LTCAVSGDST AACNSFWGWV RQPPGKCLEW VGSLSHCASY  420
WNRGWTYHNP SLKSRLTLAL DTPKNLVFLK LNSVTAADTA TYYCARFGGE VLRYTDWPKP  480
AWVDLWGRGT LVTVSSGGGG SGGGGSGGGG SGGGGSQSAL TQPPSASGSP GQSITISCTG  540
TSNNFVSWYQ QHAGKAPKLV IYDVNKRPSG VPDRFSGSKS GNTASLTVSG LQTDDEAVYY  600
```

```
CGSLVGNWDV IFGCGTKLTV L                                               621

SEQ ID NO: 157          moltype = AA   length = 621
FEATURE                 Location/Qualifiers
source                  1..621
                        mol_type = protein
                        organism = synthetic construct
SEQUENCE: 157
QSALTQPPSA SGSPGQSITI SCTGTSNNFV SWYQQHAGKA PKLVIYDVNK RPSGVPDRFS    60
GSKSGNTASL TVSGLQTDDE AVYYCGSLVG NWDVIFGCGT KLTVLGGGGS GGGGSGGGGS    120
GGGGSQPQLQ ESGPTLVEAS ETLSLTCAVS GDSTAACNSF WGWVRQPPGK CLEWVGSLSH    180
CASYWNRGWT YHNPSLKSRL TLALDTPKNL VFLKLNSVTA ADTATYYCAR FGGEVLRYTD    240
WPKPAWVDLW GRGTLVTVSS GGGGSGGGGS GGGGSGGGGS KKVVYGKKGD TVELTCTASQ    300
KKNIQFHWKN SNQIKILGNQ GSFLTKGPSK LNDRVDSRRS LWDQGNFPLI IKNLKPEDSD    360
TYICEVEDQK EEVQLVVVGG GGGSGGGGSG GGGSDKTHTC PPCPAPELLG GPSVFLFPPK    420
PKDTLMISRT PEVTCVVVDV SHEDPEVKFN WYVDGVEVHN AKTKPREEQY NSTYRVVSVL    480
TVLHQDWLNG KEYKCKVSNK ALPAPIEKTI SKAKGQPREP QVYTLPPSRD ELTKNQVSLT    540
CLVKGFYPSD IAVEWESNGQ PENNYKTTPP VLDSDGSFFL YSKLTVDKSR WQQGNVFSCS    600
VLHEALHSHY TQKSLSLSPG K                                              621

SEQ ID NO: 158          moltype = AA   length = 346
FEATURE                 Location/Qualifiers
source                  1..346
                        mol_type = protein
                        organism = synthetic construct
SEQUENCE: 158
KKVVYGKCGD TVELTCTASQ KKNIQFHWKN SNQIKILGNQ GSFLTKGPSK LNDRVDSRRS    60
LWDQGNFPLI IKNLKPEDSD TYICEVEDQK EEVQLVVVCG GGGSGGGGSG GGGSGGGGSD    120
KTHTCPPCPA PELLGGPSVF LFPPKPKDTL MISRTPEVTC VVVDVSHEDP EVKFNWYVDG    180
VEVHNAKTKP REEQYNSTYR VVSVLTVLHQ DWLNGKEYKC KVSNKALPAP IEKTISKAKG    240
QPREPQVYTL PPSRDELTKN QVSLTCLVKG FYPSDIAVEW ESNGQPENNY KTTPPVLDSD    300
GSFFLYSKLT VDKSRWQQGN VFSCSVLHEA LHSHYTQKSL SLSPGK                   346

SEQ ID NO: 159          moltype = AA   length = 5
FEATURE                 Location/Qualifiers
source                  1..5
                        mol_type = protein
                        organism = synthetic construct
SEQUENCE: 159
DNYWS                                                                 5

SEQ ID NO: 160          moltype = AA   length = 16
FEATURE                 Location/Qualifiers
source                  1..16
                        mol_type = protein
                        organism = synthetic construct
SEQUENCE: 160
YVHDSGDTNY NPSLKS                                                     16

SEQ ID NO: 161          moltype = AA   length = 24
FEATURE                 Location/Qualifiers
source                  1..24
                        mol_type = protein
                        organism = synthetic construct
SEQUENCE: 161
TKHGRRIYGV VAFKEWFTYF YMDV                                            24

SEQ ID NO: 162          moltype = AA   length = 11
FEATURE                 Location/Qualifiers
source                  1..11
                        mol_type = protein
                        organism = synthetic construct
SEQUENCE: 162
GEESLGSRSV I                                                          11

SEQ ID NO: 163          moltype = AA   length = 7
FEATURE                 Location/Qualifiers
source                  1..7
                        mol_type = protein
                        organism = synthetic construct
SEQUENCE: 163
NNNDRPS                                                               7

SEQ ID NO: 164          moltype = AA   length = 12
FEATURE                 Location/Qualifiers
source                  1..12
                        mol_type = protein
                        organism = synthetic construct
SEQUENCE: 164
```

-continued

```
HIWDSRRPTN WV                                                      12

SEQ ID NO: 165              moltype = AA   length = 5
FEATURE                     Location/Qualifiers
source                      1..5
                            mol_type = protein
                            organism = synthetic construct
SEQUENCE: 165
DAYWS                                                              5

SEQ ID NO: 166              moltype = AA   length = 16
FEATURE                     Location/Qualifiers
source                      1..16
                            mol_type = protein
                            organism = synthetic construct
SEQUENCE: 166
YVHHSGDTNY NPSLKR                                                  16

SEQ ID NO: 167              moltype = AA   length = 24
FEATURE                     Location/Qualifiers
source                      1..24
                            mol_type = protein
                            organism = synthetic construct
SEQUENCE: 167
ALHGKRIYGI VALGELFTYF YMDV                                         24

SEQ ID NO: 168              moltype = AA   length = 11
FEATURE                     Location/Qualifiers
source                      1..11
                            mol_type = protein
                            organism = synthetic construct
SEQUENCE: 168
GKESIGSRAV Q                                                       11

SEQ ID NO: 169              moltype = AA   length = 7
FEATURE                     Location/Qualifiers
source                      1..7
                            mol_type = protein
                            organism = synthetic construct
SEQUENCE: 169
NNQDRPA                                                            7

SEQ ID NO: 170              moltype = AA   length = 12
FEATURE                     Location/Qualifiers
source                      1..12
                            mol_type = protein
                            organism = synthetic construct
SEQUENCE: 170
HIYDARGGTN WV                                                      12

SEQ ID NO: 171              moltype = AA   length = 7
FEATURE                     Location/Qualifiers
source                      1..7
                            mol_type = protein
                            organism = synthetic construct
SEQUENCE: 171
ACTYFWG                                                            7

SEQ ID NO: 172              moltype = AA   length = 22
FEATURE                     Location/Qualifiers
source                      1..22
                            mol_type = protein
                            organism = synthetic construct
SEQUENCE: 172
SLSHCQSFWG SGWTFHNPSL KS                                           22

SEQ ID NO: 173              moltype = AA   length = 19
FEATURE                     Location/Qualifiers
source                      1..19
                            mol_type = protein
                            organism = synthetic construct
SEQUENCE: 173
FDGEVLVYNH WPKPAWVDL                                               19

SEQ ID NO: 174              moltype = AA   length = 9
FEATURE                     Location/Qualifiers
source                      1..9
                            mol_type = protein
                            organism = synthetic construct
```

```
SEQUENCE: 174
NGTATNFVS                                                                    9

SEQ ID NO: 175          moltype = AA  length = 7
FEATURE                 Location/Qualifiers
source                  1..7
                        mol_type = protein
                        organism = synthetic construct
SEQUENCE: 175
GVDKRPP                                                                       7

SEQ ID NO: 176          moltype = AA  length = 10
FEATURE                 Location/Qualifiers
source                  1..10
                        mol_type = protein
                        organism = synthetic construct
SEQUENCE: 176
GSLVGNWDVI                                                                   10

SEQ ID NO: 177          moltype = AA  length = 7
FEATURE                 Location/Qualifiers
source                  1..7
                        mol_type = protein
                        organism = synthetic construct
SEQUENCE: 177
ACDYFWG                                                                       7

SEQ ID NO: 178          moltype = AA  length = 22
FEATURE                 Location/Qualifiers
source                  1..22
                        mol_type = protein
                        organism = synthetic construct
SEQUENCE: 178
GLSHCAGYYN TGWTYHNPSL KS                                                     22

SEQ ID NO: 179          moltype = AA  length = 19
FEATURE                 Location/Qualifiers
source                  1..19
                        mol_type = protein
                        organism = synthetic construct
SEQUENCE: 179
FDGEVLVYHD WPKPAWVDL                                                         19

SEQ ID NO: 180          moltype = AA  length = 9
FEATURE                 Location/Qualifiers
source                  1..9
                        mol_type = protein
                        organism = synthetic construct
SEQUENCE: 180
TGTSNRFVS                                                                     9

SEQ ID NO: 181          moltype = AA  length = 7
FEATURE                 Location/Qualifiers
source                  1..7
                        mol_type = protein
                        organism = synthetic construct
SEQUENCE: 181
GVNKRPS                                                                       7

SEQ ID NO: 182          moltype = AA  length = 10
FEATURE                 Location/Qualifiers
source                  1..10
                        mol_type = protein
                        organism = synthetic construct
SEQUENCE: 182
SSLVGNWDVI                                                                   10

SEQ ID NO: 183          moltype = AA  length = 7
FEATURE                 Location/Qualifiers
source                  1..7
                        mol_type = protein
                        organism = synthetic construct
SEQUENCE: 183
RCNYFWG                                                                       7

SEQ ID NO: 184          moltype = AA  length = 22
FEATURE                 Location/Qualifiers
source                  1..22
                        mol_type = protein
```

-continued

```
                          organism = synthetic construct
SEQUENCE: 184
SLSHCRSYYN TDWTYHNPSL KS                                              22

SEQ ID NO: 185           moltype = AA  length = 19
FEATURE                  Location/Qualifiers
source                   1..19
                         mol_type = protein
                         organism = synthetic construct
SEQUENCE: 185
FGGEVLVYRD WPKPAWVDL                                                  19

SEQ ID NO: 186           moltype = AA  length = 9
FEATURE                  Location/Qualifiers
source                   1..9
                         mol_type = protein
                         organism = synthetic construct
SEQUENCE: 186
TGTSNNFVS                                                             9

SEQ ID NO: 187           moltype = AA  length = 7
FEATURE                  Location/Qualifiers
source                   1..7
                         mol_type = protein
                         organism = synthetic construct
SEQUENCE: 187
EVNKRPS                                                               7

SEQ ID NO: 188           moltype = AA  length = 10
FEATURE                  Location/Qualifiers
source                   1..10
                         mol_type = protein
                         organism = synthetic construct
SEQUENCE: 188
SSLVGNWDVI                                                            10

SEQ ID NO: 189           moltype = AA  length = 7
FEATURE                  Location/Qualifiers
source                   1..7
                         mol_type = protein
                         organism = synthetic construct
SEQUENCE: 189
TGHYYWG                                                               7

SEQ ID NO: 190           moltype = AA  length = 16
FEATURE                  Location/Qualifiers
source                   1..16
                         mol_type = protein
                         organism = synthetic construct
SEQUENCE: 190
HIHYTTAVLH NPSLKS                                                     16

SEQ ID NO: 191           moltype = AA  length = 19
FEATURE                  Location/Qualifiers
source                   1..19
                         mol_type = protein
                         organism = synthetic construct
SEQUENCE: 191
SGGDILYYYE WQKPHWFSP                                                  19

SEQ ID NO: 192           moltype = AA  length = 14
FEATURE                  Location/Qualifiers
source                   1..14
                         mol_type = protein
                         organism = synthetic construct
SEQUENCE: 192
NGTSSDIGGW NFVS                                                       14

SEQ ID NO: 193           moltype = AA  length = 7
FEATURE                  Location/Qualifiers
source                   1..7
                         mol_type = protein
                         organism = synthetic construct
SEQUENCE: 193
EVNKRPS                                                               7

SEQ ID NO: 194           moltype = AA  length = 10
FEATURE                  Location/Qualifiers
source                   1..10
```

-continued

```
                         mol_type = protein
                         organism = synthetic construct
SEQUENCE: 194
SSLFGRWDVV                                                    10

SEQ ID NO: 195          moltype = AA   length = 7
FEATURE                 Location/Qualifiers
source                  1..7
                        mol_type = protein
                        organism = synthetic construct
SEQUENCE: 195
TGHHYWG                                                       7

SEQ ID NO: 196          moltype = AA   length = 16
FEATURE                 Location/Qualifiers
source                  1..16
                        mol_type = protein
                        organism = synthetic construct
SEQUENCE: 196
HIHYNTAVLH NPALKS                                             16

SEQ ID NO: 197          moltype = AA   length = 19
FEATURE                 Location/Qualifiers
source                  1..19
                        mol_type = protein
                        organism = synthetic construct
SEQUENCE: 197
SGGDILYYIE WQKPHWFYP                                          19

SEQ ID NO: 198          moltype = AA   length = 14
FEATURE                 Location/Qualifiers
source                  1..14
                        mol_type = protein
                        organism = synthetic construct
SEQUENCE: 198
SGTGSDIGSW NFVS                                               14

SEQ ID NO: 199          moltype = AA   length = 7
FEATURE                 Location/Qualifiers
source                  1..7
                        mol_type = protein
                        organism = synthetic construct
SEQUENCE: 199
EVNRRRS                                                       7

SEQ ID NO: 200          moltype = AA   length = 10
FEATURE                 Location/Qualifiers
source                  1..10
                        mol_type = protein
                        organism = synthetic construct
SEQUENCE: 200
SSLSGRWDIV                                                    10

SEQ ID NO: 201          moltype = AA   length = 12
FEATURE                 Location/Qualifiers
source                  1..12
                        mol_type = protein
                        organism = synthetic construct
SEQUENCE: 201
GTDWGENDFH YG                                                 12

SEQ ID NO: 202          moltype = AA   length = 17
FEATURE                 Location/Qualifiers
source                  1..17
                        mol_type = protein
                        organism = synthetic construct
SEQUENCE: 202
SIHWRGRTTH YKTSFRS                                            17

SEQ ID NO: 203          moltype = AA   length = 18
FEATURE                 Location/Qualifiers
source                  1..18
                        mol_type = protein
                        organism = synthetic construct
SEQUENCE: 203
HKYHDIFRVV PVAGWFDP                                           18

SEQ ID NO: 204          moltype = AA   length = 11
FEATURE                 Location/Qualifiers
```

```
source                    1..11
                          mol_type = protein
                          organism = synthetic construct
SEQUENCE: 204
RASQNVKNNL A                                                              11

SEQ ID NO: 205            moltype = AA  length = 7
FEATURE                   Location/Qualifiers
source                    1..7
                          mol_type = protein
                          organism = synthetic construct
SEQUENCE: 205
DASSRAG                                                                   7

SEQ ID NO: 206            moltype = AA  length = 9
FEATURE                   Location/Qualifiers
source                    1..9
                          mol_type = protein
                          organism = synthetic construct
SEQUENCE: 206
QQYEEWPRT                                                                 9

SEQ ID NO: 207            moltype = AA  length = 12
FEATURE                   Location/Qualifiers
source                    1..12
                          mol_type = protein
                          organism = synthetic construct
SEQUENCE: 207
GGEWGDSDYH WG                                                             12

SEQ ID NO: 208            moltype = AA  length = 16
FEATURE                   Location/Qualifiers
source                    1..16
                          mol_type = protein
                          organism = synthetic construct
SEQUENCE: 208
SIHWRGTTHY NAPFRG                                                         16

SEQ ID NO: 209            moltype = AA  length = 18
FEATURE                   Location/Qualifiers
source                    1..18
                          mol_type = protein
                          organism = synthetic construct
SEQUENCE: 209
HKYHDIVMVV PIAGWFDP                                                       18

SEQ ID NO: 210            moltype = AA  length = 11
FEATURE                   Location/Qualifiers
source                    1..11
                          mol_type = protein
                          organism = synthetic construct
SEQUENCE: 210
RASQSVKNNL A                                                              11

SEQ ID NO: 211            moltype = AA  length = 7
FEATURE                   Location/Qualifiers
source                    1..7
                          mol_type = protein
                          organism = synthetic construct
SEQUENCE: 211
DTSSRAS                                                                   7

SEQ ID NO: 212            moltype = AA  length = 9
FEATURE                   Location/Qualifiers
source                    1..9
                          mol_type = protein
                          organism = synthetic construct
SEQUENCE: 212
QQYEEWPRT                                                                 9

SEQ ID NO: 213            moltype = AA  length = 5
FEATURE                   Location/Qualifiers
source                    1..5
                          mol_type = protein
                          organism = synthetic construct
SEQUENCE: 213
DVWLN                                                                     5

SEQ ID NO: 214            moltype = AA  length = 19
```

-continued

```
FEATURE              Location/Qualifiers
source               1..19
                     mol_type = protein
                     organism = synthetic construct
SEQUENCE: 214
RIKSRTDGGT TDYAASVKG                                                     19

SEQ ID NO: 215       moltype = AA  length = 20
FEATURE              Location/Qualifiers
source               1..20
                     mol_type = protein
                     organism = synthetic construct
SEQUENCE: 215
DGFIMIRGVS EDYYYYYMDV                                                    20

SEQ ID NO: 216       moltype = AA  length = 13
FEATURE              Location/Qualifiers
source               1..13
                     mol_type = protein
                     organism = synthetic construct
SEQUENCE: 216
SGSSSNIGNN YVL                                                           13

SEQ ID NO: 217       moltype = AA  length = 7
FEATURE              Location/Qualifiers
source               1..7
                     mol_type = protein
                     organism = synthetic construct
SEQUENCE: 217
GNNKRPS                                                                   7

SEQ ID NO: 218       moltype = AA  length = 12
FEATURE              Location/Qualifiers
source               1..12
                     mol_type = protein
                     organism = synthetic construct
SEQUENCE: 218
ATWDSGLSAD WV                                                            12

SEQ ID NO: 219       moltype = AA  length = 5
FEATURE              Location/Qualifiers
source               1..5
                     mol_type = protein
                     organism = synthetic construct
SEQUENCE: 219
SYVMH                                                                     5

SEQ ID NO: 220       moltype = AA  length = 17
FEATURE              Location/Qualifiers
source               1..17
                     mol_type = protein
                     organism = synthetic construct
SEQUENCE: 220
AISSDGETTY HANSVKG                                                       17

SEQ ID NO: 221       moltype = AA  length = 14
FEATURE              Location/Qualifiers
source               1..14
                     mol_type = protein
                     organism = synthetic construct
SEQUENCE: 221
DRYYETSGSN AFDV                                                          14

SEQ ID NO: 222       moltype = AA  length = 11
FEATURE              Location/Qualifiers
source               1..11
                     mol_type = protein
                     organism = synthetic construct
SEQUENCE: 222
QASQDISNYL N                                                             11

SEQ ID NO: 223       moltype = AA  length = 7
FEATURE              Location/Qualifiers
source               1..7
                     mol_type = protein
                     organism = synthetic construct
SEQUENCE: 223
TASNLET                                                                   7
```

-continued

```
SEQ ID NO: 224        moltype = AA   length = 10
FEATURE               Location/Qualifiers
source                1..10
                      mol_type = protein
                      organism = synthetic construct
SEQUENCE: 224
QQYDNLGDLS                                                        10

SEQ ID NO: 225        moltype = AA   length = 5
FEATURE               Location/Qualifiers
source                1..5
                      mol_type = protein
                      organism = synthetic construct
SEQUENCE: 225
NFAIH                                                             5

SEQ ID NO: 226        moltype = AA   length = 17
FEATURE               Location/Qualifiers
source                1..17
                      mol_type = protein
                      organism = synthetic construct
SEQUENCE: 226
GRVPVVGIYK YGKKFHD                                                17

SEQ ID NO: 227        moltype = AA   length = 21
FEATURE               Location/Qualifiers
source                1..21
                      mol_type = protein
                      organism = synthetic construct
SEQUENCE: 227
WRGCGMCPYD TSSYYNDASD V                                           21

SEQ ID NO: 228        moltype = AA   length = 12
FEATURE               Location/Qualifiers
source                1..12
                      mol_type = protein
                      organism = synthetic construct
SEQUENCE: 228
RASQNISSSW IA                                                     12

SEQ ID NO: 229        moltype = AA   length = 7
FEATURE               Location/Qualifiers
source                1..7
                      mol_type = protein
                      organism = synthetic construct
SEQUENCE: 229
AASARAA                                                           7

SEQ ID NO: 230        moltype = AA   length = 9
FEATURE               Location/Qualifiers
source                1..9
                      mol_type = protein
                      organism = synthetic construct
SEQUENCE: 230
QYYGGSFFT                                                         9

SEQ ID NO: 231        moltype = AA   length = 5
FEATURE               Location/Qualifiers
source                1..5
                      mol_type = protein
                      organism = synthetic construct
SEQUENCE: 231
AHTMN                                                             5

SEQ ID NO: 232        moltype = AA   length = 17
FEATURE               Location/Qualifiers
source                1..17
                      mol_type = protein
                      organism = synthetic construct
SEQUENCE: 232
SISTSSTYRD YADAVKG                                                17

SEQ ID NO: 233        moltype = AA   length = 14
FEATURE               Location/Qualifiers
source                1..14
                      mol_type = protein
                      organism = synthetic construct
SEQUENCE: 233
KGSDRLSDND PFDA                                                   14
```

-continued

```
SEQ ID NO: 234            moltype = AA   length = 11
FEATURE                   Location/Qualifiers
source                    1..11
                          mol_type = protein
                          organism = synthetic construct
SEQUENCE: 234
RASQSIETWL A                                                           11

SEQ ID NO: 235            moltype = AA   length = 7
FEATURE                   Location/Qualifiers
source                    1..7
                          mol_type = protein
                          organism = synthetic construct
SEQUENCE: 235
KASTLKT                                                                7

SEQ ID NO: 236            moltype = AA   length = 9
FEATURE                   Location/Qualifiers
source                    1..9
                          mol_type = protein
                          organism = synthetic construct
SEQUENCE: 236
QHYAGYSAT                                                              9

SEQ ID NO: 237            moltype = AA   length = 5
FEATURE                   Location/Qualifiers
source                    1..5
                          mol_type = protein
                          organism = synthetic construct
SEQUENCE: 237
SSYWS                                                                  5

SEQ ID NO: 238            moltype = AA   length = 16
FEATURE                   Location/Qualifiers
source                    1..16
                          mol_type = protein
                          organism = synthetic construct
SEQUENCE: 238
YTHHSGDTNY APSLKS                                                      16

SEQ ID NO: 239            moltype = AA   length = 24
FEATURE                   Location/Qualifiers
source                    1..24
                          mol_type = protein
                          organism = synthetic construct
SEQUENCE: 239
TLHGRRIYGV VAFNEFFTYF YWEV                                             24

SEQ ID NO: 240            moltype = AA   length = 11
FEATURE                   Location/Qualifiers
source                    1..11
                          mol_type = protein
                          organism = synthetic construct
SEQUENCE: 240
GGESIGSRAV Q                                                           11

SEQ ID NO: 241            moltype = AA   length = 7
FEATURE                   Location/Qualifiers
source                    1..7
                          mol_type = protein
                          organism = synthetic construct
SEQUENCE: 241
NNQDRPP                                                                7

SEQ ID NO: 242            moltype = AA   length = 12
FEATURE                   Location/Qualifiers
source                    1..12
                          mol_type = protein
                          organism = synthetic construct
SEQUENCE: 242
HIWDSRRPTN WV                                                          12

SEQ ID NO: 243            moltype = AA   length = 5
FEATURE                   Location/Qualifiers
source                    1..5
                          mol_type = protein
                          organism = synthetic construct
SEQUENCE: 243
```

-continued

```
SSYWS                                                           5

SEQ ID NO: 244          moltype = AA   length = 16
FEATURE                 Location/Qualifiers
source                  1..16
                        mol_type = protein
                        organism = synthetic construct
SEQUENCE: 244
YTHHSGDTNY APSLKS                                               16

SEQ ID NO: 245          moltype = AA   length = 24
FEATURE                 Location/Qualifiers
source                  1..24
                        mol_type = protein
                        organism = synthetic construct
SEQUENCE: 245
TLHGRRIYGV VAFNEYYTYF YWPT                                      24

SEQ ID NO: 246          moltype = AA   length = 11
FEATURE                 Location/Qualifiers
source                  1..11
                        mol_type = protein
                        organism = synthetic construct
SEQUENCE: 246
GGESIGSRAV Q                                                    11

SEQ ID NO: 247          moltype = AA   length = 7
FEATURE                 Location/Qualifiers
source                  1..7
                        mol_type = protein
                        organism = synthetic construct
SEQUENCE: 247
NNQDRPP                                                         7

SEQ ID NO: 248          moltype = AA   length = 12
FEATURE                 Location/Qualifiers
source                  1..12
                        mol_type = protein
                        organism = synthetic construct
SEQUENCE: 248
HIWDSRRPTN WE                                                   12

SEQ ID NO: 249          moltype = AA   length = 5
FEATURE                 Location/Qualifiers
source                  1..5
                        mol_type = protein
                        organism = synthetic construct
SEQUENCE: 249
SSYWS                                                           5

SEQ ID NO: 250          moltype = AA   length = 16
FEATURE                 Location/Qualifiers
source                  1..16
                        mol_type = protein
                        organism = synthetic construct
SEQUENCE: 250
YTHHSGDTNY APSLKS                                               16

SEQ ID NO: 251          moltype = AA   length = 24
FEATURE                 Location/Qualifiers
source                  1..24
                        mol_type = protein
                        organism = synthetic construct
SEQUENCE: 251
TLHGRRIYGV VAFNEYYTYF YWPT                                      24

SEQ ID NO: 252          moltype = AA   length = 14
FEATURE                 Location/Qualifiers
source                  1..14
                        mol_type = protein
                        organism = synthetic construct
SEQUENCE: 252
TGTSSDIGAS DYVS                                                 14

SEQ ID NO: 253          moltype = AA   length = 7
FEATURE                 Location/Qualifiers
source                  1..7
                        mol_type = protein
                        organism = synthetic construct
```

```
SEQUENCE: 253
DVTKRPS                                                                       7

SEQ ID NO: 254          moltype = AA  length = 10
FEATURE                 Location/Qualifiers
source                  1..10
                        mol_type = protein
                        organism = synthetic construct
SEQUENCE: 254
SSDAGRHTLL                                                                     10

SEQ ID NO: 255          moltype = AA  length = 132
FEATURE                 Location/Qualifiers
source                  1..132
                        mol_type = protein
                        organism = synthetic construct
SEQUENCE: 255
QVHLQESGPG LVKPSETLSL TCNVSGTLVR DNYWSWIRQP LGKQPEWIGY VHDSGDTNYN   60
PSLKSRVHLS LDKSKNLVSL RLTGVTAADS AIYYCATTKH GRRIYGVVAF KEWFTYFYMD  120
VWGKGTSVTV SS                                                      132

SEQ ID NO: 256          moltype = AA  length = 105
FEATURE                 Location/Qualifiers
source                  1..105
                        mol_type = protein
                        organism = synthetic construct
SEQUENCE: 256
TFVSVAPGQT ARITCGEESL GSRSVIWYQQ RPGQAPSLII YNNNDRPSGI PDRFSGSPGS   60
TFGTTATLTI TSVEAGDEAD YYCHIWDSRR PTNWVFGEGT TLIVL                  105

SEQ ID NO: 257          moltype = AA  length = 462
FEATURE                 Location/Qualifiers
source                  1..462
                        mol_type = protein
                        organism = synthetic construct
SEQUENCE: 257
QVHLQESGPG LVKPSETLSL TCNVSGTLVR DNYWSWIRQP LGKQPEWIGY VHDSGDTNYN   60
PSLKSRVHLS LDKSKNLVSL RLTGVTAADS AIYYCATTKH GRRIYGVVAF KEWFTYFYMD  120
VWGKGTSVTV SSASTKGPSV FPLAPSSKST SGGTAALGCL VKDYFPEPVT VSWNSGALTS  180
GVHTFPAVLQ SSGLYSLSSV VTVPSSSLGT QTYICNVNHK PSNTKVDKKV EPKSCDKTHT  240
CPPCPAPELL GGPSVFLFPP KPKDTLMISR TPEVTCVVVD VSHEDPEVKF NWYVDGVEVH  300
NAKTKPREEQ YNSTYRVVSV LTVLHQDWLN GKEYKCKVSN KALPAPIEKT ISKAKGQPRE  360
PQVYTLPPSR DELTKNQVSL TCLVKGFYPS DIAVEWESNG QPENNYKTTP PVLDSDGSFF  420
LYSKLTVDKS RWQQGNVFSC SVMHEALHNH YTQKSLSLSP GK                     462

SEQ ID NO: 258          moltype = AA  length = 462
FEATURE                 Location/Qualifiers
source                  1..462
                        mol_type = protein
                        organism = synthetic construct
SEQUENCE: 258
QVHLQESGPG LVKPSETLSL TCNVSGTLVR DNYWSWIRQP LGKQPEWIGY VHDSGDTNYN   60
PSLKSRVHLS LDKSKNLVSL RLTGVTAADS AIYYCATTKH GRRIYGVVAF KEWFTYFYMD  120
VWGKGTSVTV SSASTKGPSV FPLAPSSKST SGGTAALGCL VKDYFPEPVT VSWNSGALTS  180
GVHTFPAVLQ SSGLYSLSSV VTVPSSSLGT QTYICNVNHK PSNTKVDKKV EPKSCDKTHT  240
CPPCPAPELL GGPSVFLFPP KPKDTLMISR TPEVTCVVVD VSHEDPEVKF NWYVDGVEVH  300
NAKTKPREEQ YNSTYRVVSV LTVLHQDWLN GKEYKCKVSN KALPAPIEKT ISKAKGQPRE  360
PQVYTLPPSR DELTKNQVSL TCLVKGFYPS DIAVEWESNG QPENNYKTTP PVLDSDGSFF  420
LYSKLTVDKS RWQQGNVFSC SVLHEALHSH YTQKSLSLSP GK                     462

SEQ ID NO: 259          moltype = AA  length = 211
FEATURE                 Location/Qualifiers
source                  1..211
                        mol_type = protein
                        organism = synthetic construct
SEQUENCE: 259
TFVSVAPGQT ARITCGEESL GSRSVIWYQQ RPGQAPSLII YNNNDRPSGI PDRFSGSPGS   60
TFGTTATLTI TSVEAGDEAD YYCHIWDSRR PTNWVFGEGT TLIVLGQPKA APSVTLFPPS  120
SEELQANKAT LVCLISDFYP GAVTVAWKAD SSPVKAGVET TTPSKQSNNK YAASSYLSLT  180
PEQWKSHRSY SCQVTHEGST VEKTVAPTEC S                                 211

SEQ ID NO: 260          moltype = AA  length = 132
FEATURE                 Location/Qualifiers
source                  1..132
                        mol_type = protein
                        organism = synthetic construct
SEQUENCE: 260
QLHLQESGPG LVKPPETLSL TCSVSGASIN DAYWSWIRQS PGKRPEWVGY VHHSGDTNYN   60
PSLKRRVTFS LDTAKNEVSL KLVDLTAADS ATYFCARALH GKRIYGIVAL GELFTYFYMD  120
```

-continued

```
VWGKGTAVTV SS                                                       132

SEQ ID NO: 261           moltype = AA   length = 105
FEATURE                  Location/Qualifiers
source                   1..105
                         mol_type = protein
                         organism = synthetic construct
SEQUENCE: 261
SSMSVSPGET AKISCGKESI GSRAVQWYQQ KPGQPPSLII YNNQDRPAGV PERFSASPDF   60
RPGTTATLTI TNVDAEDEAD YYCHIYDARG GTNWVFDRGT TLTVL                   105

SEQ ID NO: 262           moltype = AA   length = 462
FEATURE                  Location/Qualifiers
source                   1..462
                         mol_type = protein
                         organism = synthetic construct
SEQUENCE: 262
QLHLQESGPG LVKPPETLSL TCSVSGASIN DAYWSWIRQS PGKRPEWVGY VHHSGDTNYN   60
PSLKRRVTFS LDTAKNEVSL KLVDLTAADS ATYFCARALH GKRIYGIVAL GELFTYFYMD   120
VWGKGTAVTV SSASTKGPSV FPLAPSSKST SGGTAALGCL VKDYFPEPVT VSWNSGALTS   180
GVHTFPAVLQ SSGLYSLSSV VTVPSSSLGT QTYICNVNHK PSNTKVDKKV EPKSCDKTHT   240
CPPCPAPELL GGPCVFLFPP KPKDTLMISR TPEVTCVVVD VSHEDPEVKF NWYVDGVEVH   300
NAKTKPREEQ YNSTYRVVSV LTVLHQDWLN GKEYKCKVSN KALPAPIEKT ISKAKGQPRE   360
PQVYTLPPSR DELTKNQVSL TCLVKGFYPS DIAVEWESNG QPENNYKTTP PVLDSDGSFF   420
LYSKLTVDKS RWQQGNVFSC SVMHEALHNH YTQKSLSLSP GK                     462

SEQ ID NO: 263           moltype = AA   length = 462
FEATURE                  Location/Qualifiers
source                   1..462
                         mol_type = protein
                         organism = synthetic construct
SEQUENCE: 263
QLHLQESGPG LVKPPETLSL TCSVSGASIN DAYWSWIRQS PGKRPEWVGY VHHSGDTNYN   60
PSLKRRVTFS LDTAKNEVSL KLVDLTAADS ATYFCARALH GKRIYGIVAL GELFTYFYMD   120
VWGKGTAVTV SSASTKGPSV FPLAPSSKST SGGTAALGCL VKDYFPEPVT VSWNSGALTS   180
GVHTFPAVLQ SSGLYSLSSV VTVPSSSLGT QTYICNVNHK PSNTKVDKKV EPKSCDKTHT   240
CPPCPAPELL GGPSVFLFPP KPKDTLMISR TPEVTCVVVD VSHEDPEVKF NWYVDGVEVH   300
NAKTKPREEQ YNSTYRVVSV LTVLHQDWLN GKEYKCKVSN KALPAPIEKT ISKAKGQPRE   360
PQVYTLPPSR DELTKNQVSL TCLVKGFYPS DIAVEWESNG QPENNYKTTP PVLDSDGSFF   420
LYSKLTVDKS RWQQGNVFSC SVLHEALHSH YTQKSLSLSP GK                     462

SEQ ID NO: 264           moltype = AA   length = 211
FEATURE                  Location/Qualifiers
source                   1..211
                         mol_type = protein
                         organism = synthetic construct
SEQUENCE: 264
SSMSVSPGET AKISCGKESI GSRAVQWYQQ KPGQPPSLII YNNQDRPAGV PERFSASPDF   60
RPGTTATLTI TNVDAEDEAD YYCHIYDARG GTNWVFDRGT TLTVLGQPKA APSVTLFPPS   120
SEELQANKAT LVCLISDFYP GAVTVAWKAD SSPVKAGVET TTPSKQSNNK YAASSYLSLT   180
PEQWKSHRSY SCQVTHEGST VEKTVAPTEC S                                 211

SEQ ID NO: 265           moltype = AA   length = 137
FEATURE                  Location/Qualifiers
source                   1..137
                         mol_type = protein
                         organism = synthetic construct
SEQUENCE: 265
QSQLQESGPR LVEASETLSL TCNVSGESTG ACTYFWGWVR QAPGKGLEWI GSLSHCQSFW   60
GSGWTFHNPS LKSRLTISLD TPKNQVFLKL TSLTAADTAT YYCARFDGEV LVYNHWPKPA   120
WVDLWGRGIP VTVTVSS                                                 137

SEQ ID NO: 266           moltype = AA   length = 105
FEATURE                  Location/Qualifiers
source                   1..105
                         mol_type = protein
                         organism = synthetic construct
SEQUENCE: 266
QSALTQPPSA SGSPGQSITI SCNGTATNFV SWYQQFPDKA PKLIIFGVDK RPPGVPDRFS   60
GSRSGTTASL TVSRLQTDDE AVYYCGSLVG NWDVIFGGGT TLTVL                  105

SEQ ID NO: 267           moltype = AA   length = 467
FEATURE                  Location/Qualifiers
source                   1..467
                         mol_type = protein
                         organism = synthetic construct
SEQUENCE: 267
QSQLQESGPR LVEASETLSL TCNVSGESTG ACTYFWGWVR QAPGKGLEWI GSLSHCQSFW   60
GSGWTFHNPS LKSRLTISLD TPKNQVFLKL TSLTAADTAT YYCARFDGEV LVYNHWPKPA   120
```

-continued

```
WVDLWGRGIP VTVTVSSAST KGPSVFPLAP SSKSTSGGTA ALGCLVKDYF PEPVTVSWNS  180
GALTSGVHTF PAVLQSSGLY SLSSVVTVPS SSLGTQTYIC NVNHKPSNTK VDKKVEPKSC  240
DKTHTCPPCP APELLGGPSV FLFPPKPKDT LMISRTPEVT CVVVDVSHED PEVKFNWYVD  300
GVEVHNAKTK PREEQYNSTY RVVSVLTVLH QDWLNGKEYK CKVSNKALPA PIEKTISKAK  360
GQPREPQVYT LPPSRDELTK NQVSLTCLVK GFYPSDIAVE WESNGQPENN YKTTPPVLDS  420
DGSFFLYSKL TVDKSRWQQG NVFSCSVMHE ALHNHYTQKS LSLSPGK              467

SEQ ID NO: 268          moltype = AA   length = 467
FEATURE                 Location/Qualifiers
source                  1..467
                        mol_type = protein
                        organism = synthetic construct
SEQUENCE: 268
QSQLQESGPR LVEASETLSL TCNVSGESTG ACTYFWGWVR QAPGKGLEWI GSLSHCQSFW  60
GSGWTFHNPS LKSRLTISLD TPKNQVFLKL TSLTAADTAT YYCARFDGEV LVYNHWPKPA  120
WVDLWGRGIP VTVTVSSAST KGPSVFPLAP SSKSTSGGTA ALGCLVKDYF PEPVTVSWNS  180
GALTSGVHTF PAVLQSSGLY SLSSVVTVPS SSLGTQTYIC NVNHKPSNTK VDKKVEPKSC  240
DKTHTCPPCP APELLGGPSV FLFPPKPKDT LMISRTPEVT CVVVDVSHED PEVKFNWYVD  300
GVEVHNAKTK PREEQYNSTY RVVSVLTVLH QDWLNGKEYK CKVSNKALPA PIEKTISKAK  360
GQPREPQVYT LPPSRDELTK NQVSLTCLVK GFYPSDIAVE WESNGQPENN YKTTPPVLDS  420
DGSFFLYSKL TVDKSRWQQG NVFSCSVLHE ALHSHYTQKS LSLSPGK              467

SEQ ID NO: 269          moltype = AA   length = 211
FEATURE                 Location/Qualifiers
source                  1..211
                        mol_type = protein
                        organism = synthetic construct
SEQUENCE: 269
QSALTQPPSA SGSPGQSITI SCNGTATNFV SWYQQFPDKA PKLIIFGVDK RPPGVPDRFS  60
GSRSGTTASL TVSRLQTDDE AVYYCGSLVG NWDVIFGGGT TLTVLGQPKA APSVTLFPPS  120
SEELQANKAT LVCLISDFYP GAVTVAWKAD SSPVKAGVET TTPSKQSNNK YAASSYLSLT  180
PEQWKSHRSY SCQVTHEGST VEKTVAPTEC S                              211

SEQ ID NO: 270          moltype = AA   length = 137
FEATURE                 Location/Qualifiers
source                  1..137
                        mol_type = protein
                        organism = synthetic construct
SEQUENCE: 270
QPQLQESGPG LVEASETLSL TCTVSGDSTA ACDYFWGWVR QPPGKGLEWI GGLSHCAGYY  60
NTGWTYHNPS LKSRLTISLD TPKNQVFLKL NSVTAADTAI YYCARFDGEV LVYHDWPKPA  120
WVDLWGRGTL VTVTVSS                                             137

SEQ ID NO: 271          moltype = AA   length = 105
FEATURE                 Location/Qualifiers
source                  1..105
                        mol_type = protein
                        organism = synthetic construct
SEQUENCE: 271
QSALTQPPSA SGSPGQSISI SCTGTSNRFV SWYQQHPGKA PKLVIYGVNK RPSGVPDRFS  60
GSKSGNTASL TVSGLQTDDE AVYYCSSLVG NWDVIFGGGT KLTVL                105

SEQ ID NO: 272          moltype = AA   length = 467
FEATURE                 Location/Qualifiers
source                  1..467
                        mol_type = protein
                        organism = synthetic construct
SEQUENCE: 272
QPQLQESGPG LVEASETLSL TCTVSGDSTA ACDYFWGWVR QPPGKGLEWI GGLSHCAGYY  60
NTGWTYHNPS LKSRLTISLD TPKNQVFLKL NSVTAADTAI YYCARFDGEV LVYHDWPKPA  120
WVDLWGRGTL VTVTVSSAST KGPSVFPLAP SSKSTSGGTA ALGCLVKDYF PEPVTVSWNS  180
GALTSGVHTF PAVLQSSGLY SLSSVVTVPS SSLGTQTYIC NVNHKPSNTK VDKKVEPKSC  240
DKTHTCPPCP APELLGGPSV FLFPPKPKDT LMISRTPEVT CVVVDVSHED PEVKFNWYVD  300
GVEVHNAKTK PREEQYNSTY RVVSVLTVLH QDWLNGKEYK CKVSNKALPA PIEKTISKAK  360
GQPREPQVYT LPPSRDELTK NQVSLTCLVK GFYPSDIAVE WESNGQPENN YKTTPPVLDS  420
DGSFFLYSKL TVDKSRWQQG NVFSCSVMHE ALHNHYTQKS LSLSPGK              467

SEQ ID NO: 273          moltype = AA   length = 467
FEATURE                 Location/Qualifiers
source                  1..467
                        mol_type = protein
                        organism = synthetic construct
SEQUENCE: 273
QPQLQESGPG LVEASETLSL TCTVSGDSTA ACDYFWGWVR QPPGKGLEWI GGLSHCAGYY  60
NTGWTYHNPS LKSRLTISLD TPKNQVFLKL NSVTAADTAI YYCARFDGEV LVYHDWPKPA  120
WVDLWGRGTL VTVTVSSAST KGPSVFPLAP SSKSTSGGTA ALGCLVKDYF PEPVTVSWNS  180
GALTSGVHTF PAVLQSSGLY SLSSVVTVPS SSLGTQTYIC NVNHKPSNTK VDKKVEPKSC  240
DKTHTCPPCP APELLGGPSV FLFPPKPKDT LMISRTPEVT CVVVDVSHED PEVKFNWYVD  300
GVEVHNAKTK PREEQYNSTY RVVSVLTVLH QDWLNGKEYK CKVSNKALPA PIEKTISKAK  360
```

-continued

```
GQPREPQVYT LPPSRDELTK NQVSLTCLVK GFYPSDIAVE WESNGQPENN YKTTPPVLDS    420
DGSFFLYSKL TVDKSRWQQG NVFSCSVLHE ALHSHYTQKS LSLSPGK                  467

SEQ ID NO: 274           moltype = AA  length = 211
FEATURE                  Location/Qualifiers
source                   1..211
                         mol_type = protein
                         organism = synthetic construct
SEQUENCE: 274
QSALTQPPSA SGSPGQSISI SCTGTSNRFV SWYQQHPGKA PKLVIYGVNK RPSGVPDRFS    60
GSKSGNTASL TVSGLQTDDE AVYYCSSLVG NWDVIFGGGT KLTVLGQPKA APSVTLFPPS    120
SEELQANKAT LVCLISDFYP GAVTVAWKAD SSPVKAGVET TTPSKQSNNK YAASSYLSLT    180
PEQWKSHRSY SCQVTHEGST VEKTVAPTEC S                                   211

SEQ ID NO: 275           moltype = AA  length = 135
FEATURE                  Location/Qualifiers
source                   1..135
                         mol_type = protein
                         organism = synthetic construct
SEQUENCE: 275
QPQLQESGPG LVEASETLSL TCTVSGDSTG RCNYFWGWVR QPPGKGLEWI GSLSHCRSYY    60
NTDWTYHNPS LKSRLTISLD TPKNQVFLRL TSVTAADTAT YYCARFGGEV LVYRDWPKPA    120
WVDLWGRGTL VTVSS                                                     135

SEQ ID NO: 276           moltype = AA  length = 105
FEATURE                  Location/Qualifiers
source                   1..105
                         mol_type = protein
                         organism = synthetic construct
SEQUENCE: 276
QSALTQPPSA SGSPGQSITI SCTGTSNNFV SWYQQYPGKA PKLVIYEVNK RPSGVPDRFS    60
GSKSGSTASL TVSGLQADDE GVYYCSSLVG NWDVIFGGGT KLTVL                    105

SEQ ID NO: 277           moltype = AA  length = 465
FEATURE                  Location/Qualifiers
source                   1..465
                         mol_type = protein
                         organism = synthetic construct
SEQUENCE: 277
QPQLQESGPG LVEASETLSL TCTVSGDSTG RCNYFWGWVR QPPGKGLEWI GSLSHCRSYY    60
NTDWTYHNPS LKSRLTISLD TPKNQVFLRL TSVTAADTAT YYCARFGGEV LVYRDWPKPA    120
WVDLWGRGTL VTVSSASTKG PSVFPLAPSS KSTSGGTAAL GCLVKDYFPE PVTVSWNSGA    180
LTSGVHTFPA VLQSSGLYSL SSVVTVPSSS LGTQTYICNV NHKPSNTKVD KKVEPKSCDK    240
THTCPPCPAP ELLGGPSVFL FPPKPKDTLM ISRTPEVTCV VVDVSHEDPE VKFNWYVDGV    300
EVHNAKTKPR EEQYNSTYRV VSVLTVLHQD WLNGKEYKCK VSNKALPAPI EKTISKAKGQ    360
PREPQVYTLP PSRDELTKNQ VSLTCLVKGF YPSDIAVEWE SNGQPENNYK TTPPVLDSDG    420
SFFLYSKLTV DKSRWQQGNV FSCSVMHEAL HNHYTQKSLS LSPGK                    465

SEQ ID NO: 278           moltype = AA  length = 465
FEATURE                  Location/Qualifiers
source                   1..465
                         mol_type = protein
                         organism = synthetic construct
SEQUENCE: 278
QPQLQESGPG LVEASETLSL TCTVSGDSTG RCNYFWGWVR QPPGKGLEWI GSLSHCRSYY    60
NTDWTYHNPS LKSRLTISLD TPKNQVFLRL TSVTAADTAT YYCARFGGEV LVYRDWPKPA    120
WVDLWGRGTL VTVSSASTKG PSVFPLAPSS KSTSGGTAAL GCLVKDYFPE PVTVSWNSGA    180
LTSGVHTFPA VLQSSGLYSL SSVVTVPSSS LGTQTYICNV NHKPSNTKVD KKVEPKSCDK    240
THTCPPCPAP ELLGGPSVFL FPPKPKDTLM ISRTPEVTCV VVDVSHEDPE VKFNWYVDGV    300
EVHNAKTKPR EEQYNSTYRV VSVLTVLHQD WLNGKEYKCK VSNKALPAPI EKTISKAKGQ    360
PREPQVYTLP PSRDELTKNQ VSLTCLVKGF YPSDIAVEWE SNGQPENNYK TTPPVLDSDG    420
SFFLYSKLTV DKSRWQQGNV FSCSVLHEAL HSHYTQKSLS LSPGK                    465

SEQ ID NO: 279           moltype = AA  length = 211
FEATURE                  Location/Qualifiers
source                   1..211
                         mol_type = protein
                         organism = synthetic construct
SEQUENCE: 279
QSALTQPPSA SGSPGQSITI SCTGTSNNFV SWYQQYPGKA PKLVIYEVNK RPSGVPDRFS    60
GSKSGSTASL TVSGLQADDE GVYYCSSLVG NWDVIFGGGT KLTVLGQPKA APSVTLFPPS    120
SEELQANKAT LVCLISDFYP GAVTVAWKAD SSPVKAGVET TTPSKQSNNK YAASSYLSLT    180
PEQWKSHRSY SCQVTHEGST VEKTVAPTEC S                                   211

SEQ ID NO: 280           moltype = AA  length = 129
FEATURE                  Location/Qualifiers
source                   1..129
                         mol_type = protein
                         organism = synthetic construct
```

-continued

```
SEQUENCE: 280
QVQLQESGPG LVKPAETLSL TCSVSGESIN TGHYYWGWVR QVPGKGLEWI GHIHYTTAVL   60
HNPSLKSRLT IKIYTLRNQI TLRLSNVTAA DTAVYHCVRS GGDILYYYEW QKPHWFSPWG  120
PGIHVTVSS                                                          129

SEQ ID NO: 281        moltype = AA   length = 110
FEATURE               Location/Qualifiers
source                1..110
                      mol_type = protein
                      organism = synthetic construct
SEQUENCE: 281
QSALTQPPSA SGSLGQSVTI SCNGTSSDIG GWNFVSWYQQ FPGRAPRLII FEVNKRPSGV   60
PGRFSGSKSG NSASLTVSGL QSDDEGQYFC SSLFGRWDVV FGGGTKLTVL             110

SEQ ID NO: 282        moltype = AA   length = 459
FEATURE               Location/Qualifiers
source                1..459
                      mol_type = protein
                      organism = synthetic construct
SEQUENCE: 282
QVQLQESGPG LVKPAETLSL TCSVSGESIN TGHYYWGWVR QVPGKGLEWI GHIHYTTAVL   60
HNPSLKSRLT IKIYTLRNQI TLRLSNVTAA DTAVYHCVRS GGDILYYYEW QKPHWFSPWG  120
PGIHVTVSSA STKGPSVFPL APSSKSTSGG TAALGCLVKD YFPEPVTVSW NSGALTSGVH  180
TFPAVLQSSG LYSLSSVVTV PSSSLGTQTY ICNVNHKPSN TKVDKKVEPK SCDKTHTCPP  240
CPAPELLGGP SVFLFPPKPK DTLMISRTPE VTCVVVDVSH EDPEVKFNWY VDGVEVHNAK  300
TKPREEQYNS TYRVVSVLTV LHQDWLNGKE YKCKVSNKAL PAPIEKTISK AKGQPREPQV  360
YTLPPSRDEL TKNQVSLTCL VKGFYPSDIA VEWESNGQPE NNYKTTPPVL DSDGSFFLYS  420
KLTVDKSRWQ QGNVFSCSVM HEALHNHYTQ KSLSLSPGK                         459

SEQ ID NO: 283        moltype = AA   length = 459
FEATURE               Location/Qualifiers
source                1..459
                      mol_type = protein
                      organism = synthetic construct
SEQUENCE: 283
QVQLQESGPG LVKPAETLSL TCSVSGESIN TGHYYWGWVR QVPGKGLEWI GHIHYTTAVL   60
HNPSLKSRLT IKIYTLRNQI TLRLSNVTAA DTAVYHCVRS GGDILYYYEW QKPHWFSPWG  120
PGIHVTVSSA STKGPSVFPL APSSKSTSGG TAALGCLVKD YFPEPVTVSW NSGALTSGVH  180
TFPAVLQSSG LYSLSSVVTV PSSSLGTQTY ICNVNHKPSN TKVDKKVEPK SCDKTHTCPP  240
CPAPELLGGP SVFLFPPKPK DTLMISRTPE VTCVVVDVSH EDPEVKFNWY VDGVEVHNAK  300
TKPREEQYNS TYRVVSVLTV LHQDWLNGKE YKCKVSNKAL PAPIEKTISK AKGQPREPQV  360
YTLPPSRDEL TKNQVSLTCL VKGFYPSDIA VEWESNGQPE NNYKTTPPVL DSDGSFFLYS  420
KLTVDKSRWQ QGNVFSCSVL HEALHSHYTQ KSLSLSPGK                         459

SEQ ID NO: 284        moltype = AA   length = 216
FEATURE               Location/Qualifiers
source                1..216
                      mol_type = protein
                      organism = synthetic construct
SEQUENCE: 284
QSALTQPPSA SGSLGQSVTI SCNGTSSDIG GWNFVSWYQQ FPGRAPRLII FEVNKRPSGV   60
PGRFSGSKSG NSASLTVSGL QSDDEGQYFC SSLFGRWDVV FGGGTKLTVL GQPKAAPSVT  120
LFPPSSEELQ ANKATLVCLI SDFYPGAVTV AWKADSSPVK AGVETTTPSK QSNNKYAASS  180
YLSLTPEQWK SHRSYSCQVT HEGSTVEKTV APTECS                           216

SEQ ID NO: 285        moltype = AA   length = 129
FEATURE               Location/Qualifiers
source                1..129
                      mol_type = protein
                      organism = synthetic construct
SEQUENCE: 285
QVQLQESGPG LVKPSETLSL TCTVSGDSIN TGHHYWGWVR QVPGKGPEWI AHIHYNTAVL   60
HNPALKSRVT ISIFTLKNLI TLSLSNVTAA DTAVYFCVRS GGDILYYIEW QKPHWFYPWG  120
PGILVTVSS                                                          129

SEQ ID NO: 286        moltype = AA   length = 110
FEATURE               Location/Qualifiers
source                1..110
                      mol_type = protein
                      organism = synthetic construct
SEQUENCE: 286
QSALTQPPSA SGSLGQSLTI SCSGTGSDIG SWNFVSWYQQ FPGRAPNLII FEVNRRRSGV   60
PDRFSGSKSG NTASLTVSGL RSEDEAEYFC SSLSGRWDIV FGGGTKVTVL             110

SEQ ID NO: 287        moltype = AA   length = 459
FEATURE               Location/Qualifiers
source                1..459
                      mol_type = protein
                      organism = synthetic construct
```

```
SEQUENCE: 287
QVQLQESGPG LVKPSETLSL TCTVSGDSIN TGHHYWGWVR QVPGKGPEWI AHIHYNTAVL    60
HNPALKSRVT ISIFTLKNLI TLSLSNVTAA DTAVYFCVRS GGDILYYIEW QKPHWFYPWG   120
PGILVTVSSA STKGPSVFPL APSSKSTSGG TAALGCLVKD YFPEPVTVSW NSGALTSGVH   180
TFPAVLQSSG LYSLSSVVTV PSSSLGTQTY ICNVNHKPSN TKVDKKVEPK SCDKTHTCPP   240
CPAPELLGGP SVFLFPPKPK DTLMISRTPE VTCVVVDVSH EDPEVKFNWY VDGVEVHNAK   300
TKPREEQYNS TYRVVSVLTV LHQDWLNGKE YKCKVSNKAL PAPIEKTISK AKGQPREPQV   360
YTLPPSRDEL TKNQVSLTCL VKGFYPSDIA VEWESNGQPE NNYKTTPPVL DSDGSFFLYS   420
KLTVDKSRWQ QGNVFSCSVM HEALHNHYTQ KSLSLSPGK                         459

SEQ ID NO: 288          moltype = AA   length = 459
FEATURE                 Location/Qualifiers
source                  1..459
                        mol_type = protein
                        organism = synthetic construct
SEQUENCE: 288
QVQLQESGPG LVKPSETLSL TCTVSGDSIN TGHHYWGWVR QVPGKGPEWI AHIHYNTAVL    60
HNPALKSRVT ISIFTLKNLI TLSLSNVTAA DTAVYFCVRS GGDILYYIEW QKPHWFYPWG   120
PGILVTVSSA STKGPSVFPL APSSKSTSGG TAALGCLVKD YFPEPVTVSW NSGALTSGVH   180
TFPAVLQSSG LYSLSSVVTV PSSSLGTQTY ICNVNHKPSN TKVDKKVEPK SCDKTHTCPP   240
CPAPELLGGP SVFLFPPKPK DTLMISRTPE VTCVVVDVSH EDPEVKFNWY VDGVEVHNAK   300
TKPREEQYNS TYRVVSVLTV LHQDWLNGKE YKCKVSNKAL PAPIEKTISK AKGQPREPQV   360
YTLPPSRDEL TKNQVSLTCL VKGFYPSDIA VEWESNGQPE NNYKTTPPVL DSDGSFFLYS   420
KLTVDKSRWQ QGNVFSCSVL HEALHSHYTQ KSLSLSPGK                         459

SEQ ID NO: 289          moltype = AA   length = 216
FEATURE                 Location/Qualifiers
source                  1..216
                        mol_type = protein
                        organism = synthetic construct
SEQUENCE: 289
QSALTQPPSA SGSLGQSLTI SCSGTGSDIG SWNFVSWYQQ FPGRAPNLII FEVNRRRSGV    60
PDRFSGSKSG NTASLTVSGL RSEDEAEYFC SSLSGRWDIV FGGGTKVTVL GQPKAAPSVT   120
LFPPSSEELQ ANKATLVCLI SDFYPGAVTV AWKADSSPVK AGVETTTPSK QSNNKYAASS   180
YLSLTPEQWK SHRSYSCQVT HEGSTVEKTV APTECS                            216

SEQ ID NO: 290          moltype = AA   length = 134
FEATURE                 Location/Qualifiers
source                  1..134
                        mol_type = protein
                        organism = synthetic construct
SEQUENCE: 290
QLQLQESGPG LVKPSETLSL TCTVSGGSMR GTDWGENDFH YGWIRQSSAK GLEWIGSIHW    60
RGRTTHYKTS FRSRATLSID TSNNRFSLTF SFVTAADTAV YYCARHKYHD IFRVVPVAGW   120
FDPWGQGLLV TVSS                                                    134

SEQ ID NO: 291          moltype = AA   length = 107
FEATURE                 Location/Qualifiers
source                  1..107
                        mol_type = protein
                        organism = synthetic construct
SEQUENCE: 291
EIVMTQSPPT LSVSPGETAT LSCRASQNVK NNLAWYQLKP GQAPRLLIFD ASSRAGGIPD    60
RFSGSGYGTD FTLTVNSVQS EDFGDYFCQQ YEEWPRTFGQ GTKVDIK                107

SEQ ID NO: 292          moltype = AA   length = 464
FEATURE                 Location/Qualifiers
source                  1..464
                        mol_type = protein
                        organism = synthetic construct
SEQUENCE: 292
QLQLQESGPG LVKPSETLSL TCTVSGGSMR GTDWGENDFH YGWIRQSSAK GLEWIGSIHW    60
RGRTTHYKTS FRSRATLSID TSNNRFSLTF SFVTAADTAV YYCARHKYHD IFRVVPVAGW   120
FDPWGQGLLV TVSSASTKGP SVFPLAPSSK STSGGTAALG CLVKDYFPEP VTVSWNSGAL   180
TSGVHTFPAV LQSSGLYSLS SVVTVPSSSL GTQTYICNVN HKPSNTKVDK VEPKSCDKT   240
HTCPPCPAPE LLGGPSVFLF PPKPKDTLMI SRTPEVTCVV VDVSHEDPEV KFNWYVDGVE   300
VHNAKTKPRE EQYNSTYRVV SVLTVLHQDW LNGKEYKCKV SNKALPAPIE KTISKAKGQP   360
REPQVYTLPP SRDELTKNQV SLTCLVKGFY PSDIAVEWES NGQPENNYKT TPPVLDSDGS   420
FFLYSKLTVD KSRWQQGNVF SCSVMHEALH NHYTQKSLSL SPGK                   464

SEQ ID NO: 293          moltype = AA   length = 464
FEATURE                 Location/Qualifiers
source                  1..464
                        mol_type = protein
                        organism = synthetic construct
SEQUENCE: 293
QLQLQESGPG LVKPSETLSL TCTVSGGSMR GTDWGENDFH YGWIRQSSAK GLEWIGSIHW    60
RGRTTHYKTS FRSRATLSID TSNNRFSLTF SFVTAADTAV YYCARHKYHD IFRVVPVAGW   120
FDPWGQGLLV TVSSASTKGP SVFPLAPSSK STSGGTAALG CLVKDYFPEP VTVSWNSGAL   180
```

```
TSGVHTFPAV LQSSGLYSLS SVVTVPSSSL GTQTYICNVN HKPSNTKVDK KVEPKSCDKT  240
HTCPPCPAPE LLGGPSVFLF PPKPKDTLMI SRTPEVTCVV VDVSHEDPEV KFNWYVDGVE  300
VHNAKTKPRE EQYNSTYRVV SVLTVLHQDW LNGKEYKCKV SNKALPAPIE KTISKAKGQP  360
REPQVYTLPP SRDELTKNQV SLTCLVKGFY PSDIAVEWES NGQPENNYKT TPPVLDSDGS  420
FFLYSKLTVD KSRWQQGNVF SCSVLHEALH SHYTQKSLSL SPGK  464
```

```
SEQ ID NO: 294             moltype = AA   length = 214
FEATURE                    Location/Qualifiers
source                     1..214
                           mol_type = protein
                           organism = synthetic construct
SEQUENCE: 294
EIVMTQSPPT LSVSPGETAT LSCRASQNVK NNLAWYQLKP GQAPRLLIFD ASSRAGGIPD  60
RFSGSGYGTD FTLTVNSVQS EDFGDYFCQQ YEEWPRTFGQ GTKVDIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC  214
```

```
SEQ ID NO: 295             moltype = AA   length = 133
FEATURE                    Location/Qualifiers
source                     1..133
                           mol_type = protein
                           organism = synthetic construct
SEQUENCE: 295
EVHLEESGPG LVRPSETLSL TCTASGGSIR GGEWGDSDYH WGWVRHSPEK GLEWIGSIHW  60
RGTTHYNAPF RGRGRLSIDL SRNQFSLRLT SVTAEDTAVY YCVKHKYHDI VMVVPIAGWF  120
DPWGQGLQVT VSS  133
```

```
SEQ ID NO: 296             moltype = AA   length = 107
FEATURE                    Location/Qualifiers
source                     1..107
                           mol_type = protein
                           organism = synthetic construct
SEQUENCE: 296
EIMMTQSPAI LSVSPGDRAT LSCRASQSVK NNLAWYQKRP GQAPRLLIFD TSSRASGIPA  60
RFSGGGSGTE FTLTVNSMQS EDFATYYCQQ YEEWPRTFGQ GTKVEIK  107
```

```
SEQ ID NO: 297             moltype = AA   length = 463
FEATURE                    Location/Qualifiers
source                     1..463
                           mol_type = protein
                           organism = synthetic construct
SEQUENCE: 297
EVHLEESGPG LVRPSETLSL TCTASGGSIR GGEWGDSDYH WGWVRHSPEK GLEWIGSIHW  60
RGTTHYNAPF RGRGRLSIDL SRNQFSLRLT SVTAEDTAVY YCVKHKYHDI VMVVPIAGWF  120
DPWGQGLQVT VSSASTKGPS VFPLAPSSKS TSGGTAALGC LVKDYFPEPV TVSWNSGALT  180
SGVHTFPAVL QSSGLYSLSS VVTVPSSSLG TQTYICNVNH KPSNTKVDKK VEPKSCDKTH  240
TCPPCPAPEL LGGPSVFLFP PKPKDTLMIS RTPEVTCVVV DVSHEDPEVK FNWYVDGVEV  300
HNAKTKPREE QYNSTYRVVS VLTVLHQDWL NGKEYKCKVS NKALPAPIEK TISKAKGQPR  360
EPQVYTLPPS RDELTKNQVS LTCLVKGFYP SDIAVEWESN GQPENNYKTT PPVLDSDGSF  420
FLYSKLTVDK SRWQQGNVFS CSVMHEALHN HYTQKSLSLS PGK  463
```

```
SEQ ID NO: 298             moltype = AA   length = 463
FEATURE                    Location/Qualifiers
source                     1..463
                           mol_type = protein
                           organism = synthetic construct
SEQUENCE: 298
EVHLEESGPG LVRPSETLSL TCTASGGSIR GGEWGDSDYH WGWVRHSPEK GLEWIGSIHW  60
RGTTHYNAPF RGRGRLSIDL SRNQFSLRLT SVTAEDTAVY YCVKHKYHDI VMVVPIAGWF  120
DPWGQGLQVT VSSASTKGPS VFPLAPSSKS TSGGTAALGC LVKDYFPEPV TVSWNSGALT  180
SGVHTFPAVL QSSGLYSLSS VVTVPSSSLG TQTYICNVNH KPSNTKVDKK VEPKSCDKTH  240
TCPPCPAPEL LGGPSVFLFP PKPKDTLMIS RTPEVTCVVV DVSHEDPEVK FNWYVDGVEV  300
HNAKTKPREE QYNSTYRVVS VLTVLHQDWL NGKEYKCKVS NKALPAPIEK TISKAKGQPR  360
EPQVYTLPPS RDELTKNQVS LTCLVKGFYP SDIAVEWESN GQPENNYKTT PPVLDSDGSF  420
FLYSKLTVDK SRWQQGNVFS CSVLHEALHS HYTQKSLSLS PGK  463
```

```
SEQ ID NO: 299             moltype = AA   length = 214
FEATURE                    Location/Qualifiers
source                     1..214
                           mol_type = protein
                           organism = synthetic construct
SEQUENCE: 299
EIMMTQSPAI LSVSPGDRAT LSCRASQSVK NNLAWYQKRP GQAPRLLIFD TSSRASGIPA  60
RFSGGGSGTE FTLTVNSMQS EDFATYYCQQ YEEWPRTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC  214
```

```
SEQ ID NO: 300             moltype = AA   length = 131
FEATURE                    Location/Qualifiers
```

```
source                        1..131
                              mol_type = protein
                              organism = synthetic construct
SEQUENCE: 300
EVQLVESGGG LVKPGGSLRL TCVASGFTFS DVWLNWVRQA PGKGLEWVGR IKSRTDGGTT   60
DYAASVKGRF TISRDDSKNT LYLQMNSLKT EDTAVYSCTT DGFIMIRGVS EDYYYYYMDV  120
WGKGTTVTVS S                                                      131

SEQ ID NO: 301               moltype = AA  length = 111
FEATURE                      Location/Qualifiers
source                        1..111
                              mol_type = protein
                              organism = synthetic construct
SEQUENCE: 301
QSVLTQPPSV SAAPGQKVTI SCSGSSSNIG NNYVLWYQQF PGTAPKLLIY GNNKRPSGIP   60
DRFSGSKSGT SATLGITGLQ TGDEADYFCA TWDSGLSADW VFGGGTKLTV L          111

SEQ ID NO: 302               moltype = AA  length = 461
FEATURE                      Location/Qualifiers
source                        1..461
                              mol_type = protein
                              organism = synthetic construct
SEQUENCE: 302
EVQLVESGGG LVKPGGSLRL TCVASGFTFS DVWLNWVRQA PGKGLEWVGR IKSRTDGGTT   60
DYAASVKGRF TISRDDSKNT LYLQMNSLKT EDTAVYSCTT DGFIMIRGVS EDYYYYYMDV  120
WGKGTTVTVS SASTKGPSVF PLAPSSKSTS GGTAALGCLV KDYFPEPVTV SWNSGALTSG  180
VHTFPAVLQS SGLYSLSSVV TVPSSSLGTQ TYICNVNHKP SNTKVDKKVE PKSCDKTHTC  240
PPCPAPELLG GPSVFLFPPK PKDTLMISRT PEVTCVVVDV SHEDPEVKFN WYVDGVEVHN  300
AKTKPREEQY NSTYRVVSVL TVLHQDWLNG KEYKCKVSNK ALPAPIEKTI SKAKGQPREP  360
QVYTLPPSRD ELTKNQVSLT CLVKGFYPSD IAVEWESNGQ PENNYKTTPP VLDSDGSFFL  420
YSKLTVDKSR WQQGNVFSCS VMHEALHNHY TQKSLSLSPG K                    461

SEQ ID NO: 303               moltype = AA  length = 461
FEATURE                      Location/Qualifiers
source                        1..461
                              mol_type = protein
                              organism = synthetic construct
SEQUENCE: 303
EVQLVESGGG LVKPGGSLRL TCVASGFTFS DVWLNWVRQA PGKGLEWVGR IKSRTDGGTT   60
DYAASVKGRF TISRDDSKNT LYLQMNSLKT EDTAVYSCTT DGFIMIRGVS EDYYYYYMDV  120
WGKGTTVTVS SASTKGPSVF PLAPSSKSTS GGTAALGCLV KDYFPEPVTV SWNSGALTSG  180
VHTFPAVLQS SGLYSLSSVV TVPSSSLGTQ TYICNVNHKP SNTKVDKKVE PKSCDKTHTC  240
PPCPAPELLG GPSVFLFPPK PKDTLMISRT PEVTCVVVDV SHEDPEVKFN WYVDGVEVHN  300
AKTKPREEQY NSTYRVVSVL TVLHQDWLNG KEYKCKVSNK ALPAPIEKTI SKAKGQPREP  360
QVYTLPPSRD ELTKNQVSLT CLVKGFYPSD IAVEWESNGQ PENNYKTTPP VLDSDGSFFL  420
YSKLTVDKSR WQQGNVFSCS VLHEALHSHY TQKSLSLSPG K                    461

SEQ ID NO: 304               moltype = AA  length = 217
FEATURE                      Location/Qualifiers
source                        1..217
                              mol_type = protein
                              organism = synthetic construct
SEQUENCE: 304
QSVLTQPPSV SAAPGQKVTI SCSGSSSNIG NNYVLWYQQF PGTAPKLLIY GNNKRPSGIP   60
DRFSGSKSGT SATLGITGLQ TGDEADYFCA TWDSGLSADW VFGGGTKLTV LGQPKAAPSV  120
TLFPPSSEEL QANKATLVCL ISDFYPGAVT VAWKADSSPV KAGVETTTPS KQSNNKYAAS  180
SYLSLTPEQW KSHRSYSCQV THEGSTVEKT VAPTECS                          217

SEQ ID NO: 305               moltype = AA  length = 123
FEATURE                      Location/Qualifiers
source                        1..123
                              mol_type = protein
                              organism = synthetic construct
SEQUENCE: 305
QVQLVQSGGG LVQPGGSLRL SCAAFGFNFS SYVMHWVRQA PGQGLEYLSA ISSDGETTYH   60
ANSVKGRFTS SRDNSKNTLF LQMGSLRTED VAVYYCARDR YYETSGSNAF DVWGQGTMVV  120
VSS                                                              123

SEQ ID NO: 306               moltype = AA  length = 108
FEATURE                      Location/Qualifiers
source                        1..108
                              mol_type = protein
                              organism = synthetic construct
SEQUENCE: 306
NSVLTQSPSS LSASVGDRVT ITCQASQDIS NYLNWYQHKP GKAPKLLIYT ASNLETGVPS   60
RFSGGGSGTH FSFTITSLQP EDAATYFCQQ YDNLGDLSFG GGTKVEIK             108

SEQ ID NO: 307               moltype = AA  length = 453
FEATURE                      Location/Qualifiers
```

-continued

```
source                   1..453
                         mol_type = protein
                         organism = synthetic construct
SEQUENCE: 307
QVQLVQSGGG LVQPGGSLRL SCAAFGFNFS SYVMHWVRQA PGQGLEYLSA ISSDGETTYH   60
ANSVKGRFTS SRDNSKNTLF LQMGSLRTED VAVYYCARDR YYETSGSNAF DVWGQGTMVV  120
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH TCPPCPAPEL  240
LGGPSVFLFP PKPKDTLMIS RTPEVTCVVV DVSHEDPEVK FNWYVDGVEV HNAKTKPREE  300
QYNSTYRVVS VLTVLHQDWL NGKEYKCKVS NKALPAPIEK TISKAKGQPR EPQVYTLPPS  360
RDELTKNQVS LTCLVKGFYP SDIAVEWESN GQPENNYKTT PPVLDSDGSF FLYSKLTVDK  420
SRWQQGNVFS CSVMHEALHN HYTQKSLSLS PGK                                453

SEQ ID NO: 308           moltype = AA  length = 453
FEATURE                  Location/Qualifiers
source                   1..453
                         mol_type = protein
                         organism = synthetic construct
SEQUENCE: 308
QVQLVQSGGG LVQPGGSLRL SCAAFGFNFS SYVMHWVRQA PGQGLEYLSA ISSDGETTYH   60
ANSVKGRFTS SRDNSKNTLF LQMGSLRTED VAVYYCARDR YYETSGSNAF DVWGQGTMVV  120
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH TCPPCPAPEL  240
LGGPSVFLFP PKPKDTLMIS RTPEVTCVVV DVSHEDPEVK FNWYVDGVEV HNAKTKPREE  300
QYNSTYRVVS VLTVLHQDWL NGKEYKCKVS NKALPAPIEK TISKAKGQPR EPQVYTLPPS  360
RDELTKNQVS LTCLVKGFYP SDIAVEWESN GQPENNYKTT PPVLDSDGSF FLYSKLTVDK  420
SRWQQGNVFS CSVLHEALHS HYTQKSLSLS PGK                                453

SEQ ID NO: 309           moltype = AA  length = 215
FEATURE                  Location/Qualifiers
source                   1..215
                         mol_type = protein
                         organism = synthetic construct
SEQUENCE: 309
NSVLTQSPSS LSASVGDRVT ITCQASQDIS NYLNWYQHKP GKAPKLLIYT ASNLETGVPS   60
RFSGGGSGTH FSFTITSLQP EDAATYFCQQ YDNLGDLSFG GGTKVEIKRT VAAPSVFIFP  120
PSDEQLKSGT ASVVCLLNNF YPREAKVQWK VDNALQSGNS QESVTEQDSK DSTYSLSSTL  180
TLSKADYEKH KVYACEVTHQ GLSSPVTKSF NRGEC                              215

SEQ ID NO: 310           moltype = AA  length = 130
FEATURE                  Location/Qualifiers
source                   1..130
                         mol_type = protein
                         organism = synthetic construct
SEQUENCE: 310
QVQLVQSGAE VRKPGSSVTI SCKPVGGTFT NFAIHWVRQA PGQGLEWVGG RVPVVGIYKY   60
GKKFHDRLRL YEDDPMKTVF LELRSLTSDD TGVYYCTRWR GCGMCPYDTS SYYNDASDVW  120
GPGTKVIVSA                                                         130

SEQ ID NO: 311           moltype = AA  length = 108
FEATURE                  Location/Qualifiers
source                   1..108
                         mol_type = protein
                         organism = synthetic construct
SEQUENCE: 311
EIVLTQSPVT LSLSSGETGT LSCRASQNIS SSWIAWYQQR RGQVPRLLIS AASARAAGIP   60
DRFTGRGSGT DFTLTITRLE PEDFGVYSCQ YYGGSFFTFG PGTQVDVK               108

SEQ ID NO: 312           moltype = AA  length = 460
FEATURE                  Location/Qualifiers
source                   1..460
                         mol_type = protein
                         organism = synthetic construct
SEQUENCE: 312
QVQLVQSGAE VRKPGSSVTI SCKPVGGTFT NFAIHWVRQA PGQGLEWVGG RVPVVGIYKY   60
GKKFHDRLRL YEDDPMKTVF LELRSLTSDD TGVYYCTRWR GCGMCPYDTS SYYNDASDVW  120
GPGTKVIVSA ASTKGPSVFP LAPSSKSTSG GTAALGCLVK DYFPEPVTVS WNSGALTSGV  180
HTFPAVLQSS GLYSLSSVVT VPSSSLGTQT YICNVNHKPS NTKVDKKVEP KSCDKTHTCP  240
PCPAPELLGG PSVFLFPPKP KDTLMISRTP EVTCVVVDVS HEDPEVKFNW YVDGVEVHNA  300
KTKPREEQYN STYRVVSLT VLHQDWLNGK EYKCKVSNKA LPAPIEKTIS KAKGQPREPQ  360
VYTLPPSRDE LTKNQVSLTC LVKGFYPSDI AVEWESNGQP ENNYKTTPPV LDSDGSFFLY  420
SKLTVDKSRW QQGNVFSCSV MHEALHNHYT QKSLSLSPGK                         460

SEQ ID NO: 313           moltype = AA  length = 460
FEATURE                  Location/Qualifiers
source                   1..460
                         mol_type = protein
                         organism = synthetic construct
SEQUENCE: 313
```

```
QVQLVQSGAE VRKPGSSVTI SCKPVGGTFT NFAIHWVRQA PGQGLEWVGG RVPVVGIYKY  60
GKKFHDRLRL YEDDPMKTVF LELRSLTSDD TGVYYCTRWR GCGMCPYDTS SYYNDASDVW 120
GPGTKVIVSA ASTKGPSVFP LAPSSKSTSG GTAALGCLVK DYFPEPVTVS WNSGALTSGV 180
HTFPAVLQSS GLYSLSSVVT VPSSSLGTQT YICNVNHKPS NTKVDKKVEP KSCDKTHTCP 240
PCPAPELLGG PSVFLPPPKP KDTLMISRTP EVTCVVVDVS HEDPEVKFNW YVDGVEVHNA 300
KTKPREEQYN STYRVVSVLT VLHQDWLNGK EYKCKVSNKA LPAPIEKTIS KAKGQPREPQ 360
VYTLPPSRDE LTKNQVSLTC LVKGFYPSDI AVEWESNGQP ENNYKTTPPV LDSDGSFFLY 420
SKLTVDKSRW QQGNVFSCSV LHEALHSHYT QKSLSLSPGK                       460

SEQ ID NO: 314            moltype = AA  length = 215
FEATURE                   Location/Qualifiers
source                    1..215
                          mol_type = protein
                          organism = synthetic construct
SEQUENCE: 314
EIVLTQSPVT LSLSSGETGT LSCRASQNIS SSWIAWYQQR RGQVPRLLIS AASARAAGIP  60
DRFTGRGSGT DFTLTITRLE PEDFGVYSCQ YYGGSFFTFG PGTQVDVKRT VAAPSVFIFP 120
PSDEQLKSGT ASVVCLLNNF YPREAKVQWK VDNALQSGNS QESVTEQDSK DSTYSLSSTL 180
TLSKADYEKH KVYACEVTHQ GLSSPVTKSF NRGEC                           215

SEQ ID NO: 315            moltype = AA  length = 123
FEATURE                   Location/Qualifiers
source                    1..123
                          mol_type = protein
                          organism = synthetic construct
SEQUENCE: 315
EVQLVESGGG LVKAGGSLIL SCGVSNFRIS AHTMNWVRRV PGGGLEWVAS ISTSSTYRDY  60
ADAVKGRFTV SRDDLEDFVY LQMHKMRVED TAIYYCARKG SDRLSDNDPF DAWGPGTVVT 120
VSP                                                              123

SEQ ID NO: 316            moltype = AA  length = 107
FEATURE                   Location/Qualifiers
source                    1..107
                          mol_type = protein
                          organism = synthetic construct
SEQUENCE: 316
DVVMTQSPST LSASVGDTIT ITCRASQSIE TWLAWYQQKP GKAPKLLIYK ASTLKTGVPS  60
RFSGSGSGTE FTLTISGLQF DDFATYHCQH YAGYSATFGQ GTRVEIK               107

SEQ ID NO: 317            moltype = AA  length = 453
FEATURE                   Location/Qualifiers
source                    1..453
                          mol_type = protein
                          organism = synthetic construct
SEQUENCE: 317
EVQLVESGGG LVKAGGSLIL SCGVSNFRIS AHTMNWVRRV PGGGLEWVAS ISTSSTYRDY  60
ADAVKGRFTV SRDDLEDFVY LQMHKMRVED TAIYYCARKG SDRLSDNDPF DAWGPGTVVT 120
VSPASTKGPS VFPLAPSSKS TSGGTAALGC LVKDYFPEPV TVSWNSGALT SGVHTFPAVL 180
QSSGLYSLSS VVTVPSSSLG TQTYICNVNH KPSNTKVDKK VEPKSCDKTH TCPPCPAPEL 240
LGGPSVFLFP PKPKDTLMIS RTPEVTCVVV DVSHEDPEVK FNWYVDGVEV HNAKTKPREE 300
QYNSTYRVVS VLTVLHQDWL NGKEYKCKVS NKALPAPIEK TISKAKGQPR EPQVYTLPPS 360
RDELTKNQVS LTCLVKGFYP SDIAVEWESN GQPENNYKTT PPVLDSDGSF FLYSKLTVDK 420
SRWQQGNVFS CSVMHEALHN HYTQKSLSLS PGK                             453

SEQ ID NO: 318            moltype = AA  length = 453
FEATURE                   Location/Qualifiers
source                    1..453
                          mol_type = protein
                          organism = synthetic construct
SEQUENCE: 318
EVQLVESGGG LVKAGGSLIL SCGVSNFRIS AHTMNWVRRV PGGGLEWVAS ISTSSTYRDY  60
ADAVKGRFTV SRDDLEDFVY LQMHKMRVED TAIYYCARKG SDRLSDNDPF DAWGPGTVVT 120
VSPASTKGPS VFPLAPSSKS TSGGTAALGC LVKDYFPEPV TVSWNSGALT SGVHTFPAVL 180
QSSGLYSLSS VVTVPSSSLG TQTYICNVNH KPSNTKVDKK VEPKSCDKTH TCPPCPAPEL 240
LGGPSVFLFP PKPKDTLMIS RTPEVTCVVV DVSHEDPEVK FNWYVDGVEV HNAKTKPREE 300
QYNSTYRVVS VLTVLHQDWL NGKEYKCKVS NKALPAPIEK TISKAKGQPR EPQVYTLPPS 360
RDELTKNQVS LTCLVKGFYP SDIAVEWESN GQPENNYKTT PPVLDSDGSF FLYSKLTVDK 420
SRWQQGNVFS CSVLHEALHS HYTQKSLSLS PGK                             453

SEQ ID NO: 319            moltype = AA  length = 214
FEATURE                   Location/Qualifiers
source                    1..214
                          mol_type = protein
                          organism = synthetic construct
SEQUENCE: 319
DVVMTQSPST LSASVGDTIT ITCRASQSIE TWLAWYQQKP GKAPKLLIYK ASTLKTGVPS  60
RFSGSGSGTE FTLTISGLQF DDFATYHCQH YAGYSATFGQ GTRVEIKRTV AAPSVFIFPP 120
SDEQLKSGTA SVVCLLNNFY PREAKVQWKV DNALQSGNSQ ESVTEQDSKD STYSLSSTLT 180
LSKADYEKHK VYACEVTHQG LSSPVTKSFN RGEC                            214
```

```
SEQ ID NO: 320          moltype = AA  length = 132
FEATURE                 Location/Qualifiers
source                  1..132
                        mol_type = protein
                        organism = synthetic construct
SEQUENCE: 320
QMQLQESGPG LVKPGETLSL TCSVSGASIS SSYWSWLRET PGKGLEWIGY THHSGDTNYA   60
PSLKSRVHLG LHPSKNQVSL SLTSVTAADT AVYYCARTLH GRRIYGVVAF NEFFTYFYWE  120
VWGKGTQVTV SS                                                      132

SEQ ID NO: 321          moltype = AA  length = 105
FEATURE                 Location/Qualifiers
source                  1..105
                        mol_type = protein
                        organism = synthetic construct
SEQUENCE: 321
SDISVAPGET VRISCGGESI GSRAVQWYQH RAGQAPKLII YNNQDRPPGI PERFSGSPDI   60
DFGTTATLTI TNVEAGDEAT YYCHIWDSRR PTNWVFGGGT TLTVL                  105

SEQ ID NO: 322          moltype = AA  length = 462
FEATURE                 Location/Qualifiers
source                  1..462
                        mol_type = protein
                        organism = synthetic construct
SEQUENCE: 322
QMQLQESGPG LVKPGETLSL TCSVSGASIS SSYWSWLRET PGKGLEWIGY THHSGDTNYA   60
PSLKSRVHLG LHPSKNQVSL SLTSVTAADT AVYYCARTLH GRRIYGVVAF NEFFTYFYWE  120
VWGKGTQVTV SSASTKGPSV FPLAPSSKST SGGTAALGCL VKDYFPEPVT VSWNSGALTS  180
GVHTFPAVLQ SSGLYSLSSV VTVPSSSLGT QTYICNVNHK PSNTKVDKKV EPKSCDKTHT  240
CPPCPAPELL GGPSVFLFPP KPKDTLMISR TPEVTCVVVD VSHEDPEVKF NWYVDGVEVH  300
NAKTKPREEQ YNSTYRVVSV LTVLHQDWLN GKEYKCKVSN KALPAPIEKT ISKAKGQPRE  360
PQVYTLPPSR DELTKNQVSL TCLVKGFYPS DIAVEWESNG QPENNYKTTP PVLDSDGSFF  420
LYSKLTVDKS RWQQGNVFSC SVMHEALHNH YTQKSLSLSP GK                     462

SEQ ID NO: 323          moltype = AA  length = 462
FEATURE                 Location/Qualifiers
source                  1..462
                        mol_type = protein
                        organism = synthetic construct
SEQUENCE: 323
QMQLQESGPG LVKPGETLSL TCSVSGASIS SSYWSWLRET PGKGLEWIGY THHSGDTNYA   60
PSLKSRVHLG LHPSKNQVSL SLTSVTAADT AVYYCARTLH GRRIYGVVAF NEFFTYFYWE  120
VWGKGTQVTV SSASTKGPSV FPLAPSSKST SGGTAALGCL VKDYFPEPVT VSWNSGALTS  180
GVHTFPAVLQ SSGLYSLSSV VTVPSSSLGT QTYICNVNHK PSNTKVDKKV EPKSCDKTHT  240
CPPCPAPELL GGPSVFLFPP KPKDTLMISR TPEVTCVVVD VSHEDPEVKF NWYVDGVEVH  300
NAKTKPREEQ YNSTYRVVSV LTVLHQDWLN GKEYKCKVSN KALPAPIEKT ISKAKGQPRE  360
PQVYTLPPSR DELTKNQVSL TCLVKGFYPS DIAVEWESNG QPENNYKTTP PVLDSDGSFF  420
LYSKLTVDKS RWQQGNVFSC SVLHEALHSH YTQKSLSLSP GK                     462

SEQ ID NO: 324          moltype = AA  length = 211
FEATURE                 Location/Qualifiers
source                  1..211
                        mol_type = protein
                        organism = synthetic construct
SEQUENCE: 324
SDISVAPGET VRISCGGESI GSRAVQWYQH RAGQAPKLII YNNQDRPPGI PERFSGSPDI   60
DFGTTATLTI TNVEAGDEAT YYCHIWDSRR PTNWVFGGGT TLTVLGQPKA APSVTLFPPS  120
SEELQANKAT LVCLISDFYP GAVTVAWKAD SSPVKAGVET TTPSKQSNNK YAASSYLSLT  180
PEQWKSHRSY SCQVTHEGST VEKTVAPTEC S                                 211

SEQ ID NO: 325          moltype = AA  length = 132
FEATURE                 Location/Qualifiers
source                  1..132
                        mol_type = protein
                        organism = synthetic construct
SEQUENCE: 325
QMQLQESGPG LVKPGETLSL TCSVSGASIS SSYWSWLRET PGKGLEWIGY THHSGDTNYA   60
PSLKSRVHLG LHPSKNQVSL SLTSVTAADT AVYYCARTLH GRRIYGVVAF NEYYTYFYWP  120
TWGKGTQVTV SS                                                      132

SEQ ID NO: 326          moltype = AA  length = 105
FEATURE                 Location/Qualifiers
source                  1..105
                        mol_type = protein
                        organism = synthetic construct
SEQUENCE: 326
SDISVAPGET VRITCGGESI GSRAVQWYQH RPGQAPRLII YNNQDRPPGI PERFSGSPDI   60
DFGTTATLTI SNVEAGDEAT YYCHIWDSRR PTNWELGPGT TLTVL                  105
```

```
SEQ ID NO: 327          moltype = AA  length = 462
FEATURE                 Location/Qualifiers
source                  1..462
                        mol_type = protein
                        organism = synthetic construct
SEQUENCE: 327
QMQLQESGPG LVKPGETLSL TCSVSGASIS SSYWSWLRET PGKGLEWIGY THHSGDTNYA  60
PSLKSRVHLG LHPSKNQVSL SLTSVTAADT AVYYCARTLH GRRIYGVVAF NEYYTYFYWP  120
TWGKGTQVTV SSASTKGPSV FPLAPSSKST SGGTAALGCL VKDYFPEPVT VSWNSGALTS  180
GVHTFPAVLQ SSGLYSLSSV VTVPSSSLGT QTYICNVNHK PSNTKVDKKV EPKSCDKTHT  240
CPPCPAPELL GGPSVFLFPP KPKDTLMISR TPEVTCVVVD VSHEDPEVKF NWYVDGVEVH  300
NAKTKPREEQ YNSTYRVVSV LTVLHQDWLN GKEYKCKVSN KALPAPIEKT ISKAKGQPRE  360
PQVYTLPPSR DELTKNQVSL TCLVKGFYPS DIAVEWESNG QPENNYKTTP PVLDSDGSFF  420
LYSKLTVDKS RWQQGNVFSC SVMHEALHNH YTQKSLSLSP GK                     462

SEQ ID NO: 328          moltype = AA  length = 462
FEATURE                 Location/Qualifiers
source                  1..462
                        mol_type = protein
                        organism = synthetic construct
SEQUENCE: 328
QMQLQESGPG LVKPGETLSL TCSVSGASIS SSYWSWLRET PGKGLEWIGY THHSGDTNYA  60
PSLKSRVHLG LHPSKNQVSL SLTSVTAADT AVYYCARTLH GRRIYGVVAF NEYYTYFYWP  120
TWGKGTQVTV SSASTKGPSV FPLAPSSKST SGGTAALGCL VKDYFPEPVT VSWNSGALTS  180
GVHTFPAVLQ SSGLYSLSSV VTVPSSSLGT QTYICNVNHK PSNTKVDKKV EPKSCDKTHT  240
CPPCPAPELL GGPSVFLFPP KPKDTLMISR TPEVTCVVVD VSHEDPEVKF NWYVDGVEVH  300
NAKTKPREEQ YNSTYRVVSV LTVLHQDWLN GKEYKCKVSN KALPAPIEKT ISKAKGQPRE  360
PQVYTLPPSR DELTKNQVSL TCLVKGFYPS DIAVEWESNG QPENNYKTTP PVLDSDGSFF  420
LYSKLTVDKS RWQQGNVFSC SVLHEALHSH YTQKSLSLSP GK                     462

SEQ ID NO: 329          moltype = AA  length = 211
FEATURE                 Location/Qualifiers
source                  1..211
                        mol_type = protein
                        organism = synthetic construct
SEQUENCE: 329
SDISVAPGET VRITCGGESI GSRAVQWYQH RPGQAPRLII YNNQDRPPGI PERFSGSPDI  60
DFGTTATLTI SNVEAGDEAT YYCHIWDSRR PTNWELGPGT TLTVLGQPKA APSVTLFPPS  120
SEELQANKAT LVCLISDFYP GAVTVAWKAD SSPVKAGVET TTPSKQSNNK YAASSYLSLT  180
PEQWKSHRSY SCQVTHEGST VEKTVAPTEC S                                 211

SEQ ID NO: 330          moltype = AA  length = 132
FEATURE                 Location/Qualifiers
source                  1..132
                        mol_type = protein
                        organism = synthetic construct
SEQUENCE: 330
QMQLQESGPG LVKPGETLSL TCSVSGASIS SSYWSWLRET PGKGLEWIGY THHSGDTNYA  60
PSLKSRVTIG LDPSKNQVSL SLTSVTAADT AVYYCARTLH GRRIYGVVAF NEYYTYFYWP  120
TWGKGTQVTV SS                                                      132

SEQ ID NO: 331          moltype = AA  length = 462
FEATURE                 Location/Qualifiers
source                  1..462
                        mol_type = protein
                        organism = synthetic construct
SEQUENCE: 331
QMQLQESGPG LVKPGETLSL TCSVSGASIS SSYWSWLRET PGKGLEWIGY THHSGDTNYA  60
PSLKSRVTIG LDPSKNQVSL SLTSVTAADT AVYYCARTLH GRRIYGVVAF NEYYTYFYWP  120
TWGKGTQVTV SSASTKGPSV FPLAPSSKST SGGTAALGCL VKDYFPEPVT VSWNSGALTS  180
GVHTFPAVLQ SSGLYSLSSV VTVPSSSLGT QTYICNVNHK PSNTKVDKKV EPKSCDKTHT  240
CPPCPAPELL GGPSVFLFPP KPKDTLMISR TPEVTCVVVD VSHEDPEVKF NWYVDGVEVH  300
NAKTKPREEQ YNSTYRVVSV LTVLHQDWLN GKEYKCKVSN KALPAPIEKT ISKAKGQPRE  360
PQVYTLPPSR DELTKNQVSL TCLVKGFYPS DIAVEWESNG QPENNYKTTP PVLDSDGSFF  420
LYSKLTVDKS RWQQGNVFSC SVMHEALHNH YTQKSLSLSP GK                     462

SEQ ID NO: 332          moltype = AA  length = 462
FEATURE                 Location/Qualifiers
source                  1..462
                        mol_type = protein
                        organism = synthetic construct
SEQUENCE: 332
QMQLQESGPG LVKPGETLSL TCSVSGASIS SSYWSWLRET PGKGLEWIGY THHSGDTNYA  60
PSLKSRVTIG LDPSKNQVSL SLTSVTAADT AVYYCARTLH GRRIYGVVAF NEYYTYFYWP  120
TWGKGTQVTV SSASTKGPSV FPLAPSSKST SGGTAALGCL VKDYFPEPVT VSWNSGALTS  180
GVHTFPAVLQ SSGLYSLSSV VTVPSSSLGT QTYICNVNHK PSNTKVDKKV EPKSCDKTHT  240
CPPCPAPELL GGPSVFLFPP KPKDTLMISR TPEVTCVVVD VSHEDPEVKF NWYVDGVEVH  300
NAKTKPREEQ YNSTYRVVSV LTVLHQDWLN GKEYKCKVSN KALPAPIEKT ISKAKGQPRE  360
```

```
PQVYTLPPSR DELTKNQVSL TCLVKGFYPS DIAVEWESNG QPENNYKTTP PVLDSDGSFF  420
LYSKLTVDKS RWQQGNVFSC SVLHEALHSH YTQKSLSLSP GK                      462

SEQ ID NO: 333            moltype = AA  length = 132
FEATURE                   Location/Qualifiers
source                    1..132
                          mol_type = protein
                          organism = synthetic construct
SEQUENCE: 333
QMQLQESGPG LVKPGETLSL TCSVSGASIS SSYWSWLRET PGKGLEWIGY THHSGDTNYA  60
PSLKSRVTIG LDPSKNQVSL SLTSVTAADT AVYYCARTLH GRRIYGVVAF NEYYTYFYWP  120
TWGKGTQVTV SS                                                      132

SEQ ID NO: 334            moltype = AA  length = 110
FEATURE                   Location/Qualifiers
source                    1..110
                          mol_type = protein
                          organism = synthetic construct
SEQUENCE: 334
QSVLTQPPSA SGSPGQSVTI SCTGTSSDIG ASDYVSWYQQ YPGEAPKVII YDVTKRPSGV  60
PDRFSGSKSG TTASLTVSGL QAEDEADYYC SSDAGRHTLL FGGGTKVTVL             110

SEQ ID NO: 335            moltype = AA  length = 451
FEATURE                   Location/Qualifiers
source                    1..451
                          mol_type = protein
                          organism = synthetic construct
SEQUENCE: 335
QVQLLESGPG LVRPSETLTL TCSVFNSRVS GYYYSWIRQP PGRGLEWIAS THFSLRPSRN  60
PSLLSRVTTS IDTERYQVFL NMRSVTAADT AVYFCARGDA SGWRADYFPH WGQGTLVVVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSCDKTHTC PPCPAPELLG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPAPIEKTI SKAKGQPREP QVYTLPPSRD  360
ELTKNQVSLT CLVKGFYPSD IAVEWESNGQ PENNYKTTPP VLDSDGSFFL YSKLTVDKSR  420
WQQGNVFSCS VMHEALHNHY TQKSLSLSPG K                                 451

SEQ ID NO: 336            moltype = AA  length = 451
FEATURE                   Location/Qualifiers
source                    1..451
                          mol_type = protein
                          organism = synthetic construct
SEQUENCE: 336
QVQLLESGPG LVRPSETLTL TCSVFNSRVS GYYYSWIRQP PGRGLEWIAS THFSLRPSRN  60
PSLLSRVTTS IDTERYQVFL NMRSVTAADT AVYFCARGDA SGWRADYFPH WGQGTLVVVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSCDKTHTC PPCPAPELLG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPAPIEKTI SKAKGQPREP QVYTLPPSRD  360
ELTKNQVSLT CLVKGFYPSD IAVEWESNGQ PENNYKTTPP VLDSDGSFFL YSKLTVDKSR  420
WQQGNVFSCS VLHEALHSHY TQKSLSLSPG K                                 451

SEQ ID NO: 337            moltype = AA  length = 216
FEATURE                   Location/Qualifiers
source                    1..216
                          mol_type = protein
                          organism = synthetic construct
SEQUENCE: 337
QSVLTQPPSA SGSPGQSVTI SCTGTSSDIG ASDYVSWYQQ YPGEAPKVII YDVTKRPSGV  60
PDRFSGSKSG TTASLTVSGL QAEDEADYYC SSDAGRHTLL FGGGTKVTVL GQPKAAPSVT  120
LFPPSSEELQ ANKATLVCLI SDFYPGAVTV AWKADSSPVK AGVETTTPSK QSNNKYAASS  180
YLSLTPEQWK SHRSYSCQVT HEGSTVEKTV APTECS                            216

SEQ ID NO: 338            moltype = AA  length = 566
FEATURE                   Location/Qualifiers
source                    1..566
                          mol_type = protein
                          organism = synthetic construct
SEQUENCE: 338
KKVVYGKCGD TVELTCTASQ KKNIQFHWKN SNQIKILGNQ GSFLTKGPSK LNDRVDSRRS  60
LWDQGNFPLI IKNLKPEDSD TYICEVEDQK EEVQLVVVCG GGGSQVHLQE SGPGLVKPSE  120
TLSLTCNVSG TLVRDNYWSW IRQPLGKQPE WIGYVHDSGD TNYNPSLKSR VHLSLDKSKN  180
LVSLRLTGVT AADSAIYYCA TTKHGRRIYG VVAFKEWFTY FYMDVWGKGT SVTVSSASTK  240
GPSVFPLAPS SKSTSGGTAA LGCLVKDYFP EPVTVSWNSG ALTSGVHTFP AVLQSSGLYS  300
LSSVVTVPSS SLGTQTYICN VNHKPSNTKV DKKVEPKSCD KTHTCPPCPA PELLGGPSVF  360
LFPPKPKDTL MISRTPEVTC VVVDVSHEDP EVKFNWYVDG VEVHNAKTKP REEQYNSTYR  420
VVSVLTVLHQ DWLNGKEYKC KVSNKALPAP IEKTISKAKG QPREPQVYTL PPSRDELTKN  480
QVSLTCLVKG FYPSDIAVEW ESNGQPENNY KTTPPVLDSD GSFFLYSKLT VDKSRWQQGN  540
VFSCSVLHEA LHSHYTQKSL SLSPGK                                       566
```

-continued

```
SEQ ID NO: 339            moltype = AA  length = 566
FEATURE                   Location/Qualifiers
source                    1..566
                          mol_type = protein
                          organism = synthetic construct
SEQUENCE: 339
KKVVYGKCGD TVELTCTASQ KKNIQFHWKN SNQIKILGNQ GSFLTKGPSK LNDRVDSRRS  60
LWDQGNFPLI IKNLKPEDSD TYICEVEDQK EEVQLVVVCG GGGSQLHLQE SGPGLVKPPE  120
TLSLTCSVSG ASINDAYWSW IRQSPGKRPE WVGYVHHSGD TNYNPSLKRR VTFSLDTAKN  180
EVSLKLVDLT AADSATYFCA RALHGKRIYG IVALGELFTY FYMDVWGKGT AVTVSSASTK  240
GPSVFPLAPS SKSTSGGTAA LGCLVKDYFP EPVTVSWNSG ALTSGVHTFP AVLQSSGLYS  300
LSSVVTVPSS SLGTQTYICN VNHKPSNTKV DKKVEPKSCD KTHTCPPCPA PELLGGPSVF  360
LFPPKPKDTL MISRTPEVTC VVVDVSHEDP EVKFNWYVDG VEVHNAKTKP REEQYNSTYR  420
VVSVLTVLHQ DWLNGKEYKC KVSNKALPAP IEKTISKAKG QPREPQVYTL PPSRDELTKN  480
QVSLTCLVKG FYPSDIAVEW ESNGQPENNY KTTPPVLDSD GSFFLYSKLT VDKSRWQQGN  540
VFSCSVLHEA LHSHYTQKSL SLSPGK                                     566

SEQ ID NO: 340            moltype = AA  length = 571
FEATURE                   Location/Qualifiers
source                    1..571
                          mol_type = protein
                          organism = synthetic construct
SEQUENCE: 340
KKVVYGKCGD TVELTCTASQ KKNIQFHWKN SNQIKILGNQ GSFLTKGPSK LNDRVDSRRS  60
LWDQGNFPLI IKNLKPEDSD TYICEVEDQK EEVQLVVVCG GGGSQSQLQE SGPRLVEASE  120
TLSLTCNVSG ESTGACTYFW GWVRQAPGKG LEWIGSLSHC QSFWGSGWTF HNPSLKSRLT  180
ISLDTPKNQV FLKLTSLTAA DTATYYCARF DGEVLVYNHW PKPAWVDLWG RGIPVTVTVS  240
SASTKGPSVF PLAPSSKSTS GGTAALGCLV KDYFPEPVTV SWNSGALTSG VHTFPAVLQS  300
SGLYSLSSVV TVPSSSLGTQ TYICNVNHKP SNTKVDKKVE PKSCDKTHTC PPCPAPELLG  360
GPSVFLFPPK PKDTMISRT PEVTCVVVDV SHEDPEVKFN WYVDGVEVHN AKTKPREEQY  420
NSTYRVVSVL TVLHQDWLNG KEYKCKVSNK ALPAPIEKTI SKAKGQPREP QVYTLPPSRD  480
ELTKNQVSLT CLVKGFYPSD IAVEWESNGQ PENNYKTTPP VLDSDGSFFL YSKLTVDKSR  540
WQQGNVFSCS VLHEALHSHY TQKSLSLSPG K                               571

SEQ ID NO: 341            moltype = AA  length = 571
FEATURE                   Location/Qualifiers
source                    1..571
                          mol_type = protein
                          organism = synthetic construct
SEQUENCE: 341
KKVVYGKCGD TVELTCTASQ KKNIQFHWKN SNQIKILGNQ GSFLTKGPSK LNDRVDSRRS  60
LWDQGNFPLI IKNLKPEDSD TYICEVEDQK EEVQLVVVCG GGGSQPQLQE SGPGLVEASE  120
TLSLTCTVSG DSTAACDYFW GWVRQPPGKG LEWIGGLSHC AGYYNTGWTY HNPSLKSRLT  180
ISLDTPKNQV FLKLNSVTAA DTAIYYCARF DGEVLVYHDW PKPAWVDLWG RGTLVTVTVS  240
SASTKGPSVF PLAPSSKSTS GGTAALGCLV KDYFPEPVTV SWNSGALTSG VHTFPAVLQS  300
SGLYSLSSVV TVPSSSLGTQ TYICNVNHKP SNTKVDKKVE PKSCDKTHTC PPCPAPELLG  360
GPSVFLFPPK PKDTMISRT PEVTCVVVDV SHEDPEVKFN WYVDGVEVHN AKTKPREEQY  420
NSTYRVVSVL TVLHQDWLNG KEYKCKVSNK ALPAPIEKTI SKAKGQPREP QVYTLPPSRD  480
ELTKNQVSLT CLVKGFYPSD IAVEWESNGQ PENNYKTTPP VLDSDGSFFL YSKLTVDKSR  540
WQQGNVFSCS VLHEALHSHY TQKSLSLSPG K                               571

SEQ ID NO: 342            moltype = AA  length = 569
FEATURE                   Location/Qualifiers
source                    1..569
                          mol_type = protein
                          organism = synthetic construct
SEQUENCE: 342
KKVVYGKCGD TVELTCTASQ KKNIQFHWKN SNQIKILGNQ GSFLTKGPSK LNDRVDSRRS  60
LWDQGNFPLI IKNLKPEDSD TYICEVEDQK EEVQLVVVCG GGGSQPQLQE SGPGLVEASE  120
TLSLTCTVSG DSTGRCNYFW GWVRQPPGKG LEWIGSLSHC RSYYNTDWTY HNPSLKSRLT  180
ISLDTPKNQV FLRLTSVTAA DTATYYCARF GGEVLVYRDW PKPAWVDLWG RGTLVTVSSA  240
STKGPSVFPL APSSKSTSGG TAALGCLVKD YFPEPVTVSW NSGALTSGVH TFPAVLQSSG  300
LYSLSSVVTV PSSSLGTQTY ICNVNHKPSN TKVDKKVEPK SCDKTHTCPP CPAPELLGGP  360
SVFLFPPKPK DTLMISRTPE VTCVVVDVSH EDPEVKFNWY VDGVEVHNAK TKPREEQYNS  420
TYRVVSVLTV LHQDWLNGKE YKCKVSNKAL PAPIEKTISK AKGQPREPQV YTLPPSRDEL  480
TKNQVSLTCL VKGFYPSDIA VEWESNGQPE NNYKTTPPVL DSDGSFFLYS KLTVDKSRWQ  540
QGNVFSCSVL HEALHSHYTQ KSLSLSPGK                                  569

SEQ ID NO: 343            moltype = AA  length = 563
FEATURE                   Location/Qualifiers
source                    1..563
                          mol_type = protein
                          organism = synthetic construct
SEQUENCE: 343
KKVVYGKCGD TVELTCTASQ KKNIQFHWKN SNQIKILGNQ GSFLTKGPSK LNDRVDSRRS  60
LWDQGNFPLI IKNLKPEDSD TYICEVEDQK EEVQLVVVCG GGGSQVQLQE SGPGLVKPAE  120
TLSLTCSVSG ESINTGHYYW GWVRQVPGKG LEWIGHIHYT TAVLHNPSLK SRLTIKIYTL  180
RNQITLRLSN VTAADTAVYH CVRSGGDILY YYEWQKPHWF SPWGPGIHVT VSSASTKGPS  240
```

```
VFPLAPSSKS TSGGTAALGC LVKDYFPEPV TVSWNSGALT SGVHTFPAVL QSSGLYSLSS  300
VVTVPSSSLG TQTYICNVNH KPSNTKVDKK VEPKSCDKTH TCPPCPAPEL LGGPSVFLFP  360
PKPKDTLMIS RTPEVTCVVV DVSHEDPEVK FNWYVDGVEV HNAKTKPREE QYNSTYRVVS  420
VLTVLHQDWL NGKEYKCKVS NKALPAPIEK TISKAKGQPR EPQVYTLPPS RDELTKNQVS  480
LTCLVKGFYP SDIAVEWESN GQPENNYKTT PPVLDSDGSF FLYSKLTVDK SRWQQGNVFS  540
CSVLHEALHS HYTQKSLSLS PGK                                          563

SEQ ID NO: 344            moltype = AA  length = 563
FEATURE                   Location/Qualifiers
source                    1..563
                          mol_type = protein
                          organism = synthetic construct
SEQUENCE: 344
QVQLQESGPG LVKPAETLSL TCSVSGESIN TGHYYWGWVR QVPGKGLEWI GHIHYTTAVL  60
HNPSLKSRLT IKIYTLRNQI TLRLSNVTAA DTAVYHCVRS GGDILYYYEW QKPHWFSPWG  120
PGIHVTVSSA STKGPSVFPL APSSKSTSGG TAALGCLVKD YFPEPVTVSW NSGALTSGVH  180
TFPAVLQSSG LYSLSSVVTV PSSSLGTQTY ICNVNHKPSN TKVDKKVEPK SCDKTHTCPP  240
CPAPELLGGP SVFLFPPKPK DTLMISRTPE VTCVVVDVSH EDPEVKFNWY VDGVEVHNAK  300
TKPREEQYNS TYRVVSVLTV LHQDWLNGKE YKCKVSNKAL PAPIEKTISK AKGQPREPQV  360
YTLPPSRDEL TKNQVSLTCL VKGFYPSDIA VEWESNGQPE NNYKTTPPVL DSDGSFFLYS  420
KLTVDKSRWQ QGNVFSCSVL HEALHSHYTQ KSLSLSPGKG GGGSKVVYG KCGDTVELTC  480
TASQKNIQF HWKNSNQIKI LGNQGSFLTK GPSKLNDRVD SRRSLWDQGN FPLIIKNLKP  540
EDSDTYICEV EDQKEEVQLV VVC                                          563

SEQ ID NO: 345            moltype = AA  length = 320
FEATURE                   Location/Qualifiers
source                    1..320
                          mol_type = protein
                          organism = synthetic construct
SEQUENCE: 345
KKVVYGKCGD TVELTCTASQ KKNIQFHWKN SNQIKILGNQ GSFLTKGPSK LNDRVDSRRS  60
LWDQGNFPLI IKNLKPEDSD TYICEVEDQK EEVQLVVVCG GGGSQSALTQ PPSASGSLGQ  120
SVTISCNGTS SDIGGWNFVS WYQQFPGRAP RLIIFEVNKR PSGVPGRFSG SKSGNSASLT  180
VSGLQSDDEG QYFCSSLFGR WDVVFGGGTK LTVLGQPKAA PSVTLFPPSS EELQANKATL  240
VCLISDFYPG AVTVAWKADS SPVKAGVETT TPSKQSNNKY AASSYLSLTP EQWKSHRSYS  300
CQVTHEGSTV EKTVAPTECS                                              320

SEQ ID NO: 346            moltype = AA  length = 320
FEATURE                   Location/Qualifiers
source                    1..320
                          mol_type = protein
                          organism = synthetic construct
SEQUENCE: 346
QSALTQPPSA SGSLGQSVTI SCNGTSSDIG GWNFVSWYQQ FPGRAPRLII FEVNKRPSGV  60
PGRFSGSKSG NSASLTVSGL QSDDEGQYFC SSLFGRWDVV FGGGTKLTVL GQPKAAPSVT  120
LFPPSSEELQ ANKATLVCLI SDFYPGAVTV AWKADSSPVK AGVETTTPSK QSNNKYAASS  180
YLSLTPEQWK SHRSYSCQVT HEGSTVEKTV APTECSGGGG SKKVVYGKCG DTVELTCTAS  240
QKKNIQFHWK NSNQIKILGN QGSFLTKGPS KLNDRVDSRR SLWDQGNFPL IIKNLKPEDS  300
DTYICEVEDQ KEEVQLVVVC                                              320

SEQ ID NO: 347            moltype = AA  length = 563
FEATURE                   Location/Qualifiers
source                    1..563
                          mol_type = protein
                          organism = synthetic construct
SEQUENCE: 347
KKVVYGKCGD TVELTCTASQ KKNIQFHWKN SNQIKILGNQ GSFLTKGPSK LNDRVDSRRS  60
LWDQGNFPLI IKNLKPEDSD TYICEVEDQK EEVQLVVVCG GGGSQVQLQE SGPGLVKPSE  120
TLSLTCTVSG DSINTGHHYW GWVRQVPGKG PEWIAHIHYN TAVLHNPALK SRVTISIFTL  180
KNLITLSLSN VTAADTAVYF CVRSGGDILY YIEWQKPHWF YPWGPGILVT VSSASTKGPS  240
VFPLAPSSKS TSGGTAALGC LVKDYFPEPV TVSWNSGALT SGVHTFPAVL QSSGLYSLSS  300
VVTVPSSSLG TQTYICNVNH KPSNTKVDKK VEPKSCDKTH TCPPCPAPEL LGGPSVFLFP  360
PKPKDTLMIS RTPEVTCVVV DVSHEDPEVK FNWYVDGVEV HNAKTKPREE QYNSTYRVVS  420
VLTVLHQDWL NGKEYKCKVS NKALPAPIEK TISKAKGQPR EPQVYTLPPS RDELTKNQVS  480
LTCLVKGFYP SDIAVEWESN GQPENNYKTT PPVLDSDGSF FLYSKLTVDK SRWQQGNVFS  540
CSVLHEALHS HYTQKSLSLS PGK                                          563

SEQ ID NO: 348            moltype = AA  length = 568
FEATURE                   Location/Qualifiers
source                    1..568
                          mol_type = protein
                          organism = synthetic construct
SEQUENCE: 348
KKVVYGKCGD TVELTCTASQ KKNIQFHWKN SNQIKILGNQ GSFLTKGPSK LNDRVDSRRS  60
LWDQGNFPLI IKNLKPEDSD TYICEVEDQK EEVQLVVVCG GGGSQLQLQE SGPGLVKPSE  120
TLSLTCTVSG GSMRGTDWGE NDFHYGWIRQ SSAKGLEWIG SIHWRGRTTH YKTSFRSRAT  180
LSIDTSNNRF SLTFSFVTAA DTAVYYCARH KYHDIFRVVP VAGWFDPWGQ GLLVTVSSAS  240
TKGPSVFPLA PSSKSTSGGT AALGCLVKDY FPEPVTVSWN SGALTSGVHT FPAVLQSSGL  300
YSLSSVVTVP SSSLGTQTYI CNVNHKPSNT KVDKKVEPKS CDKTHTCPPC PAPELLGGPS  360
```

```
VFLFPPKPKD TLMISRTPEV TCVVVDVSHE DPEVKFNWYV DGVEVHNAKT KPREEQYNST   420
YRVVSVLTVL HQDWLNGKEY KCKVSNKALP APIEKTISKA KGQPREPQVY TLPPSRDELT   480
KNQVSLTCLV KGFYPSDIAV EWESNGQPEN NYKTTPPVLD SDGSFFLYSK LTVDKSRWQQ   540
GNVFSCSVLH EALHSHYTQK SLSLSPGK                                       568

SEQ ID NO: 349          moltype = AA  length = 567
FEATURE                 Location/Qualifiers
source                  1..567
                        mol_type = protein
                        organism = synthetic construct
SEQUENCE: 349
KKVVYGKCGD TVELTCTASQ KKNIQFHWKN SNQIKILGNQ GSFLTKGPSK LNDRVDSRRS   60
LWDQGNFPLI IKNLKPEDSD TYICEVEDQK EEVQLVVVCG GGGSEVHLEE SGPGLVRPSE   120
TLSLTCTASG GSIRGGEWGD SDYHWGWVRH SPEKGLEWIG SIHWRGTTHY NAPFRGRGRL   180
SIDLSRNQFS LRLTSVTAED TAVYYCVKHK YHDIVMVVPI AGWFDPWGQG LQVTVSSAST   240
KGPSVFPLAP SSKSTSGGTA ALGCLVKDYF PEPVTVSWNS GALTSGVHTF PAVLQSSGLY   300
SLSSVVTVPS SSLGTQTYIC NVNHKPSNTK VDKKVEPKSC DKTHTCPPCP APELLGGPSV   360
FLFPPPKDT LMISRTPEVT CVVVDVSHED PEVKFNWYVD GVEVHNAKTK PREEQYNSTY   420
RVVSVLTVLH QDWLNGKEYK CKVSNKALPA PIEKTISKAK GQPREPQVYT LPPSRDELTK   480
NQVSLTCLVK GFYPSDIAVE WESNGQPENN YKTTPPVLDS DGSFFLYSKL TVDKSRWQQG   540
NVFSCSVLHE ALHSHYTQKS LSLSPGK                                       567

SEQ ID NO: 350          moltype = AA  length = 565
FEATURE                 Location/Qualifiers
source                  1..565
                        mol_type = protein
                        organism = synthetic construct
SEQUENCE: 350
KKVVYGKCGD TVELTCTASQ KKNIQFHWKN SNQIKILGNQ GSFLTKGPSK LNDRVDSRRS   60
LWDQGNFPLI IKNLKPEDSD TYICEVEDQK EEVQLVVVCG GGGSEVQLVE SGGGLVKPGG   120
SLRLTCVASG FTFSDVWLNW VRQAPGKGLE WVGRIKSRTD GGTTDYAASV KGRFTISRDD   180
SKNTLYLQMN SLKTEDTAVY SCTTDGFIMI RGVSEDYYYY YMDVWGKGTT VTVSSASTKG   240
PSVFPLAPSS KSTSGGTAAL GCLVKDYFPE PVTVSWNSGA LTSGVHTFPA VLQSSGLYSL   300
SSVVTVPSSS LGTQTYICNV NHKPSNTKVD KKVEPKSCDK THTCPPCPAP ELLGGPSVFL   360
FPPKPKDTLM ISRTPEVTCV VVDVSHEDPE VKFNWYVDGV EVHNAKTKPR EEQYNSTYRV   420
VSVLTVLHQD WLNGKEYKCK VSNKALPAPI EKTISKAKGQ PREPQVYTLP PSRDELTKNQ   480
VSLTCLVKGF YPSDIAVEWE SNGQPENNYK TTPPVLDSDG SFFLYSKLTV DKSRWQQGNV   540
FSCSVLHEAL HSHYTQKSLS LSPGK                                         565

SEQ ID NO: 351          moltype = AA  length = 557
FEATURE                 Location/Qualifiers
source                  1..557
                        mol_type = protein
                        organism = synthetic construct
SEQUENCE: 351
KKVVYGKCGD TVELTCTASQ KKNIQFHWKN SNQIKILGNQ GSFLTKGPSK LNDRVDSRRS   60
LWDQGNFPLI IKNLKPEDSD TYICEVEDQK EEVQLVVVCG GGGSQVQLVQ SGGGLVQPGG   120
SLRLSCAAFG FNFSSYVMHW VRQAPGQGLE YLSAISSDGE TTYHANSVKG RFTSSRDNSK   180
NTLFLQMGSL RTEDVAVYYC ARDRYYETSG SNAFDVWGQG TMVVVSSAST KGPSVFPLAP   240
SSKSTSGGTA ALGCLVKDYF PEPVTVSWNS GALTSGVHTF PAVLQSSGLY SLSSVVTVPS   300
SSLGTQTYIC NVNHKPSNTK VDKKVEPKSC DKTHTCPPCP APELLGGPSV FLFPPPKDT   360
LMISRTPEVT CVVVDVSHED PEVKFNWYVD GVEVHNAKTK PREEQYNSTY RVVSVLTVLH   420
QDWLNGKEYK CKVSNKALPA PIEKTISKAK GQPREPQVYT LPPSRDELTK NQVSLTCLVK   480
GFYPSDIAVE WESNGQPENN YKTTPPVLDS DGSFFLYSKL TVDKSRWQQG NVFSCSVLHE   540
ALHSHYTQKS LSLSPGK                                                  557

SEQ ID NO: 352          moltype = AA  length = 564
FEATURE                 Location/Qualifiers
source                  1..564
                        mol_type = protein
                        organism = synthetic construct
SEQUENCE: 352
KKVVYGKCGD TVELTCTASQ KKNIQFHWKN SNQIKILGNQ GSFLTKGPSK LNDRVDSRRS   60
LWDQGNFPLI IKNLKPEDSD TYICEVEDQK EEVQLVVVCG GGGSQVQLVQ SGAEVRKPGS   120
SVTISCKPVG GTFTNFAIHW VRQAPGQGLE WVGGRVPVVG IYKYGKKFHD RLRLYEDDPM   180
KTVFLELRSL TSDDTGVYYC TRWRGCGMCP YDTSSYYNDA SDVWGPGTKV IVSAASTKGP   240
SVFPLAPSS STSGGTAALG CLVKDYFPEP VTVSWNSGAL TSGVHTFPAV LQSSGLYSLS   300
SVVTVPSSSL GTQTYICNVN HKPSNTKVDK KVEPKSCDKT HTCPPCPAPE LLGGPSVFLF   360
PPKPKDTLMI SRTPEVTCVV VDVSHEDPEV KFNWYVDGVE VHNAKTKPRE EQYNSTYRVV   420
SVLTVLHQDW LNGKEYKCKV SNKALPAPIE KTISKAKGQP REPQVYTLPP SRDELTKNQV   480
SLTCLVKGFY PSDIAVEWES NGQPENNYKT TPPVLDSDGS FFLYSKLTVD KSRWQQGNVF   540
SCSVLHEALH SHYTQKSLSL SPGK                                          564

SEQ ID NO: 353          moltype = AA  length = 557
FEATURE                 Location/Qualifiers
source                  1..557
                        mol_type = protein
                        organism = synthetic construct
SEQUENCE: 353
```

```
KKVVYGKCGD  TVELTCTASQ  KKNIQFHWKN  SNQIKILGNQ  GSFLTKGPSK  LNDRVDSRRS   60
LWDQGNFPLI  IKNLKPEDSD  TYICEVEDQK  EEVQLVVVCG  GGGSEVQLVE  SGGGLVKAGG  120
SLILSCGVSN  FRISAHTMNW  VRRVPGGGLE  WVASISTSST  YRDYADAVKG  RFTVSRDDLE  180
DFVYLQMHKM  RVEDTAIYYC  ARKGSDRLSD  NDPFDAWGPG  TVVTVSPAST  KGPSVFPLAP  240
SSKSTSGGTA  ALGCLVKDYF  PEPVTVSWNS  GALTSGVHTF  PAVLQSSGLY  SLSSVVTVPS  300
SSLGTQTYIC  NVNHKPSNTK  VDKKVEPKSC  DKTHTCPPCP  APELLGGPSV  FLFPPKPKDT  360
LMISRTPEVT  CVVVDVSHED  PEVKFNWYVD  GVEVHNAKTK  PREEQYNSTY  RVVSVLTVLH  420
QDWLNGKEYK  CKVSNKALPA  PIEKTISKAK  GQPREPQVYT  LPPSRDELTK  NQVSLTCLVK  480
GFYPSDIAVE  WESNGQPENN  YKTTPPVLDS  DGSFFLYSKL  TVDKSRWQQG  NVFSCSVLHE  540
ALHSHYTQKS  LSLSPGK                                                     557
```

SEQ ID NO: 354              moltype = AA  length = 566
FEATURE                     Location/Qualifiers
source                      1..566
                            mol_type = protein
                            organism = synthetic construct
SEQUENCE: 354
```
KKVVYGKCGD  TVELTCTASQ  KKNIQFHWKN  SNQIKILGNQ  GSFLTKGPSK  LNDRVDSRRS   60
LWDQGNFPLI  IKNLKPEDSD  TYICEVEDQK  EEVQLVVVCG  GGGSQMQLQE  SGPGLVKPGE  120
TLSLTCSVSG  ASISSSYWSW  LRETPGKGLE  WIGYTHHSGD  TNYAPSLKSR  VHLGLHPSKN  180
QVSLSLTSVT  AADTAVYYCA  RTLHGRRIYG  VVAFNEFFTY  FYWEVWGKGT  QVTVSSASTK  240
GPSVFPLAPS  SKSTSGGTAA  LGCLVKDYFP  EPVTVSWNSG  ALTSGVHTFP  AVLQSSGLYS  300
LSSVVTVPSS  SLGTQTYICN  VNHKPSNTKV  DKKVEPKSCD  KTHTCPPCPA  PELLGGPSVF  360
LFPPKPKDTL  MISRTPEVTC  VVVDVSHEDP  EVKFNWYVDG  VEVHNAKTKP  REEQYNSTYR  420
VVSVLTVLHQ  DWLNGKEYKC  KVSNKALPAP  IEKTISKAKG  QPREPQVYTL  PPSRDELTKN  480
QVSLTCLVKG  FYPSDIAVEW  ESNGQPENNY  KTTPPVLDSD  GSFFLYSKLT  VDKSRWQQGN  540
VFSCSVLHEA  LHSHYTQKSL  SLSPGK                                          566
```

SEQ ID NO: 355              moltype = AA  length = 566
FEATURE                     Location/Qualifiers
source                      1..566
                            mol_type = protein
                            organism = synthetic construct
SEQUENCE: 355
```
KKVVYGKCGD  TVELTCTASQ  KKNIQFHWKN  SNQIKILGNQ  GSFLTKGPSK  LNDRVDSRRS   60
LWDQGNFPLI  IKNLKPEDSD  TYICEVEDQK  EEVQLVVVCG  GGGSQMQLQE  SGPGLVKPGE  120
TLSLTCSVSG  ASISSSYWSW  LRETPGKGLE  WIGYTHHSGD  TNYAPSLKSR  VHLGLHPSKN  180
QVSLSLTSVT  AADTAVYYCA  RTLHGRRIYG  VVAFNEYYTY  FYWPTWGKGT  QVTVSSASTK  240
GPSVFPLAPS  SKSTSGGTAA  LGCLVKDYFP  EPVTVSWNSG  ALTSGVHTFP  AVLQSSGLYS  300
LSSVVTVPSS  SLGTQTYICN  VNHKPSNTKV  DKKVEPKSCD  KTHTCPPCPA  PELLGGPSVF  360
LFPPKPKDTL  MISRTPEVTC  VVVDVSHEDP  EVKFNWYVDG  VEVHNAKTKP  REEQYNSTYR  420
VVSVLTVLHQ  DWLNGKEYKC  KVSNKALPAP  IEKTISKAKG  QPREPQVYTL  PPSRDELTKN  480
QVSLTCLVKG  FYPSDIAVEW  ESNGQPENNY  KTTPPVLDSD  GSFFLYSKLT  VDKSRWQQGN  540
VFSCSVLHEA  LHSHYTQKSL  SLSPGK                                          566
```

SEQ ID NO: 356              moltype = AA  length = 566
FEATURE                     Location/Qualifiers
source                      1..566
                            mol_type = protein
                            organism = synthetic construct
SEQUENCE: 356
```
KKVVYGKCGD  TVELTCTASQ  KKNIQFHWKN  SNQIKILGNQ  GSFLTKGPSK  LNDRVDSRRS   60
LWDQGNFPLI  IKNLKPEDSD  TYICEVEDQK  EEVQLVVVCG  GGGSQMQLQE  SGPGLVKPGE  120
TLSLTCSVSG  ASISSSYWSW  LRETPGKGLE  WIGYTHHSGD  TNYAPSLKSR  VTIGLDPSKN  180
QVSLSLTSVT  AADTAVYYCA  RTLHGRRIYG  VVAFNEYYTY  FYWPTWGKGT  QVTVSSASTK  240
GPSVFPLAPS  SKSTSGGTAA  LGCLVKDYFP  EPVTVSWNSG  ALTSGVHTFP  AVLQSSGLYS  300
LSSVVTVPSS  SLGTQTYICN  VNHKPSNTKV  DKKVEPKSCD  KTHTCPPCPA  PELLGGPSVF  360
LFPPKPKDTL  MISRTPEVTC  VVVDVSHEDP  EVKFNWYVDG  VEVHNAKTKP  REEQYNSTYR  420
VVSVLTVLHQ  DWLNGKEYKC  KVSNKALPAP  IEKTISKAKG  QPREPQVYTL  PPSRDELTKN  480
QVSLTCLVKG  FYPSDIAVEW  ESNGQPENNY  KTTPPVLDSD  GSFFLYSKLT  VDKSRWQQGN  540
VFSCSVLHEA  LHSHYTQKSL  SLSPGK                                          566
```

SEQ ID NO: 357              moltype = AA  length = 555
FEATURE                     Location/Qualifiers
source                      1..555
                            mol_type = protein
                            organism = synthetic construct
SEQUENCE: 357
```
KKVVYGKCGD  TVELTCTASQ  KKNIQFHWKN  SNQIKILGNQ  GSFLTKGPSK  LNDRVDSRRS   60
LWDQGNFPLI  IKNLKPEDSD  TYICEVEDQK  EEVQLVVVCG  GGGSQVQLLE  SGPGLVRPSE  120
TLTLTCSVFN  SRVSGYYYSW  IRQPPGRGLE  WIASTHFSLR  PSRNPSLLSR  VTTSIDTERY  180
QVFLNMRSVT  AADTAVYFCA  RGDASGWRAD  YFPHWGQGTL  VVVSSASTKG  PSVFPLAPSS  240
KSTSGGTAAL  GCLVKDYFPE  PVTVSWNSGA  LTSGVHTFPA  VLQSSGLYSL  SSVVTVPSSS  300
LGTQTYICNV  NHKPSNTKVD  KKVEPKSCDK  THTCPPCPAP  ELLGGPSVFL  FPPKPKDTLM  360
ISRTPEVTCV  VVDVSHEDPE  VKFNWYVDGV  EVHNAKTKPR  EEQYNSTYRV  VSVLTVLHQD  420
WLNGKEYKCK  VSNKALPAPI  EKTISKAKGQ  PREPQVYTLP  PSRDELTKNQ  VSLTCLVKGF  480
YPSDIAVEWE  SNGQPENNYK  TTPPVLDSDG  SFFLYSKLTV  DKSRWQQGNV  FSCSVLHEAL  540
HSHYTQKSLS  LSPGK                                                       555
```

```
SEQ ID NO: 358           moltype = AA   length = 320
FEATURE                  Location/Qualifiers
source                   1..320
                         mol_type = protein
                         organism = synthetic construct
SEQUENCE: 358
KKVVYGKCGD TVELTCTASQ KKNIQFHWKN SNQIKILGNQ GSFLTKGPSK LNDRVDSRRS    60
LWDQGNFPLI IKNLKPEDSD TYICEVEDQK EEVQLVVVCG GGGSQSVLTQ PPSASGSPGQ   120
SVTISCTGTS SDIGASDYVS WYQQYPGEAP KVIIYDVTKR PSGVPDRFSG SKSGTTASLT   180
VSGLQAEDEA DYYCSSDAGR HTLLFGGGTK VTVLGQPKAA PSVTLFPPSS EELQANKATL   240
VCLISDFYPG AVTVAWKADS SPVKAGVETT TPSKQSNNKY AASSYLSLTP EQWKSHRSYS   300
CQVTHEGSTV EKTVAPTECS                                               320

SEQ ID NO: 359           moltype = AA   length = 555
FEATURE                  Location/Qualifiers
source                   1..555
                         mol_type = protein
                         organism = synthetic construct
SEQUENCE: 359
QVQLLESGPG LVRPSETLTL TCSVFNSRVS GYYYSWIRQP PGRGLEWIAS THFSLRPSRN    60
PSLLSRVTTS IDTERYQVFL NMRSVTAADT AVYFCARGDA SGWRADYFPH WGQGTLVVVS   120
SASTKGPSVF PLAPSSKSTS GGTAALGCLV KDYFPEPVTV SWNSGALTSG VHTFPAVLQS   180
SGLYSLSSVV TVPSSSLGTQ TYICNVNHKP SNTKVDKKVE PKSCDKTHTC PPCPAPELLG   240
GPSVFLFPPK PKDTLMISRT PEVTCVVVDV SHEDPEVKFN WYVDGVEVHN AKTKPREEQY   300
NSTYRVVSVL TVLHQDWLNG KEYKCKVSNK ALPAPIEKTI SKAKGQPREP QVYTLPPSRD   360
ELTKNQVSLT CLVKGFYPSD IAVEWESNGQ PENNYKTTPP VLDSDGSFFL YSKLTVDKSR   420
WQQGNVFSCS VLHEALHSHY TQKSLSLSPG KGGGGSKKVV YGKCGDTVEL TCTASQKKNI   480
QFHWKNSNQI KILGNQGSFL TKGPSKLNDR VDSRRSLWDQ GNFPLIIKNL KPEDSDTYIC   540
EVEDQKEEVQ LVVVC                                                    555

SEQ ID NO: 360           moltype = AA   length = 320
FEATURE                  Location/Qualifiers
source                   1..320
                         mol_type = protein
                         organism = synthetic construct
SEQUENCE: 360
QSVLTQPPSA SGSPGQSVTI SCTGTSSDIG ASDYVSWYQQ YPGEAPKVII YDVTKRPSGV    60
PDRFSGSKSG TTASLTVSGL QAEDEADYYC SSDAGRHTLL FGGGTKVTVL GQPKAAPSVT   120
LFPPSSEELQ ANKATLVCLI SDFYPGAVTV AWKADSSPVK AGVETTTPSK QSNNKYAASS   180
YLSLTPEQWK SHRSYSCQVT HEGSTVEKTV APTECSGGGG SKKVVYGKCG DTVELTCTAS   240
QKKNIQFHWK NSNQIKILGN QGSFLTKGPS KLNDRVDSRR SLWDQGNFPL IIKNLKPEDS   300
DTYICEVEDQ KEEVQLVVVC                                               320

SEQ ID NO: 361           moltype = AA   length = 35
FEATURE                  Location/Qualifiers
source                   1..35
                         mol_type = protein
                         organism = Human Immunodeficiency Virus 1
SEQUENCE: 361
CTRPNNNTRK SIHIGPGRAF YTTGEIIGDI RQAHC                               35

SEQ ID NO: 362           moltype = AA   length = 561
FEATURE                  Location/Qualifiers
source                   1..561
                         mol_type = protein
                         organism = synthetic construct
SEQUENCE: 362
KKVVYGKCGD TVELTCTASQ KKNIQFHWKN SNQIKILGNQ GSFLTKGPSK LNDRVDSRRS    60
LWDQGNFPLI IKNLKPEDSD TYICEVEDQK EEVQLVVVCG GGGSQVQLVQ SGAQMKNPGA   120
SVKVSCAPSG YTFTDFYIHW LRQAPGQGLQ WMGWMNPQTG RTNTARNFQG RVTMTRDTSI   180
GTAYMELRSL TSDDTAIYYC TTGGWISLYY DSSYYPNFDH WGQGTLLTVS SASTKGPSVF   240
PLAPSSKSTS GGTAALGCLV KDYFPEPVTV SWNSGALTSG VHTFPAVLQS SGLYSLSSVV   300
TVPSSSLGTQ TYICNVNHKP SNTKVDKKVE PKSCDKTHTC PPCPAPELLG GPSVFLFPPK   360
PKDTLMISRT PEVTCVVVDV SHEDPEVKFN WYVDGVEVHN AKTKPREEQY NSTYRVVSVL   420
TVLHQDWLNG KEYKCKVSNK ALPAPIEKTI SKAKGQPREP QVYTLPPSRD ELTKNQVSLT   480
CLVKGFYPSD IAVEWESNGQ PENNYKTTPP VLDSDGSFFL YSKLTVDKSR WQQGNVFSCS   540
VLHEALHSHY TQKSLSLSPG K                                             561

SEQ ID NO: 363           moltype = AA   length = 849
FEATURE                  Location/Qualifiers
source                   1..849
                         mol_type = protein
                         organism = Human Immunodeficiency Virus 1
SEQUENCE: 363
MKVMGTKKNY QHLWRWGIML LGMLMMSSAA EQLWVTVYYG VPVWREANTT LFCASDAKAY    60
DTEVHNVWAT HACVPTDPNP QEVVMGNVTE DFNMWKNNMV EQMHEDIISL WDQSLKPCVK   120
LTPLCVTLHC TNVTISSTNG STANVTMREE MKNCSFNTTT VIRDKIQKEY ALFYKLDIVP   180
IEGKNTNTSY RLINCNTSVI TQACPKVSFE PIPIHYCAPA GFAILKCNNK TFNGKGPCRN   240
VSTVQCTHGI KPVVSTQLLL NGSLAEEDII IRSENFTNNG KNIIVQLKEP VKINCTRPGN   300
```

-continued

```
NTRRSINIGP GRAFYATGAI IGDIRKAHCN ISTEQWNNTL TQIVDKLREQ FGNKTIIFNQ  360
SSGGDPEVVM HTFNCGGEFF YCNSTQLFNS TWFNNGTSTW NSTADNITLP CRIKQVINMW  420
QEVGKAMYAP PIRGQIDCSS NITGLILTRD GGSNSSQNET FRPGGGNMKD NWRSELYKYK  480
VVKIEPLGIA PTRAKRRVVQ REKRAVTLGA VFLGFLGAAG STMGAASLTL TVQARLLLSG  540
IVQQQSNLLR AIEAQQHMLQ LTVWGIKQLQ ARVLAIERYL KDQQLLGIWG CSGKLICTTT  600
VPWNTSWSNK SYDYIWNNMT WMQWEREIDN YTGFIYTLIE ESQNQQEKNE LELLELDKWA  660
SLWNWFNITN WLWYIKLFIM IIGGLVGLRI VCAVLSIVNR VRQGYSPLSF QTRLPNPRGP  720
DRPEETEGEG GERDRDRSAR LVNGFLAIIW DDLRSLCLFS YHRLRDLLLI VARVVEILGR  780
RGWEILKYWW NLLKYWSQEL KNSAVSLLNV TAIAVAEGTD RVIEIVQRAV RAILHIPTRI  840
RQGFERALL                                                         849

SEQ ID NO: 364              moltype = AA  length = 475
FEATURE                     Location/Qualifiers
source                      1..475
                            mol_type = protein
                            organism = Human Immunodeficiency Virus 1
SEQUENCE: 364
AEQLWVIVYY GVPVWREANT TLFCASDAKA YDTEVHNVWA THACVPTDPN PQEVVMGNVT  60
EDFNMWKNNM VEQMHEDIIS LWDQSLKPCV KLTPLCVTLH CTNVTISSTN GSTANVTMRE  120
EMKNCSFNTT TVIRDKIQKE YALFYKLDIV PIEGKNTNTS YRLINCNTSV ITQACPKVSF  180
EPIPIHYCAP AGFAILKCNN KTFNGKGPCR NVSTVQCTHG IKPVVSTQLL LNGSLAEEDI  240
IIRSENFTNN GKNIIVQLKE PVKINCTRPG NNTRRSINIG PGRAFYATGA IIGDIRKAHC  300
NISTEQWNNT LTQIVDKLRE QFGNKTIIFN QSSGGDPEVV MHTFNCGGEF FYCNSTQLFN  360
STWFNNGTST WNSTADNITL PCRIKQVINM WQEVGKAMYA PPIRGQIDCS SNITGLILTR  420
DGGSNSSQNE TFRPGGGNMK DNWRSELYKY KVVKIEPLGI APTRAKRRVV QREKR       475

SEQ ID NO: 365              moltype = AA  length = 105
FEATURE                     Location/Qualifiers
source                      1..105
                            mol_type = protein
                            organism = synthetic construct
SEQUENCE: 365
SDISVAPGET VRITCGGESI GSRAVQWYQH RPGQAPRLII YNNQDRPPGI PERFSGSPDI  60
DFGTTATLTI SNVEAGDEAT YYCHIWDSRR PTNWELGPGT TLTVL                  105

SEQ ID NO: 366              moltype = AA  length = 211
FEATURE                     Location/Qualifiers
source                      1..211
                            mol_type = protein
                            organism = synthetic construct
SEQUENCE: 366
SDISVAPGET VRITCGGESI GSRAVQWYQH RPGQAPRLII YNNQDRPPGI PERFSGSPDI  60
DFGTTATLTI SNVEAGDEAT YYCHIWDSRR PTNWELGPGT TLTVLGQPKA APSVTLFPPS  120
SEELQANKAT LVCLISDFYP GAVTVAWKAD SSPVKAGVET TTPSKQSNNK YAASSYLSLT  180
PEQWKSHRSY SCQVTHEGST VEKTVAPTEC S                                 211
```